US009089475B2

(12) United States Patent
Fangrow

(10) Patent No.: US 9,089,475 B2
(45) Date of Patent: Jul. 28, 2015

(54) PRESSURE-REGULATING VIAL ADAPTORS

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

(21) Appl. No.: 14/161,591

(22) Filed: Jan. 22, 2014

(65) Prior Publication Data

US 2014/0230932 A1 Aug. 21, 2014

Related U.S. Application Data

(60) Provisional application No. 61/785,874, filed on Mar. 14, 2013, provisional application No. 61/755,800, filed on Jan. 23, 2013.

(51) Int. Cl.
*A61M 5/32* (2006.01)
*A61J 1/20* (2006.01)

(52) U.S. Cl.
CPC .......... *A61J 1/2096* (2013.01); *A61J 2001/201* (2013.01); *A61J 2001/2075* (2013.01); *A61J 2001/2082* (2013.01)

(58) Field of Classification Search
CPC ................. A61J 2001/2058; A61J 2001/2062; A61J 2001/2079; A61J 2001/2086; A61J 2001/2082; A61J 2001/2068; A61J 2001/2072; A61J 2001/2075
See application file for complete search history.

(56) References Cited

U.S. PATENT DOCUMENTS

| | | | |
|---|---|---|---|
| 2,074,223 A | 3/1937 | Horiuchi et al. | |
| 2,409,734 A | 10/1946 | Bucher et al. | |
| 2,668,533 A | 2/1954 | Evans | |

(Continued)

FOREIGN PATENT DOCUMENTS

| | | |
|---|---|---|
| CA | 1037428 | 8/1978 |
| EP | 0 829 250 | 3/1998 |

(Continued)

OTHER PUBLICATIONS

International Search Report dated Jan. 16, 2008, International Application No. PCT/US2007/008809, filed Apr. 4, 2007.

(Continued)

*Primary Examiner* — Leslie Deak
*Assistant Examiner* — Kai Weng
(74) *Attorney, Agent, or Firm* — Knobbe Martens Olson & Bear LLP

(57) ABSTRACT

In certain embodiments, a vial adaptor comprises a housing configured to couple the adaptor with a vial, an access channel, a regulator channel, and a regulator assembly. The access channel is configured to facilitate withdrawal of fluid from the vial when the adaptor is coupled to the vial. The regulator channel is configured to facilitate a flow of a regulating fluid from the regulator assembly to compensate for changes in volume of a medical fluid in the vial. In some embodiments, the regulator assembly includes a flexible member configured to expand and contract in accordance with changes in the volume of the medical fluid in the vial. In some embodiments, the flexible member is substantially free to expand and contract. In some embodiments, the flexible member is not partly or completely located in a rigid enclosure.

9 Claims, 63 Drawing Sheets

(56) References Cited

U.S. PATENT DOCUMENTS

| | | | |
|---|---|---|---|
| 2,673,013 | A | 3/1954 | Hester |
| 2,852,024 | A | 7/1954 | Ryan |
| 2,999,499 | A | 7/1958 | Willet |
| 2,793,758 | A | 3/1961 | Murrish |
| 2,999,500 | A | 9/1961 | Schurer |
| 3,291,151 | A | 12/1966 | Loken |
| RE26,488 | E | 11/1968 | Bull |
| 3,542,240 | A | 11/1970 | Soloway |
| 3,557,778 | A | 1/1971 | Hughes |
| 3,584,770 | A | 6/1971 | Taylor |
| 3,797,521 | A | 3/1974 | King |
| 3,822,700 | A | 7/1974 | Pennington |
| 3,853,157 | A | 12/1974 | Madaio |
| 3,938,520 | A | 2/1976 | Scislowicz et al. |
| 3,940,003 | A | 2/1976 | Larson |
| 3,980,082 | A | 9/1976 | Miller |
| 4,058,121 | A | 11/1977 | Choski et al. |
| 4,143,853 | A | 3/1979 | Abramson |
| 4,240,433 | A | 12/1980 | Bordow |
| 4,240,833 | A | 12/1980 | Myles |
| 4,253,459 | A | 3/1981 | Willis |
| 4,262,671 | A | 4/1981 | Kersten |
| 4,301,799 | A | 11/1981 | Pope, Jr. et al. |
| 4,334,551 | A | 6/1982 | Pfister |
| 4,349,035 | A | 9/1982 | Thomas et al. |
| 4,376,634 | A | 3/1983 | Prior et al. |
| 4,381,776 | A | 5/1983 | Latham, Jr. |
| 4,396,016 | A | 8/1983 | Becker |
| 4,410,321 | A | 10/1983 | Pearson et al. |
| 4,458,733 | A | 7/1984 | Lyons |
| 4,505,709 | A | 3/1985 | Froning et al. |
| 4,534,758 | A | 8/1985 | Akers et al. |
| 4,564,054 | A | 1/1986 | Gustavsson |
| 4,576,211 | A | 3/1986 | Valentini et al. |
| 4,588,403 | A | 5/1986 | Weiss et al. |
| 4,600,040 | A | 7/1986 | Naslund |
| 4,645,073 | A | 2/1987 | Homan |
| 4,673,404 | A | 6/1987 | Gustavsson |
| 4,730,635 | A | 3/1988 | Linden |
| 4,735,608 | A | 4/1988 | Sardam |
| 4,768,568 | A | 9/1988 | Fournier et al. |
| 4,785,859 | A | 11/1988 | Gustavsson et al. |
| 4,798,578 | A | 1/1989 | Ranford |
| 4,857,068 | A | 8/1989 | Kahn |
| 4,981,464 | A | 1/1991 | Suzuki |
| 5,006,114 | A | 4/1991 | Rogers |
| 5,060,704 | A | 10/1991 | Rohrbough |
| 5,169,393 | A | 12/1992 | Moorehead et al. |
| 5,176,673 | A | 1/1993 | Marrucchi |
| 5,349,984 | A | 9/1994 | Weinheimer et al. |
| 5,405,331 | A | 4/1995 | Behnke et al. |
| 5,445,630 | A | 8/1995 | Richmond |
| 5,478,337 | A | 12/1995 | Okamoto et al. |
| 5,580,351 | A | 12/1996 | Helgren et al. |
| 5,660,796 | A | 8/1997 | Sheehy |
| 5,685,866 | A | 11/1997 | Lopez |
| 5,700,245 | A | 12/1997 | Sancoff et al. |
| 5,725,500 | A | 3/1998 | Micheler |
| 5,749,394 | A | 5/1998 | Boehmer et al. |
| 5,766,147 | A | 6/1998 | Sancoff et al. |
| 5,772,079 | A | 6/1998 | Gueret |
| 5,776,125 | A | 7/1998 | Dudar et al. |
| 5,803,311 | A | 9/1998 | Fuchs |
| 5,833,213 | A | 11/1998 | Ryan |
| 5,890,610 | A | 4/1999 | Jansen et al. |
| 6,071,270 | A | 6/2000 | Fowles et al. |
| 6,139,534 | A | 10/2000 | Niedospial et al. |
| 6,358,236 | B1 | 3/2002 | DeFoggi et al. |
| 6,551,299 | B2 | 4/2003 | Miyoshi et al. |
| 6,572,256 | B2 | 6/2003 | Seaton et al. |
| 6,679,290 | B2 | 1/2004 | Matthews et al. |
| 6,692,478 | B1 | 2/2004 | Paradis |
| 6,715,520 | B2 | 4/2004 | Andreasson et al. |
| 6,719,719 | B2 | 4/2004 | Carmel et al. |
| 6,989,002 | B2 | 1/2006 | Guala |
| 6,997,917 | B2 | 2/2006 | Niedospial, Jr. et al. |
| 7,004,926 | B2 | 2/2006 | Navia et al. |
| 7,086,431 | B2 | 8/2006 | D'Antonio et al. |
| 7,140,401 | B2 | 11/2006 | Wilcox et al. |
| 7,192,423 | B2 | 3/2007 | Wong |
| 7,213,702 | B2 | 5/2007 | Takimoto et al. |
| 7,306,584 | B2 | 12/2007 | Wessman et al. |
| 7,354,427 | B2 | 4/2008 | Fangrow |
| 7,507,227 | B2 | 3/2009 | Fangrow |
| 7,510,547 | B2 | 3/2009 | Fangrow |
| 7,510,548 | B2 | 3/2009 | Fangrow |
| 7,513,895 | B2 | 4/2009 | Fangrow |
| 7,534,238 | B2 | 5/2009 | Fangrow |
| 7,547,300 | B2 | 6/2009 | Fangrow |
| 7,569,043 | B2 | 8/2009 | Fangrow |
| 7,618,408 | B2 | 11/2009 | Yandell |
| 7,632,261 | B2 | 12/2009 | Zinger et al. |
| 7,645,271 | B2 | 1/2010 | Fangrow |
| 7,654,995 | B2 | 2/2010 | Warren et al. |
| 7,658,733 | B2 | 2/2010 | Fangrow |
| 7,678,333 | B2 | 3/2010 | Reynolds et al. |
| 7,703,486 | B2 | 4/2010 | Costanzo |
| 7,743,799 | B2 | 6/2010 | Mosler et al. |
| 7,744,580 | B2 | 6/2010 | Reboul |
| 7,758,560 | B2 | 7/2010 | Connell et al. |
| 7,789,871 | B1 | 9/2010 | Yandell |
| D630,732 | S | 1/2011 | Lev et al. |
| 7,862,537 | B2 | 1/2011 | Zinger et al. |
| 7,879,018 | B2 | 2/2011 | Zinger et al. |
| 7,883,499 | B2 | 2/2011 | Fangrow |
| 7,887,528 | B2 | 2/2011 | Yandell |
| 7,900,659 | B2 | 3/2011 | Whitley et al. |
| D637,713 | S | 5/2011 | Nord et al. |
| 7,963,954 | B2 | 6/2011 | Kavazov |
| D641,080 | S | 7/2011 | Zinger et al. |
| 7,972,321 | B2 | 7/2011 | Fangrow |
| 7,981,089 | B2 | 7/2011 | Weilbacher |
| 7,981,101 | B2 | 7/2011 | Walsh |
| 7,998,106 | B2 | 8/2011 | Thorne, Jr. et al. |
| 8,025,653 | B2 | 9/2011 | Capitaine et al. |
| 8,029,747 | B2 | 10/2011 | Helmerson |
| 8,074,964 | B2 | 12/2011 | Mansour et al. |
| 8,100,154 | B2 | 1/2012 | Reynolds et al. |
| 8,109,285 | B2 | 2/2012 | Ehrman et al. |
| 8,123,736 | B2 | 2/2012 | Kraushaar et al. |
| 8,141,601 | B2 | 3/2012 | Fehr et al. |
| 8,156,971 | B2 | 4/2012 | Costanzo |
| 8,162,006 | B2 | 4/2012 | Guala |
| 8,162,013 | B2 | 4/2012 | Rosenquist et al. |
| 8,162,914 | B2 | 4/2012 | Kraushaar et al. |
| 8,167,863 | B2 | 5/2012 | Yow |
| 8,167,864 | B2 | 5/2012 | Browne |
| 8,177,768 | B2 | 5/2012 | Leinsing |
| 8,196,614 | B2 | 6/2012 | Kriheli |
| 8,197,459 | B2 | 6/2012 | Jansen et al. |
| 8,206,367 | B2 | 6/2012 | Warren et al. |
| 8,211,082 | B2 | 7/2012 | Hasegawa et al. |
| 8,221,382 | B2 | 7/2012 | Moy et al. |
| 8,225,826 | B2 | 7/2012 | Horppu et al. |
| 8,231,567 | B2 | 7/2012 | Tennican et al. |
| 8,241,265 | B2 | 8/2012 | Moy et al. |
| 8,262,643 | B2 | 9/2012 | Tennican |
| 8,267,127 | B2 | 9/2012 | Kriheli |
| 8,267,913 | B2 | 9/2012 | Fangrow |
| 8,281,807 | B2 | 10/2012 | Trombley, III et al. |
| 8,287,513 | B2 | 10/2012 | Ellstrom et al. |
| 8,356,644 | B2 | 1/2013 | Chong et al. |
| 8,356,645 | B2 | 1/2013 | Chong et al. |
| 8,357,137 | B2 | 1/2013 | Yandell |
| 8,381,776 | B2 | 2/2013 | Horppu |
| 8,403,905 | B2 | 3/2013 | Yow |
| 8,409,164 | B2 | 4/2013 | Fangrow |
| 8,409,165 | B2 | 4/2013 | Niedospial, Jr. et al. |
| 8,414,554 | B2 | 4/2013 | Garfield et al. |
| 8,414,555 | B2 | 4/2013 | Garfield et al. |
| 8,425,487 | B2 | 4/2013 | Beiriger et al. |
| 8,449,521 | B2 | 5/2013 | Thorne, Jr. et al. |
| 8,511,352 | B2 | 8/2013 | Kraus et al. |
| 8,512,307 | B2 | 8/2013 | Fangrow |

(56) References Cited

U.S. PATENT DOCUMENTS

| | | | |
|---|---|---|---|
| 8,523,838 | B2 | 9/2013 | Tornqvist |
| 8,540,692 | B2 | 9/2013 | Fangrow |
| 8,602,067 | B2 | 12/2013 | Kuhni et al. |
| 8,622,985 | B2 | 1/2014 | Ellstrom |
| 8,657,803 | B2 | 2/2014 | Helmerson et al. |
| 8,684,992 | B2 | 4/2014 | Sullivan et al. |
| 8,684,994 | B2 | 4/2014 | Lev et al. |
| 8,702,675 | B2 | 4/2014 | Imai |
| 8,720,496 | B2 | 5/2014 | Huwiler et al. |
| 8,753,325 | B2 | 6/2014 | Lev et al. |
| 8,795,231 | B2 | 8/2014 | Chong et al. |
| 8,821,436 | B2 | 9/2014 | Mosler et al. |
| 8,827,977 | B2 | 9/2014 | Fangrow |
| 8,864,737 | B2 | 10/2014 | Hasegawa et al. |
| 8,870,832 | B2 | 10/2014 | Raday et al. |
| 8,882,738 | B2 | 11/2014 | Fangrow et al. |
| 8,900,212 | B2 | 12/2014 | Kubo |
| 8,926,554 | B2 | 1/2015 | Okuda et al. |
| 8,945,084 | B2 | 2/2015 | Warren et al. |
| 2002/0193777 | A1 | 12/2002 | Aneas |
| 2003/0070726 | A1 | 4/2003 | Andreasson et al. |
| 2003/0153895 | A1 | 8/2003 | Leinsing |
| 2003/0216695 | A1 | 11/2003 | Yang |
| 2003/0229330 | A1 | 12/2003 | Hickle |
| 2004/0073169 | A1 | 4/2004 | Amisar et al. |
| 2004/0073189 | A1 | 4/2004 | Wyatt et al. |
| 2004/0215147 | A1 | 10/2004 | Wessman et al. |
| 2004/0236305 | A1 | 11/2004 | Jansen et al. |
| 2005/0087715 | A1 | 4/2005 | Doyle |
| 2005/0131357 | A1 | 6/2005 | Denton et al. |
| 2005/0203481 | A1 | 9/2005 | Orlu et al. |
| 2006/0025747 | A1 | 2/2006 | Sullivan et al. |
| 2006/0106360 | A1 | 5/2006 | Wong |
| 2006/0149309 | A1 | 7/2006 | Paul et al. |
| 2006/0184103 | A1 | 8/2006 | Paproski et al. |
| 2006/0184139 | A1 | 8/2006 | Quigley et al. |
| 2007/0079894 | A1 | 4/2007 | Karus et al. |
| 2007/0093775 | A1 | 4/2007 | Daly |
| 2007/0106244 | A1 | 5/2007 | Mosler et al. |
| 2007/0156112 | A1 | 7/2007 | Walsh |
| 2007/0208320 | A1 | 9/2007 | Muramatsu et al. |
| 2008/0045919 | A1 | 2/2008 | Jakob et al. |
| 2008/0071243 | A1 | 3/2008 | Yandell |
| 2008/0142388 | A1 | 6/2008 | Whitley et al. |
| 2008/0169444 | A1 | 7/2008 | Guala |
| 2008/0172003 | A1 | 7/2008 | Plishka et al. |
| 2008/0172024 | A1* | 7/2008 | Yow .............................. 604/411 |
| 2008/0311007 | A1 | 12/2008 | Helmerson |
| 2008/0312634 | A1 | 12/2008 | Helmerson et al. |
| 2009/0057258 | A1 | 3/2009 | Tornqvist |
| 2010/0049157 | A1 | 2/2010 | Fangrow |
| 2010/0059474 | A1 | 3/2010 | Brandenburger et al. |
| 2010/0147402 | A1* | 6/2010 | Tornqvist ...................... 137/513 |
| 2010/0160889 | A1 | 6/2010 | Smith et al. |
| 2010/0179506 | A1 | 7/2010 | Shemesh et al. |
| 2010/0204670 | A1 | 8/2010 | Kraushaar et al. |
| 2010/0204671 | A1 | 8/2010 | Kraushaar et al. |
| 2010/0241088 | A1 | 9/2010 | Ranalletta et al. |
| 2010/0305548 | A1 | 12/2010 | Kraushaar |
| 2011/0004183 | A1 | 1/2011 | Carrez et al. |
| 2011/0062703 | A1 | 3/2011 | Lopez et al. |
| 2011/0073249 | A1 | 3/2011 | Fangrow |
| 2011/0087164 | A1 | 4/2011 | Mosler et al. |
| 2011/0112501 | A1 | 5/2011 | Garfield et al. |
| 2011/0125128 | A1 | 5/2011 | Nord et al. |
| 2011/0175347 | A1 | 7/2011 | Okiyama |
| 2011/0178493 | A1 | 7/2011 | Okiyama |
| 2011/0184382 | A1 | 7/2011 | Cady |
| 2011/0190723 | A1 | 8/2011 | Fangrow |
| 2011/0208128 | A1 | 8/2011 | Wu et al. |
| 2011/0257621 | A1 | 10/2011 | Fangrow |
| 2011/0264037 | A1 | 10/2011 | Foshee et al. |
| 2011/0284561 | A1 | 11/2011 | Rosenquist et al. |
| 2012/0022493 | A1 | 1/2012 | Warren |
| 2012/0035580 | A1 | 2/2012 | Fangrow |
| 2012/0046636 | A1 | 2/2012 | Kriheli |
| 2012/0046637 | A1 | 2/2012 | Fangrow |
| 2012/0059346 | A1 | 3/2012 | Sheppard et al. |
| 2012/0065609 | A1 | 3/2012 | Seifert et al. |
| 2012/0065610 | A1 | 3/2012 | Seifert et al. |
| 2012/0067429 | A1 | 3/2012 | Mosler et al. |
| 2012/0078091 | A1 | 3/2012 | Suchecki |
| 2012/0078214 | A1 | 3/2012 | Finke et al. |
| 2012/0078215 | A1 | 3/2012 | Finke et al. |
| 2012/0109077 | A1 | 5/2012 | Ryan |
| 2012/0152392 | A1 | 6/2012 | Guala |
| 2012/0157960 | A1 | 6/2012 | Fangrow |
| 2012/0157964 | A1 | 6/2012 | Haimi |
| 2012/0165779 | A1 | 6/2012 | Seifert et al. |
| 2012/0179128 | A1 | 7/2012 | Takemoto et al. |
| 2012/0179129 | A1 | 7/2012 | Imai |
| 2012/0209238 | A1 | 8/2012 | Rosenquist et al. |
| 2012/0215181 | A1 | 8/2012 | Lee |
| 2012/0220977 | A1 | 8/2012 | Yow |
| 2012/0220978 | A1 | 8/2012 | Lev et al. |
| 2012/0289900 | A1 | 11/2012 | Chong et al. |
| 2012/0296306 | A1 | 11/2012 | Seifert et al. |
| 2012/0298254 | A1 | 11/2012 | Brem et al. |
| 2012/0302986 | A1 | 11/2012 | Brem et al. |
| 2012/0323172 | A1 | 12/2012 | Lev et al. |
| 2012/0323210 | A1 | 12/2012 | Lev et al. |
| 2012/0330269 | A1 | 12/2012 | Fangrow et al. |
| 2013/0033034 | A1 | 2/2013 | Trombley, III et al. |
| 2013/0053815 | A1 | 2/2013 | Mucientes et al. |
| 2013/0060226 | A1 | 3/2013 | Fini et al. |
| 2013/0066293 | A1 | 3/2013 | Garfield et al. |
| 2013/0180618 | A1 | 7/2013 | Py |
| 2013/0218121 | A1 | 8/2013 | Waller et al. |
| 2013/0226128 | A1 | 8/2013 | Fangrow |
| 2013/0228239 | A1 | 9/2013 | Cederschiöld |
| 2013/0289515 | A1 | 10/2013 | Barron, III et al. |
| 2013/0306169 | A1 | 11/2013 | Weibel |
| 2014/0014210 | A1 | 1/2014 | Cederschiöld |
| 2014/0020792 | A1 | 1/2014 | Kraus et al. |
| 2014/0124087 | A1 | 5/2014 | Anderson et al. |
| 2014/0124092 | A1 | 5/2014 | Gonnelli et al. |
| 2014/0124528 | A1 | 5/2014 | Fangrow |
| 2014/0238532 | A1 | 8/2014 | Fangrow |
| 2014/0261727 | A1 | 8/2014 | Mansour et al. |
| 2014/0231876 | A1 | 9/2014 | Mansour et al. |
| 2014/0261860 | A1 | 9/2014 | Heath et al. |
| 2014/0261877 | A1 | 9/2014 | Ivosevic et al. |
| 2014/0276649 | A1 | 9/2014 | Ivosevic et al. |
| 2015/0000787 | A1 | 1/2015 | Fangrow |
| 2015/0011963 | A1 | 1/2015 | Fangrow |

FOREIGN PATENT DOCUMENTS

| | | |
|---|---|---|
| GB | 2 000 685 | 1/1979 |
| JP | H06-66682 | 9/1994 |
| WO | WO 00/35517 | 6/2000 |
| WO | WO 2010/093581 | 8/2010 |
| WO | WO 2013/025946 | 2/2013 |
| WO | WO 2013/106757 | 7/2013 |
| WO | WO 2013/142618 | 9/2013 |
| WO | WO 2014/122643 | 8/2014 |
| WO | WO 2014/181320 | 11/2014 |

OTHER PUBLICATIONS

International Preliminary Report on Patentability issued Oct. 14, 2008 (mailed Oct. 23, 2008), International Application No. PCT/US2007/008809, filed Apr. 4, 2007.

International Invitation to Pay Additional Fees and Communication Relating to the Results of the Partial International Search dated Nov. 6, 2007, International Application No. PCT/US2007/008809, filed Apr. 4, 2007.

International Search Report and Written Opinion dated Nov. 27, 2009, International Application No. PCT/US2009/054217, filed Aug. 18, 2009.

International Preliminary Report on Patentability dated Feb. 22, 2011, International Application No. PCT/US2009/054217, filed Aug. 18, 2009.

(56) References Cited

OTHER PUBLICATIONS

International Search Report and Written Opinion dated Mar. 26, 2013, International Application No. PCT/US2013/21296.
International Search Report and Written Opinion dated Oct. 22, 2012, International Application No. PCT/US2012/05122, filed Aug. 16, 2012.
International Preliminary Report on Patentability and Written Opinion mailed Feb. 28, 2014 (issued Feb. 18), International Application No. PCT/US2012/05122, filed Aug. 16, 2012.
International Search Report and Written Opinion mailed Jun. 17, 2013, International Application No. PCT/US2013/033183.
International Search Report and Written Opinion mailed Apr. 14, 2014, International Application No. PCT/US2014/012381.
OnGuard Contained Medication System with Tevadaptor Components, B. Braud Medical, Inc., Apr. 2007.
PhaSeal, The PhaSeal® Solution, http://www.phaseal.com/siteUS/page.asp?menuitem=145&right=0, dated Jan. 9, 2006.
PhaSeal, How to Use PhaSeal®, http://www.phaseal.com/siteUS/movies.asp?main=filmsmain&right=filmsright, dated Jul. 25, 2005.
“Protection Safety Products,” IV Sets and Access Devices, Chemo-AIDE Dispensing Pin, Dec. 2002, pp. 7,21, Baxter Healthcare Corporation, Round Lake, IL.

* cited by examiner

PRESSURE-REGULATING VIAL ADAPTORS

RELATED APPLICATIONS

This application claims the benefit under 35 U.S.C. 119(e) to U.S. Provisional Application No. 61/755,800, filed Jan. 23, 2013, titled PRESSURE-REGULATING VIAL ADAPTORS and to U.S. Provisional Application No. 61/785,874, filed Mar. 14, 2013, titled PRESSURE-REGULATING VIAL ADAPTORS. The entire contents of each of the above-identified patent applications are incorporated by reference herein and made a part of this specification. Any and all priority claims identified in the Application Data Sheet, or any correction thereto, are hereby incorporated by reference under 37 CFR 1.57.

BACKGROUND

1. Field

Certain embodiments disclosed herein relate to adaptors for coupling with medicinal vials, and components thereof, and methods to contain vapors and/or to aid in regulating pressures within medicinal vials.

2. Description of Related Art

It is a common practice to store medicines or other medically related fluids in vials or other containers. In some instances, the medicines or fluids so stored are therapeutic if injected into the bloodstream, but harmful if inhaled or if contacted by exposed skin. Certain known systems for extracting potentially harmful medicines from vials suffer from various drawbacks.

SUMMARY

In some embodiments, an adaptor is configured to couple with a sealed vial and includes a housing apparatus. In some instances, the housing apparatus includes a distal extractor aperture configured to permit withdrawal of fluid from the sealed vial when the adaptor is coupled to the sealed vial. In certain cases, at least a portion of an extractor channel and at least a portion of a regulator channel pass through the housing apparatus. The adaptor can also include an enclosure, such as a regulator enclosure, in fluid communication with the regulator channel. In some configurations, the regulator enclosure is configured to move between a first orientation, in which at least a portion of the regulator enclosure is at least partially expanded or unfolded, and a second orientation, in which at least a portion of the regulator enclosure is at least partially unexpanded or folded, when a fluid is withdrawn from the sealed vial via the extractor channel. Further, the adaptor can include a volume component, such as a filler, disposed within the regulator enclosure. The filler need not fill the entire enclosure. In some embodiments, the volume occupied or encompassed by the filler can be less than the majority of the interior volume of the enclosure, or at least the majority of the interior volume of the enclosure, or substantially all of the interior volume of the enclosure. In some instances, the filler is configured to ensure an initial volume of regulator fluid within the regulator enclosure, thereby permitting the adaptor to supply regulator fluid to the sealed vial from the regulator enclosure when fluid is withdrawn from the sealed vial via the extractor aperture.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

DETAILED DESCRIPTION OF CERTAIN EMBODIMENTS

Figure 1:
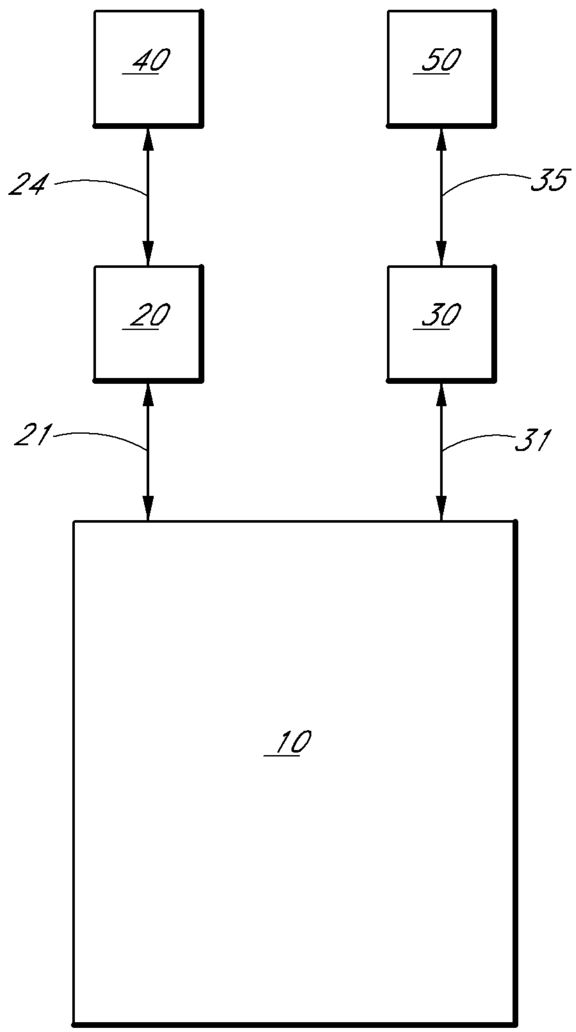
FIG. 1 schematically illustrates a system for removing fluid from and/or injecting fluid into a vial.

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The drawing showing certain embodiments can be semi-diagrammatic and not to scale and, particularly, some of the dimensions are for the clarity of presentation and are shown greatly exaggerated in the drawings.

For expository purposes, the term "horizontal" as used herein is defined as a plane parallel to the plane or surface of the floor of the area in which the device being described is used or the method being described is performed, regardless of its orientation. The term “floor” floor can be interchanged with the term “ground.” The term “vertical” refers to a direction perpendicular to the horizontal as just defined. Terms such as “above,” “below,” “bottom,” “top,” “side,” “higher,” “lower,” “upper,” “over,” and “under,” are defined with respect to the horizontal plane.

Numerous medicines and other therapeutic fluids are stored and distributed in medicinal vials or other containers of various shapes and sizes. These vials are hermetically sealed to prevent contamination or leaking of the stored fluid. The pressure differences between the interior of the sealed vials and the particular atmospheric pressure in which the fluid is later removed often give rise to various problems, as well as the release of potentially harmful vapors.

For instance, introducing a piercing member of a vial adaptor through the septum of a vial can cause the pressure within the vial to rise. This pressure increase can cause fluid to leak from the vial at the interface of the septum and piercing member or at the attachment interface of the adaptor and a medical device, such as a syringe. Also, it can be difficult to withdraw an accurate amount of fluid from a sealed vial using an empty syringe, or other medical instrument, because the fluid may be naturally urged back into the vial once the syringe plunger is released. Furthermore, as the syringe is decoupled from the vial, pressure differences can often cause an amount of fluid to spurt from the syringe or the vial.

Moreover, in some instances, introducing a fluid into the vial can cause the pressure to rise in the vial. For example, in certain cases it can be desirable to introduce a solvent (such as sterile saline) into the vial, e.g., to reconstitute a lyophilized pharmaceutical in the vial. Such introduction of fluid into the vial can cause the pressure in the vial to rise above the pressure of the surrounding environment, which can result in fluid leaking from the vial at the interface of the septum and piercing member or at the attachment interface of the adaptor and a medical device, such as a syringe. Further, the increased pressure in the vial can make it difficult to introduce an accurate amount of the fluid into the vial with a syringe, or other medical instrument. Also, should the syringe be decoupled from the vial when the pressure inside the vial is greater than the surrounding pressure (e.g., atmospheric), the pressure gradient can cause a portion of the fluid to spurt from the vial.

Additionally, in many instances, air bubbles are drawn into the syringe as fluid is withdrawn from the vial. Such bubbles are generally undesirable as they could result in an embolus if injected into a patient. To rid a syringe of bubbles after removal from the vial, medical professionals often flick the syringe, gathering all bubbles near the opening of the syringe, and then forcing the bubbles out. In so doing, a small amount of liquid is usually expelled from the syringe as well. Medical personnel generally do not take the extra step to re-couple the syringe with the vial before expelling the bubbles and fluid. In some instances, this may even be prohibited by laws and regulations. Such laws and regulations may also necessitate expelling overdrawn fluid at some location outside of the vial in certain cases. Moreover, even if extra air or fluid were attempted to be reinserted in the vial, pressure differences can sometimes lead to inaccurate measurements of withdrawn fluid.

To address these problems caused by pressure differentials, medical professionals frequently pre-fill an empty syringe with a precise volume of ambient air corresponding to the volume of fluid that they intend to withdraw from the vial. The medical professionals then pierce the vial and expel this ambient air into the vial, temporarily increasing the pressure within the vial. When the desired volume of fluid is later withdrawn, the pressure differential between the interior of the syringe and the interior of the vial is generally near equilibrium. Small adjustments of the fluid volume within the syringe can then be made to remove air bubbles without resulting in a demonstrable pressure differential between the vial and the syringe. However, a significant disadvantage to this approach is that ambient air, especially in a hospital setting, may contain various airborne viruses, bacteria, dust, spores, molds, and other unsanitary and harmful contaminants. The pre-filled ambient air in the syringe may contain one or more of these harmful substances, which may then mix with the medicine or other therapeutic fluid in the vial. If this contaminated fluid is injected directly into a patient’s bloodstream, it can be particularly dangerous because it circumvents many of the body’s natural defenses to airborne pathogens. Moreover, patients who need the medicine and other therapeutic fluids are more likely to be suffering from a diminished infection-fighting capacity.

In the context of oncology and certain other drugs, all of the foregoing problems can be especially serious. Such drugs, although helpful when injected into the bloodstream of a patient, can be extremely harmful if inhaled or touched. Accordingly, such drugs can be dangerous if allowed to spurt unpredictably from a vial due to pressure differences. Furthermore, these drugs are often volatile and may instantly aerosolize when exposed to ambient air. Accordingly, expelling a small amount of such drugs in order to clear a syringe of bubbles or excess fluid, even in a controlled manner, is generally not a viable option, especially for medical personnel who may repeat such activities numerous times each day.

Some devices use rigid enclosures for enclosing all or a portion of a volume-changing component or region for assisting in regulating pressure within a container. Although such enclosures can provide rigidity, they generally make the devices bulky and unbalanced. Coupling such a device with a vial generally can create a top-heavy, unstable system that is prone to tipping-over and possibly spilling the contents of the device and/or the vial.

Indeed, certain of such coupling devices include relatively large and/or heavy, rigid components that are cantilevered or otherwise disposed a distance from of the axial center of the device, thereby exacerbating the tendency for the device to tip-over.

Additionally, such rigid enclosures can increase the size of the device, which can require an increase in material to form the device and otherwise increase costs associated manufacturing, transporting, and/or storing the device. Further, such rigid enclosures can hamper the ability of the device to expand or contract to deliver a regulating fluid to the vial. No feature, structure, or step disclosed herein is essential or indispensible.

FIG. 1 is a schematic illustration of a container 10, such as a medicinal vial, that can be coupled with an accessor 20 and a regulator 30. In certain arrangements, the regulator 30 allows the removal of some or all of the contents of the container 10 via the accessor 20 without a significant change of pressure within the container 10.

In general, the container 10 is hermetically sealed to preserve the contents of the container 10 in a sterile environment. The container 10 can be evacuated or pressurized upon sealing. In some instances, the container 10 is partially or completely filled with a liquid, such as a drug or other medical fluid. In such instances, one or more gases can also be sealed in the container 10. In some instances, a solid or powdered substance, such as a lyophilized pharmaceutical, is disposed in the container 10.

The accessor 20 generally provides access to contents of the container 10 such that the contents may be removed or added to. In certain arrangements, the accessor 20 includes an opening between the interior and exterior of the container 10. The accessor 20 can further comprise a passageway between the interior and exterior of the container 10. In some configurations, the passageway of the accessor 20 can be selectively opened and closed. In some arrangements, the accessor 20 comprises a conduit extending through a surface of the container 10. The accessor 20 can be integrally formed with the container 10 prior to the sealing thereof or introduced to the container 10 after the container 10 has been sealed.

In some configurations, the accessor 20 is in fluid communication with the container 10, as indicated by an arrow 21. In certain of these configurations, when the pressure inside the container 10 varies from that of the surrounding environment, the introduction of the accessor 20 to the container 10 causes a transfer through the accessor 20. For example, in some arrangements, the pressure of the environment that surrounds the container 10 exceeds the pressure within the container 10, which may cause ambient air from the environment to ingress through the accessor 20 upon insertion of the accessor 20 into the container 10. In other arrangements, the pressure inside the container 10 exceeds that of the surrounding environment, causing the contents of the container 10 to egress through the accessor 20.

In some configurations, the accessor 20 is coupled with an exchange device 40. In certain instances, the accessor 20 and the exchange device 40 are separable. In some instances, the accessor 20 and the exchange device 40 are integrally formed. The exchange device 40 is configured to accept fluids and/or gases from the container 10 via the accessor 20, to introduce fluids and/or gases to the container 10 via the accessor 20, or to do some combination of the two. In some arrangements, the exchange device 40 is in fluid communication with the accessor 20, as indicated by an arrow 24. In certain configurations, the exchange device 40 comprises a medical instrument, such as a syringe.

In some instances, the exchange device 40 is configured to remove some or all of the contents of the container 10 via the accessor 20. In certain arrangements, the exchange device 40 can remove the contents independent of pressure differences, or lack thereof, between the interior of the container 10 and the surrounding environment. For example, in instances where the pressure outside of the container 10 exceeds that within the container 10, an exchange device 40 comprising a syringe can remove the contents of the container 10 if sufficient force is exerted to extract the plunger from the syringe. The exchange device 40 can similarly introduce fluids and/or gases to the container 10 independent of pressure differences between the interior of the container 10 and the surrounding environment.

In certain configurations, the regulator 30 is coupled with the container 10. The regulator 30 generally regulates the pressure within the container 10. As used herein, the term "regulate," or any derivative thereof, is a broad term used in its ordinary sense and includes, unless otherwise noted, any active, affirmative, or positive activity, or any passive, reactive, respondent, accommodating, or compensating activity that tends to effect a change. In some instances, the regulator 30 substantially maintains a pressure difference, or equilibrium, between the interior of the container 10 and the surrounding environment. As used herein, the term "maintain," or any derivative thereof, is a broad term used in its ordinary sense and includes the tendency to preserve an original condition for some period, with some small degree of variation permitted as may be appropriate in the circumstances. In some instances, the regulator 30 maintains a substantially constant pressure within the container 10. In certain instances, the pressure within the container 10 varies by no more than about 1 psi, no more than about 2 psi, no more than about 3 psi, no more than about 4 psi, or no more than about 5 psi. In still further instances, the regulator 30 equalizes pressures exerted on the contents of the container 10. As used herein, the term "equalize," or any derivative thereof, is a broad term used in its ordinary sense and includes the tendency for causing quantities to be the same or close to the same, with some small degree of variation permitted as may be appropriate in the circumstances. In certain configurations, the regulator 30 is coupled with the container 10 to allow or encourage equalization of a pressure difference between the interior of the container 10 and some other environment, such as the environment surrounding the container 10 or an environment within the exchange device 40. In some arrangements, a single device comprises the regulator 30 and the accessor 20. In other arrangements, the regulator 30 and the accessor 20 are separate units.

The regulator 30 is generally in communication with the container 10, as indicated by an arrow 31, and a reservoir 50, as indicated by another arrow 35. In some configurations, the reservoir 50 comprises at least a portion of the environment surrounding the container 10. In certain configurations, the reservoir 50 comprises a container, canister, bag, or other holder dedicated to the regulator 30. As used herein, the term "bag," or any derivative thereof, is a broad term used in its ordinary sense and includes, for example, any sack, balloon, bladder, receptacle, enclosure, diaphragm, or membrane capable of expanding and/or contracting, including structures comprising a flexible, supple, pliable, resilient, elastic, and/or expandable material. In some embodiments, the reservoir 50 includes a gas and/or a liquid. As used herein, the term "flexible," or any derivative thereof, is a broad term used in its ordinary sense and describes, for example, the ability of a component to bend, expand, contract, fold, unfold, or otherwise substantially deform or change shape when fluid is flowing into or out of the container 10 (e.g., via the accessor 20). Also, as used herein, the term "rigid," or any derivative thereof, is a broad term used in its ordinary sense and describes, for example, the ability of a component to generally avoid substantial deformation under normal usage when fluid is flowing into or out of the container 10 (e.g., via the accessor 20).

In certain embodiments, the regulator 30 provides fluid communication between the container 10 and the reservoir 50. In certain of such embodiments, the fluid in the reservoir 50 includes mainly gas so as not to appreciably dilute liquid contents of the container 10. In some arrangements, the regulator 30 comprises a filter to purify or remove contaminants from the gas or liquid entering the container 10, thereby reducing the risk of contaminating the contents of the container 10. In certain arrangements, the filter is hydrophobic such that air can enter the container 10 but fluid cannot escape therefrom. In some configurations, the regulator 30 comprises an orientation-actuated or orientation-sensitive check valve which selectively inhibits fluid communication between the container 10 and the filter. In some configurations, the regulator 30 comprises a check valve which selectively inhibits fluid communication between the container 10 and the filter when the valve and/or the container 10 are oriented so that the regulator 30 is held above (e.g., further from the floor than) the regulator 30.

In some embodiments, the regulator 30 prevents fluid communication between the container 10 and the reservoir 50. In certain of such embodiments, the regulator 30 serves as an interface between the container 10 and the reservoir 50. In some arrangements, the regulator 30 comprises a substantially impervious bag for accommodating ingress of gas and/or liquid to the container 10 or egress of gas and/or liquid from the container 10.

Figure 2:
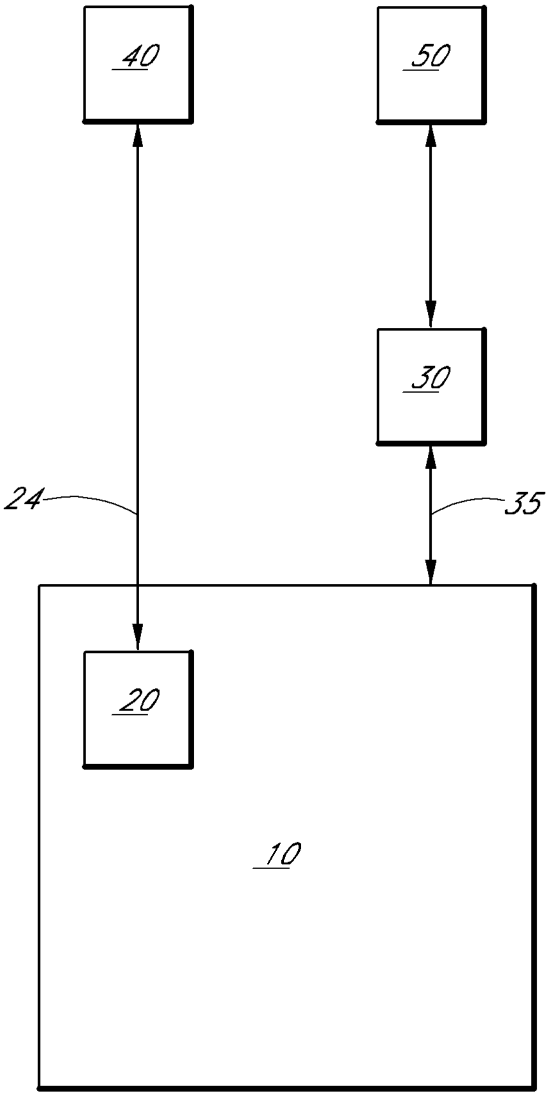
FIG. 2 schematically illustrates another system for removing fluid from and/or injecting fluid into a vial.

As schematically illustrated in FIG. 2, in certain embodiments, the accessor 20, or some portion thereof, is located within the container 10. As detailed above, the accessor 20 can be integrally formed with the container 10 or separate therefrom. In some embodiments, the regulator 30, or some portion thereof, is located outside the container 10. In some arrangements, the regulator 30 is integrally formed with the container 10. It is possible to have any combination of the accessor 20, or some portion thereof, entirely within, partially within, or outside of the container 10 and/or the regulator 30, or some portion thereof, entirely within, partially within, or outside of the container 10.

In certain embodiments, the accessor 20 is in fluid communication with the container 10. In further embodiments, the accessor 20 is in fluid communication with the exchange device 40, as indicated by the arrow 24.

The regulator 30 can be in fluid or non-fluid communication with the container 10. In some embodiments, the regulator 30 is located entirely outside the container 10. In certain of such embodiments, the regulator 30 comprises a closed bag configured to expand or contract external to the container 10 to maintain a substantially constant pressure within the container 10. In some embodiments, the regulator 30 is in communication, either fluid or non-fluid, with the reservoir 50, as indicated by the arrow 35.

Figure 2A:
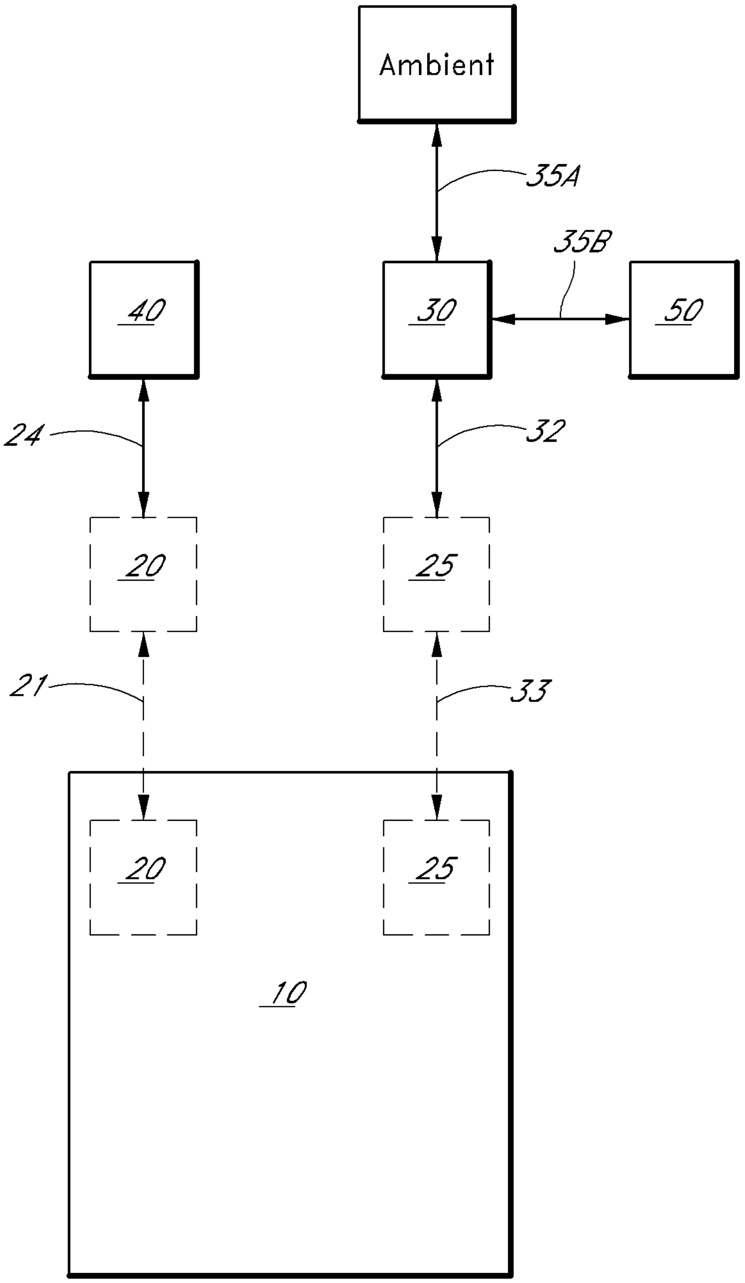
FIG. 2A schematically illustrates another system for removing fluid from and/or injecting fluid into a vial.
Figure 2B:
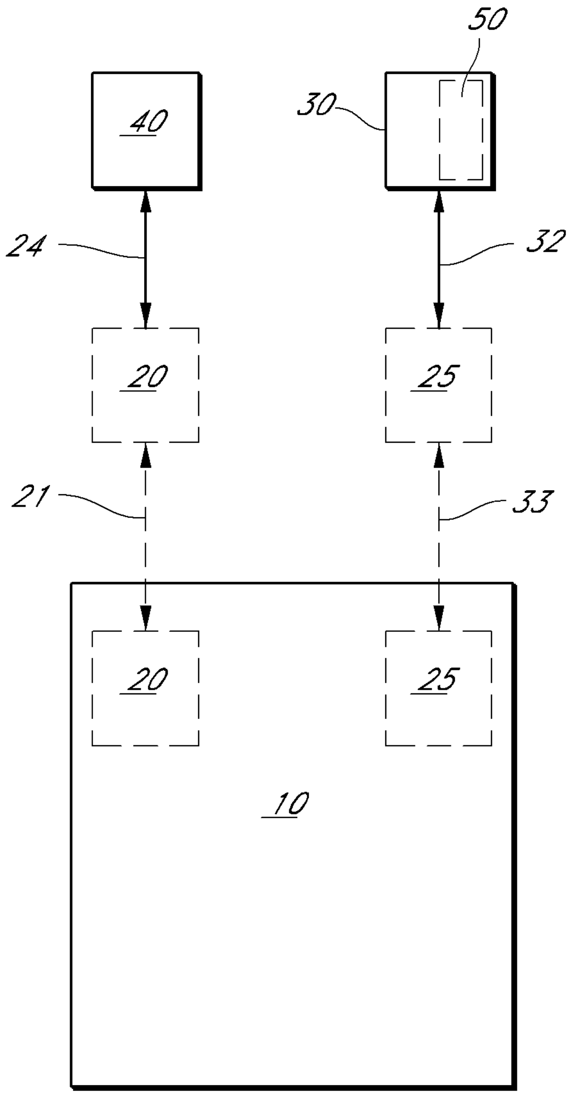
FIG. 2B schematically illustrates another system for removing fluid from and/or injecting fluid into a vial, wherein the flexible enclosure is in a contracted position.

As schematically illustrated in FIG. 2A, in certain embodiments, the accessor 20, or some portion thereof, can be located within the container 10. In some embodiments, the accessor 20, or some portion thereof, can be located outside the container 10. In some embodiments, a valve 25, or some portion thereof, can be located outside the container 10. In some embodiments, the valve 25, or some portion thereof, can be located within the container 10. In some embodiments, the regulator 30 is located entirely outside the container 10. In some embodiments, the regulator 30, or some portion thereof, can be located within the container 10. It is possible to have any combination of the accessor 20, or some portion thereof, entirely within, partially within, or outside of the container 10 and/or the valve 25, or some portion thereof, entirely within, partially within, or outside of the container 10. It is also possible to have any combination of the accessor 20, or some portion thereof, entirely within, partially within, or outside of the container 10 and/or the regulator 30, or some portion thereof, entirely within, partially within, or outside of the container 10.

The accessor 20 can be in fluid communication with the container 10, as indicated by the arrow 21. In some embodiments, the accessor 20 can be in fluid communication with the exchange device 40, as indicated by the arrow 24.

In certain embodiments, the regulator 30 can be in fluid or non-fluid communication with a valve 25, as indicated by the arrow 32. In some embodiments, the valve 25 can be integrally formed with the container 10 or separate therefrom. In some embodiments, the valve 25 can be integrally formed with the regulator 30 or separate therefrom. In certain embodiments, the valve 25 can be in fluid or non-fluid communication with the container 10, as indicated by the arrow 33.

In some embodiments the regulator 30 can be in fluid or non-fluid communication with the ambient surroundings, as indicated by the arrow 35A. In some embodiments, the regulator 30 can be in fluid or non-fluid communication with a reservoir 50, as indicated by the arrow 35B. In some embodiments, the reservoir 50 can comprise a bag or other flexible enclosure. In some embodiments, the reservoir 50 comprises a rigid container surrounding a flexible enclosure. In some embodiments, the reservoir 50 comprises a partially-rigid enclosure.

According to some configurations, the regulator 30 can comprise a filter. In some embodiments, the filter can selectively inhibit passage of liquids and/or contaminants between the valve 25 and the reservoir 50 or the ambient surroundings. In some embodiments, the filter can selectively inhibit passage of liquids and/or contaminants between the reservoir 50 or ambient surroundings and the valve 25.

In some embodiments, the valve 25 can be a one-way check valve. In some embodiments, the valve 25 can be a two-way valve. According to some configurations, the valve 25 can selectively inhibit liquid communication between the filter and/or reservoir 50 and the container 10. In some embodiments, the valve 25 can selectively inhibit liquid communication between the container 10 and the filter and/or reservoir 50 when the container 10 is oriented above the exchange device 40.

Figure 3:
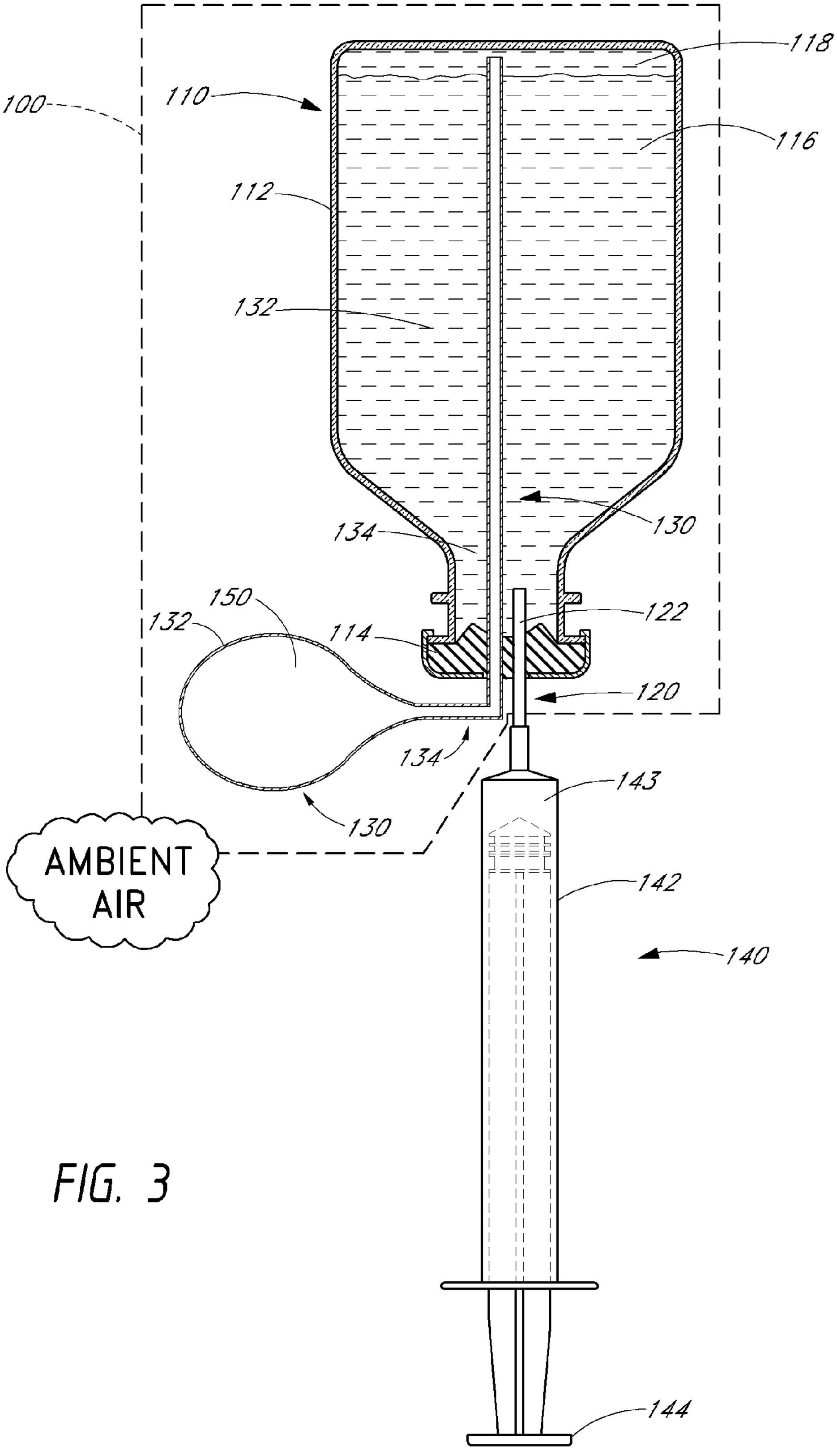
FIG. 3 illustrates another system for removing fluid from and/or injecting fluid into a vial.

FIG. 3 illustrates an embodiment of a system 100 comprising a vial 110, an accessor 120, and a regulator 130. The vial 110 comprises a body 112 and a cap 114. In the illustrated embodiment, the vial 110 contains a medical fluid 116 and a relatively small amount of sterilized air 118. In certain arrangements, the fluid 116 is removed from the vial 110 when the vial 110 is oriented with the cap 114 facing downward (e.g., the cap 114 is between the fluid and the floor). The accessor 120 comprises a conduit 122 fluidly connected at one end to an exchange device 140, such as a standard syringe 142 with a plunger 144. The conduit 122 extends through the cap 114 and into the fluid 116. The regulator 130 comprises a bag 132 and a conduit 134. The bag 132 and the conduit 134 are in fluid communication with a reservoir 150, which comprises an amount of cleaned and/or sterilized air. The outside surface of the bag 132 is generally in contact with the ambient air surrounding both the system 100 and the exchange device 140. The bag 132 comprises a substantially impervious material such that the fluid 116, the air 118 inside the vial 110, and the reservoir 150 do not contact the ambient air.

In the illustrated embodiment, areas outside of the vial 110 are at atmospheric pressure. Accordingly, the pressure on the syringe plunger 144 is equal to the pressure on the interior of the bag 132, and the system 100 is in general equilibrium. The plunger 144 can be withdrawn to fill a portion of the syringe 142 with the fluid 116. Withdrawing the plunger 144 increases the effective volume of the vial 110, thereby decreasing the pressure within the vial 110. Such a decrease of pressure within the vial 110 increases the difference in pressure between the vial 110 and the syringe 142, which causes the fluid 116 to flow into the syringe 142 and the reservoir 150 to flow into the vial 110. Additionally, the decrease of pressure within the vial 110 increases the difference in pressure between the interior and exterior of the bag 132, which causes the bag 132 to decrease in internal volume or contract, which in turn encourages an amount of regulatory fluid through the conduit 134 and into the vial 110. In effect, the bag 132 contracts outside the vial 110 to a new volume that compensates for the volume of the fluid 116 withdrawn from the vial 110. Thus, once the plunger 144 ceases from being withdrawn from the vial 110, the system is again in equilibrium. As the system 100 operates near equilibrium, withdrawal of the fluid 116 can be facilitated. Furthermore, due to the equilibrium of the system 100, the plunger 144 remains at the position to which it has been withdrawn, thereby allowing removal of an accurate amount of the fluid 116 from the vial 110.

In certain arrangements, the decreased volume of the bag 132 is approximately equal to the volume of liquid removed from the vial 110. In some arrangements, the volume of the bag 132 decreases at a slower rate as greater amounts of fluid are withdrawn from the vial 110 such that the volume of fluid withdrawn from the vial 110 is greater than the decreased volume of the bag 132.

In some arrangements, the bag 132 can be substantially and/or completely deflated, such that there is substantially no volume inside the bag 132. In some instances, such deflation of the bag 132 effectively creates a difference in pressure between the inside of the bag 132 and the inside of the vial 110. For example, a vacuum (relative to ambient) inside the vial 110 can be created when the bag 132 is deflated. In some instances, such deflation of the bag 132 creates substantially no restoring force that tends to create a pressure differential between the inside of the bag 132 and the inside of the vial 110, such as when the bag 132 is generally non-resilient.

In certain embodiments, the syringe 142 comprises fluid contents 143. A portion of the fluid contents 143 can be introduced into the vial 110 by depressing (e.g., toward the vial) the plunger 144, which can be desirable in certain instances. For example, in some instances, it is desirable to introduce a solvent and/or compounding fluid into the vial 110. In certain instances, more of the fluid 116 than desired initially might be withdrawn inadvertently. In some instances, some of the air 118 in the vial 110 initially might be withdrawn, creating unwanted bubbles within the syringe 142. It may thus be desirable to inject some of the withdrawn fluid 116 and/or air 118 back into the vial 110.

Depressing the plunger 144 encourages the fluid contents 143 of the syringe into the vial 110, which decreases the effective volume of the vial 110, thereby increasing the pressure within the vial 110. An increase of pressure within the vial 110 increases the difference in pressure between the exterior and interior of the bag 132, which causes the air 118 to flow into the bag 132, which in turn causes the bag 132 to expand. In effect, the bag 132 expands or increases to a new volume that compensates for the volume of the contents 143 of the syringe 142 introduced into the vial 110. Thus, once the plunger 144 ceases from being depressed, the system is again in equilibrium. As the system 100 operates near equilibrium, introduction of the contents 143 can be facilitated. Moreover, due to the equilibrium of the system 100, the plunger 144 generally remains at the position to which it is depressed, thereby allowing introduction of an accurate amount of the contents 143 of the syringe 142 into the vial 110.

In certain arrangements, the increased volume of the bag 132 is approximately equal to the volume of air 118 removed from the vial 110. In some arrangements, the volume of the bag 132 increases at a slower rate as greater amounts of the contents 143 are introduced into the vial 110, such that the volume of the contents 143 introduced into the vial 110 is greater than the increased volume of the bag 132.

In some arrangements, the bag 132 can stretch to expand beyond a resting volume. In some instances, the stretching gives rise to a restorative force that effectively creates a difference in pressure between the inside of the bag 132 and the inside of the vial 110. For example, a slight overpressure (relative to ambient) inside the vial 110 can be created when the bag 132 is stretched.

Figure 4:
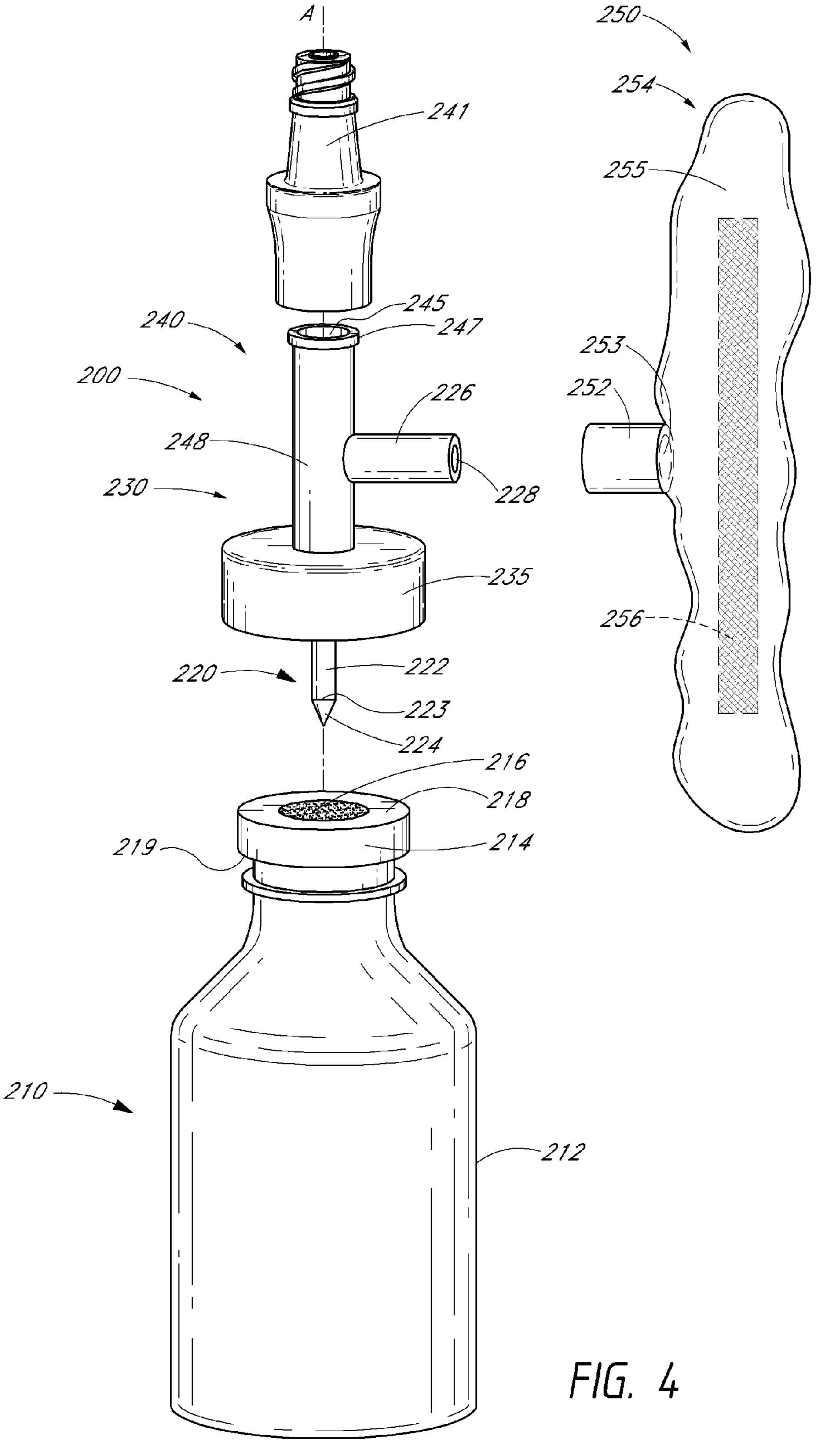
FIG. 4 illustrates a perspective view of a vial adaptor and a vial.

FIG. 4 illustrates an embodiment of a vial adaptor 200 for coupling with a vial 210. The vial 210 can comprise any suitable container for storing medical fluids. In some instances, the vial 210 comprises any of a number of standard medical vials known in the art, such as those produced by Abbott Laboratories of Abbott Park, Ill. In some embodiments, the vial 210 is capable of being hermetically sealed. In some configurations, the vial 210 comprises a body 212 and a cap 214. The body 212 preferably comprises a rigid, substantially impervious material, such as plastic or glass. In some embodiments, the cap 214 comprises a septum 216 and a casing 218. The septum 216 can comprise an elastomeric material capable of deforming in such a way when punctured by an item that it forms a substantially airtight seal around that item. For example, in some instances, the septum 216 comprises silicone rubber or butyl rubber. The casing 218 can comprise any suitable material for sealing the vial 210. In some instances, the casing 218 comprises metal that is crimped around the septum 216 and a portion of the body 212 in order to form a substantially airtight seal between the septum 216 and the vial 210. In certain embodiments, the cap 214 defines a ridge 219 that extends outwardly from the top of the body 212.

In certain embodiments, the adaptor 200 comprises an axial centerline A and a piercing member 220 having a proximal end 221 (see FIG. 5) and a distal end 223. As used herein the term, “proximal,” or any derivative thereof, refers to a direction along the axial length of the piercing member 220 that is toward the cap 214 when the piercing member 220 is inserted in the vial 210; the term “distal,” or any derivative thereof, indicates the opposite direction. In some configurations, the piercing member 220 comprises a sheath 222. The sheath 222 can be substantially cylindrical, as shown, or it can assume other geometric configurations. In some instances, the sheath 222 tapers toward the distal end 223. In some arrangements, the distal end 223 defines a point that can be centered with respect to the axial centerline A or offset therefrom. In certain embodiments, the distal end 223 is angled from one side of the sheath 222 to the opposite side. The sheath 222 can comprise a rigid material, such as metal or plastic, suitable for insertion through the septum 216. In certain embodiments the sheath 222 comprises polycarbonate plastic.

In some configurations, the piercing member 220 comprises a tip 224. The tip 224 can have a variety of shapes and configurations. In some instances, the tip 224 is configured to facilitate insertion of the sheath 222 through the septum 216 via an insertion axis. In some embodiments, the insertion axis corresponds to the direction in which the force required to couple the adaptor 200 with the vial 210 is applied when coupling the adaptor 200 with the vial 210. The insertion axis can be substantially perpendicular to a plane in which the cap 214 lies. In some embodiments, as illustrated in FIG. 4, the insertion axis is substantially parallel to the axial centerline A of the adaptor 200. Furthermore, in some embodiments, the insertion axis is substantially parallel to the piercing member 220. As illustrated, the tip 224, or a portion thereof, can be substantially conical, coming to a point at or near the axial center of the piercing member 220. In some configurations, the tip 224 angles from one side of the piercing member 220 to the other. In some instances, the tip 224 is separable from the sheath 222. In other instances, the tip 224 and the sheath 222 are permanently joined, and can be unitarily formed. In various embodiments, the tip 224 comprises acrylic plastic, ABS plastic, or polycarbonate plastic.

In some embodiments, the adaptor 200 comprises a cap connector 230. As illustrated, the cap connector 230 can substantially conform to the shape of the cap 214. In certain configurations, the cap connector 230 comprises a rigid material, such as plastic or metal, that substantially maintains its shape after minor deformations. In some embodiments, the cap connector 230 comprises polycarbonate plastic. In some arrangements, the cap connector 230 comprises a sleeve 235 configured to snap over the ridge 219 and tightly engage the cap 214. As more fully described below, in some instances, the cap connector 230 comprises a material around an interior surface of the sleeve 235 for forming a substantially airtight seal with the cap 214. The cap connector 230 can be or can include adhesive tape, as known to those of skill in the art. In some embodiments, the cap connector 230 comprises an elastic material that is stretched over the ridge 219 to form a seal around the cap 214. In some embodiments, the cap connector 230 resembles or is identical to the structures shown in FIGS. 6 and 7 of and described in the specification of U.S. Pat. No. 5,685,866, the entire contents of which are hereby incorporated by reference herein and are made a part of this specification.

In certain embodiments, the adaptor 200 comprises a connector interface 240 for coupling the adaptor 200 with a medical connector 241, another medical device (not shown), or any other instrument used in extracting fluid from or injecting fluid into the vial 210. In certain embodiments, the connector interface 240 comprises a sidewall 248 that defines a proximal portion of an access channel 245 through which fluid may flow. In some instances, the access channel 245 extends through the cap connector 230 and through a portion of the piercing member 220 such that the connector interface 240 is in fluid communication with the piercing member 220. The sidewall 248 can assume any suitable configuration for coupling with the medical connector 241, a medical device, or another instrument. In the illustrated embodiment, the sidewall 248 is substantially cylindrical and extends generally proximally from the cap connector 230.

In certain configurations, the connector interface 240 comprises a flange 247 to aid in coupling the adaptor 200 with the medical connector 241, a medical device, or another instrument. The flange 247 can be configured to accept any suitable medical connector 241, including connectors capable of sealing upon removal of a medical device therefrom. In some instances, the flange 247 is sized and configured to accept the Clave® connector, available from ICU Medical, Inc. of San Clemente, Calif. Certain features of the Clave® connector are disclosed in U.S. Pat. No. 5,685,866, the entire contents of which are incorporated by reference herein. Connectors of many other varieties, including other needle-less connectors, can also be used. The connector 241 can be permanently or separably attached to the connector interface 240. In other arrangements, the flange 247 is threaded, configured to accept a Luer connector, or otherwise shaped to attach directly to a medical device, such as a syringe, or to other instruments.

In certain embodiments, the connector interface 240 is generally centered on the axial center of the adaptor 200. Such a configuration provides vertical stability to a system comprising the adaptor 200 coupled with the vial 210, thereby making the coupled system less likely to tip-over. Accordingly, the adaptor 200 is less likely to cause leaks, or spills, or disorganization of supplies occasioned by accidental bumping or tipping of the adaptor 200 or the vial 210.

In some embodiments, the piercing member 220, the cap connector 230, and the connector interface 240 are integrally formed of a unitary piece of material, such as polycarbonate plastic. In other embodiments, one or more of the piercing member 220, the cap connector 230, and the connector interface 240 comprise a separate piece. The separate pieces can be joined in any suitable manner, such as by glue, epoxy, ultrasonic welding, etc. Connections between joined pieces can create substantially airtight bonds between the pieces. In some arrangements, any of the piercing member 220, the cap connector 230, or the connector interface 240 can comprise more than one piece. Details and examples of some embodiments of piercing members 220, cap connectors 230, and connector interfaces 240 are provided in U.S. Pat. No. 7,547,300 and U.S. Patent Application Publication No. 2010/0049157, the entirety of each of which is incorporated herein by reference.

Figure 5:
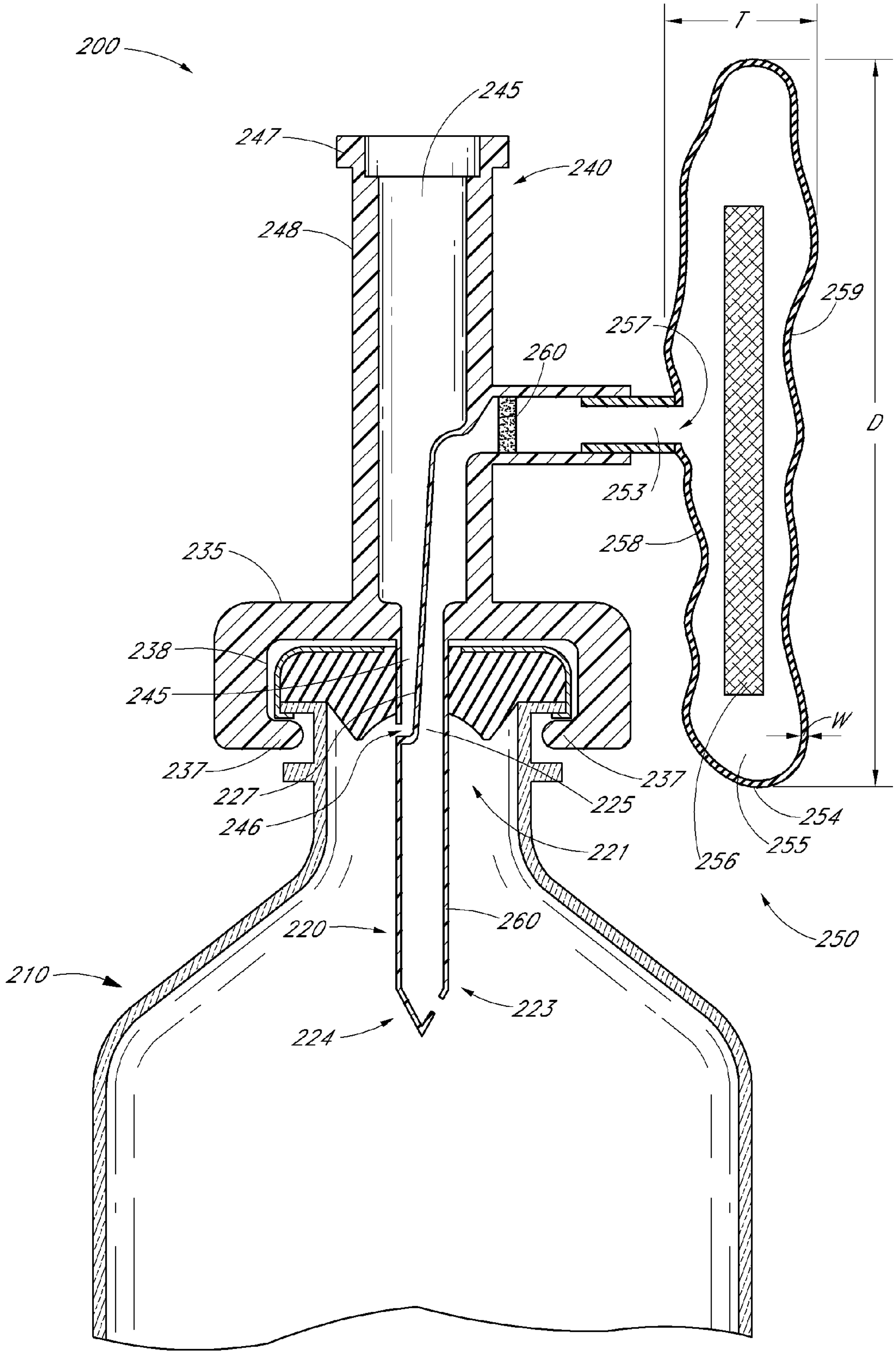
FIG. 5 illustrates a partial cross-sectional view of the vial adaptor of FIG. 4, coupled with a vial, in a high-volume stage.

In certain embodiments, the adaptor 200 comprises a regulator channel 225, which extends through the connector interface 240 and/or the cap connector 230, and through the piercing member 220 (see, e.g., FIG. 5). In the illustrated embodiment, the regulator channel 225 passes through a lumen 226 that extends radially outward from the connector interface 240. In some embodiments, the channel 225 is formed as a part of the cap connector 230. In certain embodiments, the regulator channel 225 terminates in a regulator aperture 228.

In some embodiments, the adaptor 200 includes a regulator assembly 250. In certain embodiments, the regulator assembly 250 comprises a coupling 252. The coupling 252 can be configured to connect the regulator assembly 250 with the remainder of the adaptor 200. For example, the coupling 252 can connect with the lumen 226 in substantially airtight engagement, thereby placing the coupling 252 in fluid communication with the regulator channel 225. In some instances, the coupling 252 and the lumen 226 engage with a slip or interference fit. In certain embodiments, the coupling 252 and the lumen 226 comprise complimentary threads, such that the coupling 252 can be threadably connected with the lumen 226. In some embodiments, the coupling 252 includes a passage 253 that extends through the coupling 252.

In the illustrated embodiment, the regulator assembly comprises a bag 254 with an interior chamber 255. The bag 254 is generally configured to stretch, flex, unfold, or otherwise expand and contract or cause a change in interior volume. In some cases, the bag 254 includes one or more folds, pleats, or the like. In certain arrangements, the interior chamber 255 of the bag 254 is in fluid communication with the regulator channel 225, thereby allowing fluid to pass from the regulator channel 225 into the interior chamber 255 and/or from the interior chamber 255 into the regulator channel 225. In some arrangements, the interior chamber 255 is in fluid communication with the passage 253 of the coupling 252.

In certain embodiments, the regulator assembly 250 comprises a filler 256, which can be located in the inner chamber 255 of the bag 254. As used herein, the term "filler," or any derivative thereof, is a broad term used in its ordinary sense and includes, for example, any support, stuffing, spacing, wadding, padding, lining, enclosure, reservoir, or other structure configured to inhibit or prevent the bag 254 from fully deflating at ambient pressure, or a combination of structures. In certain configurations, the filler 256 occupies substantially the entire volume of the entire inner chamber 255. In other arrangements, the filler 256 occupies only a portion of the volume of the inner chamber 255. In some configurations, the filler 256 comprises a network of woven or non-woven fibers. In some embodiments, the filler 256 is porous, such that regulating fluid (e.g., air) in the inner chamber 255 can enter a network or plurality of hollows within the filler 256. For example, in some cases, the filler 256 is a sponge-like material. In certain configurations, the filler 256 is configured to be compressed by the bag 254, without causing damage to the bag 254. In some embodiments the filler 256 has a lower durometer than the bag 254.

As illustrated, the filler 256 can be positioned in the bag 254. In certain embodiments, the filler 256 is positioned at about the radial center in the bag 254. In other instances, the position of the filler 256 is offset with respect to the center of the bag 254. In some embodiments, the position of the filler 256 changes relative to the bag 254. For example, in some embodiments, the filler 256 moves (e.g., by force of gravity) relative to the bag 254 when the bag 254 changes volume, such as when the bag 254 expands. Such a configuration can, for example, enhance the ability of the bag 254 to expand and can decrease the likelihood of the bag 254 becoming snagged on or bound-up by the filler 256.

In other embodiments, the position of the filler 256 is substantially constant with respect to the bag 254 and/or a coupling 252. In some such embodiments, the filler 256 moves substantially in unison with the bag 254. For example, the filler 256 can be configured to expand and contract at substantially the same rate as the bag 254. In certain embodiments, the filler 256 is bonded with the bag 254. In some such cases, the filler 256 is adhered or at least partially adhered to at least a portion of the bag 254. In some cases, at least a portion of the filler 256 is formed as a part of the bag 254. In certain embodiments, at least a portion of the filler 256 is maintained in position by one or more flexible legs that abut an inner surface of the bag 254. In some configurations, at least a portion of the filler 256 is maintained in position by one or more beams that connect with the coupling 252. In certain arrangements, at least a portion of the filler 256 is joined with the coupling 252.

Figure 6:
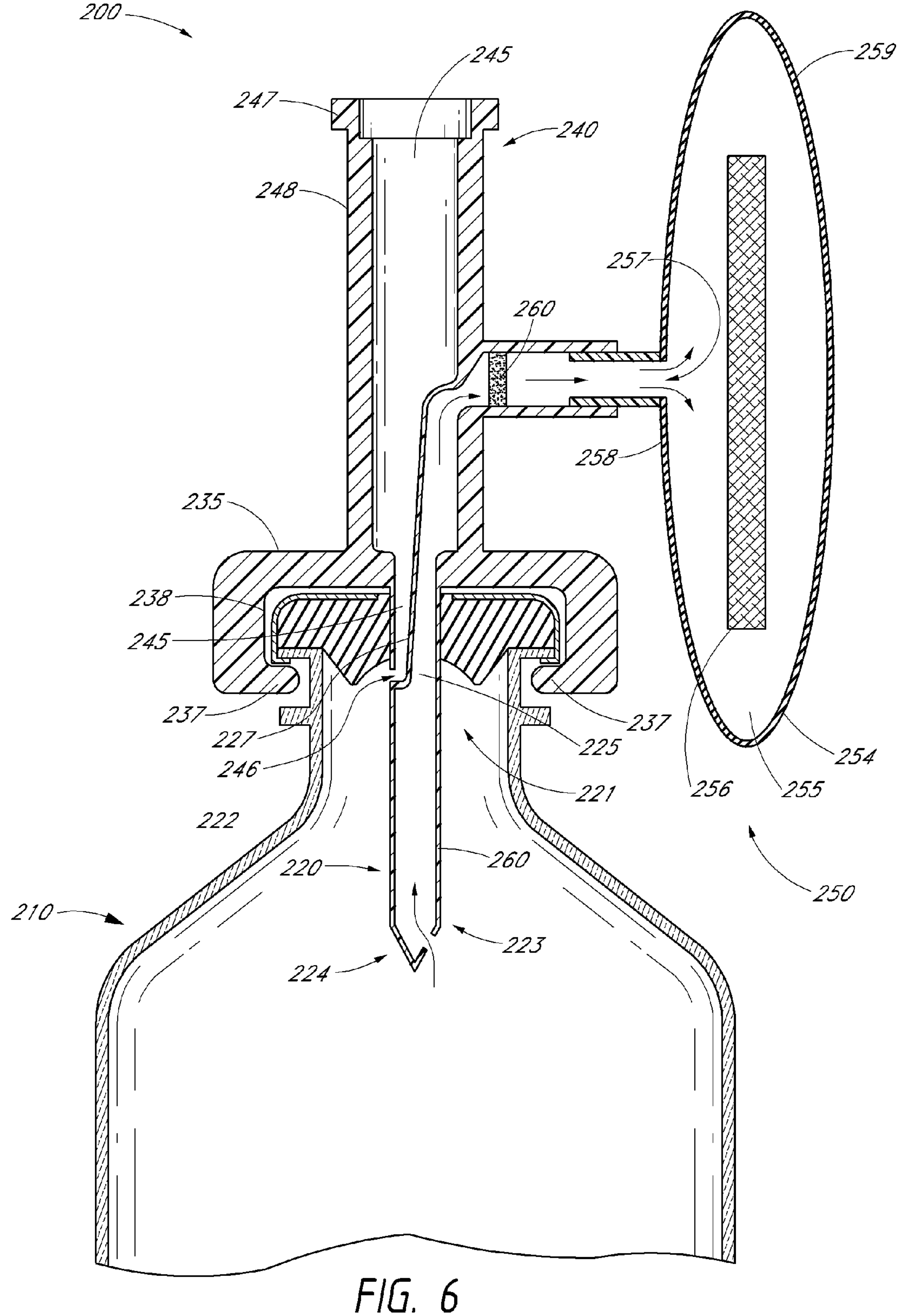
FIG. 6 illustrates a partial cross-sectional view of the vial adaptor of FIG. 4 coupled with a vial in an expanded stage.

FIGS. 5 and 6 illustrate cross-sections of the vial adaptor 200 coupled with the vial 210. FIG. 5 illustrates a non-fully expanded condition and FIG. 6 illustrates a fully-expanded condition. In the illustrated embodiment, the cap connector 230 firmly secures the adaptor 200 to the cap 214 and the piercing member 220 extends through the septum 216 into the interior of the vial 210. Additionally, the regulator assembly 250 is engaged with the connector interface 240 such that the inner chamber 255 of the bag 254 is in fluid communication with the regulator channel 255 through the coupling 252. In some embodiments, the piercing member 220 is oriented substantially perpendicularly with respect to the cap 214 when the adaptor 200 and the vial 210 are coupled. Other configurations are also contemplated.

In certain embodiments, the cap connector 230 comprises one or more projections 237 that aid in securing the adaptor 200 to the vial 210. The one or more projections 237 extend toward an axial center of the cap connector 230. In some configurations, the one or more projections 237 comprise a single circular flange extending around the interior of the cap connector 230. The cap connector 230 can be sized and configured such that an upper surface of the one or more projections 237 abuts a lower surface of the ridge 219, helping secure the adaptor 200 in place.

The one or more projections 237 can be rounded, chamfered, or otherwise shaped to facilitate the coupling of the adaptor 200 and the vial 210. For example, as the adaptor 200 having rounded projections 237 is introduced to the vial 210, a lower surface of the rounded projections 237 abuts a top surface of the cap 214. As the adaptor 200 is advanced onto the vial 210, the rounded surfaces cause the cap connector 230 to expand radially outward. As the adaptor 200 is advanced further onto the vial 210, a resilient force of the deformed cap connector 220 seats the one or more projections 237 under the ridge 219, securing the adaptor 200 in place.

In some embodiments, the cap connector 230 is sized and configured such that an inner surface 238 of the cap connector 230 contacts the cap 214. In some embodiments, a portion of the cap connector 230 contacts the cap 214 in substantially airtight engagement. In certain embodiments, a portion of the inner surface 238 surrounding either the septum 216 or the casing 218 is lined with a material, such as rubber or plastic, to ensure the formation of a substantially airtight seal between the adaptor 200 and the vial 210.

In the embodiment illustrated, the piercing member 220 comprises the sheath 222 and the tip 224. The sheath 222 is generally sized and dimensioned to be inserted through the septum 216 without breaking and, in some instances, with relative ease. Accordingly, in various embodiments, the sheath 222 has a cross-sectional area of between about 0.025 and about 0.075 square inches, between about 0.040 and about 0.060 square inches, or between about 0.045 and about 0.055 square inches. In other embodiments, the cross-sectional area is less than about 0.075 square inches, less than about 0.060 square inches, or less than or equal to about 0.055 square inches. In still other embodiments, the cross-sectional area is greater than or equal to about 0.025 square inches, greater than or equal to about 0.035 square inches, or greater than or equal to about 0.045 square inches. In some embodiments, the cross-sectional area is about 0.050 square inches.

The sheath 222 can assume any of a number of cross-sectional geometries, such as, for example, oval, ellipsoidal, square, rectangular, hexagonal, or diamond-shaped. The cross-sectional geometry of the sheath 222 can vary along a length thereof in size and/or shape. In some embodiments, the sheath 222 has substantially circular cross-sections along a substantial portion of a length thereof. A circular geometry provides the sheath 222 with substantially equal strength in all radial directions, thereby preventing bending or breaking that might otherwise occur upon insertion of the sheath 222. The symmetry of an opening created in the septum 216 by the circular sheath 222 prevents pinching that might occur with angled geometries, allowing the sheath 222 to more easily be inserted through the septum 216. Advantageously, the matching circular symmetries of the piercing member 220 and the opening in the septum 216 ensure a tight fit between the piercing member 220 and the septum 216, even if the adaptor 200 is inadvertently twisted. Accordingly, the risk of dangerous liquids or gases escaping the vial 210, or of impure air entering the vial 210 and contaminating the contents thereof, can be reduced in some instances with a circularly symmetric configuration.

In some embodiments, the sheath 222 is hollow. In the illustrated embodiment, the inner and outer surfaces of the sheath 222 substantially conform to each other such that the sheath 222 has a substantially uniform thickness. In various embodiments, the thickness is between about 0.015 inches and about 0.040 inches, between about 0.020 inches and about 0.030 inches, or between about 0.024 inches and about 0.026 inches. In other embodiments, the thickness is greater than or equal to about 0.015 inches, greater than or equal to about 0.020 inches, or greater than or equal to about 0.025 inches. In still other embodiments, the thickness is less than or equal to about 0.040 inches, less than or equal to about 0.035 inches, or less than or equal to about 0.030 inches. In some embodiments, the thickness is about 0.025 inches.

In some embodiments, the inner surface of the sheath 222 varies in configuration from that of the outer surface of the sheath 222. Accordingly, in some arrangements, the thickness varies along the length of the sheath 222. In various embodiments, the thickness at one end, such as a proximal end, of the sheath is between about 0.015 inches and about 0.050 inches, between about 0.020 inches and about 0.040 inches, or between about 0.025 inches and about 0.035 inches, and the thickness at another end, such as the distal end 223, is between about 0.015 inches and 0.040 inches, between about 0.020 inches and 0.030 inches, or between about 0.023 inches and about 0.027 inches. In some embodiments, the thickness at one end of the sheath 222 is greater than or equal to about 0.015 inches, greater than or equal to about 0.020 inches, or greater than or equal to about 0.025 inches, and the thickness at another end thereof is greater than or equal to about 0.015 inches, greater than or equal to about 0.020 inches, or greater than or equal to about 0.025 inches. In still other embodiments, the thickness at one end of the sheath 222 is less than or equal to about 0.050 inches, less than or equal to about 0.040 inches, or less than or equal to about 0.035 inches, and the thickness at another end thereof is less than or equal to about 0.045 inches, less than or equal to about 0.035 inches, or less than or equal to about 0.030 inches. In some embodiments, the thickness at a proximal end of the sheath 222 is about 0.030 inches and the thickness at the distal end 223 is about 0.025 inches. In some arrangements, the cross-section of the inner surface of the sheath 222 is shaped differently from that of the outer surface. The shape and thickness of the sheath 222 can be altered, e.g., to optimize the strength of the sheath 222.

In some instances, the length of the sheath 222, as measured from a distal surface of the cap connector 230 to the distal end 223, is between about 0.8 inches to about 1.4 inches, between about 0.9 inches and about 1.3 inches, or between about 1.0 inches and 1.2 inches. In other instances, the length is greater than or equal to about 0.8 inches, greater than or equal to about 0.9 inches, or greater than or equal to about 1.0 inches. In still other instances, the length is less than or equal to about 1.4 inches, less than or equal to about 1.3 inches, or less than or equal to about 1.2 inches. In some embodiments, the length is about 1.1 inches.

In certain embodiments, the sheath 222 at least partially encloses one or more channels. For example, in the embodiment of FIG. 5, the sheath 22 partially encloses the regulator channel 225 and the access channel 245. In some arrangements, the sheath 222 defines the outer boundary of a distal portion of the regulator channel 225 and the outer boundary of a distal portion of the access channel 245. An inner wall 227 extending from an inner surface of the sheath 222 to a distal portion of the medical connector interface 240 defines an inner boundary between the regulator channel 225 and the access channel 245.

In the embodiment shown, the access channel 245 extends from an access aperture 246 formed in the sheath 222, through the cap connector 230, and through the connector interface 240. Thus, when a medical device, such as a syringe, is connected with the medical connector 241, which in turn is coupled with the connector interface 240, the medical device is in fluid communication with the inside of the vial 210. In such arrangements, the contents of the vial 210 and the contents of the medical device can be exchanged between the vial 210 and the medical device.

In the illustrated embodiment, the regulator channel 225 extends from a distal end 223 of the sheath 222, through the cap connector 230, through a portion of the connector interface 240, through the lumen 226, and terminates at the regulator aperture 228. In certain arrangements, such as in the arrangement shown, the regulator aperture 228 is in fluid communication with the passage 253 of the coupling 252, which is in fluid communication with the inner chamber 255 of the bag 254. Thus, in such arrangements, the inner chamber 255 is in fluid communication with the regulator channel 225. Additionally, because in the illustrated embodiment the filler 256 is located in the inner chamber 255, the filler 256 is also in fluid communication with the regulator channel 225.

In certain configurations, the adaptor 200 comprises a filter 260. In the embodiment illustrated, the filter 260 is located in the regulator channel 225 within the lumen 226. In other embodiments, the filter 260 is located in the regulator channel 225 in the sheath 222. In yet other embodiments, the filter 260 is located in the passage 253 in the coupling 252. Still further embodiments have the filter 260 positioned in the inner chamber 255 of the bag 254. Generally, the filter 260 is chemically or mechanically held in position, e.g., by adhesive or a snap ring. Certain embodiments include a plurality of filters 260. For example, certain embodiments have a first filter located in the lumen 226 and a second filter located in the coupling 252.

In some arrangements, the filter 260 is a hydrophobic membrane, which is generally configured to allow gases to pass therethrough, but to inhibit or prevent passage of liquids therethrough. In some configurations, gases (e.g., sterilized air) are able to pass through the filter 260 so as to move between the vial 210 and the bag 254, but liquid from the vial 210 is blocked by the filter 260. Embodiments of the adaptor 200 in which the filter 260 is located in the regulator channel 225 can therefore reduce the likelihood of liquid spilling from the vial 210 even if the regulator assembly 250 is detached.

In certain configurations, the filter 260 can remove particles and/or contaminants from the gas that passes through the filter. For example, in certain embodiments, the filter 260 is configured to remove nearly all or about 99.9% of airborne particles 0.3 micrometers in diameter. In some cases, the filter 260 is configured to remove microbes. In some embodiments, the filter 260 comprises nylon, polypropylene, polyvinylidene fluoride, polytetrafluoroethylene, or other plastics. In some embodiments, the filter 260 includes activated carbon, e.g., activated charcoal. In certain configurations, the filter 260 comprises a mat of regularly or randomly arranged fibers, e.g., fiberglass. In some arrangements, the filter 260 comprises Gortex® material or Teflon® material.

In the illustrated embodiment, the lumen 226 is a hollow cylindrical member extending radially outward from the connector interface 240. In other embodiments, the lumen 226 comprises other shapes, such as conical. The lumen 226 can have a variety of cross-sectional shapes, such as circular, square, rectangular, elliptical, diamond, star-shaped, polygonal, or irregular. As shown, in some embodiments, the lumen 226 extends radially outward less than the sleeve 235 of the cap connector 230. However, in certain configurations, the lumen 226 extends radially outward beyond the sleeve 235 of the cap connector 230. Such a configuration can, for example, facilitate a connection with the regulator assembly 250 such that the regulator assembly 250 is spaced-apart from the remainder of the adaptor 200 and from the vial 210.

In some embodiments, the coupling 252 has a shape that is corresponding or complementary with the shape of the lumen 226. For example, in some cases, the lumen 226 has a triangular shape and the coupling 252 has a triangular shape as well. The coupling 252 can have most any cross-sectional shape, such as circular, square, rectangular, elliptical, diamond, star-shaped, polygonal, or irregular. In certain configurations, the coupling 252 and the lumen 226 are correspondingly shaped to promote an orientation of the coupling 252 (and thus the regulator assembly 250) relative to the lumen 226 (and thus the remainder of the adaptor 200), as discussed below.

The coupling 252 can be configured to engage the lumen 226. For example, in the embodiments illustrated, the coupling 252 is configured to be received by the lumen 226. In other cases, the coupling 252 is configured to receive the lumen 226. In some instances, the coupling 252 and the lumen 226 connect with a slip fit or a press fit. In some configurations, the coupling 252 and the lumen 226 connect with a hose-barb connection. In certain arrangements, the coupling 252 and the lumen 226 connect with a threaded connection. For example, in certain cases the coupling 252 and the lumen 226 have corresponding standard luer lock connections. In some embodiments, the connection between the coupling 252 and the lumen 226 is substantially airtight, so as to inhibit or prevent outside air from entering the regulator channel 225. Such a configuration can reduce the likelihood that microbes or impurities will enter vial 210, thereby enhancing patient safety by reducing the likelihood of contaminating the medical fluid.

In some arrangements, the connection between the coupling 252 and the lumen 226 includes a feedback device to alert the user that the connection has been made. For example, in certain arrangements, the connection between the coupling 252 and the lumen 226 includes a detent mechanism, e.g., a ball detent, which can provide a tactile indication that the connection has been made. Some embodiments include an audible signal, e.g., a click, snap, or the like, to indicate that coupling 252 has been connected with the lumen 226.

In some embodiments, the connection between the coupling 252 and the lumen 226 is substantially permanent. For example, in certain configurations, the coupling 252 and lumen 226 are sonically welded. In some cases, the coupling 252 and lumen 226 are permanently attached with an adhesive, such as glue, epoxy, double-sided tape, solvent bond, or otherwise. In some embodiments, the coupling 252 and lumen 226 joined with a permanent snap fit mechanism (e.g., a generally 90° hook and a corresponding generally 90° valley), such that the coupling 252 and lumen 226 are substantially restrained from being separated after the snap mechanism has been engaged. Permanent connection of the coupling 252 and lumen 226 can encourage one-time-use of the adaptor 200, including one-time-use of the regulator assembly 250. Further, permanent connection of the regulator assembly 250 and with the remainder of the adaptor 200 reduces the total number of unique parts to be inventoried, maintained, and prepared prior to use. In some embodiments, the coupling 252 is formed substantially monolithically with (e.g., molded during the same operation as) the remainder of the adaptor 200.

In some cases, the coupling 252 and lumen 226 are connected during the process of manufacturing the adaptor 200, e.g., at the factory. In some configurations, the regulator assembly 250 is a separate item from the remainder of the adaptor 200 and is configured to be connected with the remainder of the adaptor 200 by a user. For example, the piercing member 220, cap connector 230, and connector interface 240 may be provided in a first package and the regulator assembly 250 may be provided in a second package. In some user-connected configurations, the connection is substantially permanent. For example, in some cases one of the coupling 252 and the lumen 226 includes an adhesive (e.g., double-sided tape) which substantially permanently bonds the coupling 252 and the lumen 226 when the user connects the coupling 252 and the lumen 226. On the other hand, in certain user-connected embodiments, the coupling 252 is configured to be detachable from the lumen 226, even after the coupling 252 has been connected with the lumen 226. For example, in certain embodiments the coupling 252 and the lumen 226 are releasably joined with threads or a release mechanism, such as a detent or a set-screw. Such a configuration can facilitate operations (e.g., voluminous pharmaceutical compounding operations) in which the transfer of a volume of regulating fluid from the regulator assembly 250 into the vial 210 is desired that is greater that the volume of regulating fluid contained in the regulator assembly 250, as discussed below. In some embodiments, when the regulator assembly 250 is detached, the contents therein are sealed off from the environment, such as by way of a one-way valve.

In the illustrated embodiment, the coupling 252 is joined with the bag 254. In some cases, the bag 254 and coupling 252 are welded or joined with adhesive. As shown, the connection of the bag 254 and the coupling 252 generally fluidly connects the passage 253 with the inner chamber 255 of the bag 254. To facilitate fluid communication, the bag 254 can include a bag aperture 257, such as a slit or hole. In some cases, the bag aperture 257 is produced with a hot implement, such as a soldering iron.

The bag 254 is generally configured to unfold, unroll, expand, contract, inflate, deflate, compress, and/or decompress. The bag 254 can comprise any of a wide variety of flexible and/or expandable materials. For example, in certain embodiments, the bag 254 comprises polyester, polyethylene, polypropylene, saran, latex rubber, polyisoprene, silicone rubber, vinyl, polyurethane, or other materials. In certain embodiments, the bag 254 comprises a material having a metal component to further inhibit fluid (including gas or air) leakage through the material of the bag, e.g., metalized biaxially-oriented polyethylene terephthalate (also known as PET and available under the trade name Mylar®). In some embodiments, the bag 254 comprises a laminate. For example, the bag 254 can be constructed of a layer of 0.36 Mil (7.8#) metalized (e.g., aluminum) PET film and a layer of 0.65 Mil (9.4#) linear low-density polyethylene. In some embodiments, the bag 254 comprises a material capable of forming a substantially airtight seal with the coupling 252. In certain embodiments, the bag 254 is transparent or substantially transparent. In other embodiments, the bag 254 is opaque. In many instances, the bag 254 comprises a material that is generally impervious to liquid and air. In certain embodiments, the bag 254 comprises a material that is inert with respect to the intended contents of the vial 210. For example, in certain cases, the bag 254 comprises a material that does not react with certain drugs used in chemotherapy. In some embodiments, the bag 254 comprises latex-free silicone having a durometer that is between about 10 and about 40.

In certain configurations, the bag 254 includes a coating. For example, in some embodiments, the bag 254 includes a coating that reduces the porosity of the bag 254. In some cases, the coating is evaporated aluminum or gold. In some cases, the coating includes a water soluble plastic configured to form a barrier to inhibit passage of gases thereacross. In certain instances, the coating is applied to the outside of the bag 254. In other instances, the coating is applied to the inside of the bag 254. In some cases, the coating is applied to the inside and the outside of the bag 254. In some embodiments, the coating is a polyolefin.

In certain embodiments, the bag 254 is located entirely outside of the vial 210. In certain arrangements, the bag 254 is positioned entirely outside of the remainder of the adaptor (e.g., the piercing member 220, cap connector 230, and connector interface 240). In some embodiments, the bag 254 is substantially free to expand in generally any direction. For example, in the embodiment illustrated, there is no rigid enclosure surrounding or partially surrounding a portion of the bag 254. In some instances, a rigid housing does not contain a substantial portion of the bag 254. In some embodiments, in the fully deflated state, the bag 254 is not within a rigid enclosure. In certain configurations, the bag 254 is substantially free to expand in generally any direction, e.g., proximally, distally, radially away from the vial 210, radially toward the vial 210, etc.

In some embodiments, the bag 254 is configured to freely expand without being constrained by, for example, a rigid enclosure. Such unconstrained expansion of the bag 254 can reduce the force needed to expand the bag 254. For instance, as the bag 254 does not contact a rigid enclosure, there is no frictional force between the bag 254 and such an enclosure, which could otherwise increase the force needed to expand the bag 254. In certain aspects, unconstrained expansion of the bag 254 reduces the likelihood of the bag 254 being damaged during expansion. For example, because the bag 254 does not contact a rigid enclosure, there is less risk of the bag 254 being damaged (e.g., pierced, torn, or snagged on a burr or other defect of such an enclosure) during expansion or deflation. Further, unconstrained movement of the bag 254 lessens the chance of a coating on the bag 254 being smeared or rubbed-off. In some embodiments, the bag 254 does not bump, rub, slide against, or otherwise statically or dynamically contact a rigid surface of the adaptor 200 during expansion. In certain configurations, the bag 254 contacts only the coupling 252, regulating fluid, and ambient air.

In certain embodiments, the bag 254 includes a first side 258 and a second side 259. In some instances, the first side 258 is closer to the connector interface 240 than the second side 259. In some cases, the first side 258 is bonded with the coupling 252, but the second side 259 is not. In certain configurations, the first side 258 connects with the second side 259. In some such cases, the first side 258 connects with the second side 259 at a peripheral edge of each of the sides 258, 259. In certain instances, the second side 259 does not touch a rigid surface during expansion of the bag 254. In some configurations, substantially all or a majority of the surface area of the bag 254 that is exposed to the ambient environment is flexible. In certain embodiments, generally the entire bag 254 is flexible.

In some embodiments, each of the sides 258, 259 includes an inner surface and an outer surface. As illustrated in FIG. 6, the inner surface of each of the sides 258, 259 can be in contact with the inner chamber 255, and the outer surface of each of the sides 258, 259 can be in contact with the ambient environment.

In certain instances, the inner surface of each of the sides 258, 259 is oriented towards the inside of the bag 254. As used herein, the phrase "oriented towards," or any derivative thereof, is a broad term used in its ordinary sense and describes, for example, generally aligning or positioning something in the direction of the member indicated. For example, if a first member is oriented towards a second member, then the first member is generally aligned or positioned in the direction of the second member. In the case of a side or a surface being oriented toward a member, the side or surface is aligned or positioned such that a normal from the side or surface intersects the member. In certain configurations, the first side 258 is oriented towards the connector interface 240.

In certain instances, the outer surface of each of the sides 258, 259 is oriented outwardly from the bag 254. In some cases, the second side 259 is oriented away from the connector interface 240. In some such cases, a normal extending from the outer surface of the second side 259 does not intersect the connector interface 240.

In certain embodiments, the second side 259 is oriented opposite from the first side 258. As used herein, the term "opposite," or any derivative thereof, is a broad term used in its ordinary sense and describes, for example, something at the other end, side, or region from a member. For example, each side in a rectangle is opposite one other side and non-opposite two other sides. In some instances, the second side 259 is oriented away from the connector interface 240. In such instances, a normal extending from the outer surface of the second side 259 does not intersect the connector interface 240.

In some embodiments, the bag 254 includes a first layer and a second layer. As used herein, the term "layer," or any derivative thereof, is a broad term used in its ordinary sense and describes, for example, a thickness, ply, or stratum of material. In some embodiments, a layer can include multiple components, plies, or strata of material. In some instances, the first layer is the first side 258 and the second layer is the second side 259. In certain configurations, the first and second layers are connected. For example, a periphery of the first layer can be connected to or formed unitarily or monolithically with a periphery of the second layer. Such configurations can, for example, aid in forming the bag 254, e.g., by rendering the bag 254 substantially airtight at the periphery. In some instances, the first layer is a first sheet of metalized PET and the second layer is a second sheet of metalized PET, and the first and second layers are bonded (e.g., heat sealed) together at the peripheries. In certain embodiments, the first and second layers each have a central portion. For example, in a configuration in which the first and second layers are each substantially circular in peripheral shape, the central portions can be at about the radial center of each of the first and second layers. In certain instances, the central portion of the first layer is unattached or not connected with the central portion of the second layer. Thus, in some such instances, the first and second portions can move relative to each other.

In some embodiments, one or both of the first and second layers include one or more sub-layers. For example, the first and/or second layers can each include a plastic sub-layer and a metal sub-layer. In certain embodiments, the first and second sub-layers have interfacing surfaces that are bonded together. In some cases, substantially the entire area of the interfacing are bonded. Generally, the sub-layers are not configured to receive a substantial volume or any appreciable volume (e.g., of regulating fluid) therebetween. On the other hand, in some embodiments, the first and second layers are configured to receive the regulating fluid therebetween. For example, in a configuration in which the first layer is the first side 258 and the second layer is the second side 259, the regulating fluid can be received between the first and second layers (see FIG. 6).

In various embodiments, the adaptor 200 does not include a rigid enclosure that wholly or partially contains the bag 254. For example, any volume of the bag inside a rigid enclosure may encompass (if at all) less than half of the bag 254 or a very small portion of the volume of the bag (e.g., smaller than or equal to the volume inside the piercing member on the adapter or smaller than or equal to the volume inside the cap of the connector). In some embodiments, any volume of the bag inside a rigid enclosure (if at all) is less than or equal to half of the volume inside a vial or vials to which the adapter is configured to be connected. A rigid enclosure can increase the weight and total material of the adaptor 200, thereby increasing material and manufacturing costs. Moreover, since rigid enclosures may be positioned a distance apart from the axial center of the adaptor, omitting a rigid enclosure can eliminate the moment of force that is imposed by the weight of such an enclosure. Thus, the adaptor 200 can promote stability and reduce the chance of tipping-over. Stability of the adaptor and vial can be particularly important in dealing with cytotoxic drugs, as tipping could increase the likelihood of spills or other unintended exposure and/or release.

Certain embodiments of the adaptor 200 have a center of mass that is not substantially disposed from the axial center of the adaptor 200, when the regulator assembly 250 is connected with the remainder of the adaptor 200 and the adaptor 200 is mated with the vial 210. For instance, some embodiments of the adaptor 200 have center of mass that is less than or equal to about 0.50 inches, less than or equal to about 0.25 inches, less than or equal to about 0.125 inches, or less than or equal to about 0.063 inches apart from the axial center of the adaptor 200.

In some instances, the bag 254 is expandable to substantially fill a range of volumes such that a single adaptor 200 can be configured to operate with vials 210 of various sizes. In some embodiments, the bag 254 is configured to hold a volume equal to at least about 30, at least about 70, or at least about 90 percent of the volume of fluid contained within the vial 210 prior to the coupling of the adaptor 200 and the vial 210. In some embodiments, the bag 254 is configured to hold a volume equal to about 70 percent of the volume of fluid contained within the vial 210 prior to the coupling of the adaptor 200 and the vial 210. In various embodiments, the fluid in the bag 254 is a gas. For example, air, sterilized air, cleaned air, nitrogen, oxygen, inert gas (e.g., argon) or otherwise. In some embodiments, the sterilized air can be supplied by providing ambient air within the bag and then sterilizing the bag and air together.

The bag 254 has a fully expanded configuration (FIG. 6) and at least one non-fully expanded configuration (FIG. 5). In certain instances, in the fully expanded configuration, the volume of the inner chamber 255 of the bag 254 is at its maximum recommended volume. In certain instances, in the fully expanded configuration, the bag 254 contains at least about 100 mL, at least about 200 mL, or at least about 300 mL of fluid. In certain instances, in the fully expanded configuration, the bag 254 holds at least about 250 mL of fluid. In certain embodiments, in the fully expanded configuration, the bag 254 contains at least 180 mL of fluid In certain instances, in a non-fully expanded configuration, the bag 254 contains less than or equal to about 5 mL, less than or equal to about 40 mL, less than or equal to about 100 mL, or less than or equal to about 250 mL of fluid. In some instances, a non-fully expanded configuration of the bag 254 is a fully deflated configuration, in which the volume of the inner chamber 255 of the bag 254 is about zero. In some such instances, in the fully deflated configuration, the bag 254 contains substantially no fluid.

The bag 254 further has an initial configuration (e.g., the configuration prior to any regulating fluid being transferred between the vial 210 and the bag 254). Generally, the bag 254 contains a volume of fluid in the initial configuration to facilitate rapid and accurate withdrawal of fluid from the vial 210 upon connection of the adaptor 200 with the vial 210. In certain embodiments, in the initial configuration, the bag 254 contains at least about 10 mL, at least about 50 mL, or at least about 90 mL of fluid. In certain embodiments, in the initial configuration, the bag 254 contains at least about 60 mL of fluid. In some embodiments, in the initial configuration, the bag 254 contains a volume of fluid that generally corresponds to the volume of a standard medical device or devices to which the adapter is configured to attach. For example, in certain instances, in the initial configuration, the bag 254 holds at least about 30 mL of fluid, which corresponds to the volume of a 30 mL syringe. In such instances, upon connection of the adaptor 200 with the vial 210, about 30 mL of fluid are immediately available to be transferred between the bag 254 to the vial 210, thereby allowing 30 mL of fluid to be immediately transferred between the vial 210 and the syringe. In some embodiments, the bag 254 has an initial volume of at least about the volume inside the cap plus inside of the piercing member, or at least about twice as large as the volume insider the cap plus inside of the piercing member In various arrangements, the bag 254 has an outer dimension (e.g., diameter or cross-sectional width or height) D of between about 1.0 inches and about 6.0 inches, between about 2.0 inches and about 5.0 inches, or between about 3.0 inches and about 4.0 inches. In some arrangements, the outer dimension is greater than or equal to about 3.0 inches, greater than or equal to about 4.0 inches, or greater than or equal to about 6.0 inches. In other arrangements, the outer diameter is less than or equal to about 8.0 inches, less than or equal to about 7.5 inches, or less than or equal to about 7.0 inches. In some embodiments, an outer dimension of the bag is greater than or equal to about the height or cross-sectional width of the vial or vials to which the adapter is configured to attach. In various arrangements, the bag 254 has a maximum total thickness T of between about 0.50 inches and about 2.00 inches, between about 0.60 inches and about 0.90 inches, and between about 0.70 inches and about 0.80 inches. In other arrangements, the maximum total thickness is less than about 1.00 inches, less than about 0.90 inches, or less than about 0.80 inches. In some arrangements, the maximum total thickness is about 0.75 inches. In certain instances, the diameter of the bag 254 is greater than the maximum total thickness of the bag 254. In certain instances, the diameter of the bag 254 is greater than twice the maximum total thickness of the bag 254. In some instances, it is desirable to prevent the bag 254 from bearing against the vial 210. Accordingly, in some instances, the bag 254 is configured (e.g., dimensioned) such that even in the fully expanded state, the bag 254 is spaced apart from the vial 210.

In some configurations, the bag 254 has a wall thickness W between about 0.001 and about 0.025 inches, between about 0.001 and about 0.010 inches, or between about 0.010 and about 0.025 inches. In other configurations, the wall thickness is greater than about 0.001 inches, greater than about 0.005 inches, greater than about 0.010 inches, greater than about 0.015 inches, or greater than about 0.020 inches. In still other configurations, the wall thickness is less than about 0.025 inches, less than about 0.020 inches, less than about 0.015 inches, less than about 0.010 inches, or less than about 0.005 inches. In some configurations, the wall thickness is about 0.015 inches. In some embodiments, the wall thickness is substantially constant. In some embodiments, the wall thickness can vary. For example, in some configurations, the wall thickness increases in an area of the bag 254 around the coupling 252.

In some configurations, such as in the non-fully expanded configuration, the bag 254 is substantially irregularly shaped, as shown in FIG. 5. In other configurations, the bag 254 has shape that is generally spherical, generally conical, generally cylindrical, generally torroidal, or otherwise. For example, in some embodiments, in the fully expanded configuration, the bag 254 is shaped as a generally oblate spheroid. In certain instances, the bag 254 is substantially bulbous. In some arrangements, the bag 254 has a convex shape. In some configurations, the bag 254 has a concave shape. In some configurations, the shape of the bag 254 generally conforms to the shape of the filler 256. In some arrangements, the bag 254 generally conforms to the shape of the filler 256 in a non-fully expanded configuration and deviates from the shape of the filler 256 in the fully expanded configuration.

The filler 256 can be configured to occupy various volumes within the bag 254. For example, in some arrangements, the filler 256 occupies a volume greater than or equal to about 30, about 75, or about 90 percent of the volume of the bag 254. In certain arrangements, the filler 256 is configured to maintain a space between the first and second sides 258, 259 of the bag 254. In certain arrangements, the filler 256 is configured to ensure that the volume of the inner chamber 255 is not zero.

In general, the filler 256 is configured to provide a ready supply of regulating fluid, e.g., sterilized air, to the vial 210. As discussed above, when the adaptor 200 is engaged with the vial 210 and a medical device (such as a syringe), and a portion of the fluid in the vial 210 is transferred from the vial 210 through the adaptor 200 into the medical device, the reduction in fluid volume in the vial 210 causes a pressure decrease in the vial 210, thereby creating a pressure gradient between the interior and exterior of the vial 210. This pressure gradient can cause surrounding air—which can contain microbes, impurities, and other contaminants—to leak into the vial 210 at the interface of the septum 216 and piercing member 220 or at the attachment interface of the adaptor 200 and a medical device. Further, such a pressure gradient can produce a restoring force that hinders the ability to withdraw an accurate amount of fluid from the vial 210. However, the filler 256 can provide a ready supply of regulating fluid to the adaptor 200 to replace some or all of the fluid volume that has been transferred out to generally maintain equilibrium in the vial 210, thereby lessening or preventing the aforementioned problems.

In certain arrangements, as fluid is removed from the vial 210 though the extraction channel 245, a corresponding amount of regulating fluid from the filler 256 can substantially concurrently be introduced through the bag aperture 257, the passage 253 in the coupling 252, the regulator channel 225, and into the vial 210, thereby maintaining equilibrium. In some arrangements, the filler 256 includes a ready supply of regulating fluid prior to the regulator assembly 250 being connected with the remainder of the adaptor 200. In some aspects, the filler 256 provides a reservoir of regulating fluid to the adaptor 200. In certain arrangements, the filler 256 is configured such that a substantial portion of the first and second sides 258, 259 of the bag 254 do not contact each other.

In some configurations, the filler 256 has a similar shape as the bag 254. For example, in some cases, in the fully expanded configuration, the bag 254 and the filler 256 are each generally shaped as an oblate spheroid. In other configurations, the filler 256 has a shape that is different than the bag 254. For example, in certain instances, in the fully expanded configuration, the bag 254 has a substantially spheroidal shape and the filler 256 has a substantially cylindrical shape. In some such instances, the longitudinal axis of the cylindrically shaped filler 256 is generally parallel with the axial centerline of the adaptor 200. In other such instances, the longitudinal axis of the cylindrically shaped filler 256 is orthogonal to the axial centerline of the adaptor 200.

In certain embodiments, the filler 256 is configured to be deformed by the bag 254 when the bag 254 deflates. For example, in some instances, when the bag 254 deflates, the filler 256 decreases in volume by at least about 30, at least about 50, or at least about 90 percent. In certain instances, when the bag 254 is in the fully expanded configuration, the filler 256 has a first shape (e.g., spheroidal) and when the bag 254 is in the fully deflated configuration, the filler 256 has a second shape (e.g., disk-like).

In some such embodiments, the filler 256 is configured to be crushable or compressible and then return substantially to its original shape. For example, when the bag 254 deflates from the fully deflated configuration, the bag 254 substantially collapses the filler 256, but during subsequent expansion of the bag 254, the filler 256 returns to about its original shape. In other embodiments, the filler 256 is configured to be permanently deformed when it is crushed. For example, in some cases, the filler 256 comprises a thin-walled hollow member (e.g., an aluminum foil ball), which is configured to be permanently or irreversibly deformed, crushed, or otherwise decreased in volume during deflation of the bag 254. This can provide an indicator that the adaptor 200 has already been used. In some embodiments, the filler 256 substantially maintains its shape when the bag 254 deflates.

In certain arrangements, the filler 256 is configured to contain a volume of gas, such as sterilized air. In certain cases, the filler 256 is porous. In some instances, the filler 256 is a sponge or sponge-like material. In certain arrangements, the filler 256 comprises cotton wadding. In certain configurations, the filler 256 comprises a mat of regularly or randomly arranged fibers configured to provide a network of chambers or spaces therein. In some embodiments, the filler 256 is made of low density foam. For example, in certain embodiments, the filler 256 is made of polyurethane-ether foam, and has a weight of, for example, about 1.05 pounds per cubic foot and an indentation load deflection (ILD) of, for example, about 38. In some embodiments, the filler 256 is made of polyether, polyester, polyethylene, or ether-like-ester (ELE). In some cases, the filler 256 is made of nylon, polypropylene, polyvinylidene fluoride, polytetrafluoroethylene, or other plastics. In certain embodiments, the filler 256 is a metal, e.g., aluminum or stainless steel. In certain embodiments, the filler 256 is treated with an anti-microbial or other compound to enhance sterility. In certain cases, the filler 256 comprises a sealed chamber, e.g., containing sterilized air, which is configured to open when a fluid is withdrawn from the vial 210. In some embodiments, the filler 256 can be configured to bind with, absorb, generally neutralize, or otherwise chemically and/or mechanically interact with the fluid (such as vapors) entering the bag.

In various arrangements, at ambient pressure, the filler 256 has an outer dimension (e.g., a diameter or cross-sectional width or height) of between about 1.0 inches and about 6.0 inches, between about 2.0 inches and about 5.0 inches, or between about 3.0 inches and about 4.0 inches. In some arrangements, at ambient pressure the outer diameter of the filler 256 is greater than or equal to about 3.0 inches, greater than or equal to about 4.0 inches, or greater than or equal to about 6.0 inches. In certain embodiments, the diameter of the filler 256 at ambient pressure is about 4.00 inches. In other arrangements, at ambient pressure the outer diameter is less than or equal to about 8.0 inches, less than or equal to about 7.5 inches, or less than or equal to about 7.0 inches. In various arrangements, at ambient pressure the filler 256 has a maximum total thickness of between about 0.05 inches and about 0.99 inches, between about 0.20 inches and about 0.60 inches, and between about 0.25 inches and about 0.35 inches. In certain embodiments, the thickness of the filler 256 at ambient pressure is about 0.30 inches. In some arrangements, the maximum total thickness of the filler 256 at ambient pressure is about 1.00 inches. In some embodiments, at ambient pressure the diameter and thickness of the filler 256 are about the same as the diameter D and thickness T of the bag 254.

With continued reference to FIGS. 5 and 6, certain processes for using the adaptor 200 comprise inserting the piercing member 220 through the septum 216 until the cap connector 230 is firmly in place. Accordingly, the coupling of the adaptor 200 and the vial 210 can be accomplished in one simple step. In certain instances, the medical connector 241 is coupled with the medical connector interface 240. A medical device or other instrument (not shown), such as a syringe, can be coupled with the interface 240 or, if present, with the medical connector 241 (see FIG. 4). For convenience, reference will be made hereafter only to a syringe as an example of a medical device suitable for attachment to the medical connector interface 240, although numerous medical devices or other instruments can be used in connection with the adaptor 200 or the medical connector 241. In some instances, the syringe is placed in fluid communication with the vial 210. In some instances, the vial 210, the adaptor 200, the syringe, and, if present, the medical connector 241 are inverted such that the cap 214 is pointing downward (e.g., toward the floor). Any of the above procedures, or any combination thereof, can be performed in any possible order.

In some instances, a volume of fluid is withdrawn from the vial 210 into the syringe. As described above, the pressure within the vial 210 decreases as the fluid is withdrawn. Accordingly, in some instances, the regulating fluid in the filler 256 in the bag 254 flows through the regulator channel 225 and into the vial 210. In some instances, the regulating fluid passes through the filter 260. In some instances, the transfer of the regulating fluid from the filler 256 causes the bag 254 to deflate. In some arrangements, the transfer of the regulating fluid from the filler 256 and/or elsewhere in the bag 254 into the vial 210 generally maintains equilibrium in the vial 210. In some cases, the volume of regulating fluid transferred from the filler 256 into the vial 210 is about equal to the volume of fluid withdrawn from the vial 210 into the syringe.

In certain instances, a volume of fluid is introduced into the vial 210 from the syringe. For example, in certain cases, a volume of fluid is introduced into the vial 210 to reconstitute a freeze-dried drug or for drug compounding purposes. As another example, in some instances, more fluid than is desired may inadvertently be withdrawn from the vial 210 by the syringe. As discussed above, as the fluid is introduced into the vial 210, the pressure in the vial 210 increases. Thus, in some instances, regulating fluid in the vial 210 flows through the regulator channel 225 and into the bag 254, as shown by the arrows in FIG. 6. In some instances, the regulating fluid passes through the filter 260. In some instances, the transfer of the regulating fluid from the vial 210 causes the bag 254 to inflate. In certain of such instances, as the bag 254 inflates, it stretches, unfolds, or unrolls outward. In certain embodiments, the bag 254 is sufficiently flexible so as to substantially avoid producing a restoring force (e.g., a force in opposition to expansion or contraction of the bag 254). In some embodiments, the bag 254 does exert a restoring force. In some arrangements, the transfer of the regulating fluid from the vial 210 into the bag 254 maintains equilibrium in the vial 210. In some cases, the volume of regulating fluid transferred from the vial 210 into the bag 254 is about equal to the volume of fluid introduced into the vial 210 from the syringe.

Thus, in certain embodiments, the adaptor 200 accommodates the withdrawal of fluid from, or the addition of fluid to, the vial 210 in order to maintain the pressure within the vial 210. In various instances, the pressure within the vial 210 changes no more than about 1 psi, no more than about 2 psi, no more than about 3 psi, no more than about 4 psi, or no more than about 5 psi.

In some embodiments, a process for containing gases and/or vapors includes providing the piercing member 220, cap connector 230, and connector interface 240. Generally, the process also includes piercing the septum of the vial 210 with the piercing member 220. The piercing member 220 can provide access to medical fluid in the vial 210. In certain embodiments, the process includes joining the regulator assembly 250 with the cap connector 230 or connector interface 240, thereby fluidly connecting the regulator assembly 250 and the vial 210. In some embodiments, the process also includes storing gases and/or or vapors displaced by a fluid that is introduced into the vial 210. In certain configurations, all or a portion of the gases and/or vapors are stored in the regulator assembly 250. Thus, the gases and/or vapors—which may pose substantial health hazards—can be sequestered and generally maintained apart from the ambient environment. In some embodiments, the process can include detaching the regulator assembly 250.

As is evident from the embodiments and processes described above, the adaptor 200 allows a user to introduce liquid into (including returning unwanted liquid and/or air) and withdrawn liquid from the vial 210 without significantly changing the pressure within the vial 210. As previously discussed, the capability to inject liquid into the vial can be particularly desirable in the reconstitution of lyophilized drugs. Also, as detailed earlier, the ability to inject air bubbles and excess fluid into the vial 210 can be particularly desirable in the context of oncology drugs.

Furthermore, the above discussion demonstrates that certain embodiments of the adaptor 200 can be configured to regulate the pressure within the vial 210 without introducing outside or ambient air into the vial 210. For example, in some embodiments, the bag 254 comprises a substantially impervious material that serves as a barrier, rather than a passageway, between interior of the vial 210 and the ambient environment. Some embodiments of the adaptor 200 substantially reduce the risk of introducing airborne contaminants into the bloodstream of a patient.

As noted above, in some instances, the vial 210 is oriented with the cap 214 pointing downward when liquid is removed from the vial 210. In certain embodiments, the access aperture 246 is located adjacent a bottom surface of the cap 214, thereby allowing removal of most or substantially all of the liquid in the vial 210. In other embodiments, access aperture 246 is located near the distal end 223 of the piercing member 220. In some arrangements, the adaptor 200 comprises more than one access aperture 246 to aid in the removal of substantially all of the liquid in the vial 210.

FIGS. 7-12 illustrate another embodiment of an adaptor 300. The adaptor 300 resembles or is identical to the adaptor 200 discussed above in many respects. Accordingly, numerals used to identify features of the adaptor 200 are incremented by a factor of 100 to identify like features of the adaptor 300. This numbering convention generally applies to the remainder of the figures. Any component or step disclosed in any embodiment in this specification can be used in other embodiments.

In certain embodiments, the adaptor 300 comprises a piercing member 320, a cap connector 330, a connector interface 340, and a regulator assembly 350. Further details and examples regarding some embodiments of piercing members 320, cap connectors 330, and connector interfaces 340 are provided in U.S. Patent Application Publication No. 2009/0216212, the entirety of each of which is incorporated herein by reference and is made a part of this specification. For clarity, the vial 210 is not illustrated. The adaptor 300 can mate with the vial 210 in a similar manner as the adaptor 200. For example, when the adaptor 300 is mated with the vial 210, the piercing member 320 extends through the septum 216 into the interior of the vial 210.

In some embodiments, such as in the illustrated embodiment, the cap connector 330 comprises a body portion 380, which in turn comprises a central portion 381 (that can be curved) and one or more tabs 382 (which can be opposing) attached to the central portion 381. Each of the tabs 382 can be supported at a proximal end of the tab 382 by the central portion 381 of the body portion 380. As shown, the distal end of the tabs 382 can each be unrestrained so as to allow the tab to deflect outward.

The body portion 380, including the central portion 381 and tabs 382, can help removably secure the vial adaptor 300 to the outside surface of the vial 210 and can help facilitate the removal of the vial adaptor 300 from the vial 210. In some embodiments, the body portion 380 defines only one tab 382, as opposed to a pair of opposing tabs 382, the single tab being configured to removably secure the vial adaptor 300 to the outside surface of the vial 210 and to facilitate the removal of the vial adaptor 300 from the vial 210. The single tab 382 can be of any suitable configuration, including those set forth herein.

Figure 7:
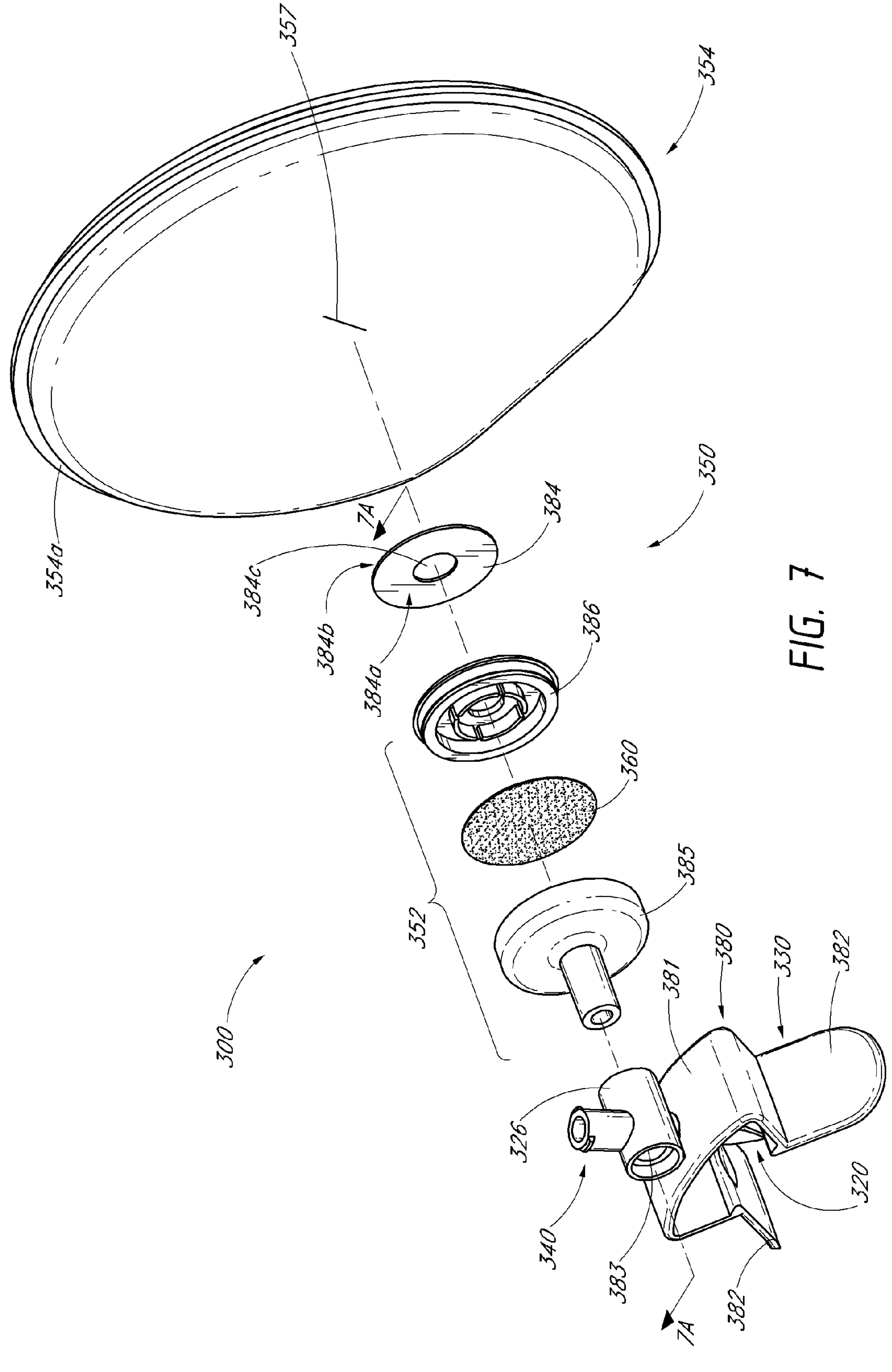
FIG. 7 illustrates an exploded perspective view of a vial adaptor.
Figure 7A:
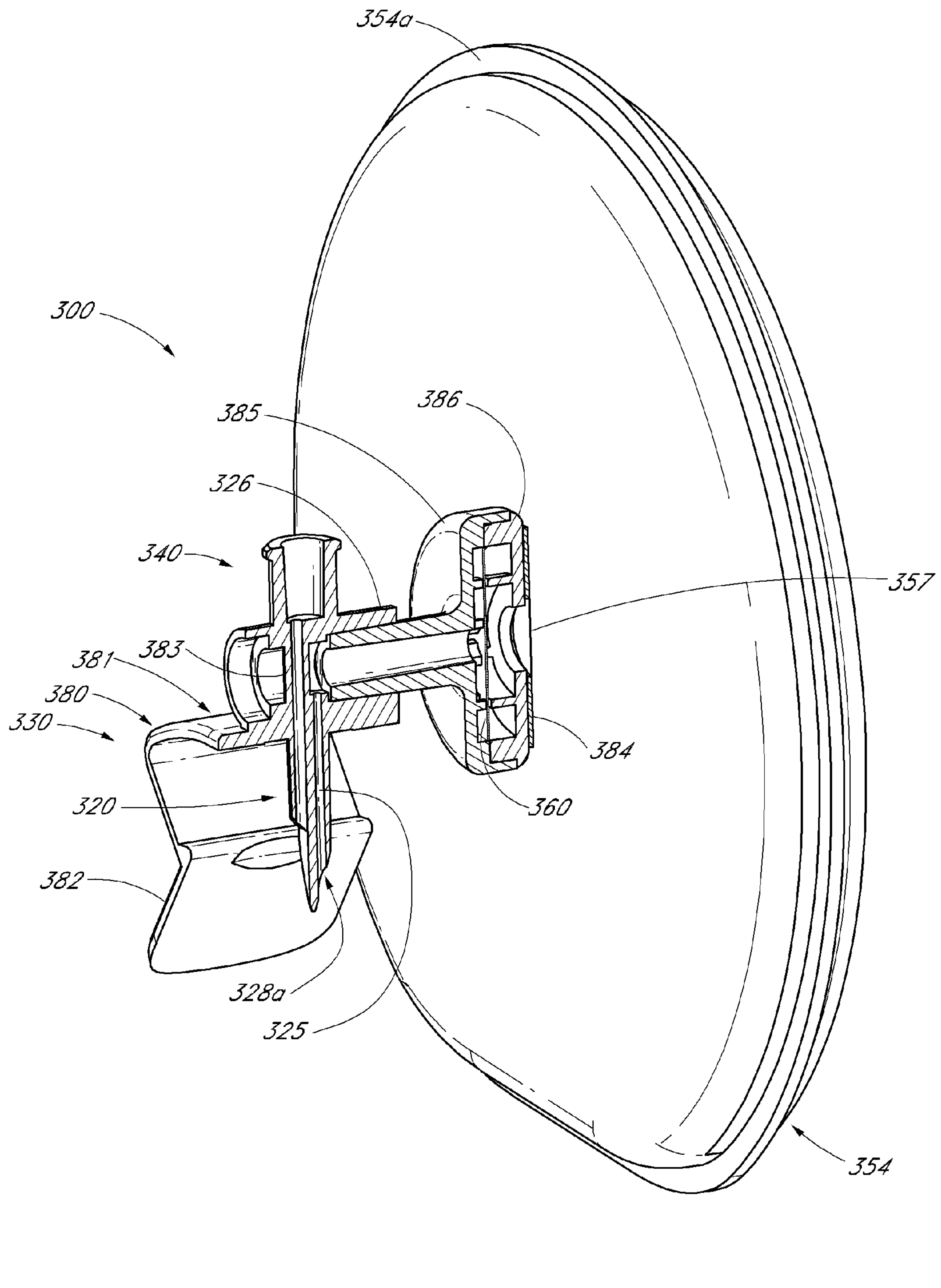
FIG. 7A illustrates an assembled perspective view of the vial adaptor of FIG. 7, including a partial cross-sectional view taken through line 7A-7A in FIG. 7.
Figure 8:
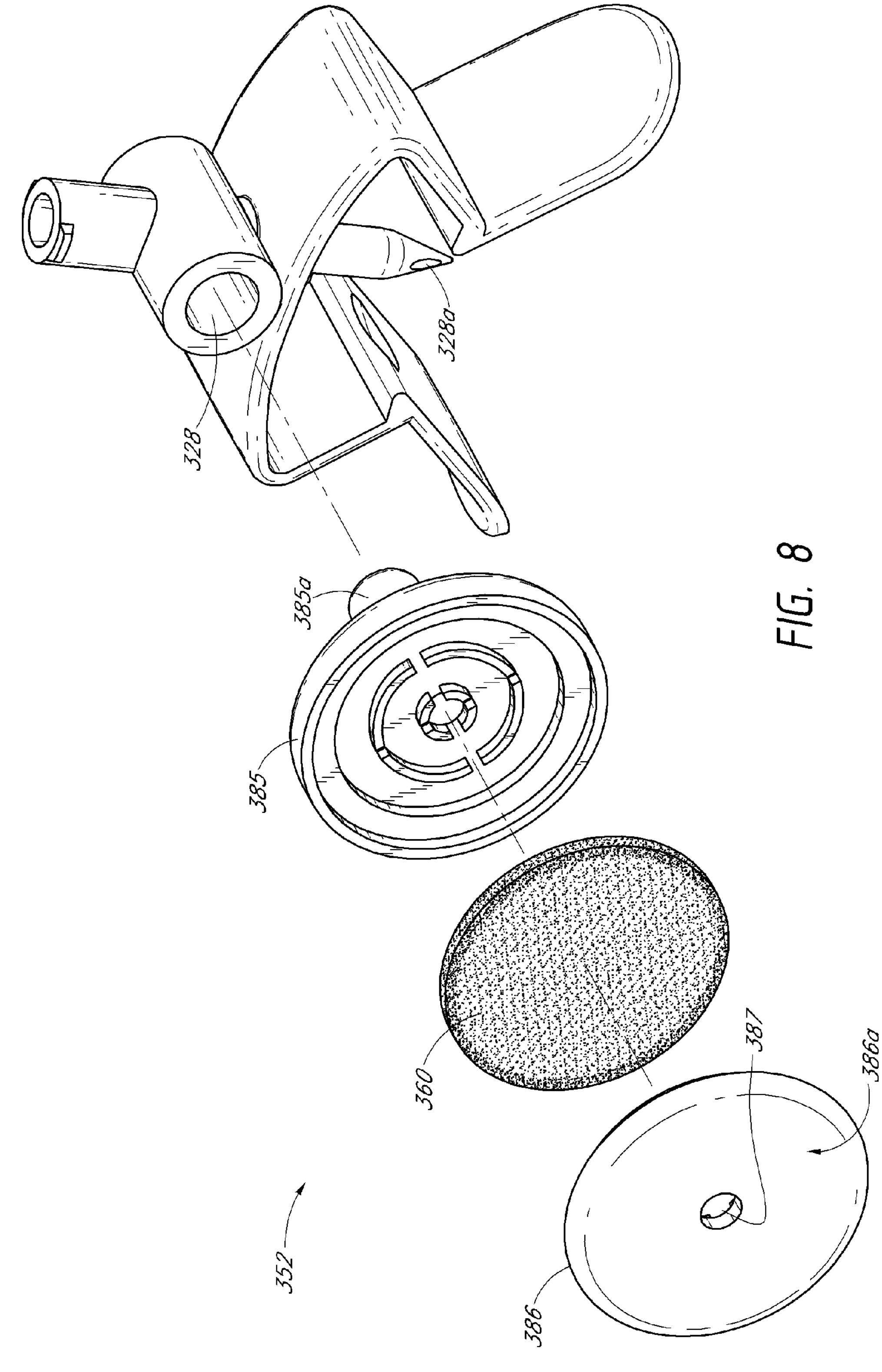
FIG. 8 illustrates an exploded perspective view of a portion of the vial adaptor of FIG. 7.

In certain configurations, such as in the configuration illustrated in FIG. 7A, the piercing member 320 is supported by the body portion 380. As illustrated, the piercing member 320 can project distally from the central portion 381 of the body portion 380. The piercing member 320 can comprise an access channel 345 and a regulator channel 325. In some embodiments, the regulator channel 325 begins at a distal regulator aperture 328*a*, passes generally through the piercing member 320, passes through a lumen 326 that extends radially outward from the connector interface 340, and terminates at a proximal regulator aperture 328 (FIG. 8). In certain instances, the lumen 326 extends radially outward from the connector interface 340 in only one direction. In some instances, the lumen 326 extends radially outward from the connector interface 340 in more than one direction, e.g., in two opposite directions.

In certain embodiments, the lumen 326 includes a barrier 383, such as a wall, cap, plug, dam, cork, partition, or otherwise. In other configurations, the barrier 383 is configured to permit fluid to flow thereacross. For example, in some cases the barrier 383 is a filter, such as a hydrophobic or activated charcoal filter. In certain configurations, the barrier is configured to inhibit or prevent fluid flow thereacross. For example, in some cases the barrier is a continuous wall. In some such configurations, the barrier 383 blocks regulating fluid from exiting the adaptor 300.

Figure 7B:
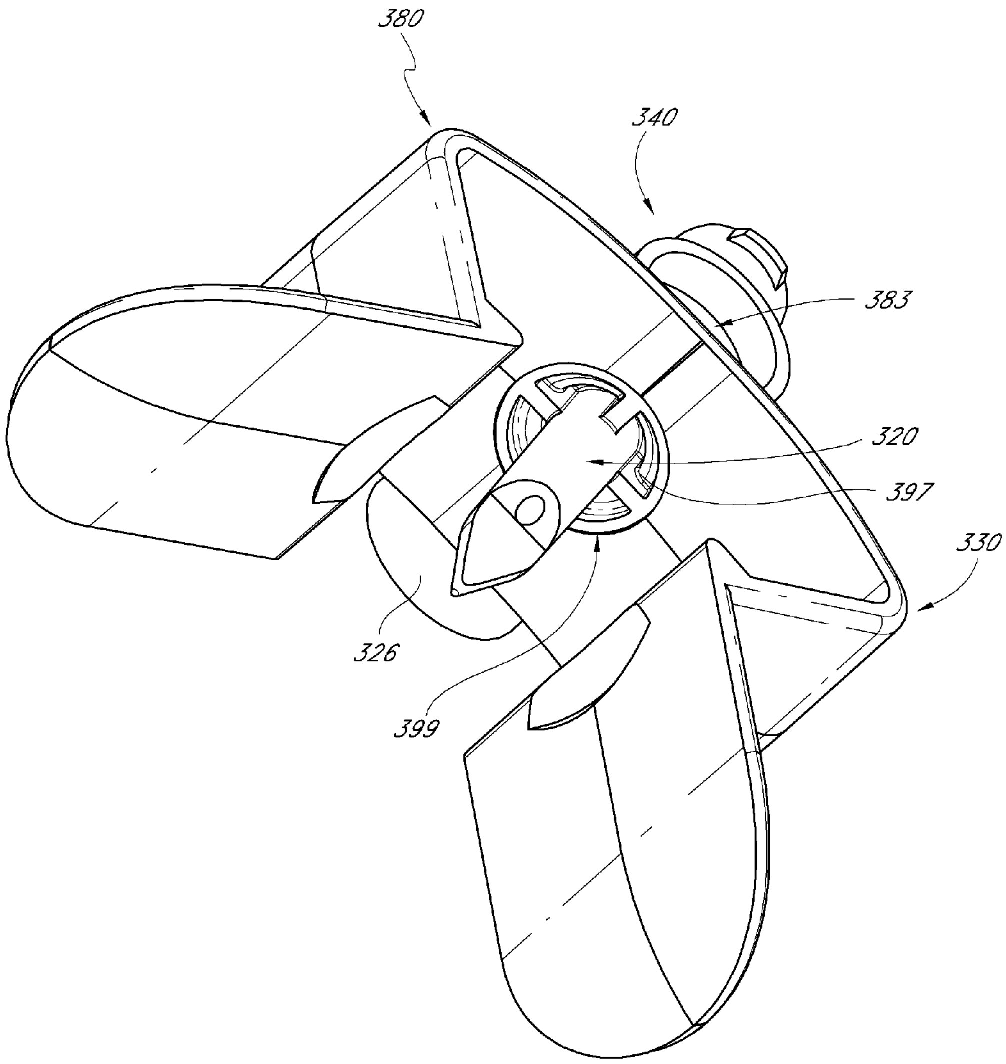
FIG. 7B illustrates an underside perspective view of a vial adaptor that comprises a recess.

As illustrated in FIG. 7B, the cap connector 330 can include one or more recesses 397 at or near an interface between the piercing member 320 and the body portion 380. In some embodiments, the one or more recesses 397 can comprise a generally annular region 399. In some embodiments, the one or more recesses 397 are formed directly in the body portion 380. The recesses 397 can help to create generally thin walls throughout the cap connector, avoiding one or more large or overly thick molded regions, and can diminish or limit the wall thickness of the cap connector 330. In some embodiments, the recess can comprise one or more structural reinforcing members, such as struts, that extend across a portion of the recess to provide structural support. In some embodiments, one or more structural reinforcing members can be manufactured separately from the structure into which they are inserted. In some embodiments, providing generally thin walls in the cap connector 330 can assist in the molding process by avoiding excessive molding cycle time for the cap connector 330 and can conserve resources and manufacturing expense. In some embodiments, providing generally thin walls in the cap connector 330 can inhibit the formation of sinks and/or voids within the cap connector 330 during molding and manufacturing of the cap connector 330.

The regulator assembly 350 can include a coupling 352, a bonding member 384, and a bag 354. In some instances, the bag includes a filler (not shown), such as the filler 254 discussed above. The bag 354 can include a bag aperture 357, which is illustrated as a linear slit but can take the form of most any opening in the bag. In certain configurations, the bag 354 is constructed of multiple sheets of material that have been joined (e.g., heat sealed) around the periphery. In some such configurations, such as shown in FIG. 8, the sealing operation produces a peripheral ridge 354*a* on the bag 354. In cases, the bag 354 is produced from a balloon having a narrowing neck portion (such as the "4 Inch Round" balloon produced by Pioneer Balloon Company of Wichita, Kans.), wherein the neck portion is removed and the bag 354 is heat sealed around the periphery to enclose (aside from the bag aperture 357) a volume therein. In some instances, removal of the neck portion produces a flattened, truncated, or otherwise asymmetrical portion of the bag 359, as shown in FIG. 7.

In certain embodiments, the bonding member 384 joins the coupling 352 with the bag 354. For example, in certain instances, the bonding member 384 includes a double-sided adhesive, e.g., a member with an adhesive surface facing the coupling 352 and an adhesive surface facing the bag 354. In the illustrated embodiment, the bonding member 384 comprises an adhesive first surface 834*a* and an adhesive second surface 834*b*. As shown, the bonding member 384 can include an aperture 384*c*. In some embodiments, the bonding member 384 is about 0.015 inches thick. In some embodiments, the bonding member 384 has a thickness of at least 0.01 inches and/or equal to or less than 0.03 inches.

In certain embodiments, the bonding member 384 is made of a flexible material, which can, for example, provide resiliency in the connection between the bonding member 384 and the coupling 352 and the bonding member 384 and the bag 354. Such resiliency can allow the coupling 352 to slightly move relative to the bag 350. Likewise, such resiliency can reduce the likelihood of the bag 354 being ripped, torn, or otherwise damaged during manipulation of the regulator assembly 350, such as in the process of connecting the regulator assembly 350 with the remainder of the adaptor 300. In certain configurations, the bonding member 384 is a foam (e.g., urethane, polyethylene, or otherwise), non-rigid plastic, rubber, paper, or cloth (e.g., cotton) material. In certain aspects, the bonding member 384 is made of doubled-sided foam tape.

In certain instances, the coupling 352 includes a base 385 and a cover 386, which in turn can include an outer face 386*a* (FIG. 8). In some embodiments, the bonding member 384 is configured to adhere to or otherwise join with the outer face 386*a*. In some embodiments, the bonding member 384 is configured to adhere to or otherwise join with the bag 354. The connections between the bonding member 384 and the outer face 386*a*, as well as the connection between the bonding member 384 and the bag 354, is substantially fluid tight (e.g., airtight) so that fluid passing between the coupling 352 and the bag 354 is inhibited from escaping. In some embodiments, the connection between the bonding member 384 and the coupling 352, and the bonding member 384 and the bag 354, is substantially permanent, such that once these components are joined they are not intended to be separated. In some embodiments, the connection between the bonding member 384 and the coupling 352, and the bonding member 384 and the bag 354, is configured to be temporary or detachable.

As shown in FIG. 8, a filter 360 can be housed between the base 385 and the cover 386. The cover 386 can be substantially sealingly received by the base 385 so that substantially all of the fluid that is permitted to flow through the filter 360 flows through an opening 387 formed in the cover 386. The base 385 and the cover 386 can be formed from any suitable material, such as plastic or metal. In some embodiments, the perimeter of the coupling 352 defines a non-circular shape, such as a square, triangular, polygonal, or other suitable or desired shape.

Figure 12:
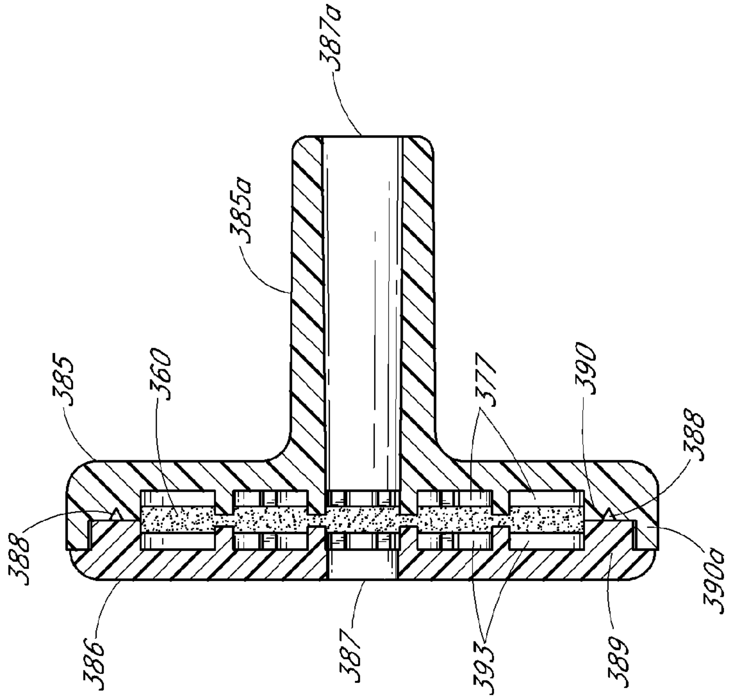
FIG. 12 illustrates a cross-sectional view of the coupling of FIG. 11, taken through line 12-12 in FIG. 11.

The cover 386 can be press-fit with or otherwise attached to the base 385 using adhesive, sonic welds, or by any other similar or suitable means. For example, as illustrated in FIG. 12, the cover 386 can be attached to the base 385 with one or more sonic welds 388. The cover 385 and the base 386 can be joined together so that an annular protrusion 389 of the cover 385 is adjacent to an annular protrusion 390 on the base 385. The protrusion 390 can have a stepped or extended lip portion 390*a* that can overlap the protrusion 389 formed on the cover 386 in the assembled configuration. The base 385 and the cover 386 can be made of various materials, such as metal or plastic. In some cases, the base 385 and the cover 386 are made of polycarbonate plastic.

In some embodiments, the cross-sectional area of the filter 360 is substantially larger than the cross-sectional area of the proximal regulator aperture 328. Such a configuration can increase the rate that regulating fluid flows through the filter 360, thereby providing sufficient regulating fluid to compensate for the introduction or withdrawal of fluid from the vial 210. As discussed above, providing sufficient regulating fluid can inhibit or avoid a pressure gradient (e.g., a vacuum) between the inside and outside of the vial and can reduce or eliminate a restoring force on the plunger of the syringe. In some embodiments, the cross-sectional area of the filter 360 is at least about 5 times greater than the cross-sectional area of the proximal regulator aperture 328. In some embodiments, the cross-sectional area of the filter 360 is between approximately 2 times greater and approximately 9 times greater than the cross-sectional area of the proximal regulator aperture 328, or to or from any values within these ranges. Similarly, in some embodiments, the cross-sectional area of the filter 360 can be approximately 400 times greater than the cross-sectional area of the distal regulator aperture 328*a*. In some embodiments, the cross-sectional area of the filter 360 can be between approximately 100 times greater and approximately 250 times greater, or between approximately 250 times greater and approximately 400 times greater, or between approximately 400 times greater and approximately 550 times greater than the cross-sectional area of the distal regulator aperture 328*a*, or to or from any values within these ranges.

The filter 360 can be configured to remove or diminish particulate matter such as dirt or other debris, germs, viruses, bacteria, and/or other forms of contamination from fluid flowing into the vial adaptor 300. The filter 360 can be formed from any suitable filter material. In some embodiments, the filter 360 can be hydrophobic and can have a mean pore size of approximately 0.1 micron, or between approximately 0.1 micron and approximately 0.5 micron.

Figure 9:
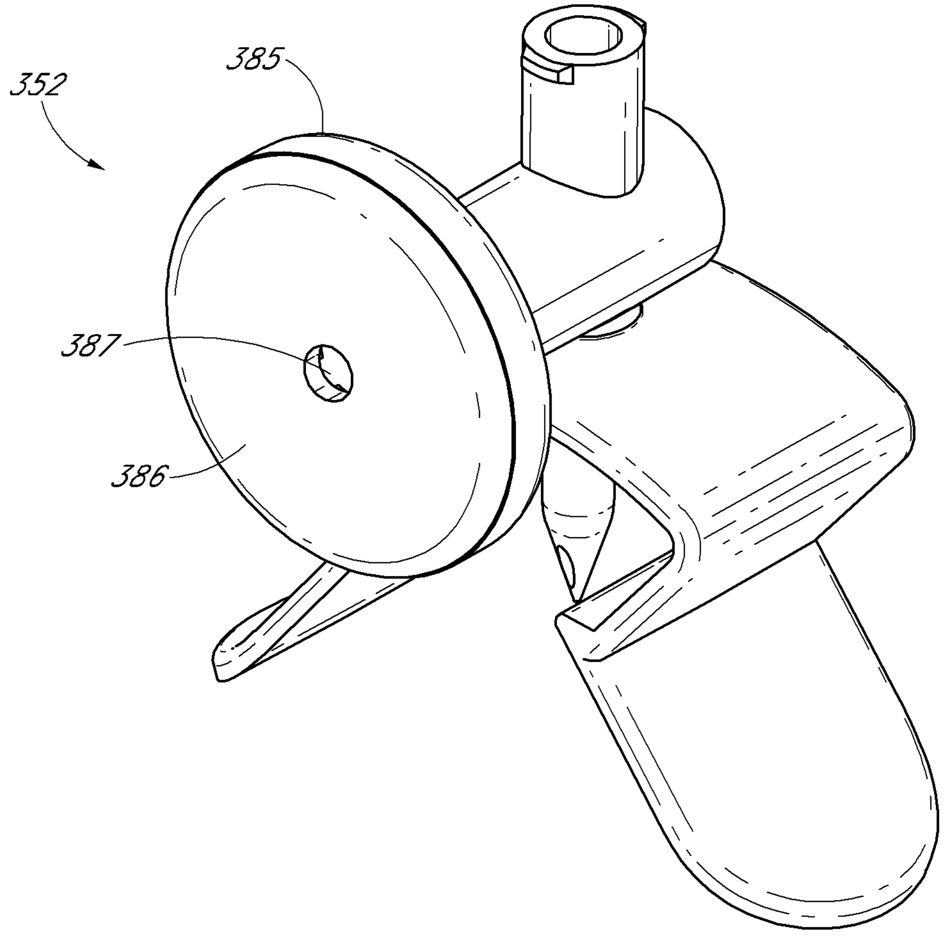
FIG. 9 illustrates an assembled perspective view of the portion of the vial adaptor of FIG. 8.

As illustrated in FIG. 9, in certain configurations, the coupling 352 can be received in the proximal regulator aperture 328. In some embodiments, a protrusion 385*a* (e.g., a boss) extending from the base 385 is configured to be substantially sealingly received within or around the outer perimeter of the proximal regulator aperture 328. The protrusion 385*a* can generally define a regulator path. In some embodiments, the protrusion 385*a* is press-fit into the proximal regulator aperture 328 so as to create a generally sealed connection between the protrusion 385*a* and the proximal regulator aperture 328. In some embodiments, adhesive, welds, or other materials or features can be used to provide the connection between the protrusion 385*a* and the proximal regulator aperture 328. In some instances, the protrusion 385*a* and the proximal regulator aperture 328 are bonded with a solvent. The protrusion 385*a* can be sized and configured to have a sufficient wall thickness and diameter to ensure that the protrusion 385*a* is not inadvertently broken during use by an inadvertent contact with coupling 352. In some embodiments, the regulator path can be in fluid communication with the regulator channel 425 when the protrusion 385*a* is connected to the proximal regulator aperture 328.

An opening 387*a* can be formed through the protrusion 385*a* so that fluid flowing between the base 385 and the cover 386 will be filtered by the filter 360 before flowing through the opening 387 or 387*a*. The size of the opening 387*a* formed through the protrusion 385*a*, as well as the opening 387 formed in the cover 386, can be designed to ensure a sufficient amount of fluid flow through the filter 360. The diameter of the proximal regulator aperture 328 can be adjusted to accommodate any desired or suitable outside diameter of the protrusion 385*a*.

Figure 10:
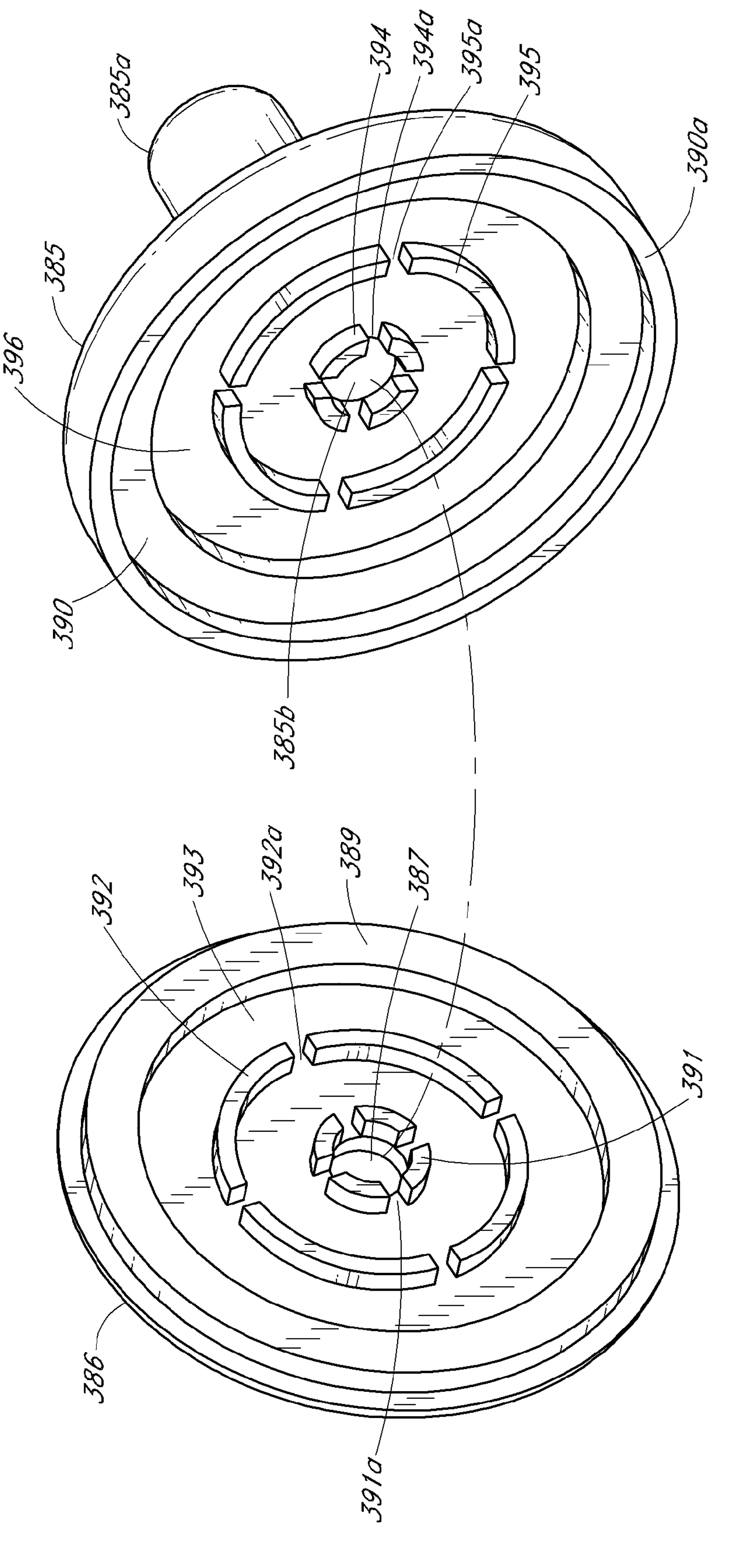
FIG. 10 illustrates an exploded perspective view of a base and a cover of a coupling of the vial adaptor of FIG. 7.
Figure 11:
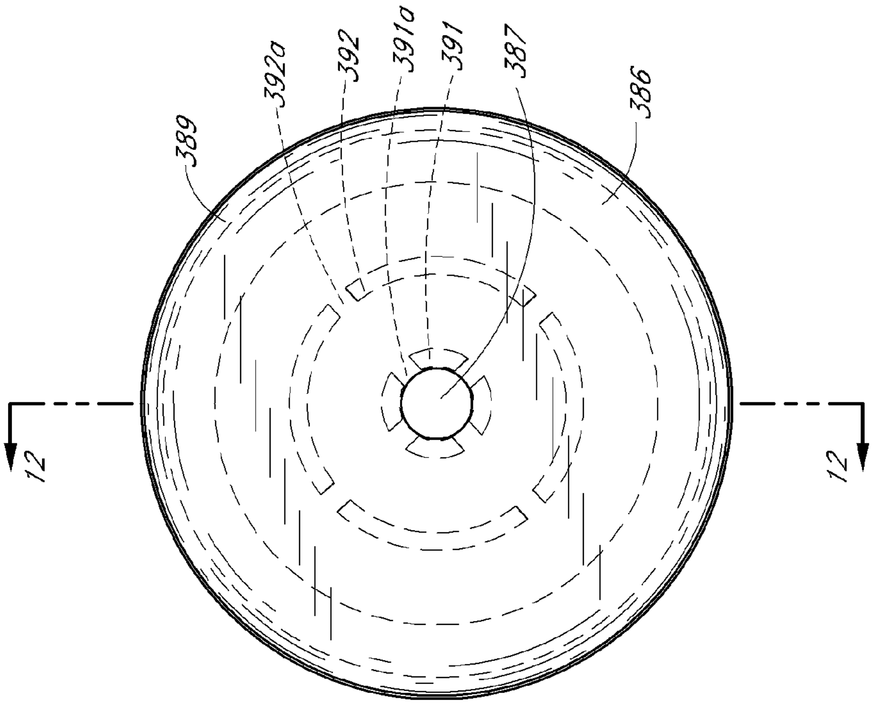
FIG. 11 illustrates a top view of the coupling of FIG. 10.

With reference to FIGS. 10, 11, and 12, the cover 386 can have a first inner annular protrusion 391 having one or more openings 391*a* therethrough, a second inner annular protrusion 392 having one or more openings 392*a* therethrough, and an outer annular protrusion 389. In some embodiments, when the cover 386 is assembled with the base 385 and the filter 360, the annular protrusions 389, 391, 392 and the openings 391*a*, 392*a* form a volume of space 393 between the inner surface of the cover 386 and the surface of the filter 360 into which regulating fluid can flow and circulate before or after passing through the filter 360. Similarly, the base 385 can have a first inner annular protrusion 394 having one or more openings 394*a* therethrough, a second inner annular protrusion 395 having one or more openings 395*a* therethrough, and an outer annular protrusion 390. In some embodiments, when the base 385 is assembled with the cover 386 and the filter 360, the annular protrusions 390, 394, 395 and the openings 394*a*, 395*a* form a volume of space 396 between the inner surface of the base 386 and the surface of the filter 360 into which the regulating fluid can flow and circulate before or after passing through the filter 360. In some configurations, the regulating fluid can access substantially the entire surface area of the filter 360.

In some embodiments, regulating fluid can flow through the opening 387 formed in the cover 386 into the space 393 defined between the cover 386 and the filter 360, through the filter 360, into the space 377 defined between the filter 360 and the base 385, through the opening 385*b* formed in the base 385, through the proximal regulator aperture 382, and into the regulator channel 325 formed in the vial adaptor 300. Likewise, in certain embodiments, regulating fluid can flow through the regulator channel 325 formed in the vial adaptor 300, through the proximal regulator aperture 382, through the opening 385*b* formed in the base 385, into the space 395 defined between the filter 360 and the base 385, through the filter 360, into the space 393 defined between the cover 386 and the filter 360, and through the opening 387 formed in the cover 386. In some instances, the opening 387 is in fluid communication with ambient air.

In some instances, the annular protrusions 390, 394, 395 are configured to maintain the shape and position of the filter 360 relative to the base 385 and the cover 386. For example, the annular protrusion 390 can be configured to maintain the filter 360 about radially centered in the base 385 and the cover 386, which can reduce the chance of fluid passing around (rather than through) the filter 360. In some configurations, the annular protrusions 394, 395 are configured to substantially inhibit the filter 360 from becoming concave shaped as regulating fluid passes through the filter 360, which can reduce the likelihood of the filter 360 being torn or otherwise damaged.

Figure 10A:
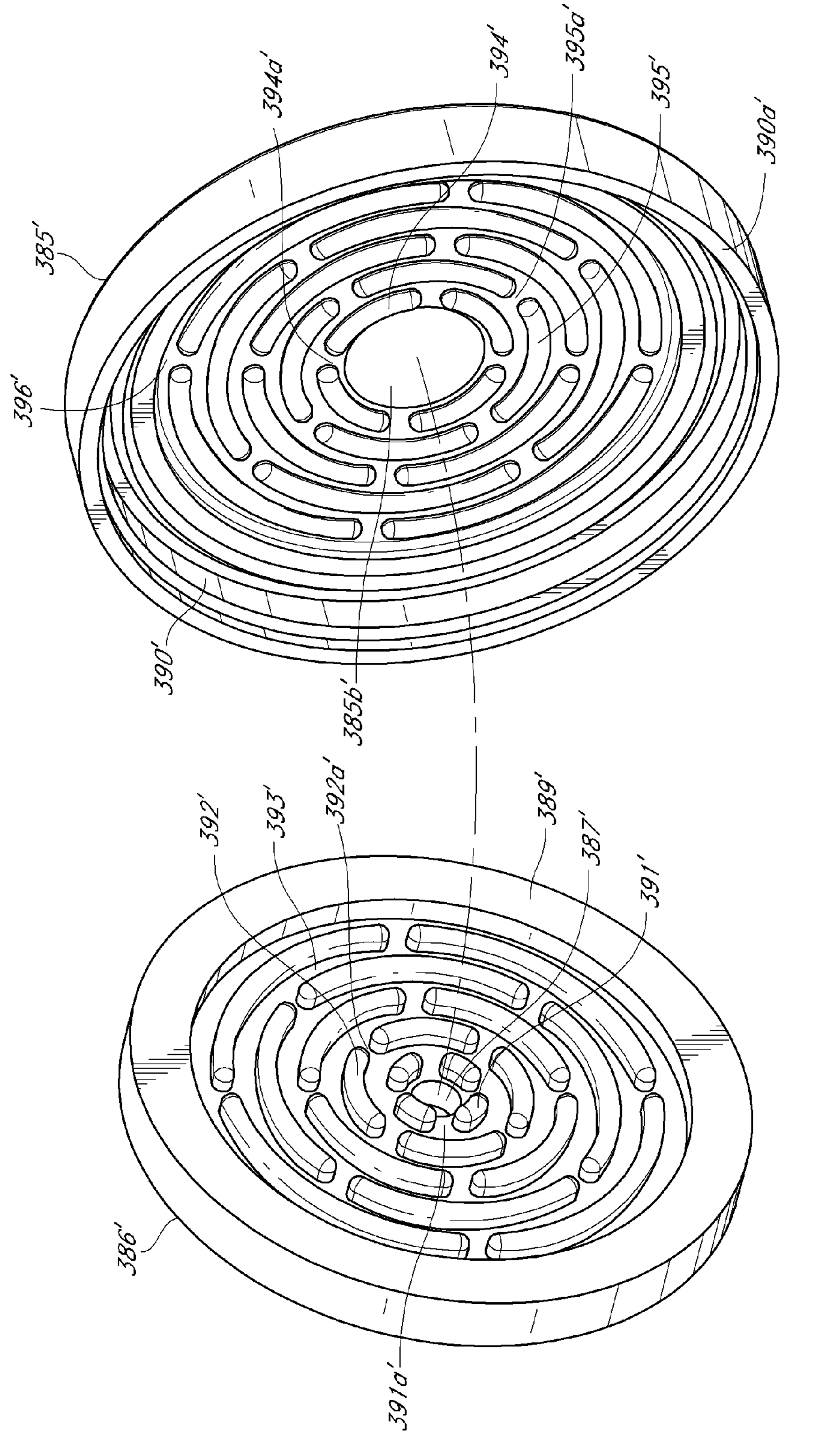
FIG. 10A illustrates an exploded perspective view of another example of a base and a cover of a coupling of a vial adaptor that can be used with any embodiment.

FIG. 10A illustrates an embodiment of a base 385' and a cover 386'. Numerical reference to components is the same as previously described, except that a prime symbol (') has been added to the reference. Where such references occur, it is to be understood that the components are the same or substantially similar to previously-described components unless otherwise indicated. For example, in some embodiments, the base 385' has an opening 385*b*'. The opening 385*b*' can be wider than an opening 387' in the cover 386'. In some embodiments, wide openings 385*b*' can allow for increased flow rates into the space 377 between the filter 360 and the base 385' from the regulator channel 382. In some embodiments, the opening 385*b*' is smaller than the opening 387' in the cover 386'.

In some embodiments, the base 385' includes a plurality of inner annular protrusions. For example, the base 385' can include a first inner annular protrusion 394'. The first inner annular protrusion 394' can have one or more openings 394*a*' circumferentially distributed about the first annular protrusion 394' at generally the same distance from the opening 391*a*'. The base 385' can include a second inner annular protrusion 395'. In some embodiments, the second inner annular protrusion 395' includes one or more openings 395*a*' distributed circumferentially about the second inner annular protrusion 395' at generally the same distance from the opening 391*a*'. The base 385' can include one or more additional inner annular protrusions. In some embodiments, the base 385' includes 6 inner annular protrusions. In some embodiments, the base 385' includes more than or less than 6 inner annular protrusions. One or more of the additional inner annular protrusions can have one or more openings.

In some embodiments, the cover 386' includes a plurality of inner annular protrusions. For example, the cover 386' can include a first inner annular protrusion 391'. The first inner annular protrusion 391' can have one or more openings 391*a*' circumferentially distributed about the first annular protrusion 391' at generally the same distance from the opening 391*a*'. The cover 386' can include a second inner annular protrusion 392'. In some embodiments, the second inner annular protrusion 392' includes one or more openings 392*a*' distributed circumferentially about the second inner annular protrusion 392' at generally the same distance from the opening 391*a*'. The cover 386' can include one or more additional inner annular protrusions. In some embodiments, cover 386' includes 6 inner annular protrusions. In some embodiments, the cover 386' includes more than or less than 6 inner annular protrusions. One or more of the additional inner annular protrusions can have one or more openings.

The protrusions 391', 392', 394', 395' and any additional inner annular protrusions on the cover 286' and the base 385' can have openings (e.g., 391*a*', 392*a*', 394*a*', 395*a*') that are arranged in circumferential patterns such that openings on adjacent inner annular protrusions are circumferentially offset from one another to produce a non-direct or tortuous flow path. For example, the openings 392*a*' can be circumferentially offset from the openings 391*a*'. In some arrangements, folding of the filter 360 into the openings 391*a*', 392*a*' can be inhibited, and/or the flow path can be encouraged to pass through a substantial portion of the filter in a circumferential or lateral direction by avoiding direct radial flow. In this description of the positioning, orientation, and/or shape of the protrusions, as with all other descriptions in this application, terms that apply to circular structures such as "circumferential" or "radial" or similar terms should be interpreted to apply to non-circular structures in a corresponding manner.

In some embodiments, the protrusions 391', 392', 394', 395' and/or any additional inner annular protrusions on the cover 386' and the base 385' can have generally rounded, chamfered, and/or filleted edges. In some such embodiments, one or more or all of the protrusions 391', 392', 394', 395' and/or any additional inner annular protrusions do not have sharp corners in order to reduce the possibility of damage to the filter 360 and to assist in the molding process.

In certain embodiments, the adaptor 300 is modularly configured. Such a configuration can, for example, facilitate manufacturability and promote user convenience by standardizing one or more parts of the adaptor 300. For example, in some instances, the configuration of the piercing member 320, cap connector 330, the connector interface 340, and the coupling 352 is substantially unchanged regardless of the volume of fluid to be transferred between the medical device and the vial 210. Such standardization can, for example, reduce the number of unique components to be purchased, stored, and inventoried, while maintaining the functionality of the adaptor 300.

In some modular embodiments, the adaptor 300 includes a first portion (e.g., the piercing member 320, cap connector 330, connector interface 340, and coupling 352—such as is shown in FIG. 9) and a second portion (e.g., the bag 354). In certain embodiments, the first portion is separate and spaced-apart from the second portion in a first arrangement, and the first portion is connected with the second portion in a second arrangement. Some embodiments can allow for variety of configurations (e.g., sizes) of the bag 354 to be mated with a common configuration of the remainder of the adaptor 300. For example, in some embodiments, 20 mL, 40 mL, and 60 mL configurations of the bag 354 are each connectable with a common configuration of the remainder of the adaptor 300. In certain embodiments, the bag 354 configuration is selectable while the remainder of the adaptor 300 is unchanged. In some cases, the configuration of the bag 354 is selected based on the volume of fluid to be transferred between the medical device (e.g., syringe) and the vial 210. For example, if about 25 mL of fluid is to be transferred from the medical device into the vial 210, then a configuration of the bag 354 that is able to contain greater than or equal to about 25 mL of fluid can be selected and connected to the remainder of the adaptor 300; if, however, it is determined that a different volume of fluid is to be transferred from the medical device into the vial 210, then the selection of the bag 354 can be changed without the need to change the remainder of the adaptor 300.

Certain modular embodiments can provide a ready supply of filtered or otherwise cleaned regulating fluid without being connected with the bag 354. For example, in some embodiments, the opening 387 of the cover 386 of the coupling 352 is in fluid communication with ambient air, thereby providing a supply of filtered air through the coupling 352, the regulator channel 325, and into the vial 210, when the piercing member 320 is disposed in the vial 210 and fluid is withdrawn through the access channel 345. In certain instances, the adaptor 300 does not include the bag 354 and/or the bonding member 384. In some embodiments, the lumen 326 is configured to connect with a filtered or otherwise cleaned regulating fluid source. For example, the lumen 326 can be configured to connect with a tube in fluid communication with a tank of sterilized air.

In some embodiments, a process of manufacturing the vial adaptor 300 includes forming the piercing member 320, cap connector 330, and connector interface 340 in a first assembly. For example, in certain embodiments, the piercing member 320, a cap connector 330, a connector interface 340 are produced by the same operation (e.g., molding, machining, or otherwise). The process can also include forming the coupling 352. For example, in some configurations, the base 385 and cover 386 are assembled with the filter 360 therebetween, as discussed above. In certain embodiments, the process also includes mating the coupling 352 with the lumen 326, such as is shown in FIG. 9. Further, the process can include joining the bonding member 384 with the outer face 386*a* of the cover 386. In some instances, the bonding member 384 is joined with the bag 354. As shown in FIG. 7, the lumen 326, the opening 387*a* in the base, the opening 387 in the cover 386, and the bag aperture 357 can be aligned, thereby allowing regulating fluid to flow between the vial 210 and the bag 354.

In some instances, the process of manufacturing the vial adaptor 300 can, for example, enable production of the adaptor 300 in discrete sub-assemblies, which can facilitate manufacturability. For example, a first sub-assembly can include the piercing member 320, cap connector 330, and connector interface 340; a second sub-assembly can include the coupling 352 (including the base 385, the cover 386, and the filter 360); and a third sub-assembly can include the bag 354 and bonding member 384. Of course, other sub-assemblies are contemplated; for example, the second sub-assembly can include the coupling 352 and the bonding member 384. In some cases, one or more of the sub-assemblies are supplied separately to the user (e.g., a healthcare worker).

Figure 13:
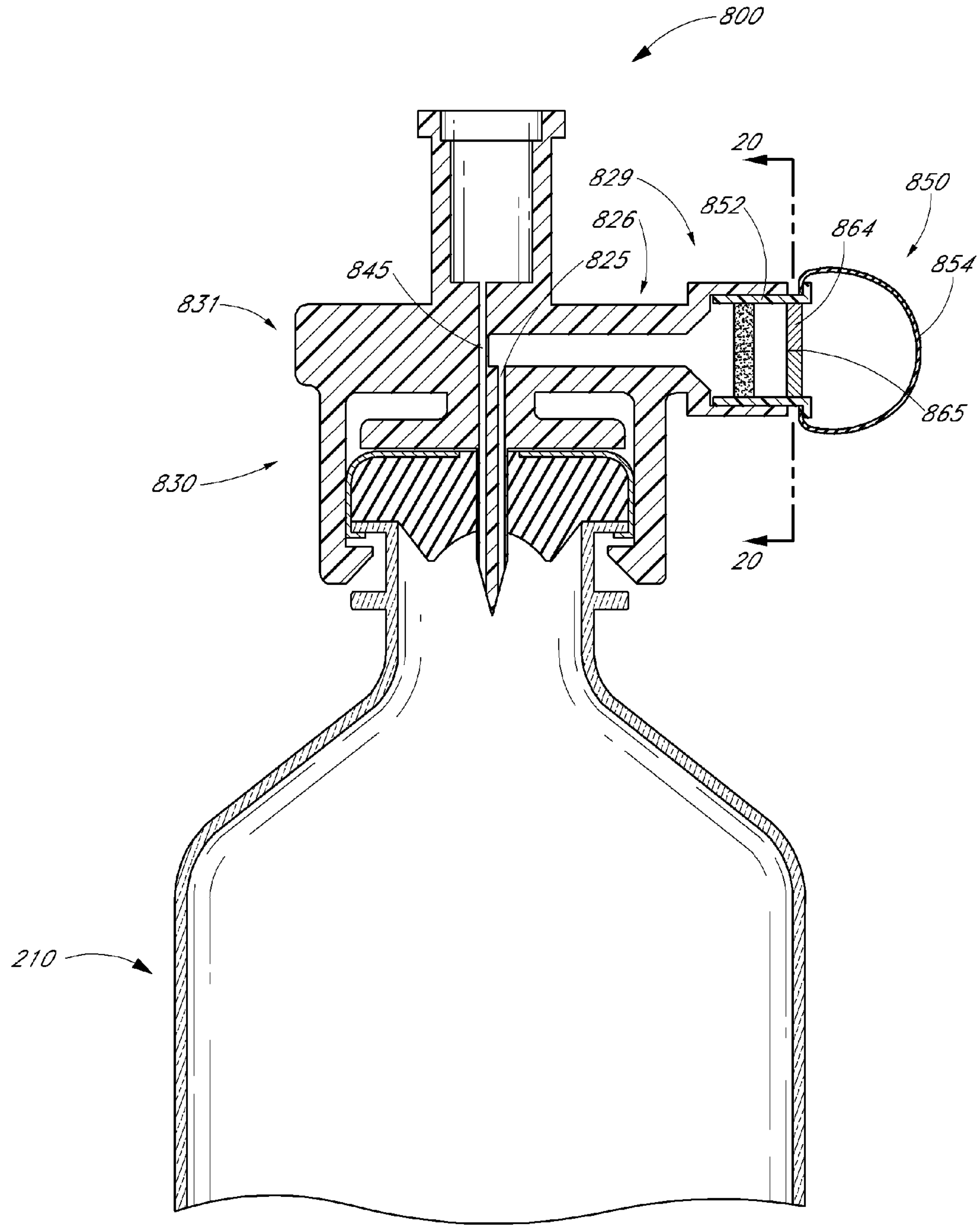
FIG. 13 illustrates a partial cross-sectional view of a vial adaptor coupled with a vial, the adaptor including a counterweight.

FIG. 13 illustrates an embodiment of an adaptor 800 that can have components or portions that are the same as or similar to the components or portions of other vial adaptors disclosed herein. The adaptor comprises a regulator assembly 850 with a seal 864, a counterweight 831, and a keyed coupling 852. As used herein, a "keyed coupling" is used in its broad and ordinary sense and includes couplings having a shape configured to match another coupling in one or more orientations. Furthermore, the illustrated embodiment of the adaptor 800 does not include a filler. In some such embodiments, the adaptor 800 includes a bag 854 that is sufficiently rigid to substantially inhibit the bag 854 from fully deflating (e.g., enclosing about zero volume).

In some embodiments, the seal 864 is configured to inhibit or prevent unintended transfer of regulating fluid out of the regulator assembly 850 and/or unintended transfer of ambient air into the regulator assembly 850. For example, in the embodiment shown, prior to the regulator assembly 850 being connected with the remainder of the adaptor 800, the seal 864 generally blocks the initial volume of regulating fluid (which may be at a pressure above ambient pressure) contained in the regulator assembly 850 from escaping into the ambient environment. Additionally, the seal 864 can generally block ambient air, which may contain microbes or impurities, from entering the regulator assembly 850.

In the illustrated embodiment, the seal 864 comprises a membrane with a slit 865. In certain instances, such as when the regulator assembly 850 is connected with the adaptor 800 and fluid is introduced or withdrawn through an access channel 845, the pressure difference between the vial 210 and the bag 854 causes the slit 865 to open, thereby allowing regulating fluid to flow between the regulator assembly 850 and the vial 210. Various other kinds and configurations of the seal 864 are contemplated. For example, in some embodiments, the seal 864 is a duck-bill valve. As another example, in some embodiments, the seal 864 comprises a substantially continuous (e.g., without a slit) membrane that is configured to rupture at a certain pressure differential (e.g., at least about 1 psi, at least about 2 psi, at least about 5 psi).

In the embodiment shown, the seal 864 is located in the coupling 852. In some other embodiments, the seal 864 is disposed in alternate locations. For example, the seal 864 can be located in a passage 826. In some arrangements, the seal 864 is configured to dislodge or detach from the adaptor 800 when fluid is introduced or withdrawn through the access channel 845. For example, in certain instances, when fluid is withdrawn from the vial 210 through the access channel 845, the seal 864 is dislodged from the regulator channel 825, thereby allowing regulating fluid to flow into the vial 210. In some such cases, the seal 864 is a tab or a sticker. In some such cases, the seal 864 separates from the adaptor 800 and falls into the vial 210.

As shown, certain configurations of the adaptor 800 include a cap connector 830, which in turn includes the counterweight 831. The counterweight 831 can, for example, enhance the stability of the mated vial 210 and adaptor 800 and reduce the chances of the combination tipping. In certain arrangements, the counterweight 831 is configured to locate the center of mass of the adaptor 800 substantially on the axial centerline of the adaptor 800 when the regulator assembly 850 is connected to the adaptor 800. In certain arrangements, the counterweight 831 has a mass that is about equal to the sum of the mass of an outwardly extending connection member 829 plus the mass of the regulator assembly 850 in the initial configuration. In some instances, the counterweight 831 comprises a mass of material generally located on the opposite side of the axial centerline as the regulator assembly 850. In some instances, the counterweight 831 comprises an area of reduced mass (e.g., grooves, notches, or thinner walls) on the same side of the axial centerline as the regulator assembly 850.

As shown in FIGS. 14A-14F, which illustrate cross-sectional views of various examples of the coupling 852, the coupling 852 can be keyed or otherwise specially shaped. The connection member 829 typically is correspondingly keyed or otherwise specially shaped. Such a configuration can be useful to signal, control, or restrict the regulator assemblies 850 that can be connected with a given adaptor 800. For example, a relatively large regulator assembly 850 (e.g., initially containing at least about 100 mL of regulating fluid) may be keyed so as not to mate with a relatively small adaptor 800 (e.g., sized and configured for to mate with vials 210 containing less than about 3 mL of fluid). In certain cases, the combination of a large regulator assembly and a small vial could be unstable and could exhibit an increased tendency to tip-over, and thus would be undesirable. However, by keying sizes of the regulator assembly 850 so as to mate only with appropriate sizes of the adaptor 800, such concerns can be reduced or avoided. In various embodiments, the coupling 852 can be male or female and the connection member 829 can be correspondingly female or male.

Figure 14A:
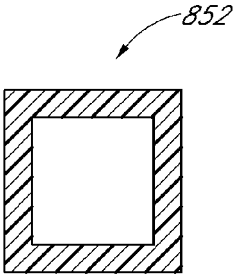
FIGS. 14A-14F illustrate cross-sectional views of a keyed coupling of the vial adaptor of FIG. 13, taken through line 20-20 in FIG. 13.
Figure 14B:
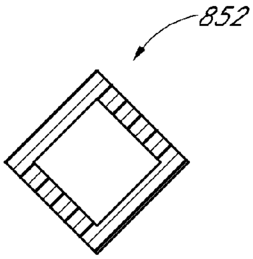
Figure 14C:
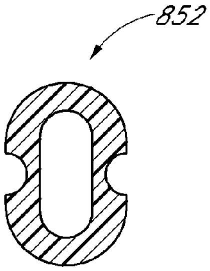
Figure 14D:
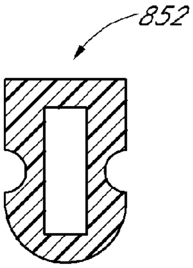
Figure 14E:
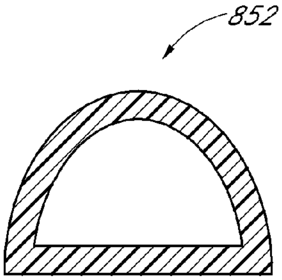
Figure 14F:
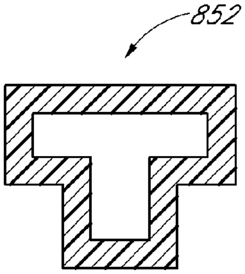

Various types of keyed couplings 852 are contemplated. In some embodiments, the shape of the coupling 852 inhibits or prevents rotation of the regulator assembly in relation to the remainder of the adaptor 800. For example, as shown in FIG. 14A, the coupling 852 can be substantially rectangular. The connection member 829 can be correspondingly rectangular to matingly engage with the coupling 852. Similarly, as shown in FIG. 14B, the coupling 852 can be substantially diamond-shaped. The connection member 829 can be correspondingly diamond-shaped to matingly engage with the coupling 852. Likewise, as shown in FIG. 14C, the coupling 852 can include notches, grooves, bumps or the like. The connection member 829 can be correspondingly shaped to matingly engage with the notches, grooves, bumps or the like of the coupling 852.

In certain embodiments, the shape of the coupling 852 establishes the orientation of the regulator assembly 850 with regard to the remainder of the adaptor 800. For example, in the embodiment illustrated in FIG. 14C, the coupling 852

(and thus the regulator assembly 850) are configured to mate with the connection member 829 in only two possible orientations. In some embodiments, such as the embodiments illustrated in FIGS. 14D, 14E, and 14F, the coupling 852 (and thus the regulator assembly 850) is configured to mate with the connection member 829 in only a single possible orientation.

Some embodiments provide feedback to alert the user that mating engagement of the coupling 852 and the connection member 829 has been achieved. For example, in certain instances, the connection between the coupling 852 and the connection member 829 includes a detent mechanism, e.g., a ball detent, which can provide tactile indication of engagement. Some embodiments include an audible signal, e.g., a click, snap, or the like, to indicate engagement.

Certain embodiments link the coupling 852 and the connection member 829 so as to inhibit or prevent subsequent separation. For example, some arrangements include an adhesive in one or both of the coupling 852 and connection member 829, such that mating engagement adheres the coupling 852 and the connection member 829 together. In certain other arrangements, mating engagement of the coupling 852 and connection member 829 engages one-way snap-fit features.

Figure 15A:
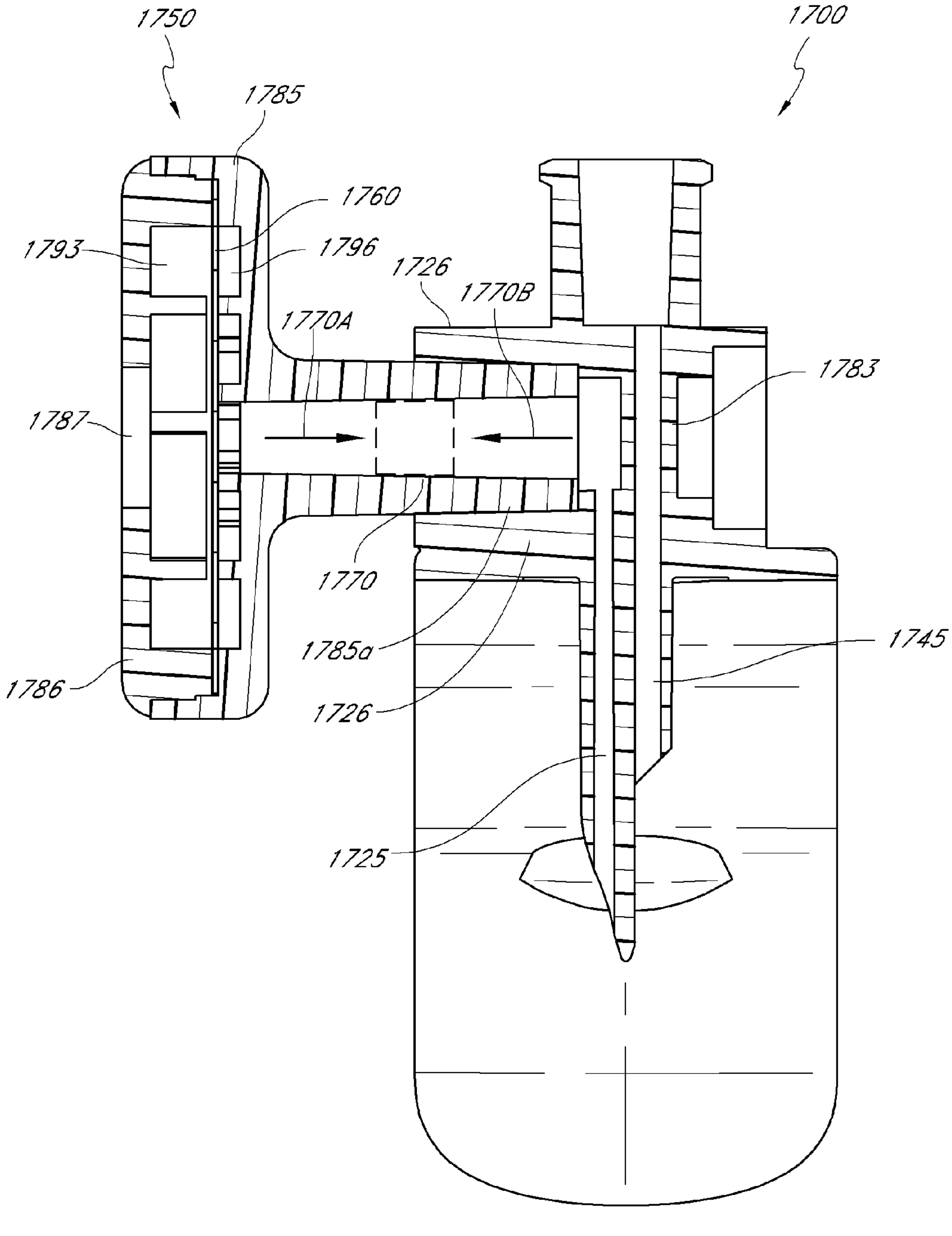
FIG. 15A illustrates a cross-sectional view of a vial adaptor.

FIG. 15A illustrates an embodiment of an adaptor 1700 that can have components or portions that are the same as or similar to the components or portions of other vial adaptors disclosed herein, and also includes a valve 1770. The adaptor 1700 is configured to engage with a vial 10. In some embodiments, the adaptor 1700 includes a regulator assembly 1750. In some configurations, the regulator assembly 1750 includes a protrusion 1785*a* which can be substantially sealingly attached to (e.g., received within or around the outer perimeter of) a lumen 1726 of the regulator assembly 1750. The protrusion 2085*a* can facilitate fluid communication between two or more features (e.g., a filter, enclosure, bag and/or valve) of the regulator assembly. In some embodiments, the protrusion 2085*a* can generally define a regulator path. The regulator path can be in fluid communication with the regulator channel a regulator channel 1725 of the regulator assembly 1750. The longitudinal axis of the protrusion 1785*a* and/or the lumen 1726 can be at least partially, substantially, or wholly perpendicular to the axial centerline of the adaptor 1700. In some embodiments, the longitudinal axis of the protrusion 1785*a* and/or the lumen 1726 is at least partially, substantially, or wholly parallel to the axial centerline of the adaptor 1700. In some embodiments, the angle between the longitudinal axis of the protrusion 1785 and the axial centerline of the adaptor 1700 is greater than or equal to about 5° and/or less than or equal to about 85°. In some embodiments, the angle is about 60°. In certain embodiments, the angle between the longitudinal axis of the protrusion 1785 and the axial centerline of the adaptor 1700 can be any angle between 0° and 90° or a variable angle that is selected by the user. Many variations are possible.

In some embodiments, the regulatory assembly includes a filter 1760. The filter 1760 can include a hydrophobic filter. In some embodiments, the valve 1770 or a portion thereof is located within a lumen 1726 of the adaptor 1700. In some embodiments, the valve 1770 or a portion thereof is located outside the lumen 1726 of the adaptor 1700 within the protrusion 1785*a* of the regulator assembly 1750.

According to some embodiments, the valve 1770 is configured to permit air or other fluid that has passed through the filter 1760 to pass into the container 10. In some embodiments, the valve 1770 is configured to selectively inhibit fluid from passing through the valve 1770 from the container 10 to the filter 1760.

In some configurations, the valve 1770 is selectively opened and/or closed depending on the orientation of the adaptor 1700. For example, the valve 1770 can be configured to allow fluid flow between the container 10 and the filter 1760 without restriction when the adaptor 1700 is positioned above (e.g., further from the floor than) a vial 10 to which the adaptor is attached. In some embodiments, the valve 1770 can be configured to prevent fluid flow from the container 10 to the filter 1760 when the vial 10 is positioned above the adaptor 1700.

In some embodiments, the valve 1770 can open and/or close in response to the effect of gravity upon the valve 1770. For example, the valve 1770 can include components that move in response to gravity to open and/or close channels within the valve 1770. In some embodiments, channels within the valve 1770 can be constructed such that the effect of gravity upon fluid within the adaptor 1700 can prevent or allow the fluid to pass through the channels within the valve 1770.

For example, the valve 1770 can comprise an orientation-sensitive or orientation-dependent roll-over valve. In some embodiments, a roll-over valve 1770 can comprise a weighted sealing member. In some embodiments, the weighted sealing member can be biased to seal and/or close the valve 1770 when the vial 10 is positioned above the adaptor 1700. In some embodiments, the sealing member can be biased to seal the valve 1770 by the force of gravity. In some embodiments, the sealing member can be biased to seal the valve 1770 through the use of a compression spring. The sealing member can be constructed such that it can transition to open the valve 1770 when the adaptor 1700 is positioned above the vial 10. For example, the weight of the sealing member can be high enough that it overcomes the force of the compression spring and moves to an open position when the adaptor 1700 is positioned above the vial 10.

In some embodiments, the valve 1770 can comprise a swing check valve. In some embodiments, the valve 1770 can comprise a weighted panel rotatably connected to the wall of the regulator channel 1925. The weighted panel can be oriented such that, when the adaptor 1700 is positioned above the vial 10, the weighted panel is rotated to an open position wherein the weighted panel does not inhibit the flow of fluid through the regulator channel 1925. In some embodiments, the weighted panel can be configured to rotate to a closed position wherein the weighted panel inhibits the flow of fluid through the regulator channel 1925 when the vial 10 is positioned above the adaptor 1700.

According to some configurations, the valve 1770 can be a check valve which can transition between two or more configurations (e.g., an open and closed configuration). In some embodiments, the valve 1770 can change configurations based on user input. For example, the valve 1770 and/or regulator assembly 1750 can include a user interface (e.g., a button, slider, knob, capacitive surface, switch, toggle, keypad, etc.) which the user can manipulate. The user interface can communicate (e.g., mechanically, electronically, and/or electromechanically) with the valve 1770 to move the valve 1770 between an opened configuration and a closed configuration. In some embodiments, the adaptor 1700 and/or regulator assembly 1750 can include a visual indicator to show whether the valve 1770 is in an open or closed configuration.

According to some embodiments, the valve 1770 is configured to act as a two-way valve. In such configurations, the valve 1770 can allow for the passage of fluid through the valve

1770 in a first direction 1770A at one pressure differential while allowing for the passage of fluid in a second direction 1770B at a different pressure differential. For example, the pressure differential required for fluid to pass in a first direction 1770A through the filter 1770 can be substantially higher than the pressure differential required for fluid to pass through the filter 1770 in a second direction 1770B.

Figure 15B:
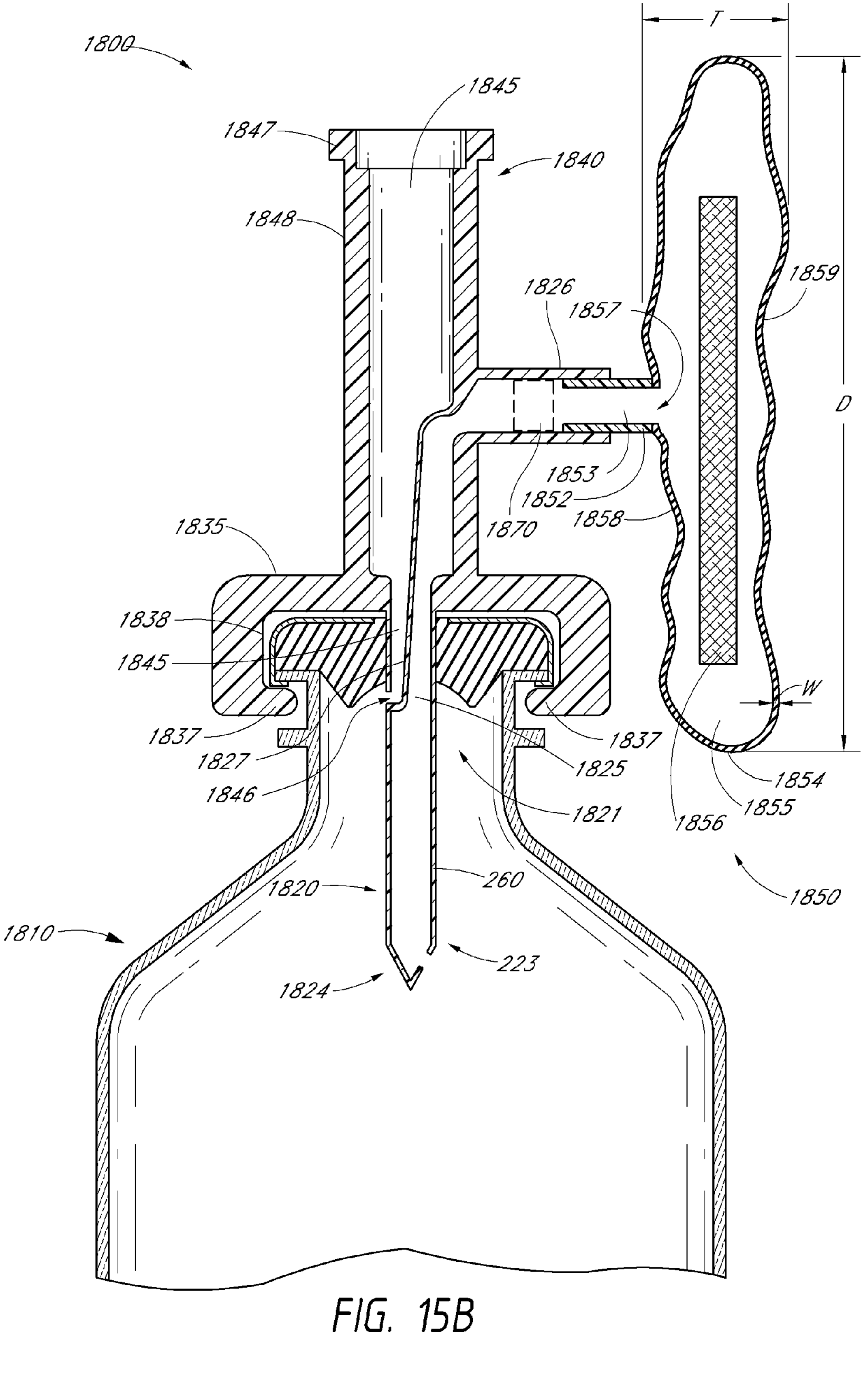
FIG. 15B illustrates a partial cross-sectional view of a vial adaptor coupled with a vial, the vial adaptor including a valve.

FIG. 15B illustrates an embodiment of an adaptor 1800 that can have components or portions that are the same as or similar to the components or portions of other vial adaptors disclosed herein. The adaptor 1800 includes a regulator assembly 1850 which, in some embodiments, can include a valve 1870. The valve 1870 can be located in a regulator channel 1825 within a lumen 1826 of the adaptor 1800 between a container 10 and a bag or other enclosure 254. In some embodiments, the valve 1879, or a portion thereof, is located outside of the lumen 1826 and within a coupling 1852 of the regulator assembly 1850. In some embodiments, the valve 1870 is configured to permit regulator fluid and/or other fluid to pass from the enclosure 1854 to the container 10. In some embodiments, the valve 1870 is configured to inhibit or prevent the passage of fluid from the container 10 to the enclosure 1854.

In some configurations, the valve 1870 is selectively opened and/or closed depending on the orientation of the adaptor 1800. For example, the valve 1870 can be configured to allow fluid flow between the container 10 and the enclosure 1854 without restriction when the adaptor 1800 is oriented above a vial 10 to which the adaptor is attached. In some embodiments, the valve 1870 is configured to prevent fluid flow from the container 10 to the enclosure 1854 when the vial 10 is positioned above the adaptor 1800. Furthermore, in some embodiments, the valve 1870 is configured to act as a two-way valve in substantially the same manner as described above with regard to the valve 1770.

Figure 15C:
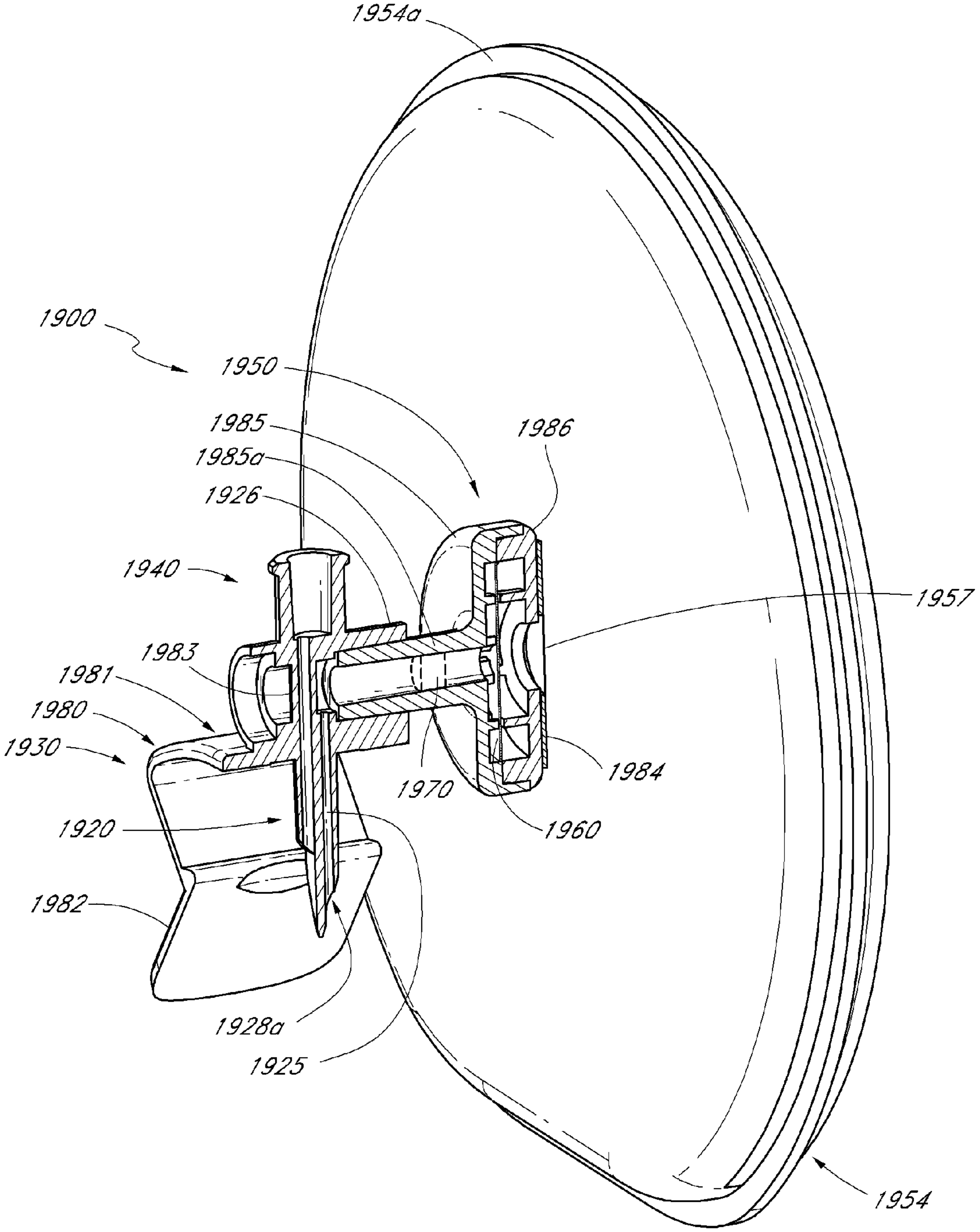
FIG. 15C illustrates an assembled perspective view of the vial adaptor of FIG. 7, the vial adaptor including a valve.

FIG. 15C illustrates an embodiment of an adaptor 1900 that can have components or portions that are the same as or similar to the components or portions of other vial adaptors disclosed herein. The adaptor 1900 can include a valve 1970 situated in a regulator channel 1925 within a protrusion **1985*a* of a regulator assembly 1950 between a container 10 and a filter 1960. In some embodiments, the valve 1970, or some portion thereof, is located in the regulator channel 1925 outside the protrusion 1985*a*. The regulator assembly 1950 can include an enclosure 1954. In some embodiments, the valve 1970 restricts the flow of fluid through the regulator channel 1925 in substantially the same way as other valves (e.g., 1770, 1870**) described herein.

Figure 16A:
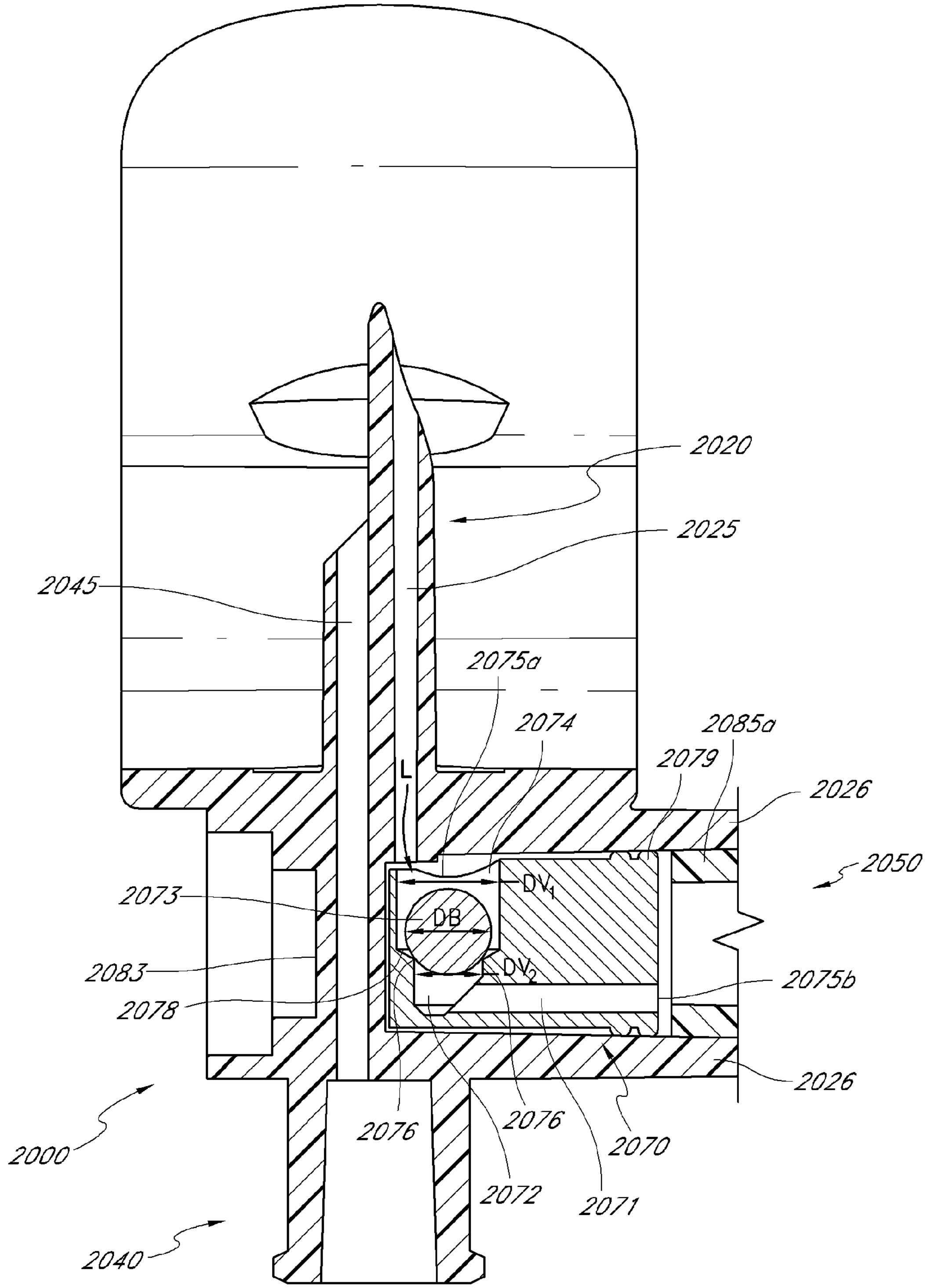
FIG. 16A illustrates a partial cross-sectional view of a portion of an inverted vial adaptor, the vial adaptor including a ball check valve.
Figure 16B:
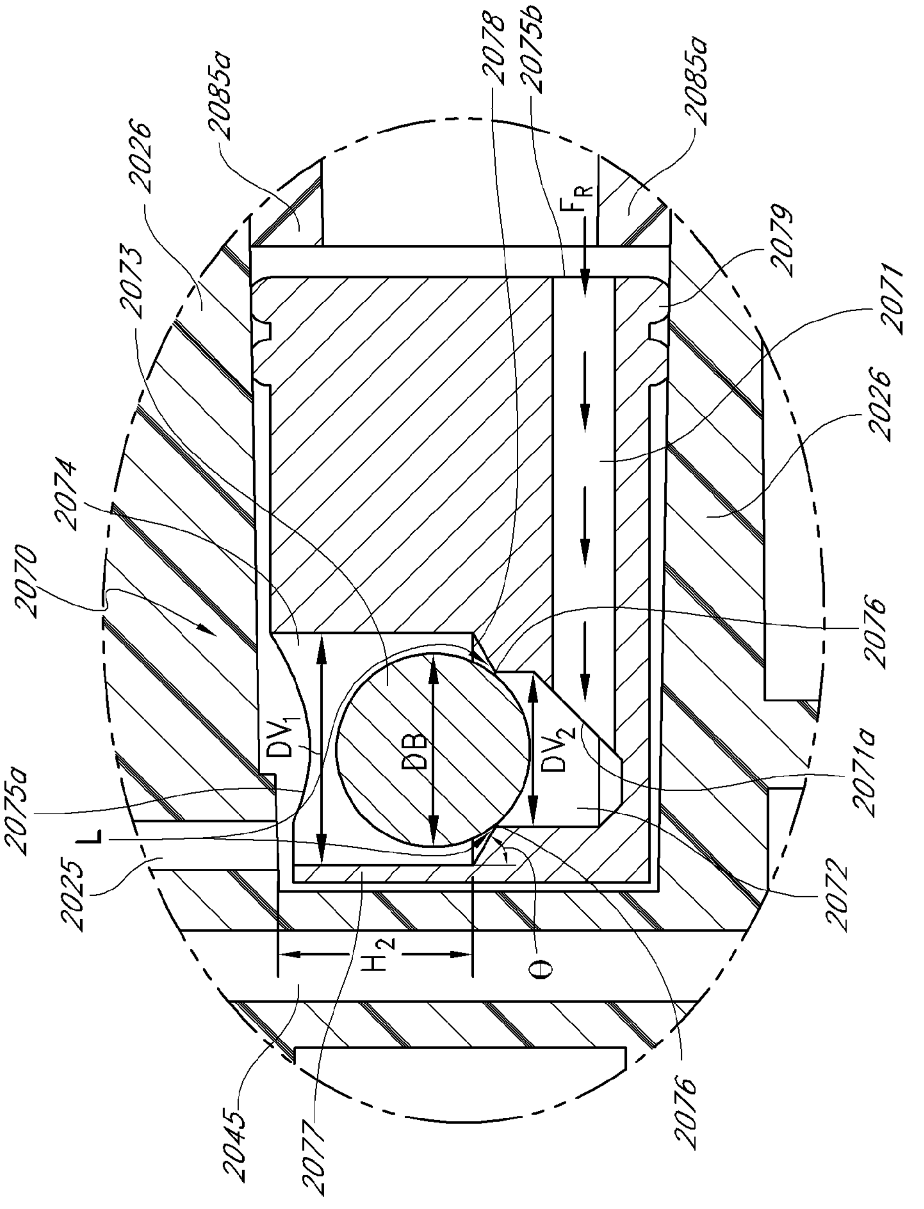
FIG. 16B illustrates a close-up cross-sectional view of the ball check valve of FIG. 16A.
Figure 16C:
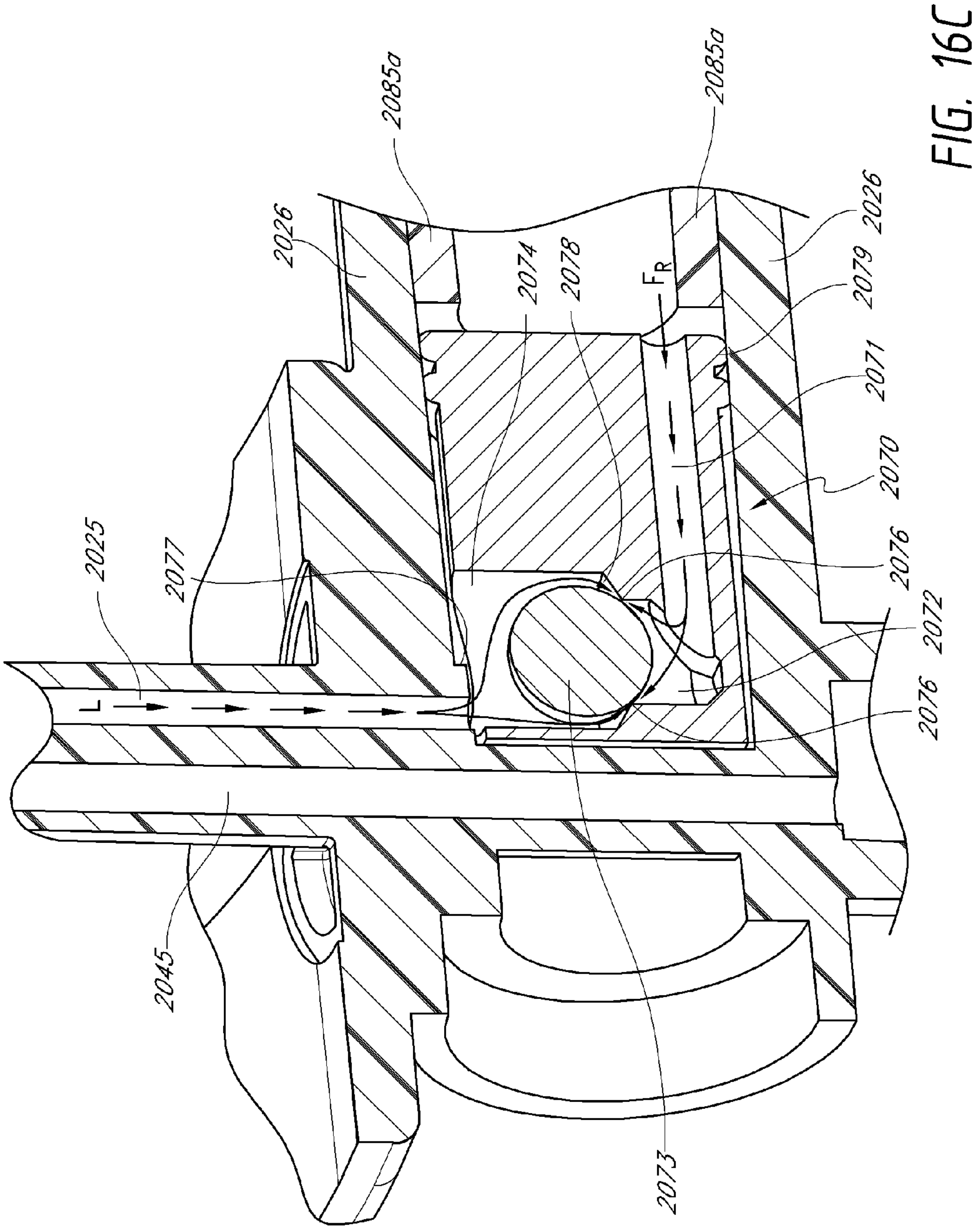
FIG. 16C illustrates a perspective cross-sectional view of the ball check valve of FIG. 16A.

FIGS. 16A-16C illustrate an embodiment of a vial adaptor 2000 that can have components or portions that are the same as or similar to the components or portions of other vial adaptors disclosed herein. In some embodiments, the vial adaptor 2000 includes a connector interface 2040 and a piercing member 2020 in partial communication with the connector interface 2040. In some embodiments, the vial adaptor 2000 includes a regulator assembly 2050.

The regulator assembly 2050 can include an orientation-actuated or orientation-dependent or orientation-sensitive occluder valve, such as a ball check valve 2070. In some embodiments, the occluder valve can be removably inserted into one or more lumens of the regulator assembly 2050 via an installation path. The installation path can be defined by the axial centerline of the lumen or portion thereof into which the occluder valve is inserted. In some embodiments, the occluder valve is configured to transition between an open configuration and a closed configuration based upon the orientation of the vial adaptor 2000 (e.g., the orientation of the vial adaptor 2000 with respect to the floor). In some such embodiments, the occluder valve is configured to transition from a first configuration corresponding with a first orientation of the vial adaptor 2000 to a second configuration corresponding with a second orientation of the vial adaptor 2000. The occluder valve can be configured to transition from the first orientation to the second orientation independent of the path of rotation of the vial adaptor 2000. In some embodiments, the occluder valve can include an occluding member configured to move about within a valve chamber. For example, the occluding member could be configured to engage with and disengage from a valve seat within the valve chamber depending on the configuration of the occluder valve and the orientation of the vial adaptor 2000. The occluding member can have an ellipsoidal shape, a spherical shape, a generally cylindrical shape with a tapered end, or any other appropriate shape.

In some configurations, the ball check valve 2070 is located in a lumen of the regulator assembly and/or in a lumen of the connector interface 2040. For example, the ball check valve 2070 can be located in a regulator channel 2025 within a lumen 2026 of the regulator assembly 2050. In some embodiments, the ball check valve 2070 is removable from the regulator channel 2025. In certain variants, the ball check valve 2070 includes a retaining member that prevents or impedes the ball 2073 from falling out of the ball check valve 2070 when it is removed from the regulator channel 2025. The ball check valve 2070 can be rotatable about its axial centerline within the regulator channel 2025. In some embodiments, the ball check valve 2070 can be installed in other lumens of the vial adaptor 2000. In some configurations, the regulator assembly 2050 includes a lumen or appendage or protrusion **2085*a* which can be substantially sealingly attached to (e.g., received within or around the outer perimeter of) the lumen 2026 of the regulator assembly 2050. The protrusion 2085*a* can facilitate fluid communication between two or more features (e.g., a filter, enclosure, bag and/or valve) of the regulator assembly. According to some configurations, the ball check valve 2070, or some portion thereof, can be located in the regulator channel 2025 within the protrusion 2085*a*. In some embodiments, the ball check valve 2070 and protrusion 2085*a* form a unitary part. In some embodiments, the ball check valve 2070 and lumen 2026** form a unitary part.

In some embodiments, the ball check valve 2070 includes a first chamber 2074 in fluid communication with the vial 10 via the regulator channel 2025. The ball check 2070 can include a second chamber 2072 in selective fluid communication with the first chamber 2074. According to some configurations, the first chamber 2074 has a substantially circular cross section with a diameter or cross-sectional distance DV1 and height H2. In some embodiments, the longitudinal axis of the first chamber 2074 is parallel to the axial centerline of the vial adaptor 2000. In some embodiments, the longitudinal axis of the first chamber 2074 is positioned at an angle away from the axial centerline of the vial adaptor 2000. The angle between the longitudinal axis of the first chamber 2074 and the axial centerline of the vial adaptor 2000 can be greater than or equal to about 15° and/or less than or equal to about 60°. In some embodiments, the angle between the longitudinal axis of the first chamber 2074 and the axial centerline of the vial adaptor 2000 is approximately 45°. Many variations are possible. In some embodiments, the second chamber 2072 also has a substantially circular cross section with a diameter or cross-sectional distance DV2. Many other variations in the structure of the first and second chambers are possible. For example, other cross-sectional shapes may be suitable.

In some embodiments, the ball check valve 2070 can include a shoulder 2078 between the first chamber 2074 and second chamber 2072. The shoulder 2078 can comprise a sloped or tapering surface configured to urge a ball 2073 to move toward an occluding position under the influence of gravity when the vial adaptor is oriented such that the vial is above the vial adaptor. In some embodiments, the angle θ between the shoulder 2078 and the wall of the first chamber 2074 is less than or equal to about 90°. In some embodiments the angle θ is less than or equal to about 75° and/or greater than or equal to about 30°. In some embodiments, the second chamber 2072 is in fluid communication with the first chamber 2074 when the ball check valve 2070 is in an open configuration. In some embodiments, the inner wall of the first chamber 2074 can gradually taper into the inside wall of the second chamber 2072 such that the first and second chambers 2074, 2072 constitute a single generally frustoconical chamber.

In some embodiments, the ball 2073 can rest on a circular seat when in the occluding position. In some embodiments, the circular seat is formed by the shoulder 2078. In some embodiments, the longitudinal axis of the circular seat is generally parallel to the longitudinal axis of the first chamber 2074. In some embodiments, the longitudinal axis of the first chamber 2074 can define a general movement path for the ball 2073 or other occluding member (e.g., the ball 2073 can generally move to and/or from the occluding position in a direction generally parallel to the longitudinal axis of the first chamber 2074). In some embodiments, the movement path of the occluding member is not substantially parallel to the installation path of the ball check valve 2070. For example, the movement path of the occluding member can be substantially perpendicular to the installation path of the ball check valve 2070. In certain variations, the longitudinal axis of the circular seat forms an angle with the respect to the longitudinal axis of the first chamber 2074. The angle formed between the longitudinal axis of the circular seat and the longitudinal axis of the first chamber 2074 can be greater than or equal to about 5° and/or less than or equal to about 30°. In some embodiments, the angle is approximately 10°. Many variations can be used. In some embodiments, the longitudinal axes of the first chamber 2074 and the circular seat are generally parallel to the axial centerline of the adaptor 2000. In some embodiments, some configurations can reduce the likelihood that the ball 2073 will "stick to" the circular seat or to the inner walls of the first chamber 2074 when the ball check valve 2070 is transitioned between the opened and closed configurations, as will be explained below.

In certain configurations, the longitudinal axis of the first chamber 2074 can be substantially parallel to the axial centerline of the ball check valve 2070. In some embodiments, the longitudinal axis of the first chamber 2074 can define the movement path of the ball 2073. As illustrated in FIG. 16C, the longitudinal axis of the first chamber 2074 can be perpendicular to the axial centerline of the ball check valve 2070. In some embodiments, the angle between the longitudinal axis of the first chamber 2074 and the axial centerline of the ball check valve 2070 is greater than or equal to about 5° and/or less than or equal to about 90°. In some embodiments, the angle is about 60°. Many variations are possible. In some embodiments, the angle between the longitudinal axis of the first chamber 2074 and axial centerline of the ball check valve 2070 is the same as the angle between the axial centerline of the ball check valve 2070 and the axial centerline of the vial adaptor 2000. In some such embodiments, the longitudinal axis of the first chamber 2074 can be aligned with the axial centerline of the vial adaptor 2000.

Figure 16D:
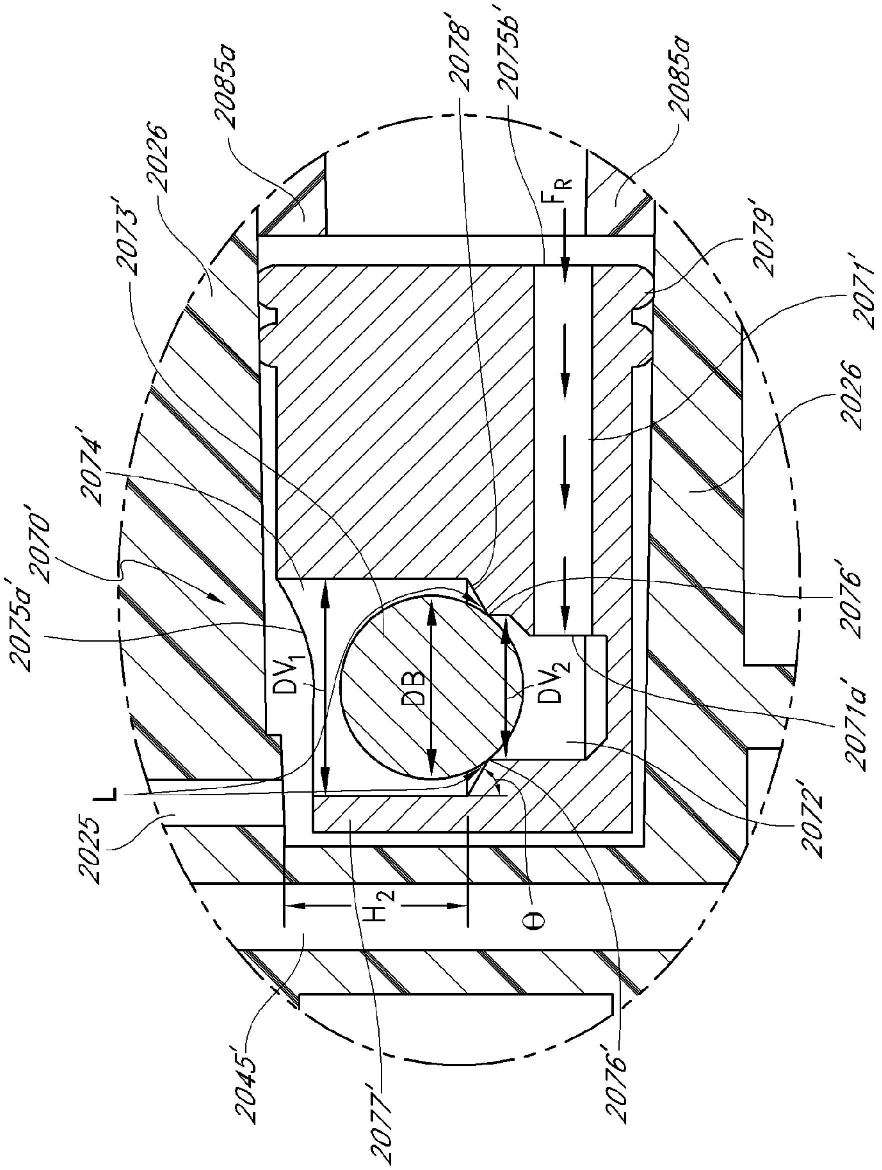
FIG. 16D illustrates a partial cross-sectional view of another ball check valve that can be used with any embodiment.

The ball check valve 2070 can also include a valve channel 2071. According to some embodiments, the valve channel 2071 is in fluid communication with the second chamber 2072. In some embodiments, the valve channel 2071 generally defines a flow path between the second chamber 2072 and a portion of the regulator channel 2025 opposite the second chamber 2072 from the first chamber 2074. The valve channel 2071 can have an interface 2071*a* with the second chamber 2072. The interface 2071*a* can be non-parallel and non-perpendicular to longitudinal axis of the first chamber 2074. FIG. 16D illustrates an embodiment of a ball check valve 2070'. Numerical reference to components is the same as previously described, except that a prime symbol (') has been added to the reference. Where such references occur, it is to be understood that the components are the same or substantially similar to previously-described components unless otherwise indicated. For example, in some embodiments, the interface 2071*a*' can be generally parallel to the longitudinal axis of the first chamber 2074. In some embodiments, the interface between the valve channel 2071 and the second chamber 2072 can be generally perpendicular to the longitudinal axis of the first chamber 2074. As illustrated in FIGS. 16A-16C, the ball check valve 2070 can include one or more sealing portions 2079. The one or more sealing portions 2079 can resist movement of the ball check valve 2070 within the regulator channel 2025. In some embodiments, the one or more sealing portions 2079 inhibit fluid from flowing around and bypassing the ball check valve 2070. In some embodiments, the one or more sealing portions 2079 include one or more annular protrusions that extend from the valve channel 2071. Many variations are possible.

As illustrated in FIG. 16A, the ball check valve 2070 has a distal opening 2075*a*. In some embodiments, the ball check valve 2070 has a plurality of distal openings. The distal opening 2075*a* defines the fluid boundary (e.g., the interface) between the first chamber 2074 and the regulator channel 2025. In some embodiments, the ball check valve 2070 includes a first valve channel in fluid communication with both the regulator channel 205 and the first chamber 2074. In such embodiments, the distal opening 2075*a* defines the fluid boundary (e.g., the interface) between the first valve channel and the regulator channel 2025. The ball check valve 2070 further includes a proximal opening 2075*b* that defines the fluid boundary (e.g., the interface) between the valve channel 2071 and the regulator channel 2025.

The ball check valve 2070 can be configured such that fluids that enter and exit the ball check valve 2070 through the distal opening 2075*a* and the proximal opening 2075*b* flow through the interfaces defined by each opening in a direction generally perpendicular to the interfaces. For example, as illustrated in FIG. 16B, regulator fluid FR that enters and/or exits the ball check valve 2070 through the proximal opening 2075*b* has a flow direction (horizontal with respect to FIG. 16B) that is generally perpendicular to the interface (vertical with respect to FIG. 16B) defined by the proximal opening 2075*b*. Similarly, the flow of liquid into and out of the ball check valve 2070 through the distal opening 2075*a* is in a direction generally perpendicular to the interface defined by the proximal opening 2075*a*. In some embodiments, the direction of flow through one or more of the distal opening 2075*a* and the proximal opening 2075*b* is oblique or perpendicular to the movement path of the ball 2073 or other occluding member. The angle formed between either interface and the movement path of the ball 2073 can be the same as the angle formed between the same interface and the insertion axis of the adaptor 2000.

According to some embodiments, the occluder valve 2070 includes a moveable occluder, such as a ball 2073. All references herein to a ball can apply to an occluder of any other shape, such as a generally cubic occluder, a generally cylindrical occluder, a generally conical occluder, combinations of these shapes, etc. In some embodiments, the ball 2073 is generally spherical or has another suitable shape. The ball 2073 can be constructed of a material with a higher density than the liquid L or other fluid within the vial 10. The ball 2073 can have a diameter DB. In some configurations, the diameter DB of the ball 2073 is less than the diameter DV1 and height H2 of the first chamber 2074. For example, in some embodiments the ratio of the diameter DB of the ball 2073 to the diameter DV1 of the first chamber 2074 is less than or equal to about 9:10 and/or greater than or equal to about 7:10. In some configurations, the diameter DB of the ball 2073 is greater than the diameter DV2 of the second chamber 2072. For example, in some embodiments the ratio of the diameter DV2 of the second chamber 2072 to the diameter DB of the ball 2073 is less than or equal to about 9:10 and/or greater than or equal to about 7:10. In some embodiments, the ball 2073 is can move between at least two positions within the first chamber 2074. For example, movement of the ball 2073 can be governed by gravity, external forces on the vial adapter, fluids within the regulator channel, other forces, or a combination of forces. The wall 2077, 2077' of the first chamber 2074, 2074' nearest the access channel 2045 can have varying wall thickness. In some embodiments, increasing the thickness of the wall 2077, 2077' can increase the durability of the ball check valve 2070, 2070'. In some embodiments, increasing the thickness of the wall 2077, 2077' can reduce the possibility of damage to the ball check valve 2070, 2070' during installation.

As illustrated in FIGS. 16A-16C, the ball 2073 in the ball check valve 2070 can be configured to rest upon the shoulder 2078 at the opening of the second chamber 2072 when the adaptor 2000 and vial 10 are oriented such that the force of gravity is influencing the fluid contained within the vial to be urged toward the vial adaptor (e.g., when at least some portion of the vial 10 is above the connector interface 2040). The ball check valve 2070 can be oriented such that the longitudinal axis of the first chamber 2074 and the longitudinal axis of the circular seat are substantially parallel to the axial centerline of the vial adaptor 2000. In such embodiments, the ball 2073 can be configured to transition to the occluding position (e.g., resting on the circular seat) in a substantially consistent manner independent of the direction of rotation of the vial 10 and the connector interface 2040. For example, in such embodiments, the manner in which the ball 2073 moves toward the shoulder 2078 or circular seat when the vial 10 is rotated from below connector interface 2040 to above the connector interface 2040 would be substantially consistent and independent of whether the vial 10 and connector interface 2040 were rotated about the longitudinal axis of the lumen 2026, about an axis perpendicular to the longitudinal axis of the lumen 2026 and to the axial centerline of the vial adaptor 2000, or about any other axis of rotation therebetween. Furthermore, in such embodiments, parallel alignment between the longitudinal axis of the first chamber 2074 and the axial centerline of the adaptor 2000 can assist the user of the adaptor 2000 in visualizing the alignment of the ball check valve 2070. In some configurations, the contact between the ball 2073 and the shoulder 2078 can form a seal 2076. The seal 2076 can put the ball check valve 2070 in a closed configuration and inhibit passage of liquid L and/or other fluid from the vial 10 through the ball check valve 2070 when the vial 10 is oriented above the connector interface 2040.

In some embodiments, the ball 2073 can be configured to move away from the shoulder 2078 when the adaptor 2000 and vial 10 are oriented such that fluid within the vial is urged away from the vial adaptor under the force of gravity (e.g., when at least a portion of the connector interface 2040 is positioned above the vial 10). In some embodiments (such as, for example, embodiments in which the longitudinal axes of the first chamber 2074 and the circular seat are parallel to the axial centerline of the vial adaptor 2000), the ball 2073 can be configured to move away from the shoulder 2078 in a substantially consistent manner independent of the direction of rotation of the vial 10 and the connector interface 2040. For example, in such embodiments, the manner in which the ball 2073 moves away from the shoulder 2078 when the vial 10 is rotated from above connector interface 2040 to below the connector interface 2040 would be substantially consistent and independent of whether the vial 10 and connector interface 2040 were rotated about the longitudinal axis of the lumen 2026, about an axis perpendicular to the longitudinal axis of the lumen 2026 and to the axial centerline of the vial adaptor 2000, or about any other axis of rotation therebetween. Movement of the ball 2073 away from the shoulder 2078 can open or break the seal 2076 and put the ball check valve 2070 in an open configuration such that the first chamber 2074 and second chamber 2072 are in fluid communication. In some embodiments, the ball check valve 2070 includes a resilient biasing member which can bias the ball 2073 toward the shoulder 2078 and thus bias the ball check valve 2070 to a closed configuration. In some configurations, the biasing member can be a spring. In some configurations, the biasing member can be a flexible member. In some embodiments, the biasing force provided by the resilient biasing member can be less than the weight of the ball 2073.

In some embodiments, the ball 2073 can move about the first chamber 2074 under the influence of gravity. In some configurations, gravity can cause the ball 2073 to move toward the second chamber 2072 and rest upon the shoulder 2078 at the opening of the second chamber 2072. As explained above, the resting of the ball 2073 upon the shoulder 2078 can create a seal 2076 which can put the ball check valve 2070 in a closed configuration and inhibit passage of liquid L and/or other fluid from the vial 10 through the ball check valve 2070. In some configurations, gravity can cause the ball 2073 to move away from the shoulder 2078. Movement of the ball 2073 away from the shoulder 2078 under the influence of gravity can open or break the seal 2076 and put the ball check valve 2070 in an open configuration such that the first chamber 2074 and second chamber 2072 are in fluid communication. Since the diameter or cross-section of the first chamber DV1 is greater than the diameter or cross-section DB of the ball 2073, fluid can flow through the first chamber, around the outside surface of the ball 2073.

Certain aspects of the operation of the ball check valve 2070 while the ball check valve 2070 is in a closed configuration will now be described. For example, in some embodiments when no fluid is being introduced to or withdrawn from the vial 10 via the access channel 2045, the pressure within the vial 10 is substantially the same as the pressure in the valve channel 2071. In such a situation, the pressure in the first chamber 2074 can be substantially the same as the pressure in the second chamber 2072. In some embodiments, positioning of the vial 10 above the connector interface 2040 can cause liquid L or other fluid to move from the vial 10 to the first chamber 2074. In some embodiments, the ball 2073 will remain at rest on the shoulder 1078 and create a seal 2076 when there is equilibrium in the pressure between the first chamber 2074 and the second chamber 2072. The seal 2076 can inhibit passage of liquid L and/or other fluid from the vial 10 through the ball check valve 2070.

In some embodiments, withdrawal of fluid from the vial 10 through the access channel 2045 can create lower pressure in the vial 10 and first chamber 2074 than the pressure within the second chamber 2072. The pressure differential can cause the ball 2073 to move away from the shoulder 2078 into the first chamber 2074. The movement of the ball 2073 away from the shoulder 2078 can break the seal 2076 and permit regulator fluid FR to pass from through the second chamber 2072 and around the ball 2073. The regulator fluid FR can then pass through the first chamber 2074 and through the regulator channel 2025 into the vial 10. In some embodiments, the regulator fluid FR is fluid which has passed through a filter in the regulator assembly 2050. In some embodiments, the regulator fluid FR is a fluid contained in the inner volume of an enclosure of the regulator assembly 2050. Passage of regulator fluid FR into the vial 10 can offset, reduce, substantially eliminate, or eliminate the pressure differential between the first chamber 2074 and the second chamber 2072 and allow the ball 2073 to return to a resting position on the shoulder 2078. In some embodiments, the passage of regulator fluid FR into the vial 10 helps to maintain equilibrium between the interior of the vial 10 and the interior of the regulator assembly 2050. The return of the ball 2073 to a resting position on the shoulder 2078 can recreate or produce the seal 2076 and prevent passage of liquid L or other fluid from the vial 10 through the ball check valve 2070.

In some embodiments, introduction of fluid to the vial 10 through the access channel 2045 (e.g., when diluents, mixing fluids, or overdrawn fluids are injected into the vial 10 via an exchange device 40) can create higher pressure in the vial 10 and first chamber 2074 than the pressure within the second chamber 2072. This difference in pressure can cause the ball 2073 to be pushed onto the shoulder 2078 and thus tighten the seal 2076. Tightening of the seal 2076 can inhibit the passage through the ball check valve 2070 of fluid L from the vial 10. In some embodiments, the tightening of the seal 2076 can cause the internal pressure within the vial 10 and first chamber 2074 to continue to increase as more fluid is introduced into the vial 10 via the access channel 2045. In some embodiments, a continual increase in pressure within the vial 10 and first chamber 2074 can dramatically increase the force required to introduce more fluid to a prohibitive level, and eventually increase the likelihood of fluid leaks from the vial 10 and adaptor 2000 or between these components. It can therefore be desirable for the ball check valve 2070 to be in an open position when fluids are injected into the vial 10.

Movement of the ball 2073 away from the shoulder 2078 can open or break the seal 2076 and put the ball check valve 2070 in an open configuration. Certain aspects of the operation of the ball check valve 2070 while the ball check valve 2070 is in an open configuration will now be described. For example, in some embodiments when no fluid is being introduced to or withdrawn from the vial 10 via the access channel 2045, the pressure within the vial 10 remains substantially constant. In some embodiments, the vial 10 is in fluid communication with and has the same substantially constant internal pressure as the first and second chambers 2074, 2072 and valve channel 2071 of the ball check valve 2070.

In some embodiments, withdrawal of fluid from the vial 10 through the access channel 2045 can lower the pressure in the vial 10 and subsequently lower the pressure in the first chamber 2074. This lowering of pressure in the vial 10 and first chamber 2074 can create a pressure differential between the first chamber 2074 and second chamber 2072 of the ball check valve 2070. The pressure differential can cause regulator fluid FR to pass through the first chamber 2074 and through the regulator channel 2025 into the vial 10. In some embodiments, the regulator fluid FR is fluid which has passed through a filter in the regulator assembly 2050. In some embodiments, the regulator fluid FR is a fluid contained in the inner volume of an enclosure of the regulator assembly 2050. Passage of regulator fluid FR into the vial 10 can offset, reduce, substantially eliminate, or eliminate the pressure differential between the first chamber 2074 and the second chamber 2072. In some embodiments, the passage of regulator fluid FR into the vial 10 helps to maintain equilibrium between the interior of the vial 10 and the interior of the regulator assembly 2050.

In some embodiments, introduction of fluid to the vial 10 through the access channel 2045 (e.g., when diluents, mixing fluids, or overdrawn fluids are injected into the vial 10 via an exchange device 40) can create higher pressure in the vial 10 and first chamber 2074 than the pressure within the second chamber 2072. This differential in pressure can cause fluid from the vial 10 to pass from the vial 10, through the ball check valve 2070 and into the regulator assembly 2050. In some embodiments, the fluid from the vial 10 can pass through the check valve 2070 and through a filter. In some embodiments, the fluid from the vial 10 passes through the check valve 2070 and into a bag or other enclosure. Passage of fluid from the vial 10 through the ball check valve 2070 can lower the pressure within the vial 10 and maintain equilibrium between the interior of the vial 10 and the interior of the regulator assembly 2050. In some embodiments, regulator fluid FR is ambient air or sterilized gas, or filtered air or gas.

In some embodiments, especially those in which portions of the vial adaptor are modular or interchangeable, the internal and/or external cross section of the lumen 2026 can include one or more alignment features. For example, the internal and/or external cross section of the lumen can be keyed or otherwise specially shaped. Some examples of potential shapes and their benefits are illustrated in FIGS. 14A-14F and discussed above. The protrusion **2085*a* and/or ball check valve 2070 can include a corresponding alignment feature (e.g. corresponding keying or other special shaping). Such a configuration can be useful to signal, control, or restrict the regulatory assembly 2050 that can be connected with, or made integral with, the adaptor 2000. For example, keying of or shaping of the ball check valve 2070 and/or the channel in which it is placed could provide a user of the adaptor 2000 with confirmation that the ball check valve 2070 is properly aligned (e.g., aligning the first chamber 2074 on the side of the vial 10) within the regulator assembly 2050. This alignment of ball check valve 2070 can allow for proper and/or predictable functioning of the regulatory assembly 2050**.

In some embodiments, the exterior of the regulator assembly 2050 can include one or more visual indicators to show the alignment of the ball check valve 2070. In some embodiments, the visual indicators include notches, words (e.g., top and/or bottom), arrows or other indicators of alignment. In some embodiments, the protrusion **2085*a*, lumen 2026, and/or body of the valve 2070 are constructed of a substantially transparent material to provide the user of the adaptor 2000** with visual confirmation of the configuration of the valve (e.g., to permit viewing the position of the ball to indicate whether the valve is in an open or closed configuration).

In some embodiments, the regulator assembly 2050 can include one or more indicators (e.g., visual or audible) to indicate when the ball 2073 is in the occluding position. For example, the regulator assembly 2050 could include one or more light sources (e.g., LED lights, chemiluminescent lights, etc.) that can be configured to emit light when the ball 2073 is in the occluding position. In some embodiments, the adaptor 2000 can include a power source (e.g., one or more batteries, AC input, DC input, photovoltaic cells, etc.) configured to supply power to at least one of the one or more indicators. In some embodiments, the ball 2073 is constructed of an electrically conductive material. In such embodiments, the ball check valve 2070 can be configured such that the ball 2073 completes a circuit between the power source and the light source when the ball 2073 is in the occluding position. In some embodiments, the adaptor 2000 can include a gyroscopic sensor configured to sense when the ball 2073 is in the occluding position. In certain such embodiments, a controller to which the sensor is connected can direct power to activate the one or more indicators when the vial 10 is held above the adaptor 2000.

Figure 17:
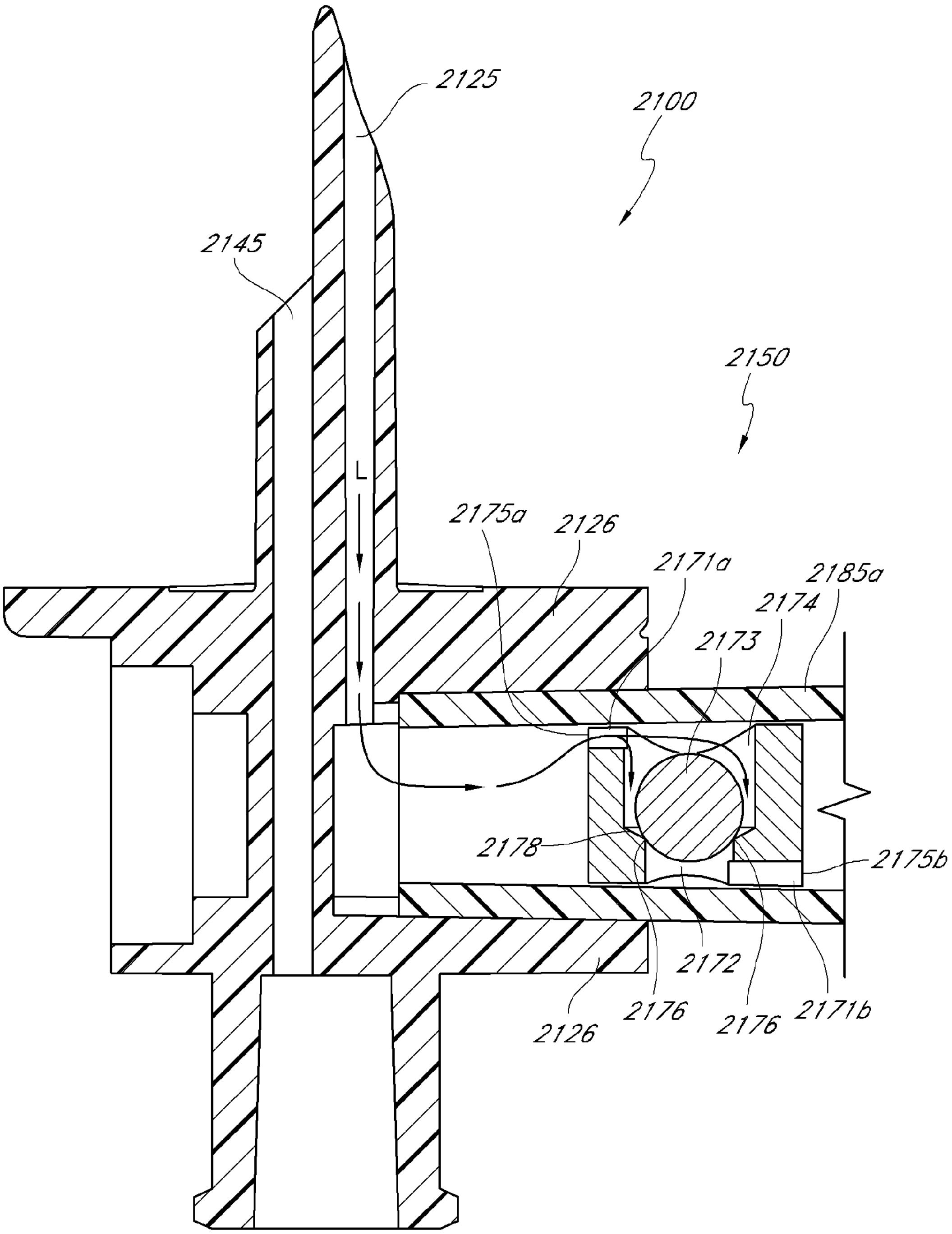
FIG. 17 illustrates a partial cross-sectional view of another vial adaptor, the vial adaptor including a ball check valve.

FIG. 17 illustrates an embodiment of an adaptor 2100 that can have components or portions that are the same as or similar to the components or portions of other vial adaptors disclosed herein. In some embodiments, a ball check valve 2170 includes a first valve channel 2171A in fluid communication with both a regulator channel 2125 and a first chamber 2174 of the ball check valve 2170. The ball check valve 2100 can include a second valve channel 2171B in fluid communication with a second chamber 2172 of the ball check valve 2170. In some embodiments, the ball check valve 2170, or some portion thereof, is positioned in the regulator channel 2125 within a protrusion **2185*a*. In some embodiments, the ball check valve 2170, or some portion thereof, is positioned in the regulator channel 2125 within a lumen 2126 of the adaptor 2100. In some embodiments, the ball check valve 2170, or some portion thereof, is positioned in the regulator channel 2125 outside a protrusion 2185*a*. In some embodiments, the ball check valve 2170, or some portion thereof, is positioned in the regulator channel 2125 outside a lumen 2126 of the adaptor 2100. In some embodiments, the ball check valve 2170 and protrusion 2185*a* form a unitary part. In some embodiments, the ball check valve 2170 and lumen 2126** form a unitary part.

Figure 18:
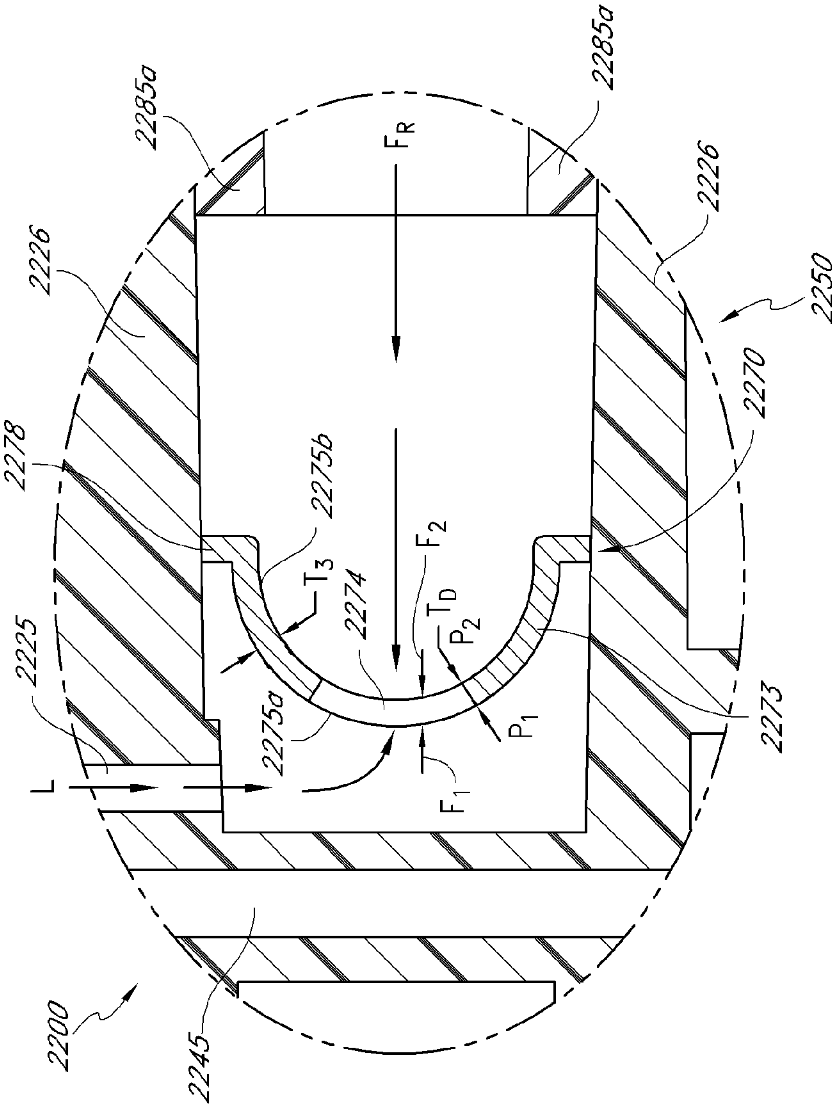
FIG. 18 illustrates a close-up cross-sectional view of a domed valve.

FIG. 18 illustrates an embodiment of an adaptor 2200 that can have components or portions that are the same as or similar to the components or portions of other vial adaptors disclosed herein. In some embodiments, a regulator assembly 2250 includes a flexible valve, such as a domed valve 2270. The domed valve 2270 can include a domed portion 2273. The domed portion 2273 can include a concave side 2275B and a convex side 2275A. In some embodiments, the domed valve 2270 can include an annular flange 2278 attached to the domed portion 2273. In some embodiments, the annular flange 2278 and domed portion 2273 constitute a unitary part. The domed portion 2273 can have a wall thickness T3. The wall thickness T3 can be substantially constant throughout the domed portion 2273. In some embodiments, the thickness T3 of the domed portion 2273 can vary across the domed valve 2270.

In some embodiments, the domed valve 2270, or some portion thereof, is positioned in a regulator channel 2225 within a lumen 2226 of the adaptor 2200. In some embodiments, the domed valve 2270, or some portion thereof, is positioned in the regulator channel 2225 outside a protrusion **2285*a*. In some embodiments, the domed valve 2270, or some portion thereof, is positioned in the regulator channel 2225 outside a lumen 2226 of the adaptor 2200. In some embodiments, the domed valve 2270 is fixed within the regulator channel 2225. The domed valve 2270 can be fixed within the regulator channel 2225 via, for example, adhesives, welding, fitted channels within the regulator channel 2225** or otherwise.

In some embodiments, the domed portion 2273 includes one or more slits 2274 or some other opening. In some embodiments, the one or more slits 2274 are biased to a closed position by the domed portion 2273 and/or annular flange 2278. The domed valve 2270 can inhibit and/or prevent the passage of fluid through the regulator channel 2225 when the one or more slits 2274 are in a closed position. In some embodiments, the one or more slits 2274 are configured to open in response to one or more cracking pressures and allow fluid to flow through the one or more slits 2274. In some embodiments, the geometry and/or material of the domed valve 2270 can cause the cracking pressure required to allow fluid to flow through the one or more slits 2274 in a first direction F1 to be substantially higher than the cracking pressure required to allow fluid to flow through the one or more slits 2274 in a second direction F2.

Certain aspects of the operation of the domed valve 2270 will now be described. For example, in some embodiments when no fluid is being introduced to or withdrawn from a vial 10 via an access channel 2245 of the adaptor 2200, the pressure within the vial 10 remains substantially constant. In some embodiments, the vial 10 is in fluid communication with and has the same substantially constant internal pressure as the pressure P1 in the regulator channel 2225 in the region of the convex side 2275A of the domed valve 2270. In some embodiments, the pressure P2 in the region of the concave side 2275B of the domed valve 2270 is substantially the same as the pressure P1 when no fluid is being introduced to or withdrawn from the vial 10. In such a configuration, the one or more slits 2274 of the domed valve 2270 can be biased closed by the domed portion 2273 of the domed valve 2270.

In some embodiments, withdrawal of fluid from the vial 10 through the access channel 2045 can lower the pressure in the vial 10 and subsequently lower the pressure P1 in the region of the convex side 2275A. This lowering of the pressure P1 can create a pressure differential between the convex side 2275A and concave side of 2275B of the domed valve 2270. In some embodiments, withdrawal of fluid from the vial 10 can create a pressure differential across the domed valve 2270 high enough to overcome the cracking pressure of the domed valve 2270 and open the one or more slits 2274 to allow fluid to flow in a second direction F2 through the domed valve 2270. In some configurations, regulator fluid FR flows in a second direction F2 through the domed valve 2270 when the one or more slits 2274 are opened and the pressure P2 on the concave side 2275B of the valve 2270 is higher than the pressure P1 on the convex side 2275A of the valve 2270. Passage of regulator fluid FR through the domed valve 2270 and/or into the vial 10 can raise the pressure within the vial 10. Raising of the pressure within the vial 10 can raise the pressure P1 in the region of the convex surface 2275A of the domed valve 2270. Raising of the pressure P1 in the region of the convex surface 2275A can lower the pressure differential across the valve 2270 below the cracking pressure and cause the one or more slits 2274 to shut. In some embodiments, the passage of regulator fluid FR in a second direction F2 through domed valve 2270 helps maintain equilibrium between the interior of the vial 10 and interior of the regulator assembly 2050 when fluid is withdrawn from the vial 10 via the access channel 2245. In some embodiments, the regulator fluid FR is fluid which has passed through a filter in the regulator assembly 2250. In some embodiments, the regulator fluid FR is a fluid contained in the inner volume of an enclosure of the regulator assembly 2250.

In some embodiments, introduction of fluid to the vial 10 through the access channel 2245 (e.g., when diluents, mixing fluids, or overdrawn fluids are injected into the vial 10 via an exchange device 40) can raise the pressure in the vial 10. Raising the pressure within the vial 10 can raise the pressure P1 in the region of the convex surface 2275A of the domed valve 2273. Raising of the pressure P1 in the region of the convex surface 2275A can create a pressure differential across the domed valve 2273. In some embodiments, introduction of fluid into the vial 10 can create a pressure differential across the domed valve 2270 high enough to overcome the cracking pressure of the domed valve 2270 and open the one or more slits 2274 to allow fluid to flow in a first direction F1 through the domed valve 2270. In some configurations, as explained above, the cracking pressure required to permit fluid to flow in the first direction F1 is substantially higher than the cracking pressure required to permit fluid to flow in a second direction F2 through the domed valve 2270. In some embodiments, flow of fluid from the vial 10 through the domed valve 2270 in a first direction F1 can lower the pressure in the vial 10. Lowering of the pressure within the vial 10 can lower the pressure P1 in the region of the convex surface 2275A and can lower the pressure differential across the valve 2270 below the cracking pressure and cause the one or more slits 2274 to shut. In some embodiments, passage of fluid through the domed valve 2270 in a first direction F1 helps maintain equilibrium between the interior of the vial 10 and the interior of the regulator assembly 2250.

Figure 19B:
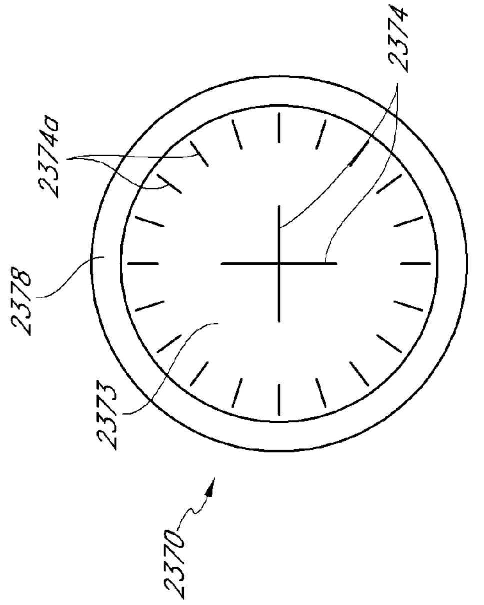
FIG. 19B illustrates an elevated view of the showerhead domed valve taken through the line B-B in FIG. 19A.
Figure 19A:
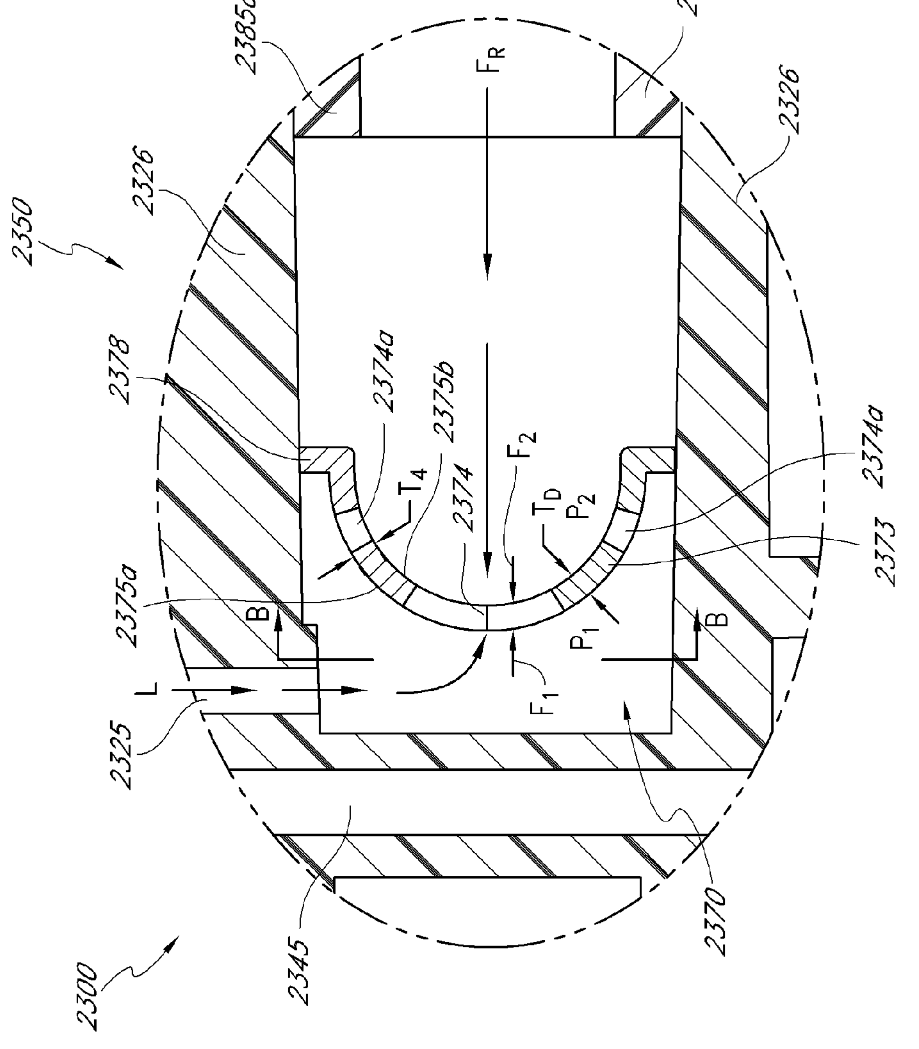
FIG. 19A illustrates a close-up cross-sectional view of a showerhead domed valve.

FIGS. 19A-19B illustrate an embodiment of an adaptor 2300 and a valve with multiple openings, such as a showerhead domed valve 2370. The adaptor 2300 can have components or portions that are the same as or similar to the components or portions of other vial adaptors disclosed herein. The showerhead domed valve 2370 can include a domed portion 2373. The domed portion 2373 can include a concave side 2375B and a convex side 2375A. In some embodiments, the showerhead domed valve 2370 can include an annular flange 2378 attached to the domed portion 2373. In some embodiments, the annular flange 2378 and domed portion 2373 constitute a unitary part. The domed portion 2373 can have a wall thickness T4. The wall thickness T4 can be substantially constant throughout the domed portion 2373. In some embodiments, the thickness T4 of the domed portion 2373 can vary across the showerhead domed valve 2370.

In some embodiments, the showerhead domed valve 2370, or some portion thereof, is positioned in a regulator channel 2325 within a lumen 2326 of the adaptor 2300. In some embodiments, the showerhead domed valve 2370, or some portion thereof, is positioned in the regulator channel 2325 outside a protrusion 2385*a*. In some embodiments, the showerhead domed valve 2370, or some portion thereof, is positioned in the regulator channel 2325 outside a lumen 2326 of the adaptor 2300. In some embodiments, the showerhead domed valve 2370 is fixed within the regulator channel 2325. The showerhead domed valve 2370 can be fixed within the regulator channel 2325 via, for example, adhesives, welding, fitted channels within the regulator channel 2325 or otherwise.

In some embodiments, the domed portion 2373 includes one or more openings or central slits 2374. In some embodiments, the one or more central slits 2374 are arranged in a generally crisscross configuration. In some embodiments, the one or more central slits 2374 are generally parallel to each other. In some embodiments, the domed portion 2373 includes one or more outer slits 2374A. In some embodiments the number of outer slits 2374A is less than or equal to about 30 and/or greater than or equal to about 4.

In some embodiments, the one or more central slits 2374 and/or outer slits 2374A are biased to a closed position by the domed portion 2373 and/or annular flange 2378. The showerhead domed valve 2370 can inhibit and/or prevent the passage of fluid through the regulator channel 2325 when the slits 2374, 2374A are in a closed position. In some embodiments, the slits 2374, 2374A are configured to open in response to one or more cracking pressures and allow fluid to flow through the slits 2374, 2374A. In some embodiments, the geometry and/or material of the showerhead domed valve 2370 can cause the cracking pressure required to allow fluid to flow through the slits 2374, 2374A in a first direction F1 to be substantially higher than the cracking pressure required to allow fluid to flow through the slits 2374, 2374A in a second direction F2. In some embodiments, the cracking pressures required to allow fluid to flow through the showerhead domed valve 2370 in a first direction F1 and second direction F2 are less than the cracking pressures required to allow fluid to flow through the domed valve 2270 in a first direction F1 and second direction F2, respectively. In some embodiments, the showerhead domed valve 2370 functions in substantially the same way as the domed valve 2270 when fluid is introduced to or removed from the vial 10 via the access channel 2345.

Figure 20A:
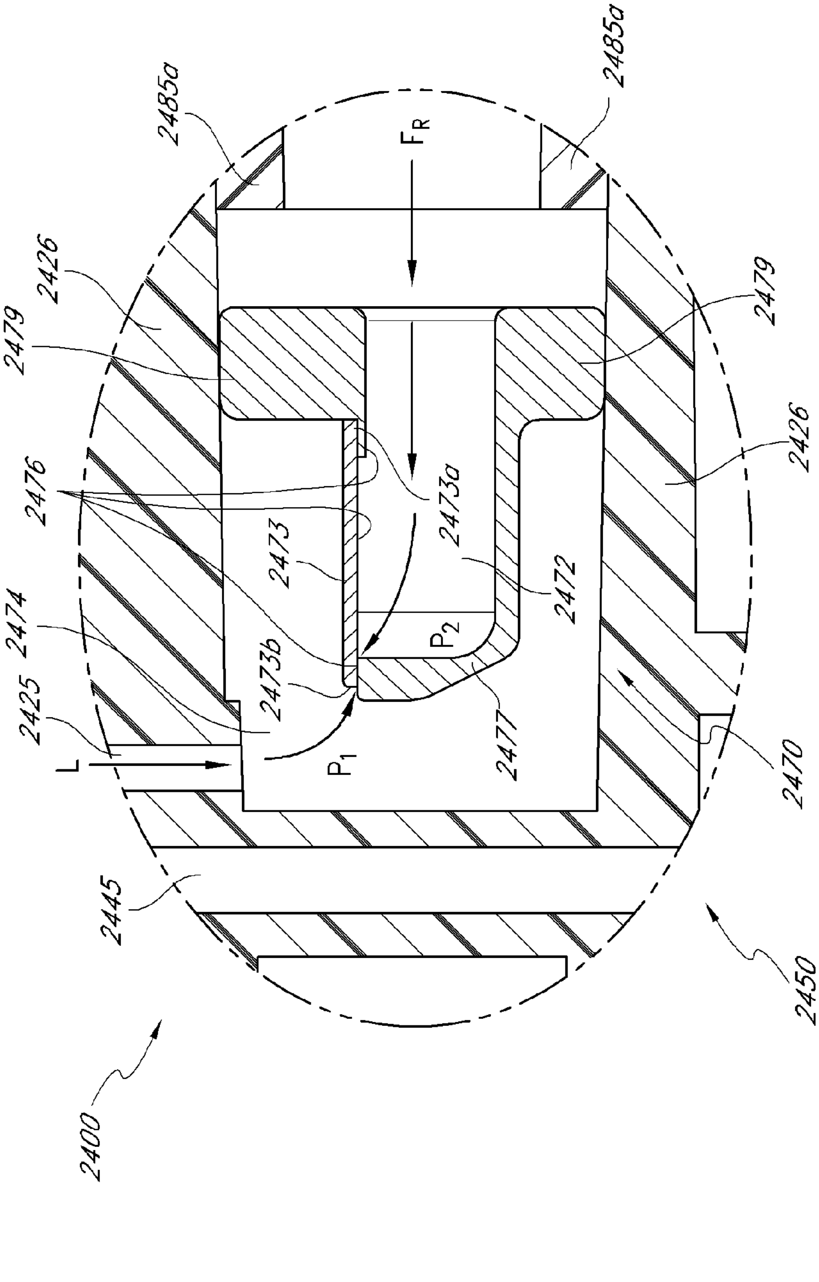
FIG. 20A illustrates a close-up cross-sectional view of a flap check valve.
Figure 20B:
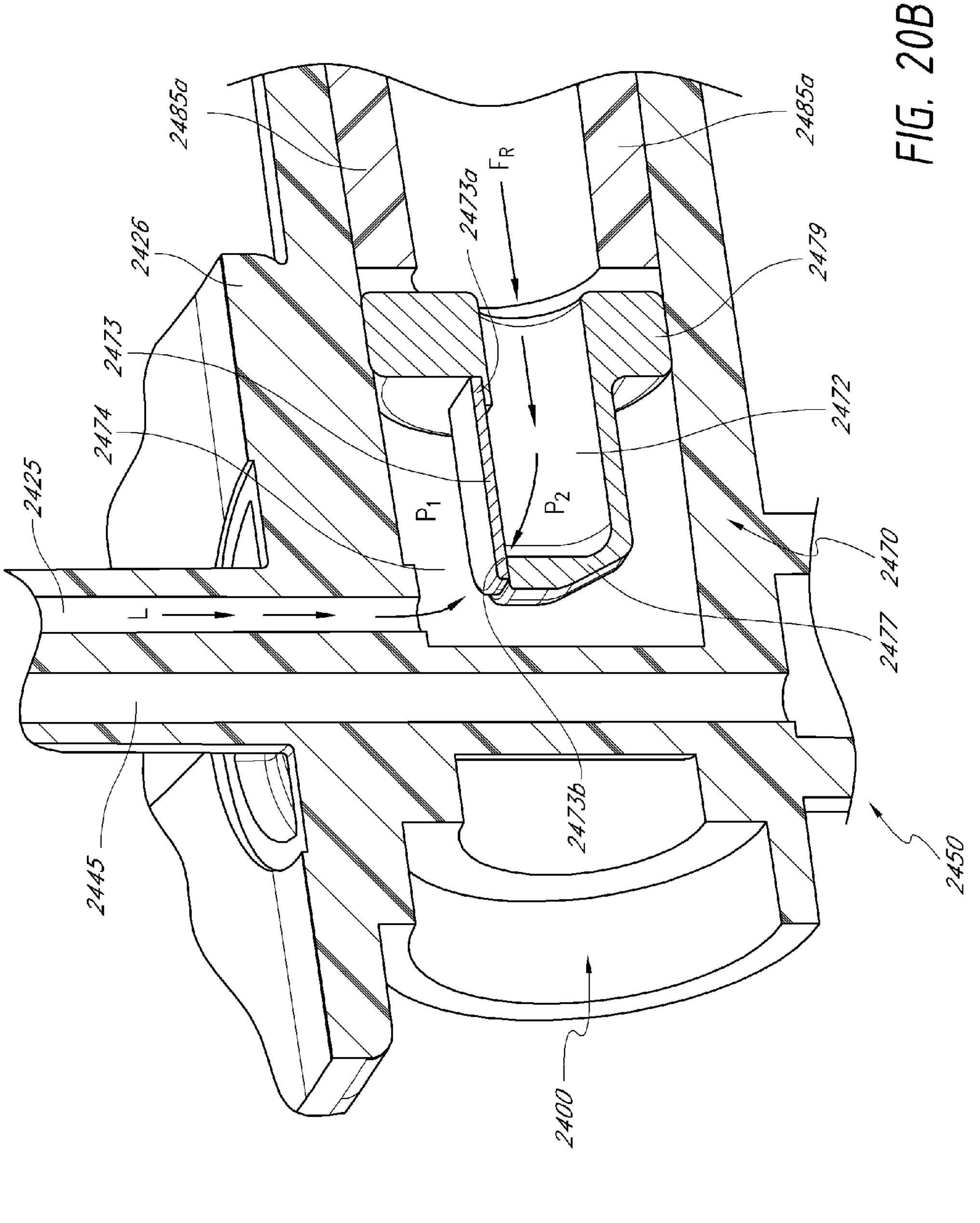
FIG. 20B illustrates a perspective cross-sectional view of the flap check valve of FIG. 20A.

FIGS. 20A-20B illustrate an embodiment of an adaptor 2400 that can have components or portions that are the same as or similar to the components or portions of other vial adaptors disclosed herein. In some embodiments, a regulator assembly 1450 includes an opening and closing occluder valve 2470, such as a flap check valve 2470, with a portion of the occluding component remaining affixed to structure within the vial adaptor 2400 as the occluder valve 2470 transitions between the open and closed states. The flap check valve 2470 can include a sealing portion 2479. The sealing portion 2479 can comprise, for example, a hollow stopper shaped to fit snugly in a regulator channel 2425 of a regulator assembly 2450, one or more annular protrusion or some other feature suitable for fixing the flap check valve 2470 in place within the regulator channel 2425. In some embodiments, flap check valve 2470, or some portion thereof, is positioned in a regulator channel 2425 within a lumen 2426 of the adaptor 2400. In some embodiments, the flap check valve 2470, or some portion thereof, is positioned in the regulator channel 2425 outside a protrusion 2485*a*. In some embodiments, the flap check valve 2470, or some portion thereof, is positioned in the regulator channel 2425 outside a lumen 2426 of the adaptor 2400. In some embodiments, the flap check valve 2470 is fixed within the regulator channel 2425.

According to some configurations, the flap check valve 2470 can include a seat portion 2477 attached to the sealing portion 2479. In some embodiments, the seat portion 2477 and sealing portion 2479 form a unitary part. In some embodiments, the seat portion 2477 and sealing portion 2479 are separate parts. The flap check valve 2470 can include a flap 2473. The flap 2473 can have a first end 2473A and a second end 2473B. The first end 2473A of the flap 2473 can be rotatably attached to the sealing portion 2479 and/or seat portion 2477.

In some embodiments, the flap 2473 can be configured to rest upon the seat portion 2477 when the adaptor 2400 and vial 10 are oriented such that the vial 10 is above the connector interface of the adaptor 2400. In some configurations, contact between the flap 2437 and the seat portion 2477 can form a seal 2476 between the interior 2472 and the exterior 2474 of the flap check valve 2470. The seal 2476 can put the flap check valve 2470 in a closed configuration and inhibit passage of liquid L and/or other fluid from the vial 10 through the flap check valve 2470. In some embodiments, the flap 2473 can be configured to rotate away from the seat portion 2477 when the adaptor 2400 and vial 10 are oriented such that the connector interface of the adaptor 2400 is above the vial 10. Movement of the flap 2473 away from the seat member 2477 can eliminate the seal 2476 and put the flap check valve 2470 in an open configuration such that the interior 2472 and exterior 2474 of the flap check valve 2470 are in fluid communication.

In some embodiments, the flap 2473 can move toward and away from the seat portion 2477 under the influence of gravity. As explained above, contact between the flap 2473 and the seat portion 2477 can form a seal 2476 between the interior 2472 and exterior 2474 of the flap check valve 2470, putting the flap check valve 2470 in a closed configuration and inhibiting passage of liquid L and/or other fluid from the vial 10 through the flap check valve 2470. In some configurations, gravity can cause the flap 2473 to move away from the seat portion 2477 and break the seal 2476. Movement of the flap 2473 away from the seat portion 2477 under the influence of gravity can eliminate the seal 2476 and put the flap check valve 2470 in an open configuration such that the exterior 2474 and interior 2472 are in fluid communication. In some embodiments, the flap 2473 is biased to the closed position. The biasing force can be provided by, for example, one or more torsion springs, or another feature suitable for biasing the flap 2473 toward the seat portion 2477 (e.g., tensile force, memory materials, magnets, etc.). In some embodiments, the biasing torque upon the flap 2473 at the first end 2473A is less than the torque created at the first end 2437A when the weight of flap 2473 is pulled away from the seat portion 2477 due to the force of gravity (e.g., when the seat portion 2477 is positioned above the flap 2473).

Certain aspects of the operation of the flap check valve 2470 while the flap check valve 2470 is in a closed configuration will now be described. For example, in some embodiments when no fluid is being introduced to or withdrawn from the vial 10 via an access channel 2445, the pressure within the vial 10 is substantially the same as the pressure in the interior 2472 of the flap check valve 2470. In such a situation, the pressure P2 in the interior 2472 of the flap check valve 2470 can be substantially the same as the pressure P1 in the exterior 2474 of the flap check valve 2470. In some embodiments, positioning of the vial 10 above the flap check valve 2470 can cause liquid L or other fluid to move from the vial 10 to the exterior 2474 of the flap check valve 2470. In some embodiments, the flap 2473 will remain at rest on the seat portion 2477 and create a seal 2476 when there is equilibrium in the pressure between the exterior 2474 and interior 2472 of the flap check valve. The seal 2476 can inhibit passage of liquid L and/or other fluid from the vial 10 through the flap check valve 2470.

In some embodiments, withdrawal of fluid from the vial 10 through the access channel 2445 can create lower pressure in the vial 10 and exterior 2474 of the flap check valve 2470 than the pressure in the interior 2472 of the flap check valve 2470. The pressure differential can cause the flap 2473 to move away from the seat portion 2477. The movement of the flap 2473 away from the seat portion 2477 can break the seal 2476 and permit regulator fluid FR to pass from through the interior 2472 of the flap check valve 2470 to the exterior 2474 of the flap check valve 2470. The regulator fluid FR can then pass through the regulator channel 2425 into the vial 10. In some embodiments, the regulator fluid FR is fluid which has passed through a filter in the regulator assembly 2450. In some embodiments, the regulator fluid FR is a fluid contained in the inner volume of an enclosure of the regulator assembly 2450. Passage of regulator fluid FR into the vial 10 can offset, reduce, substantially eliminate, or eliminate the pressure differential between the first exterior 2474 and interior 2472 of the flap check valve 2470 and allow the flap 2473 to return to a resting position on the seat portion 2477. In some embodiments, the passage of regulator fluid FR into the vial 10 helps to maintain equilibrium between the interior of the vial 10 and the interior of the regulator assembly 2450. The return of the flap 2473 to a resting position on the seat portion 2477 can recreate the seal 2476 and prevent passage of liquid L or other fluid from the vial 10 through the flap check valve 2470.

In some embodiments, introduction of fluid to the vial 10 through the access channel 2445 (e.g., when diluents, mixing fluids, or overdrawn fluids are injected into the vial 10 via an exchange device 40) can create higher pressure in the vial 10 and exterior 2474 of the flap check valve 2470 than the pressure within the interior 2472 of the flap check valve 2470. This difference in pressure can cause the flap 2473 to be pushed onto the seat portion 2477 and thus tighten the seal 2476. Tightening of the seal 2476 can inhibit the passage through the flap check valve 2470 of fluid L from the vial 10. In some embodiments, the tightening of the seal 2476 can cause the internal pressure within the vial 10 and the pressure P1 in the region of the exterior 2474 of the flap check valve 2470 to continue to increase as more fluid is introduced into the vial 10 via the access channel 2445. In some embodiments, a continual increase in pressure within the vial 10 can dramatically increase the force required to introduce more fluid to a prohibitive level, and eventually increase the likelihood of fluid leaks from the vial 10 and adaptor 2400 or between these components. It can therefore be desirable for the flap check valve 2470 to be in an open position when fluids are injected into the vial 10.

Movement of the flap 2473 away from the seat portion 2477 can eliminate the seal 2476 and put the flap check valve 2470 in an open configuration. In some embodiments, the opened flap check valve 2470 functions in much the same way as the opened ball check valve 2070 described above with regard to the passage of fluids through the flap check valve 2470 upon the introduction of fluid to or withdrawal of fluid from the vial 10 via the access channel 2445. In some embodiments, the regulator assembly 2450 can have many of the same keying, shaping, and/or alignment features described above with respect to the ball check valve 2070 (e.g., transparent materials, visual alignment indicators, shaped channels and/or a shaped valve).

Figure 21:
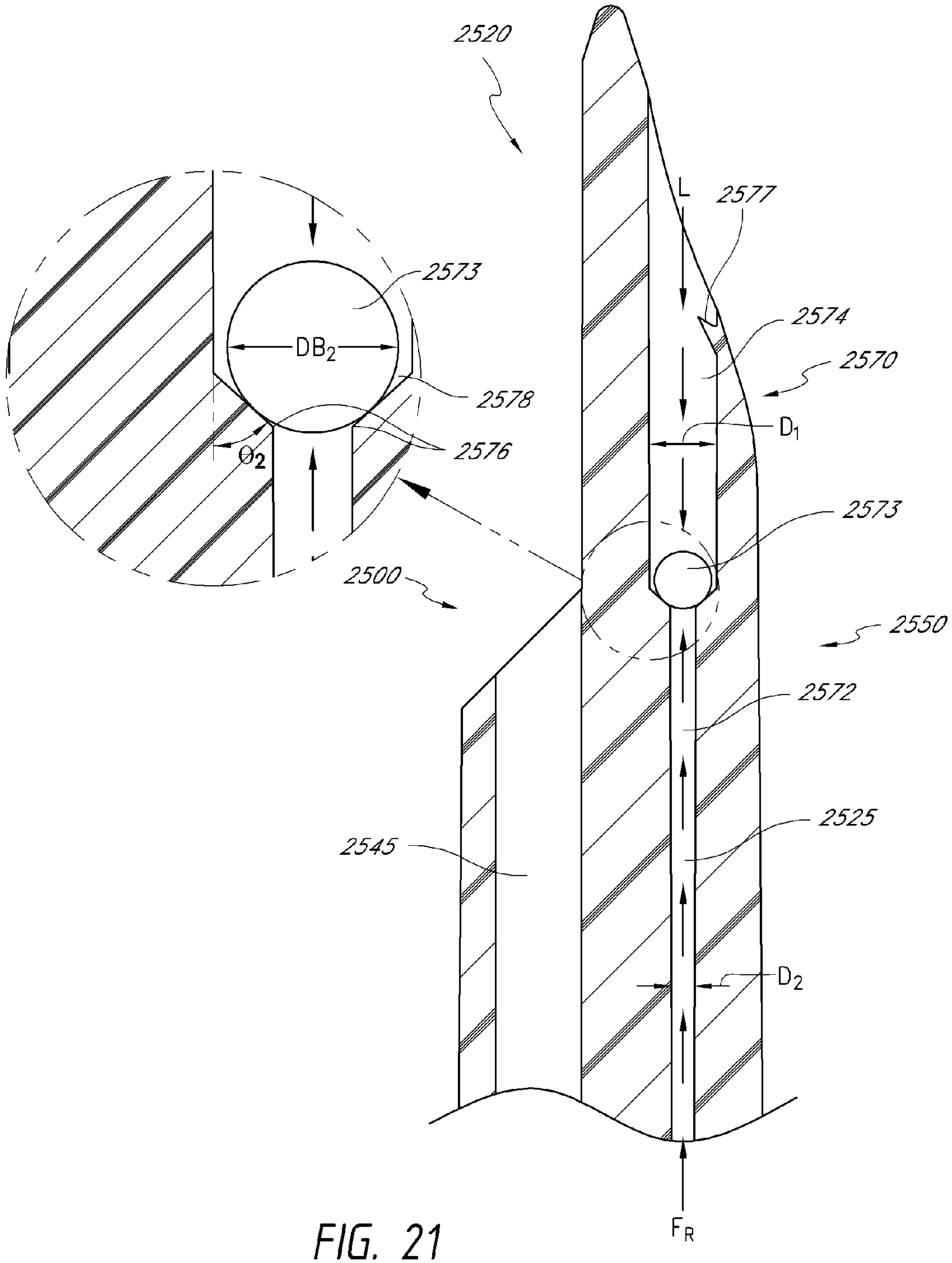
FIG. 21 illustrates a close-up cross-sectional view of a ball check valve in the piercing member of an adaptor.

FIG. 21 illustrates an embodiment of an adaptor 2500. The adaptor 2500 can include a piercing member 2520. In some embodiments, the piercing member 2520 is disposed within a vial 10. The piercing member 2520 can include an access channel 2545 in communication with an exchange device 40. In some embodiments, the piercing member 2530 includes a regulator channel 2525 which includes a gravity or orientation occluder valve, such as a ball check valve 2520. The ball check valve 2570 can include a first channel 2574 with a substantially circular cross section and a diameter D1 in fluid communication with the vial 10. In some embodiments, the ball check valve 2570 includes a second channel 2572 with a substantially circular cross section and diameter D2 in selective fluid communication with the first channel 2574. Many other variations in the structure of the first and second chambers are possible. For example, other cross-sectional shapes may be suitable.

The ball check valve 2570 can include a shoulder 2578 between the first channel 2574 and second channel 2572. In some embodiments, the angle θ2 between the shoulder 2578 and the wall of the first channel 2574 can be about 90°. In some embodiments, the angle θ2 can be less than or greater than 90°. For example, in some embodiments the angle θ2 is less than or equal to about 75° and/or greater than or equal to about 30°. In some embodiments, the second channel 2572 is in fluid communication with the first channel 2574 when the ball check valve 2570 is in an open configuration. In some embodiments, the inner wall of the first channel 2574 can gradually taper into the inside wall of the second channel 2572 such that the first and second channels 2574, 2572 constitute a single frustoconical channel.

The occluder valve can include an occluder, such as a ball 2573. In some embodiments, the ball 2573 is constructed of a material which has a higher density than the liquid L and/or other fluids within the vial 10. The ball 2573 can be spherical or some other suitable shape. In some embodiments, the ball 2573 has a diameter DB2. The diameter DB2 could be less than the diameter D1 of the first channel 2574 and more than the diameter D2 of the second channel 2572. For example, in some embodiments the ratio of the diameter DB2 of the ball 2573 to the diameter D1 of the first channel 2574 is less than or equal to about 9:10 and/or greater than or equal to about 7:10. In some embodiments the ratio of the diameter D2 of the second channel 2572 to the diameter DB2 of the ball 2573 is less than or equal to about 9:10 and/or greater than or equal to about 7:10. In some embodiments, the ball check valve 2570 can include a capture member 2577. The capture member 2577 can inhibit the ball 2570 from moving out of the first channel 2574.

In some configurations, the ball 2573 can behave in much the same way as the ball 2073 of the ball check valve 2070. For example, the ball 2573 can move within the first channel 2574 under the influence of forces in much the same way the ball 2073 can move around the first chamber 2074 of the ball check valve 2070. Resting of the ball 2573 against the shoulder 2578 of the ball check valve 2570 can create a seal 2560 which can inhibit the passage of liquid L and/or other fluids within the vial into the regulator channel 2525. In many respects, the ball check valve 2570 behaves in the same or substantially the same manner as the ball check valve 2070 under the influence of gravity, alignment of the adaptor 2570 and/or other forces.

Figure 22A:
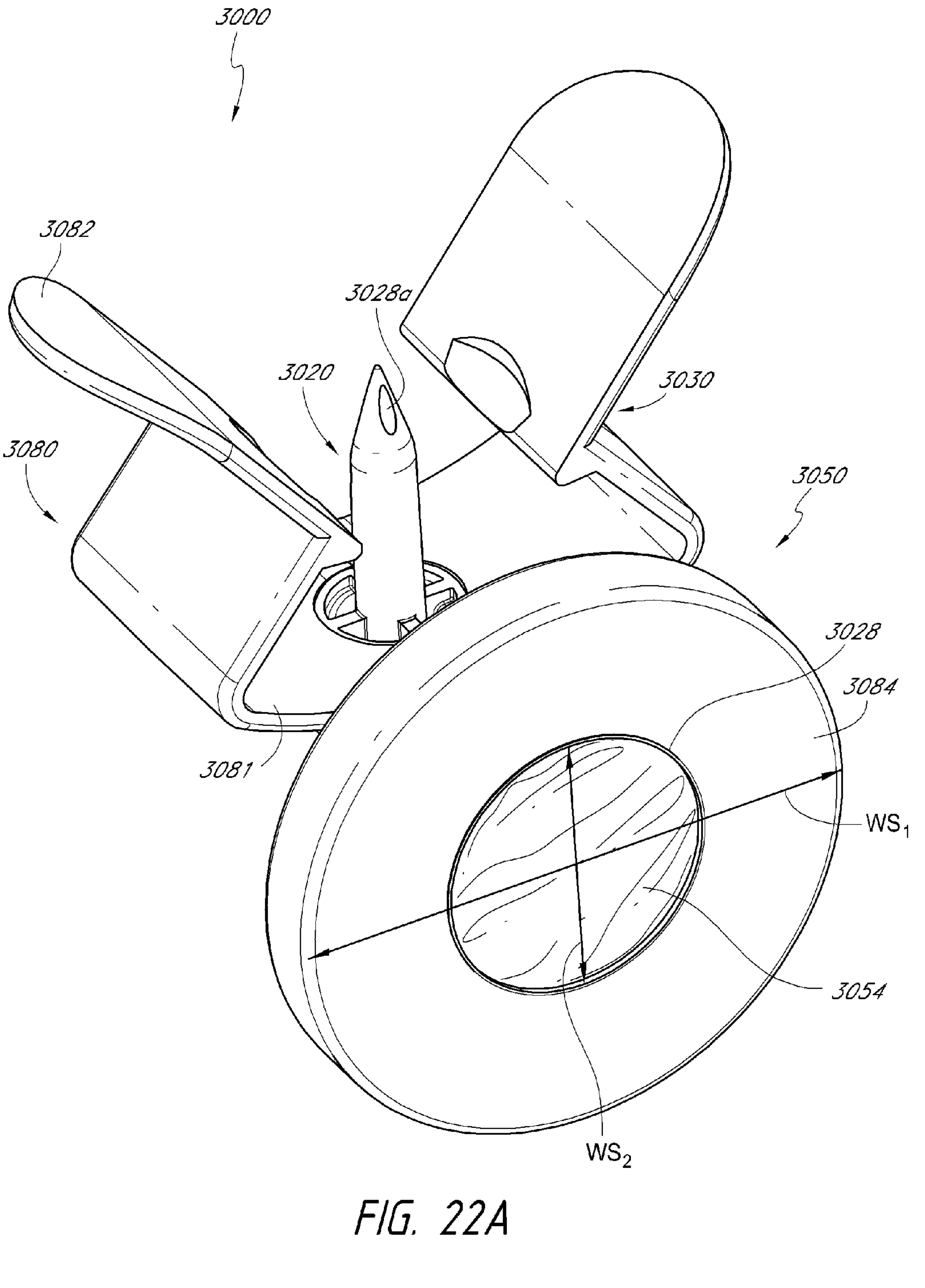
FIG. 22A illustrates a perspective view of another vial adaptor.
Figure 22B:
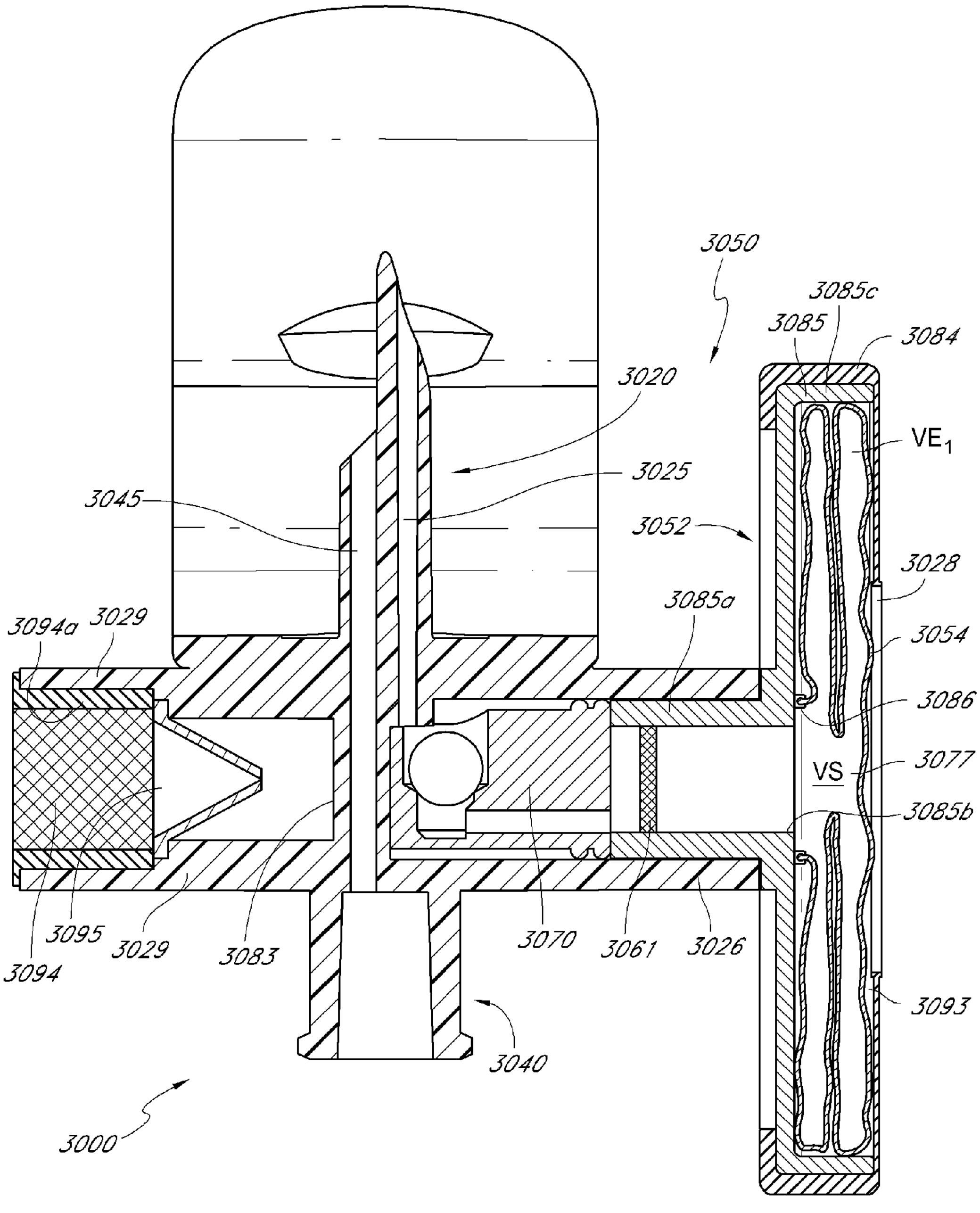
FIG. 22B illustrates a partial cross-sectional view of the vial adaptor of FIG. 22A, wherein the flexible enclosure is in the contracted position.
Figure 22C:
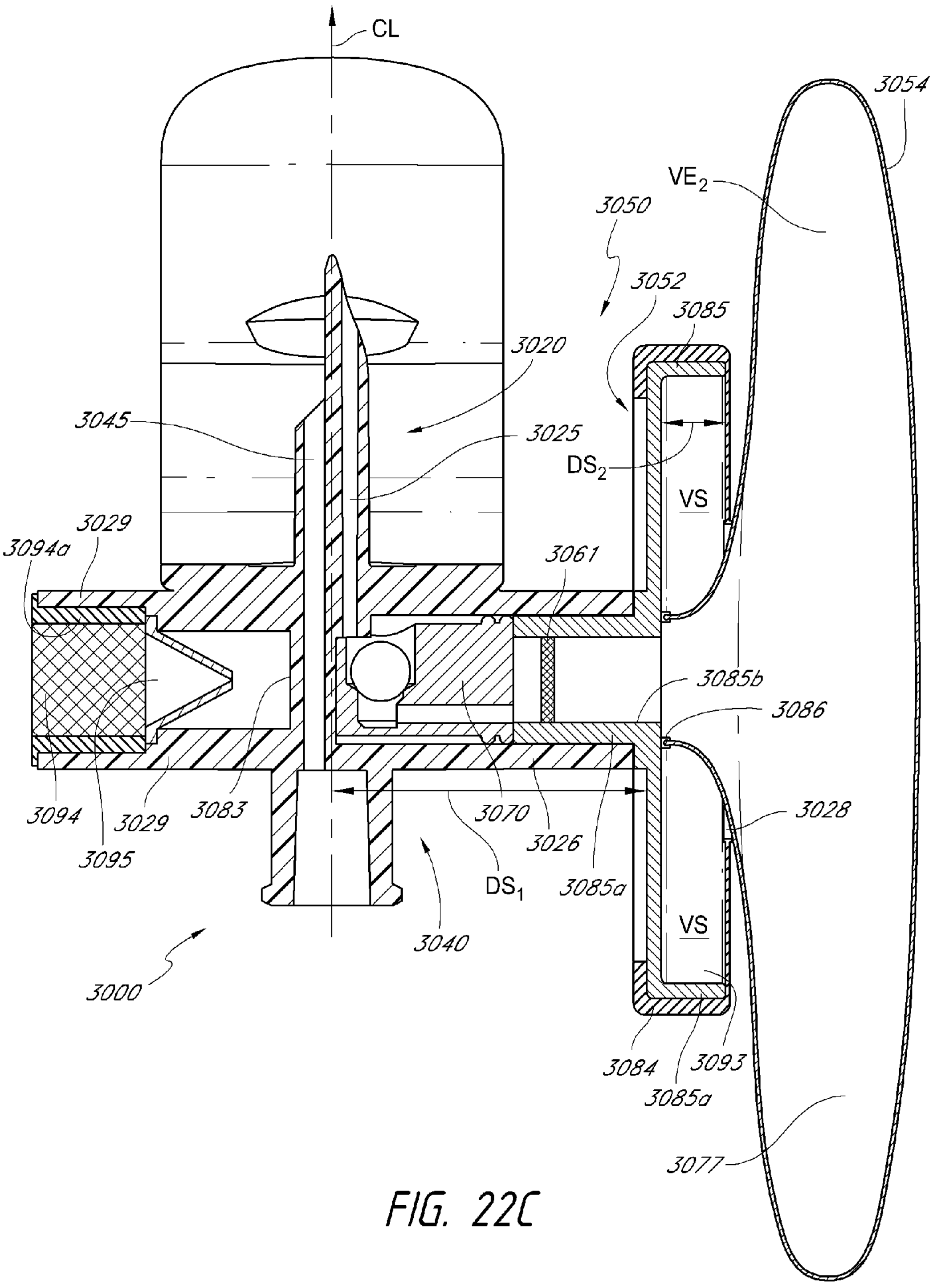
FIG. 22C illustrates a partial cross-sectional view of the vial adaptor of FIG. 22A, wherein the flexible enclosure is in the expanded position.

FIGS. 22A-22C illustrate an embodiment of a vial adaptor 3000 that can have components or portions that are the same as or similar to the components or portions of any other vial adaptors disclosed herein. In some embodiments, the vial adaptor 3000 includes a connector interface 3040 and a piercing member 3020 in partial communication with the connector interface 3040. In some embodiments, the vial adaptor 3000 includes a regulator assembly 3050. Some numerical references correspond to components in FIGS. 22A-22C that are the same as or similar to those previously described for the vial adaptors 1900 and/or 2000 (e.g., piercing member 3020 v. piercing member 2020). It is to be understood that the components can be the same in function or are similar in function to previously-described components. The adaptor 3000 of FIGS. 22A-22C shows certain variations to the adaptors 1900 and 2000 of FIGS. 26C-27D.

The piercing member 3020 can include a regulator channel 3025. In some embodiments, the regulator channel 3025 begins at a distal regulator aperture 3028*a*, passes generally through the piercing member 3020, and passes through a lumen 3026 that extends radially outward generally perpendicularly from the connector interface 3040. In certain instances, the adaptor 3000 includes a second lumen 3029 that extends radially outward from the connector interface 3040 in a direction different from that of the lumen 3026 (e.g., circumferentially offset or spaced away from). In some embodiments, the second lumen 3029 extends in a direction generally opposite that of the lumen 3026.

The adaptor 3000 can include a barrier 3083. The barrier 3083 can be positioned between the lumen 3026 and the second lumen 3029. In some embodiments, the barrier 3083 inhibits fluid communication between the lumen 3026 and the second lumen 3029. In some embodiments, the barrier 3083 includes a valve, aperture, passage, or other structure for providing fluid communication between the lumen 3026 and the second lumen 3029.

The regulator assembly 3050 can include a coupling 3052. The coupling 3052 can include a base portion 3085 and a protrusion 3085*a*. In some embodiments, at least a portion of the coupling 3052 can be constructed from thermoplastic, acrylonitrile butadiene styrene (ABS), polycarbonate, and/or some other suitable material. The base portion 3085 can have a width WS1 that is greater than the width of the protrusion 3085*a*. In some embodiments, the width WS1 can be greater than or equal to approximately 0.5 inches and/or less than or equal to approximately 5 inches. For example, the width WS1 of the base portion 3085 can be about 1.2 inches. Many variations are possible.

In some embodiments, the base portion 3085 includes a base extension 3085*c* that extends in a direction generally opposite the protrusion 3085*a*. In some embodiments, at least a portion of the base extension 3085*c* flares out in the direction generally opposite the protrusion 3085*a* (e.g., the width WS1 of the base increases in a direction away from the protrusion 3085*a*). In some embodiments, at least a portion of the base extension 3085*c* narrows in the direction generally opposite the protrusion 3085*a* (e.g., the width WS1 of the base 3085 decreases in a direction away from the protrusion 3085*a*). According to some variants, at least a portion of the base extension 3085*c* extends generally straight in the direction generally opposite the protrusion 3085*a* (e.g., the width WS1 of the base 3085 remains substantially constant in a direction away from the protrusion 3085*a*).

The protrusion 3085*a* can be configured to engage with the lumen 3026. In some embodiments, the protrusion 3085*a* is configured to removable engage with the lumen 3026 via, for example, a pressure fit, threaded coupling, or other releasable engagement. In some embodiments, the protrusion 3085*a* is attached to the lumen 3026 via an adhesive, welding, or other fixed engagement. The protrusion 3085*a* can define a protrusion lumen 3085*b*. The protrusion lumen 3085*b* can be in fluid communication with at least a portion of the lumen 3026 and/or regulator channel 3025 when the protrusion 3085*a* is engaged with the lumen 3026. In some embodiments, the width of the protrusion lumen 3085*b* can have a width that is less than the width WS1 of the base 3085. For example, the width of the protrusion lumen 3085*b* can be less than or equal to about 50% of the width WS1 of the base 3085 and/or greater than about 10% of the width WS1 of the base 3085. In some embodiments, the width of the protrusion lumen 3085*b* is approximately 25% of the width WS1 of the base 3085. Many variations are possible.

According to some variants, an enclosure cover 3084 can generally enclose or can be fitted over at least a portion of the coupling 3052. For example, as illustrated in FIGS. 22A-22C, the enclosure cover 3084 can be fitted around or generally enclose the exterior of the base 3085 of the coupling 3052. In some embodiments, the enclosure cover 3084 is constructed from a resilient, flexible, and/or stretchable material. In some embodiments, the enclosure cover 3084 is constructed from a rigid or semi-rigid material. The enclosure cover 3084 can define an expansion aperture 3028 (e.g., see FIG. 22A). The expansion aperture 3028 can have a width WS2 that is substantially smaller than the width WS1 of the base 3085 of the coupling 3052. For example, the width WS2 of the expansion aperture 3028 can be greater than or equal to about 20% of the width WS1 of the base portion 3085 and/or less than or equal to about 75% of the width WS1 of the base portion 3085. In some embodiments, the width WS2 of the expansion aperture 3028 is about 45% of the width WS1 of the base portion 3085.

The base portion 3085 and enclosure cover 3084 can combine to form a storage chamber 3093. The storage chamber 3093 can have a depth DS2. In some embodiments, the depth DS2 extends between the base portion 3085 and the portion of the enclosure cover 3084 that comprises the expansion aperture 3028 (e.g., see FIG. 22C). In some embodiments, the storage chamber 3093 has a width that is substantially equal to the width WS1 of the base portion 3085. The width of the storage chamber 3093 can be substantially less than the height of the vial 10 or other container to which the adaptor 3000 is attached. For example, in some embodiments, the width of the storage chamber 3093 can be greater than or equal to about 10% of the height of the vial 10 and/or less than or equal to about 75% of the height of the vial 10. In some embodiments, the width of the storage chamber 3093 is approximately 33% of the height of the vial 10. Many variations are possible. In some embodiments, the storage chamber 3093 can be sized and/or shaped such that the adaptor 3000 does not require a counterweight portion to balance the weight of the storage chamber 3093 to inhibit the vial 10 from tipping upon engagement between the adaptor 3000 and the vial 10.

In some embodiments, the storage chamber 3093 has a volume VS that is substantially less than the volume of the vial 10. In some embodiments, the volume VS of the storage chamber 3093 is greater than or equal to about 5% of the volume of the vial 10 and/or less than or equal to about 40% of the volume of the vial 10. In some embodiments, the volume VS of the storage chamber 3093 is approximately 15% of the volume of the vial 10. The relatively small volume VS of the storage chamber 3093 compared to the volume of the vial 10 can help reduce or eliminate the need for a counterweight on the adaptor 3000 to offset the weight of the storage chamber 3093 to maintain the balance of the vial 10 when the adaptor 3000 is connected to the vial.

The radial distance DS1 between the base portion 3085 and an axial centerline CL of the connector interface 3040 can be less than or substantially equal to the radial distance between the axial centerline CL of the interface 3040 and the radially-outward surface of the vial 10 when the adaptor 3000 is engaged with the vial 10. In some embodiments, the radial distance DS1 is greater than or equal to approximately 75% of the radial distance between the axial centerline CL of the interface 3040 and the radially-outward surface of the vial 10 and/or less than or equal to approximately 125% of the radial distance between the axial centerline CL of the interface 3040 and the radially-outward surface of the vial 10. In some embodiments, the radial distance DS1 is approximately 90% of the radial distance between the axial centerline CL of the interface 3040 and the radially-outward surface of the vial 10. The depth DS2 of the storage chamber 3093 can be approximately 20% of the radial distance DS1. In some embodiments, the sum of the radial distance DS1 and the depth DS2 is greater than or equal to approximately 85% of the radial distance between the axial centerline CL of the interface 3040 and the radially-outward surface of the vial 10 and/or less than or equal to approximately 140% of the radial distance between the axial centerline CL of the interface 3040 and the radially-outward surface of the vial 10. In some embodiments, the sum of the radial distance DS1 and the depth DS2 is approximately 105% of the radial distance between the axial centerline CL of the interface 3040 and the radially-outward surface of the vial 10.

In some embodiments, the coupling 3052 includes a flexible enclosure 3054. The flexible enclosure 3054 can be constructed from a flexible and/or stretchable material. The flexible enclosure 3054 can be fixed to a portion of the coupling 3052 at an enclosure attachment point 3086. For example, the flexible enclosure 3054 can be attached to the coupling at or near the interface between the protrusion lumen 3085*b* and the storage chamber 3093. In some embodiments, the flexible enclosure 3054 is attached to the coupling 3052 via welding, adhesive, or another coupling that provides a seal to inhibit fluid from passing into or out of the flexible enclosure 3054 through the attachment point 3086. For example, the flexible enclosure 3054 can be attached to the coupling via double-sided foam tape or some other suitable adhesive. Many variations are possible.

In some embodiments, an outer surface area (e.g., the surface area of the enclosure 3054 that is not in contact with a regulator fluid) of the enclosure 3054 can be greater than or equal to approximately 10 square inches and/or less than or equal to approximately 50 square inches. For example, in some embodiments, the outer surface area of the enclosure 3054 is approximately 23 square inches. Many variations are possible. In some embodiment, wherein the enclosure 3054 is constructed of a stretchy material, the outer surface area of the enclosure 3054 can vary over time depending on the extent to which the material of the enclosure 3054 is stretched and/or contracted.

The flexible enclosure 3054 can be configured to transition between a primarily interior or contracted configuration (e.g., FIG. 22B) and a primarily exterior or expanded configuration (e.g., FIG. 22C). In some embodiments, the diameter or cross-sectional area of the enclosure 3054 in the expanded or primarily exterior configuration is greater than or equal to about 1 inch and or less than or equal to about 8 inches. In some embodiments, the diameter or cross-sectional area of the enclosure 3054 in the expanded configuration is approximately 3.8 inches. Many variations for the diameter of the expanded enclosure 3054 are possible. The flexible enclosure 3054 can have a contracted volume VE1 when in the contracted position. The contracted volume VE1 can be less than or substantially equal to the volume VS of the storage chamber 3093. In some cases, the volume VS of the storage chamber 3093 can be greater than or equal to about 1.5 milliliters and/or less than or equal to about 10 milliliters. In some embodiments, the volume VS of the storage chamber 3093 is about 2.3 milliliters. Many variations are possible.

In some embodiments, the flexible enclosure 3054 can be folded, packed, compressed, or otherwise transitioned into a compact state when in the contacted configuration. The compacted enclosure 3054 can be inserted into and housed within the storage chamber 3093. In some embodiments, wherein the width WS2 of the expansion aperture 3028 is less than the width WS1 of the base portion 3085, the enclosure cover 3084 can inhibit accidental contact between outside instruments and/or personnel and the flexible enclosure 3054 when the flexible enclosure 3054 is housed within the storage chamber 3093. Limiting contact with the flexible enclosure 3054 can help reduce the likelihood of punctures, tearing, or other damage to the flexible enclosure 3054.

In some embodiments, the flexible enclosure 3054 transitions to the expanded or primarily exterior configuration upon introduction or diluent or other fluid to the vial 10 via an access channel 3045 in the piercing member 3020. As fluid is delivered to the vial 10, the pressure within the vial 10 can increase. Increasing pressure within the vial 10 can force fluid through the regulator channel 3025 and into the flexible enclosure 3054. The flexible enclosure 3054 can unfold and/or expand as fluid enters the flexible enclosure 3054. As illustrated in FIG. 33C, at least a portion of the flexible enclosure 3054 can extend outside of the storage chamber 3093 as the flexible enclosure 3054 transitions from the contracted to the expanded configuration. The enclosure cover 3084 can be configured to flex in the vicinity of the expansion aperture 3028 as the flexible enclosure 3054 expands outside of the storage chamber 3093. Flexure of the enclosure cover 3084 can help reduce the likelihood that the flexible enclosure 3054 is damaged upon expansion through the expansion aperture 3028.

As illustrated in FIG. 22C, in some embodiments, the outer circumference or perimeter of the flexible enclosure 3054 in the expanded or primarily exterior state can be substantially larger than the outer circumference or perimeter of the generally rigid base portion 3085 and/or the outer perimeter of the flexible or resilient enclosure cover 3084. In some embodiments, as illustrated, the front surface of the flexible enclosure 3054 in the expended or primarily exterior state can be displaced laterally substantially farther than the front surface or front edge of the base portion 3085 and/or the front surface or front edge of the enclosure cover 3084. For example, the distance from the front surface or front edge of the base portion 3085, and/or the front surface or front edge of the enclosure cover 3084, to the front surface of the flexible enclosure 3054 can be substantially greater than or equal to the thickness DS2 of the storage chamber 3093, as shown.

In some embodiments, as illustrated in FIG. 22C, the majority of the volume inside of the flexible enclosure 3054 in the expanded or primarily exterior state is positioned outside of the base portion 3085 and/or outside of the enclosure 3054. In the example shown in FIG. 22C, the flexible enclosure 3054 is not positioned within or generally within a rigid housing in the expanded or primarily exterior state.

As shown in FIG. 22C, in some embodiments, the flexible enclosure 3054 has a front surface and a rear surface in the expanded or primarily exterior state. The front surface is separate from and spaced from the rear surface. Each of the front and rear surfaces can comprise a generally convex shape. As illustrated, the front surface can be positioned entirely outside of the base portion 3085 and/or of the enclosure 3054, and a portion of or a majority of the rear surface can be positioned outside of the base portion 3085 and/or of the enclosure 3054.

As illustrated in FIG. 22C, the flexible enclosure 3054 comprises a rear opening that can contact the rearmost surface of the base portion 3085 or the rearmost surface of the storage chamber 3093. The diameter or cross-sectional area of the opening of the flexible enclosure 3054 can be substantially smaller than the largest diameter or cross-sectional area of the flexible enclosure 3054. In some embodiments, as illustrated, the air or other fluid within the flexible enclosure 3054 is not in communication with air or other fluid within the remainder of the storage chamber 3093. The flexible enclosure 3054 can be configured as shown such that: (a) it begins in a first region at the attachment point between the flexible enclosure 3054 and the storage chamber 3093; (b) it moves in a first direction upon expansion of the interior fluid (such as air); (c) in the contraction phase, it returns in a second direction that is generally opposite from the first direction toward the first region; and (d) it stops at or near the first region during or at the conclusion of the contraction phase and it does not extend further in the second direction beyond the first region during or after the contraction phase.

According to some variants, expansion of the flexible enclosure 3054 can help to maintain substantially constant pressure within the vial 10. The flexible enclosure 3054 can be sized and shaped such that the expanded volume VE2 of the enclosure 3054 (e.g., the maximum capacity of the flexible enclosure 3054) is greater than about 25% of the volume of the vial 10 and/or less than about 75% of the volume of the vial 10. In some embodiments, the expanded volume VE2 of the flexible enclosure 3054 is approximately 50% of the volume of the vial 10. Many variations on the relative size of the expanded volume VE2 of the flexible enclosure compared to the volume of the vial 10 are possible. In some embodiments, the expanded volume VE2 of the enclosure 3054 is greater than or equal to about 25 milliliters and/or less than or equal to about 200 milliliters. For example, in some embodiments, the expanded volume VE2 of the enclosure 3054 is about 100 milliliters. Many variations are possible.

Withdrawal of fluid from the vial 10 via the access channel 3045 can create a pressure deficit within the regulator channel 3025 as the pressure within the vial 10 is decreased. Creation of a pressure deficit within the regulator channel 3025 can pull at least a portion of the fluid from the expanded flexible enclosure 3054 into the vial 10. In some such embodiments, transfer of fluid from the flexible enclosure 3054 to the vial 10 can help to maintain substantially constant pressure within the vial 10.

In some embodiments, a filter 3061 can be interposed between the regulator aperture 3028*a* and the flexible enclosure 3054. For example, the filter 3061 can be positioned within the extension aperture 3085*b*. In some embodiments, the filter 3061 is positioned within the lumen 3026. The filter 3061 can be a hydrophobic and/or antimicrobial filter. In some embodiments, the filter is constructed from sintered polyethylene or some other suitable material. In some cases, the filter 3061 can inhibit the passage of liquid from the vial to the flexible enclosure.

The regulator assembly 3050 can include a valve 3070. The valve 3070 can be positioned within the regulator channel 3025 and/or within the extension lumen 3085*b*. The valve 3070 can be a ball check valve similar to or substantially the same as ball check valve 2070 described above. In some embodiments, the valve 3070 is similar to or the same as the ball check valve 2070', ball check valve 2170, domed valve 2270, showerhead domed valve 2370, flap check valve 2470, ball check valve 2570, or any other suitable valve disclosed herein or otherwise. The valve 3070 can inhibit the passage of liquid from the vial 10 into the flexible enclosure 3054.

Withdrawal of fluid from the vial 10 prior to expansion of the flexible enclosure 3054 can create a pressure deficit within the regulator channel 3025 as the pressure within the vial 10 is decreased. Creation of a pressure deficit within the regulator channel 3025 can "pull" the flexible enclosure 3054 toward the extension lumen 3085*b* due to the pressure gradient between the interior of the flexible enclosure 3054 and the exterior of the flexible enclosure 3054. In some embodiments, as explained above, the flexible closure 3054 is folded when in the initial contracted configuration. In some embodiments, the folding/layering of the flexible enclosure 3054 and/or the material properties of the flexible enclosure 3054 can inhibit the flexible enclosure 3054 from being pulled into the extension lumen 3085*b*.

In some embodiments, the second lumen 3029 is in fluid communication with the regulator channel 3025 and vial 10. In some embodiments, a one-way valve 3095 (e.g., a duckbill valve, a dome valve, or similar valve) is located within the second lumen 3029. The one-way valve 3095 can be configured to inhibit fluid from passing out of the adaptor 3000 via the second lumen 3029. In some embodiments, the one-way valve 3095 is configured to permit fluid passage through the one-way valve 3095 into the lumen 3029 from the exterior of the adaptor 3000 when a pre-determined pressure gradient (e.g., a cracking pressure) is applied to the one-way valve 3095. For example, the one-way valve 3095 can be configured to permit fluid passage into the vial 10 when fluid is removed from the vial 10 via the access channel 3045 and the flexible enclosure 3054 is in the contracted configuration. In some such configurations, the passage of fluid through the one-way valve 3095 into the vial 10 can help to maintain a substantially constant pressure within the vial 10 upon withdrawal of fluid from the vial 10.

In some embodiments, a filter 3094 can be positioned between ambient and the one-way valve 3095. The filter 3094 can be a hydrophobic and/or antimicrobial filter. In some embodiments, the filter 3094 can inhibit the passages of germs or other contaminants from ambient into the vial 10 via the one-way valve 3095. In some embodiments, the filter 3094 is held in place at least partially within the lumen 3029 by a filter retainer 3094*a*. In some embodiments, the filter retainer 3094*a* retains the one-way valve 3095 in place within the lumen 3029.

Figure 22D:
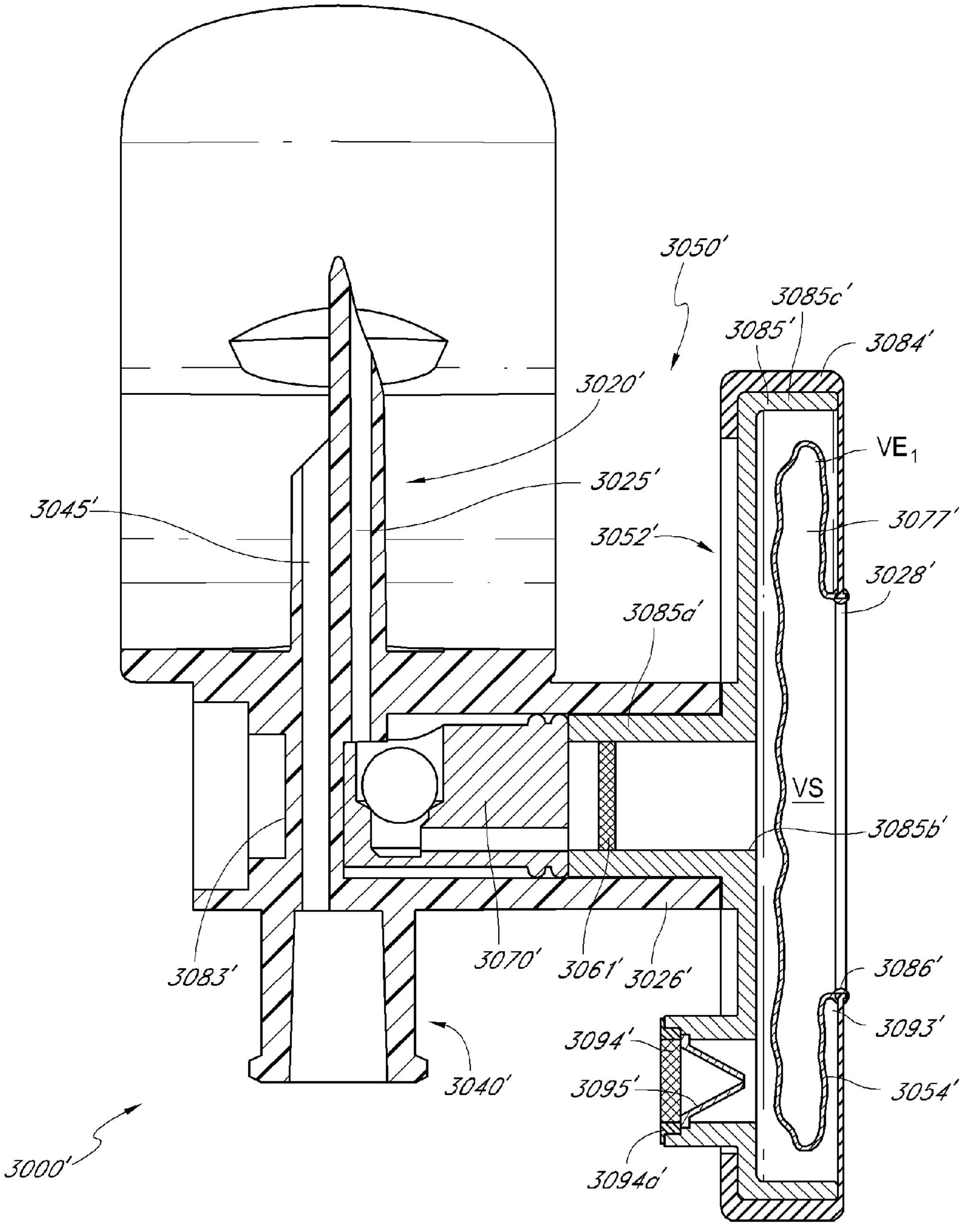
FIG. 22D illustrates a partial cross-sectional view of another vial adaptor, wherein the flexible enclosure is in the contracted position.

FIG. 22D illustrates an embodiment of an adaptor 3000' and a coupling 3052'. Numerical reference to components is the same as previously described, except that a prime symbol (') has been added to the reference. Where such references occur, it is to be understood that the components are the same or substantially similar to previously-described components unless otherwise indicated. For example, the coupling 3052' can include a flexible enclosure 3054'. In some embodiments, the coupling 3052' includes an enclosure cover 3084' that defines an expansion aperture 3028'. The coupling 3052' and cover 3084' can define a storage chamber 3093' configured to house the flexible enclosure 3054' when the flexible enclosure 3054' is in a contracted configuration. The flexible enclosure 3054' can be connected to the cover 3084' at or near the expansion aperture 3028'. In some embodiments, the flexible enclosure 3054' is attached to a base portion 3085' of the coupling 3052'.

The coupling 3052' can include a valve 3095' that is structurally and/or functionally similar to or identical to the valve 3095 described above. The valve 3095' can provide selective fluid communication between ambient and storage chamber 3093'. In some embodiments, a filter 3095' is positioned between the valve 3095' and ambient. The filter 3095' can be held in place by a filter retainer 3095*a'*.

Figure 22E:
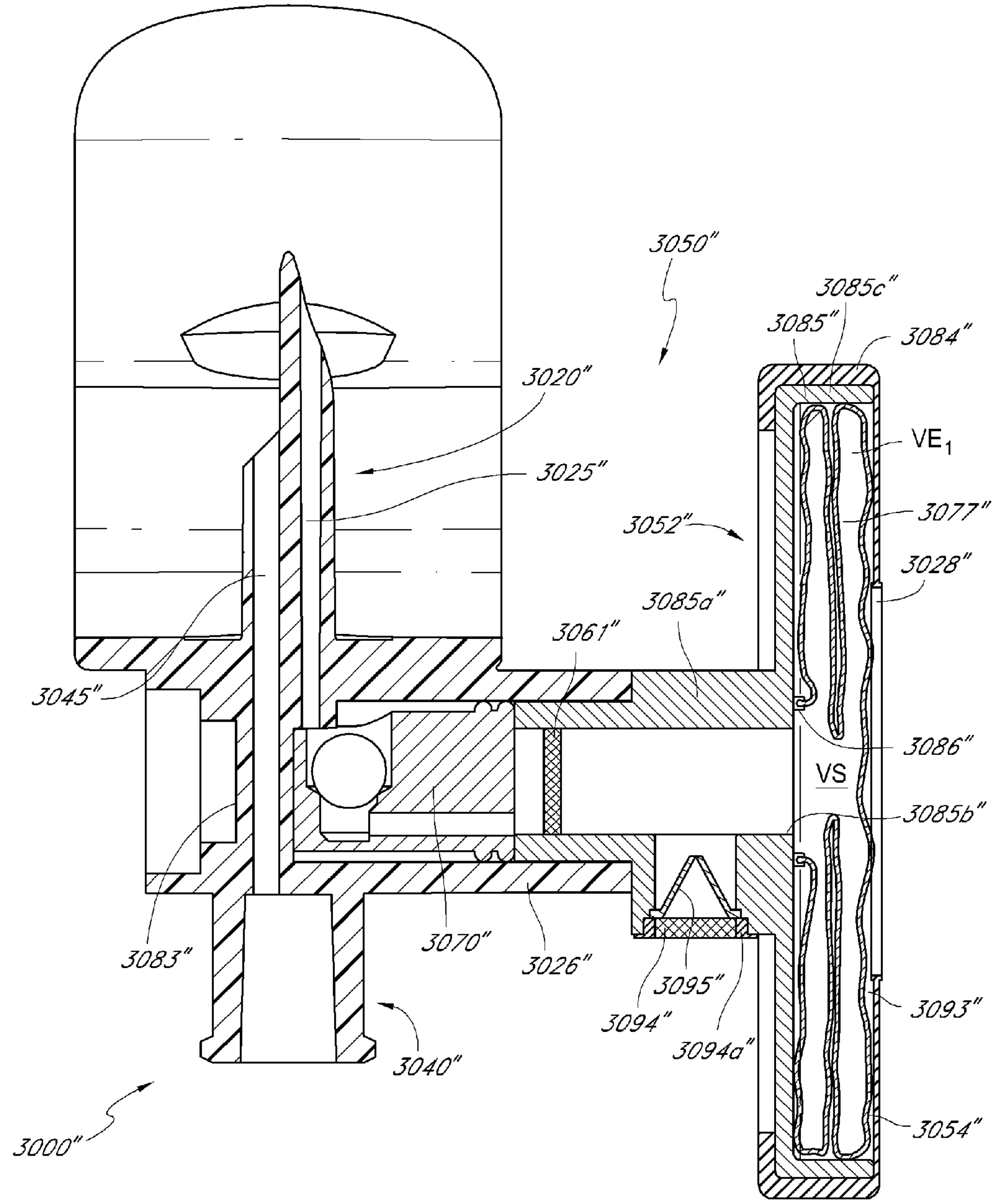
FIG. 22E illustrates a partial cross-sectional view of another vial adaptor, wherein the flexible enclosure is in the contracted position.

FIG. 22E illustrates an embodiment of an adaptor 3000" and a coupling 3052". Corresponding numerical references for components that are the same as or similar to those previously described are used, except that a prime symbol (") has been added to the reference. Where such references occur, it is to be understood that the components are the same or substantially similar to previously-described components unless otherwise indicated. For example, the coupling 3052" can include a flexible enclosure 3054". In some embodiments, the coupling 3052" includes an enclosure cover 3084" that defines an expansion aperture 3028". The coupling 3052" and cover 3084" can define a storage chamber 3093" configured to house the flexible enclosure 3054" when the flexible enclosure 3054" is in a contracted configuration. The coupling 3052" can include a protrusion 3085*a*" configured to engage with a lumen 3026" of the adaptor 3000". In some embodiments, the protrusion 3085*a*" includes a valve 3095". The valve 3095" can be structurally and/or functionally similar to or identical to the valve 3095 described above. The valve 3095" can be configured to selectively allow fluid communication between ambient and the storage chamber 3093".

Figure 23A:
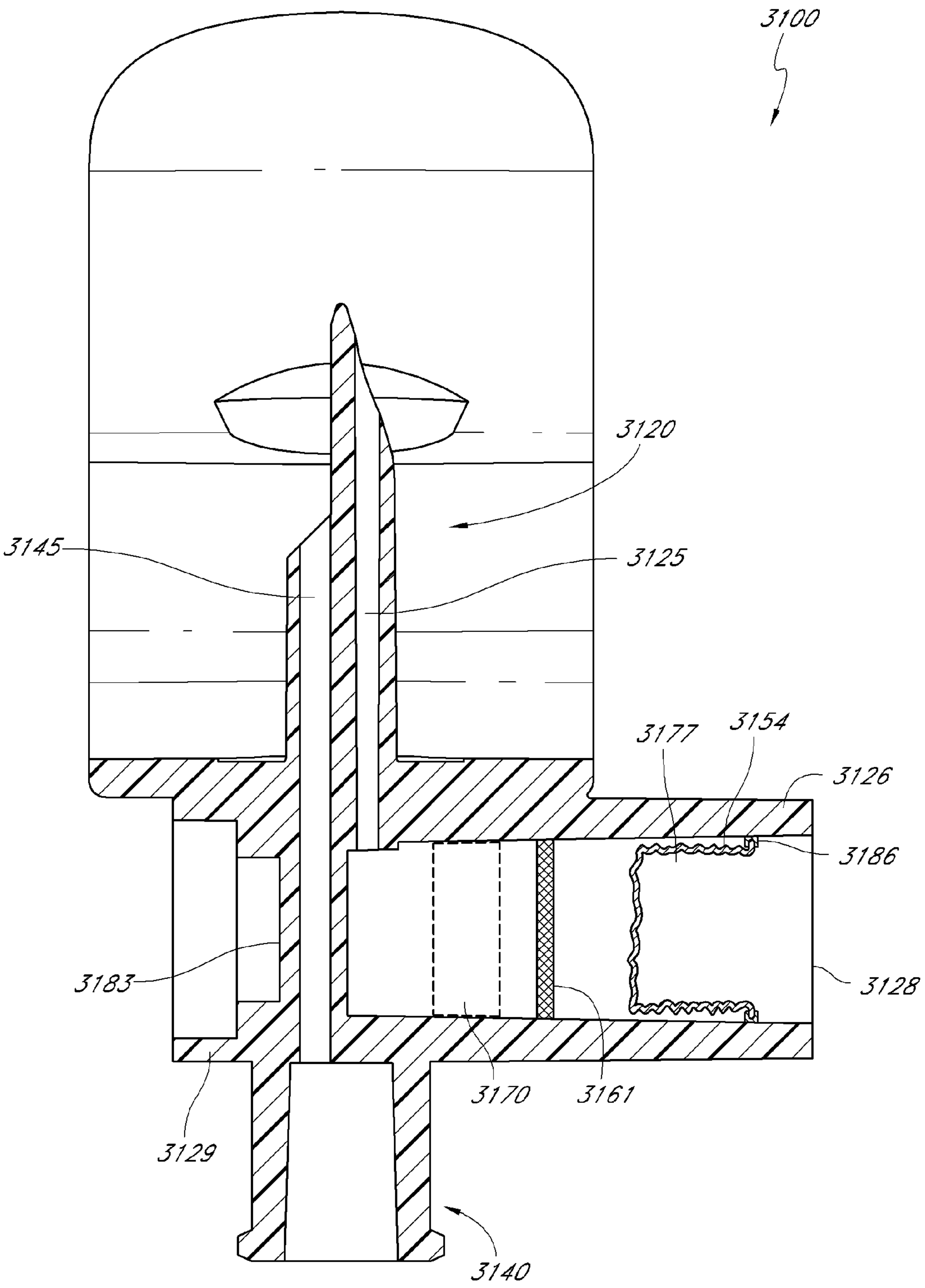
FIG. 23A illustrates a partial cross-sectional view of another vial adaptor, wherein the flexible enclosure is in the contracted position.
Figure 23B:
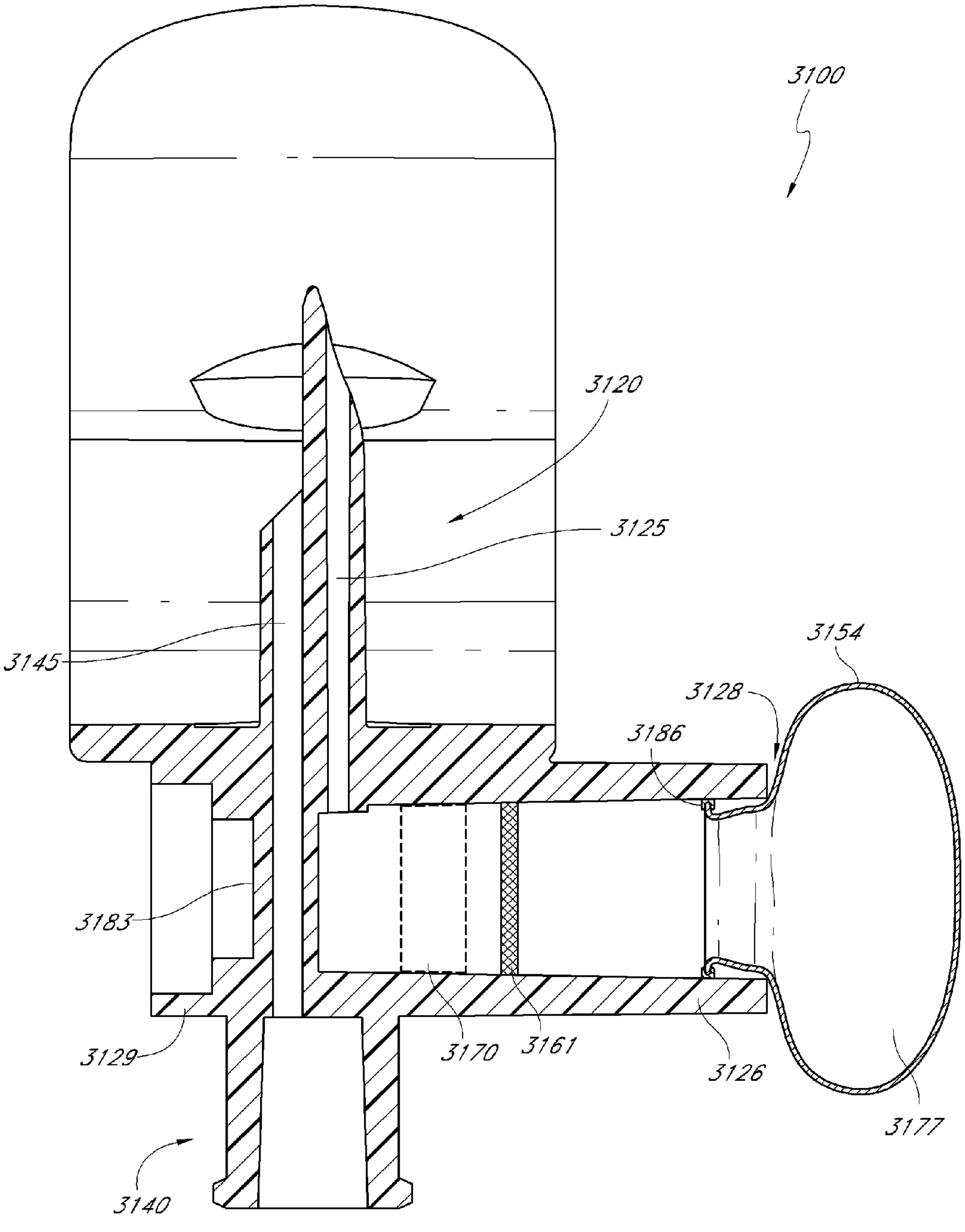
FIG. 23B illustrates a partial cross-sectional view of the vial adaptor of FIG. 23A, wherein the flexible enclosure is in the expanded position.

FIGS. 23A-23B illustrate an embodiment of a vial adaptor 3100 that can have components or portions that are the same as or similar to the components or portions of other vial adaptors disclosed herein. In some embodiments, the vial adaptor 3100 includes a connector interface 3140 and a piercing member 3120 in partial communication with the connector interface 3140. In some embodiments, the vial adaptor 3100 includes a regulator assembly 3150. Some numerical references to components in FIGS. 23A-23B are the same as or similar to those previously described for the vial adaptor 3000 (e.g., piercing member 3120 v. piercing member 3020). It is to be understood that the components can be the same in function or are similar in function to previously-described components. The adaptor 3100 of FIGS. 23A-23B shows certain variations to the adaptor 3000 of FIGS. 22A-22C.

The adaptor 3100 can include a flexible enclosure 3154 at least partially housed within a lumen 3126 that extends radially outward from the connector interface 3140. In some embodiments, the flexible enclosure 3154 transitions from a contracted configuration (e.g., see FIG. 23A) to an expanded configuration (e.g., see FIG. 23B) when fluid is introduced to a vial 10 via an access channel 3145 in the piercing member 3120 when the adaptor 3100 is coupled with the vial 10. Upon withdrawal of fluid from the vial 10 via the access channel 3145, the flexible enclosure 3154 can transition to the contracted configuration. In some embodiments, expansion and/or contraction of the flexible enclosure 3154 helps to maintain a substantially constant pressure in the vial 10 as fluid is introduced into and withdrawn from the vial 10 via the access channel 3145.

In some embodiments, the adaptor 3100 includes a valve 3170. The valve 3170 can be positioned within the regulator channel 3125 and/or within the lumen 3126. In some embodiments, the valve 3170 is similar to or the same as the ball check valve 2070, ball check valve 2070', ball check valve 2170, domed valve 2270, showerhead domed valve 2370, flap check valve 2470, ball check valve 2570, and/or any other suitable valve disclosed herein or otherwise. The valve 3170 can inhibit the passage of liquid from the vial 10 into the flexible enclosure 3154.

A filter 3161 can be positioned within the regulator channel 3125 and/or within the lumen 3126. The filter 3161 can be hydrophobic and/or antimicrobial. In some embodiments, the filter 3161 prevents liquid from passing between the interior of the vial 10 and the interior of flexible enclosure.

Figure 24A:
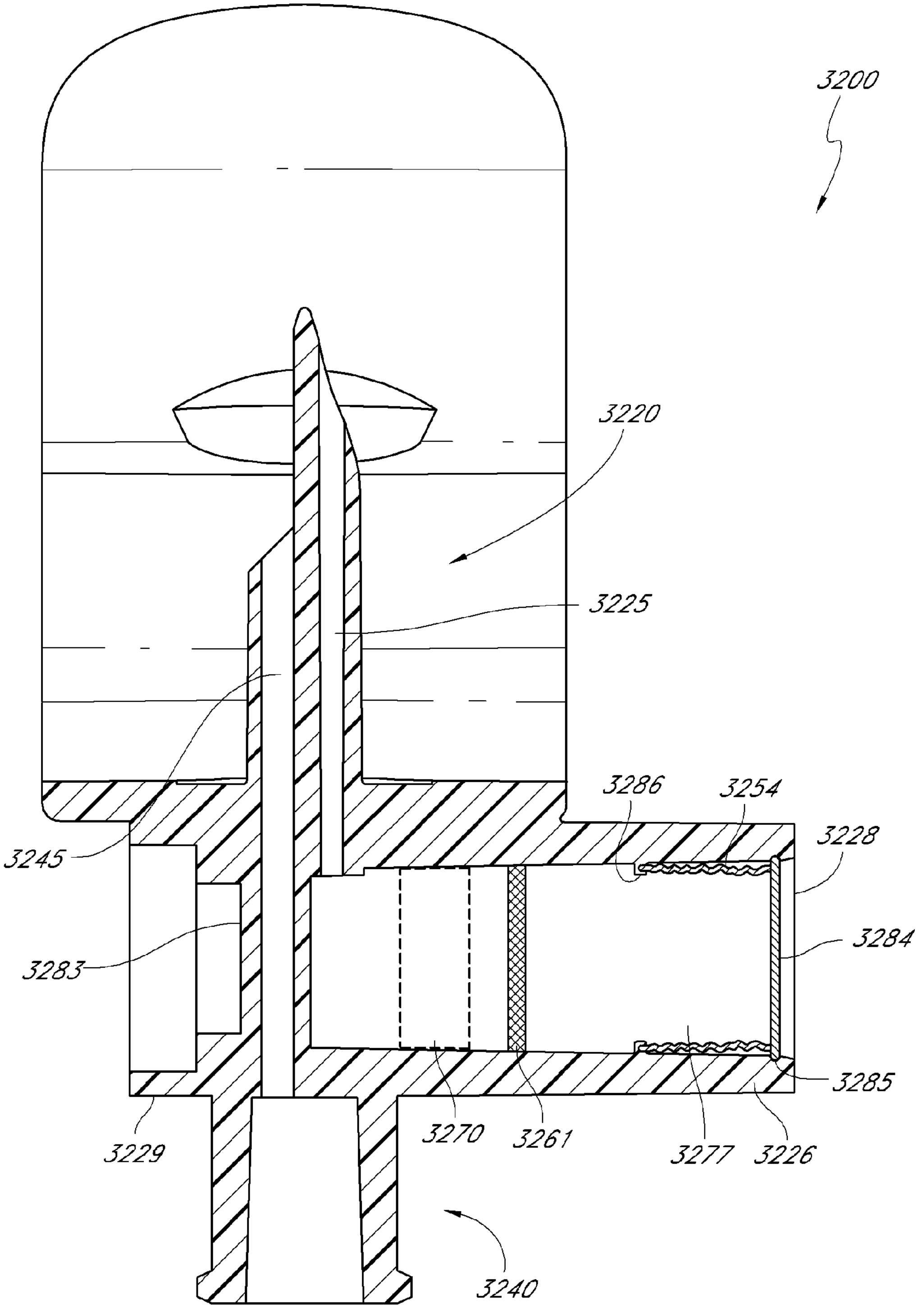
FIG. 24A illustrates a partial cross-sectional view of another vial adaptor, wherein the flexible enclosure is in the contracted position.
Figure 24B:
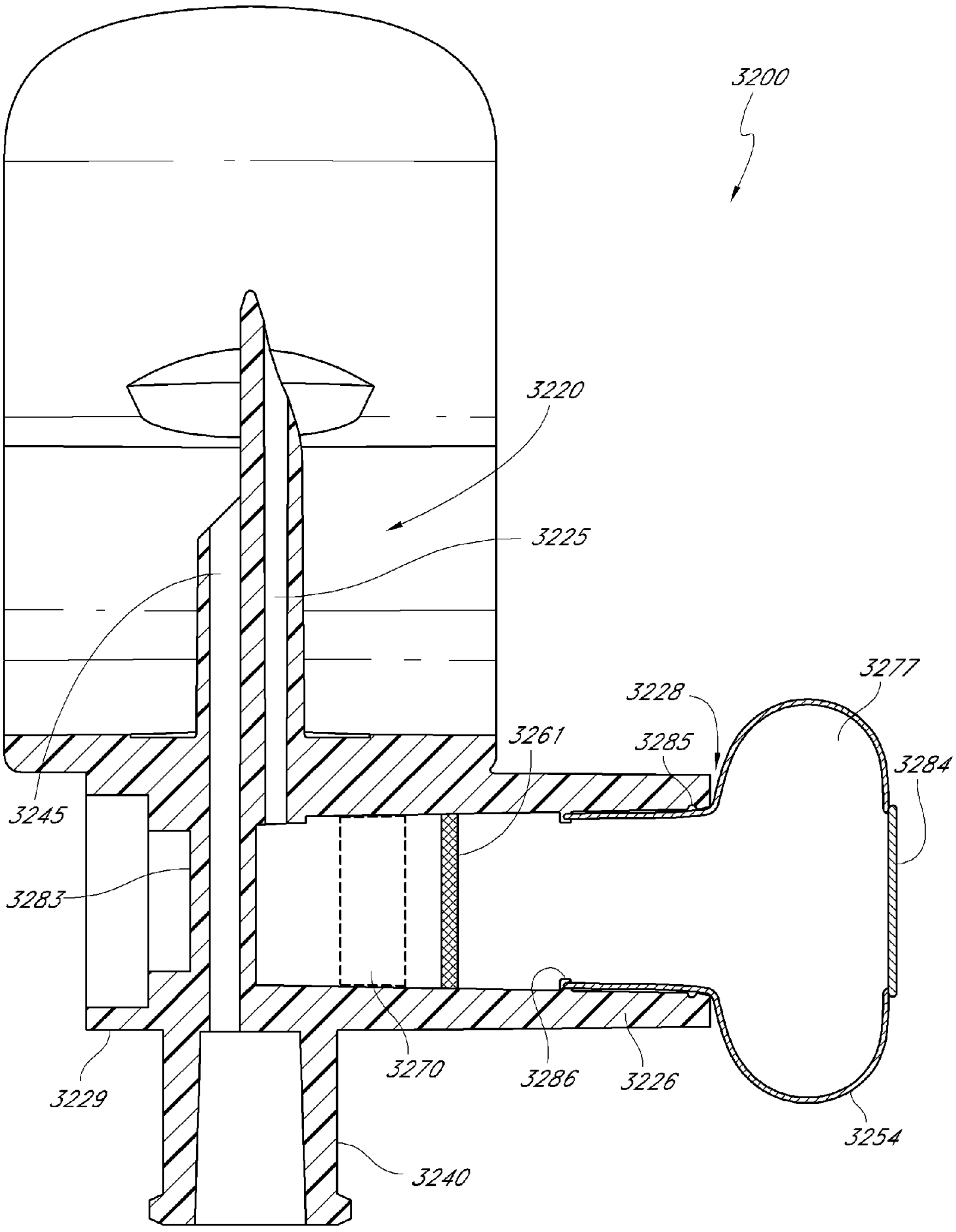
FIG. 24B illustrates a partial cross-sectional view of the vial adaptor of FIG. 4A, wherein the flexible enclosure is in the expanded position.

FIGS. 24A-24B illustrate an embodiment of a vial adaptor 3200 that can have components or portions that are the same as or similar to the components or portions of other vial adaptors disclosed herein. In some embodiments, the vial adaptor 3200 includes a connector interface 3240 and a piercing member 3220 in partial communication with the connector interface 3240. In some embodiments, the vial adaptor 3200 includes a regulator assembly 3250. Some numerical references to components in FIGS. 24A-24B are the same as or similar to those previously described for the vial adaptor 3100 (e.g., piercing member 3220 v. piercing member 3120). It is to be understood that the components can be the same in function or are similar in function to previously-described components. The adaptor 3200 of FIGS. 24A-24B shows certain variations to the adaptor 3100 of FIGS. 23A-23B.

The vial adaptor 3200 can include a flexible enclosure 3254. The flexible enclosure can include an enclosure cover portion 3284. The enclosure cover portion 3284 can be constructed of a resilient and/or semi-rigid material. In some embodiments, the enclosure cover portion 3284 is attached to the flexible enclosure 3254 via adhesives, welding, or some other fluid-tight attachment. In some embodiments, the cover portion 3284 is integrally formed with the flexible enclosure 3254.

The cover portion 3284 can be configured to releasably engage with one or more cover engagement features of the lumen 3226. For example, the cover engagement features 3285 can be one or more annular or semi-annular recesses 3285 within the lumen 3226. The cover portion 3284 can be configured to sit within the one or more recesses 3285 such that, upon an increase in pressure within the regulator channel 3225 (e.g., when fluid is introduced via an access channel 3245 of the adaptor 3200 into the vial 10 to which the adaptor 3200 is connected), the cover portion 3284 is flexed and pushed out of the one or more recesses 3285 and out of the lumen 3226. Release of the cover portion 3284 from the one or more recesses 3285 and out of the lumen 3226 can permit the flexible enclosure 3254 to transition to the expanded configuration (e.g., see FIG. 24B).

In some embodiments, the one or more recesses 3285 are configured such that the pressure differential needed to move the cover portion 3284 out of the one or more recesses 3285 in a direction radially away from the connector interface 3240 is less than the pressure differential need to move the cover portion 3284 out of the one or more recesses 3285 in a direction radially toward from the connector interface 3240.

Figure 25A:
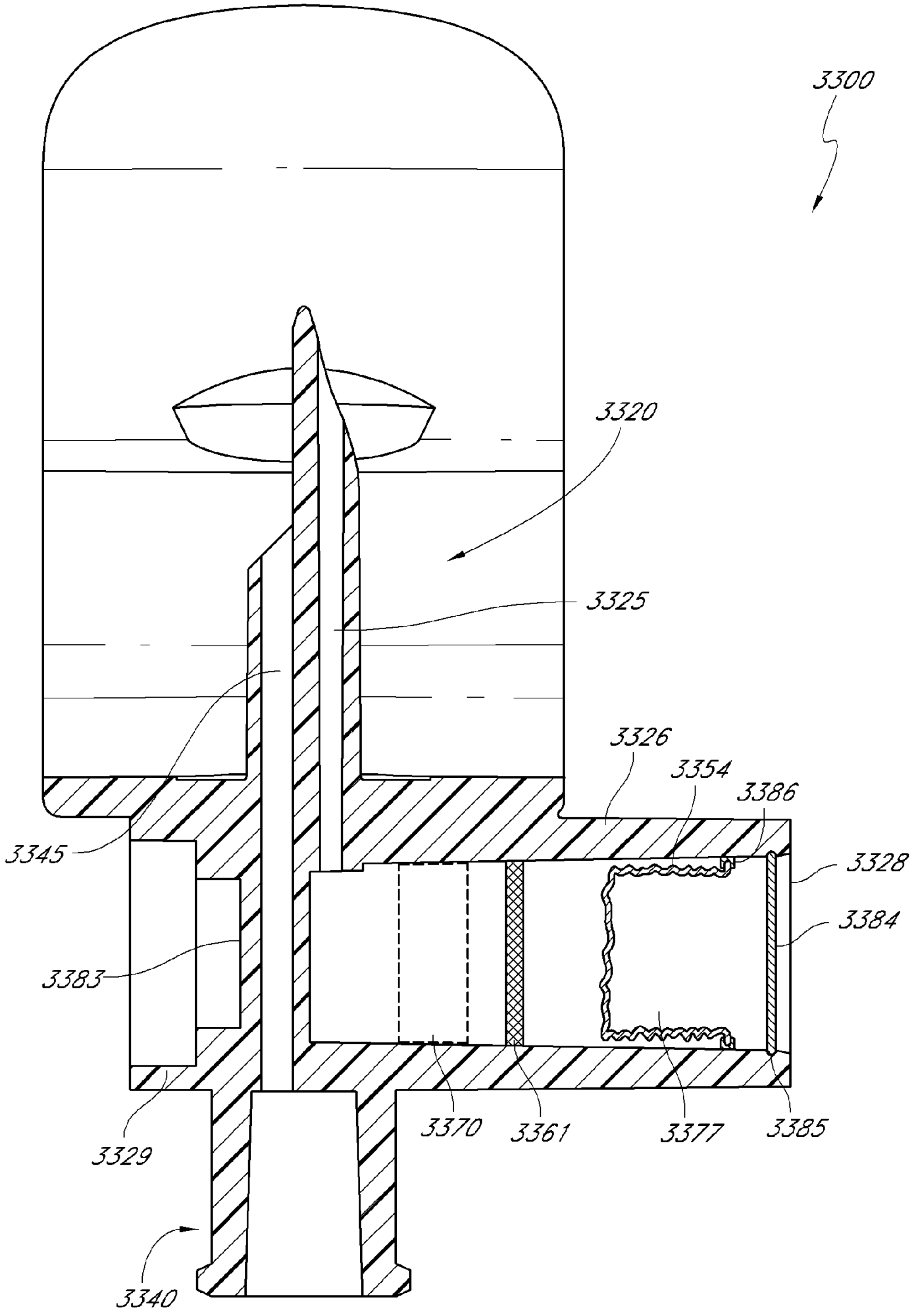
FIG. 25A illustrates a partial cross-sectional view of another vial adaptor, wherein the flexible enclosure is in the contracted position.
Figure 25B:
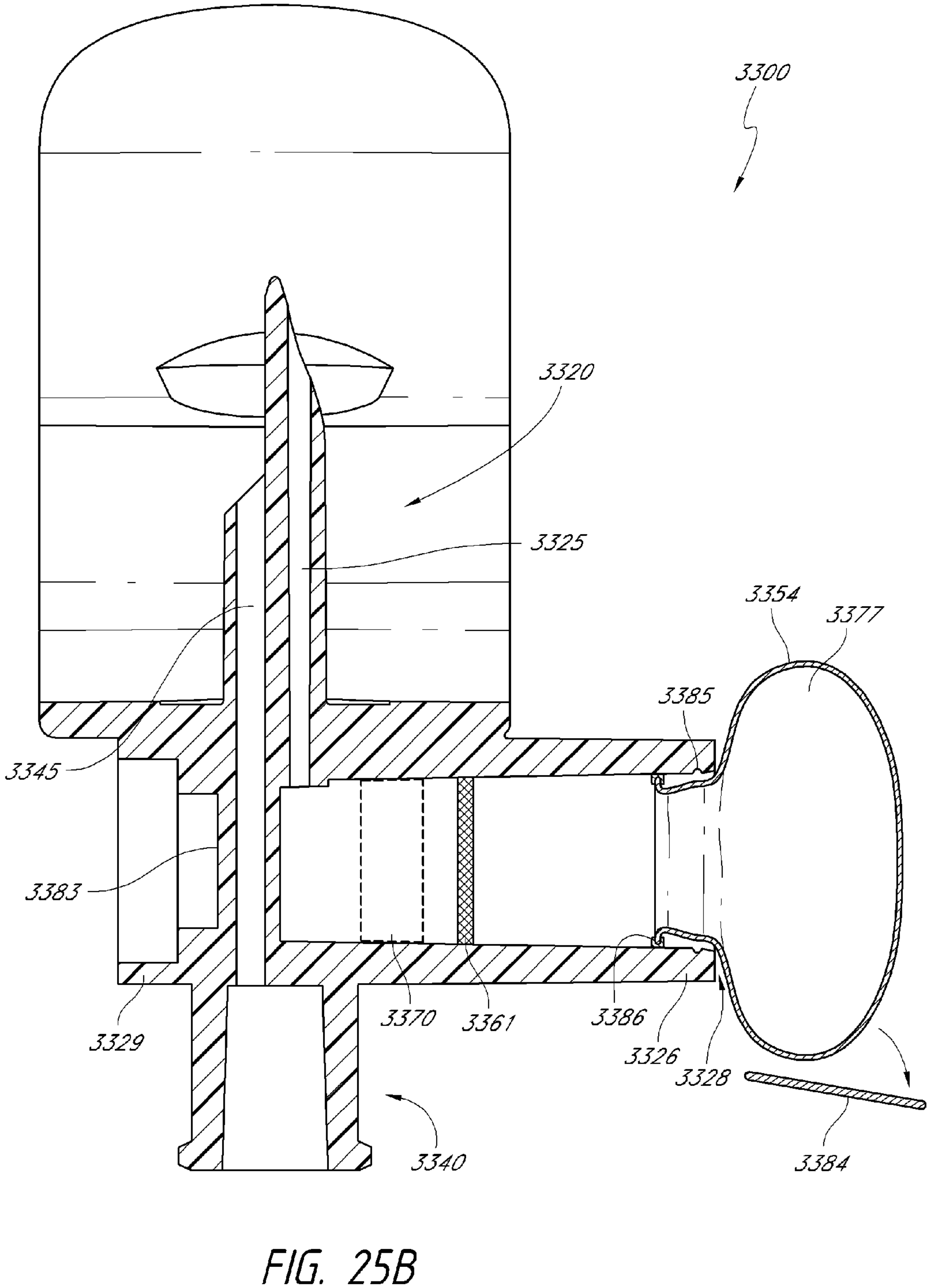
FIG. 25B illustrates a partial cross-sectional view of the vial adaptor of FIG. 25A, wherein the flexible enclosure is in the expanded position.

FIGS. 25A-25B illustrate an embodiment of a vial adaptor 3300 that can have components or portions that are the same as or similar to the components or portions of other vial adaptors disclosed herein. In some embodiments, the vial adaptor 3300 includes a connector interface 3340 and a piercing member 3320 in partial communication with the connector interface 3340. In some embodiments, the vial adaptor 3300 includes a regulator assembly 3350. Some numerical references to components in FIGS. 25A-25B are the same as or similar to those previously described for the vial adaptor 3200 (e.g., piercing member 3320 v. piercing member 3220). It is to be understood that the components can be the same in function or are similar in function to previously-described components. The adaptor 3300 of FIGS. 25A-25B shows certain variations to the adaptor 3200 of FIGS. 24A-24B.

The adaptor 3300 can include an enclosure cover 3384 configured to releasably engage with one or more recesses 3385 within a lumen 3326 of the adaptor 3300. In some embodiments, the adaptor 3300 has a flexible enclosure 3354. The flexible enclosure 3354 can be housed within the lumen 3326. Introduction of fluid into the vial 10 to which the adaptor 3300 is coupled can increase the pressure within the regulator channel 3325 and/or lumen 3326. Increasing the pressure within the regulator channel 3325 and/or lumen 3326 can cause the flexible enclosure 3354 to expand toward the enclosure cover 3384. Expansion of the flexible enclosure 3354 toward the enclosure cover 3384 can bring the enclosure 3354 into contact with the cover 3384 and can push the cover 3384 out from engagement with the one or more recesses 3385 (e.g., see FIG. 25B). Disengagement of the enclosure cover 3384 from the one or more recesses 3385 can permit the flexible enclosure 3354 to expand outside of the lumen 3326.

Figure 26A:
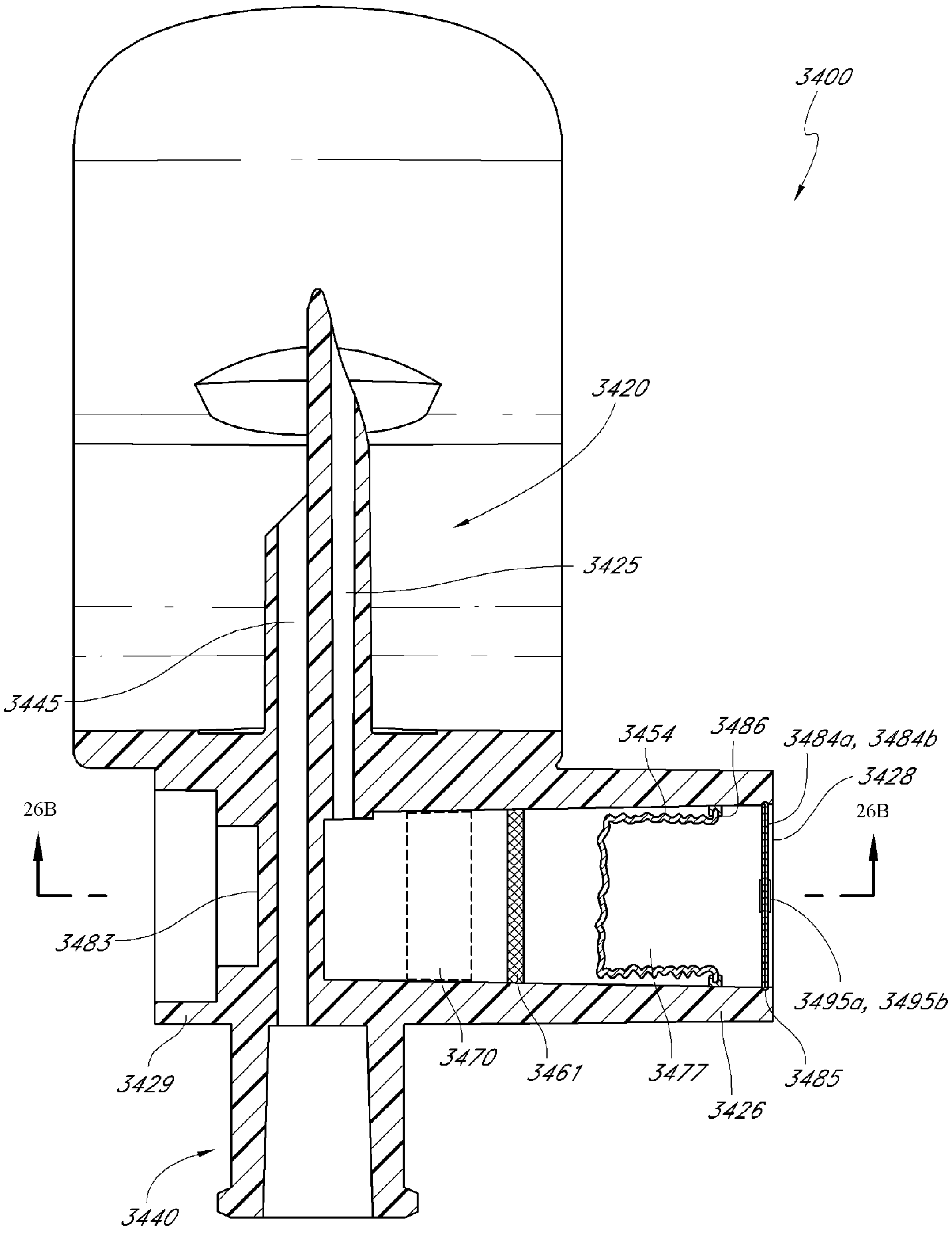
FIG. 26A illustrates a front partial cross-sectional view of another vial adaptor, wherein the flexible enclosure is in the contracted position.
Figure 26B:
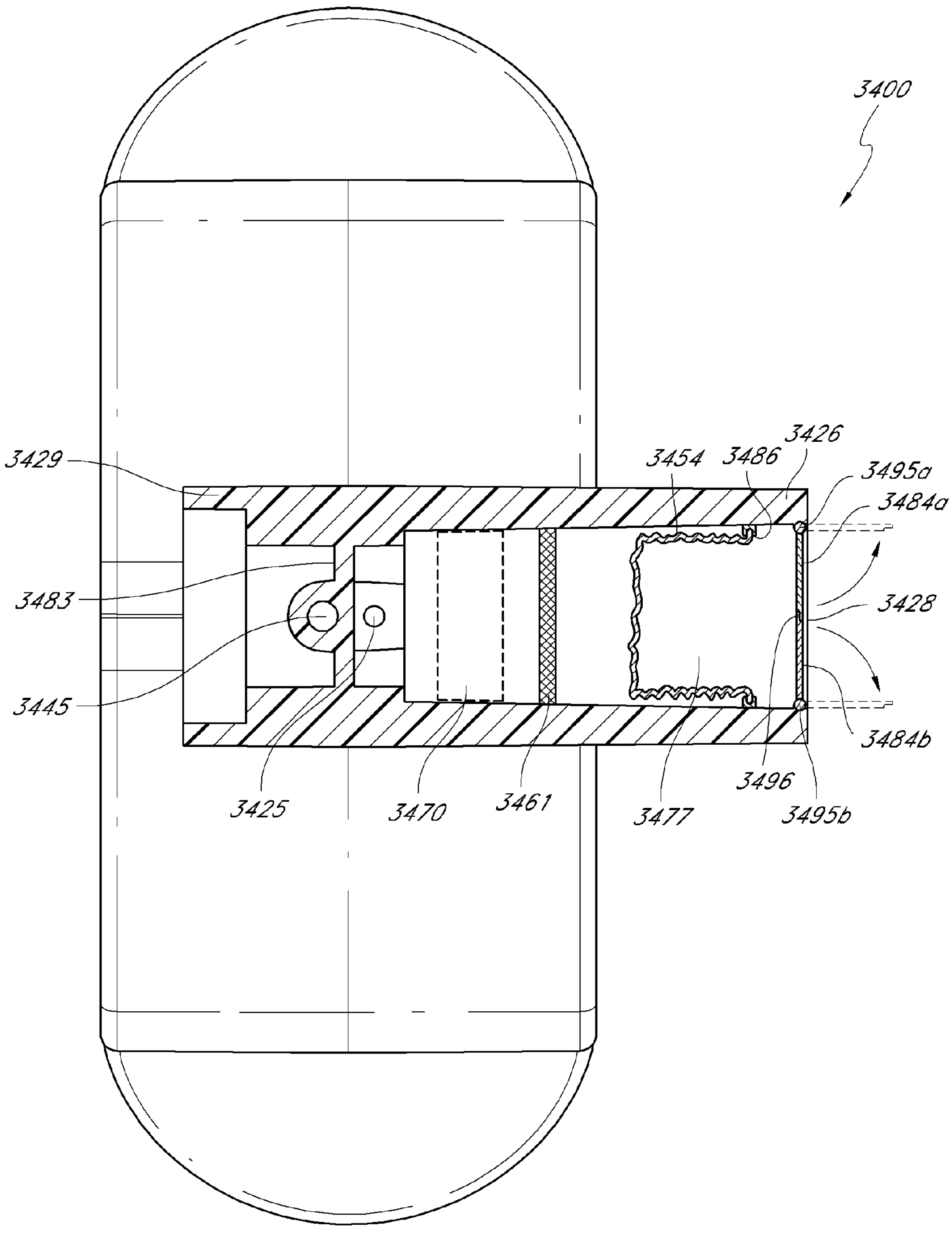
FIG. 26B illustrates a top partial cross-sectional view of the vial adaptor of FIG. 26A along the cut plane 26B-26B, wherein the flexible enclosure is in the contracted position.
Figure 26C:
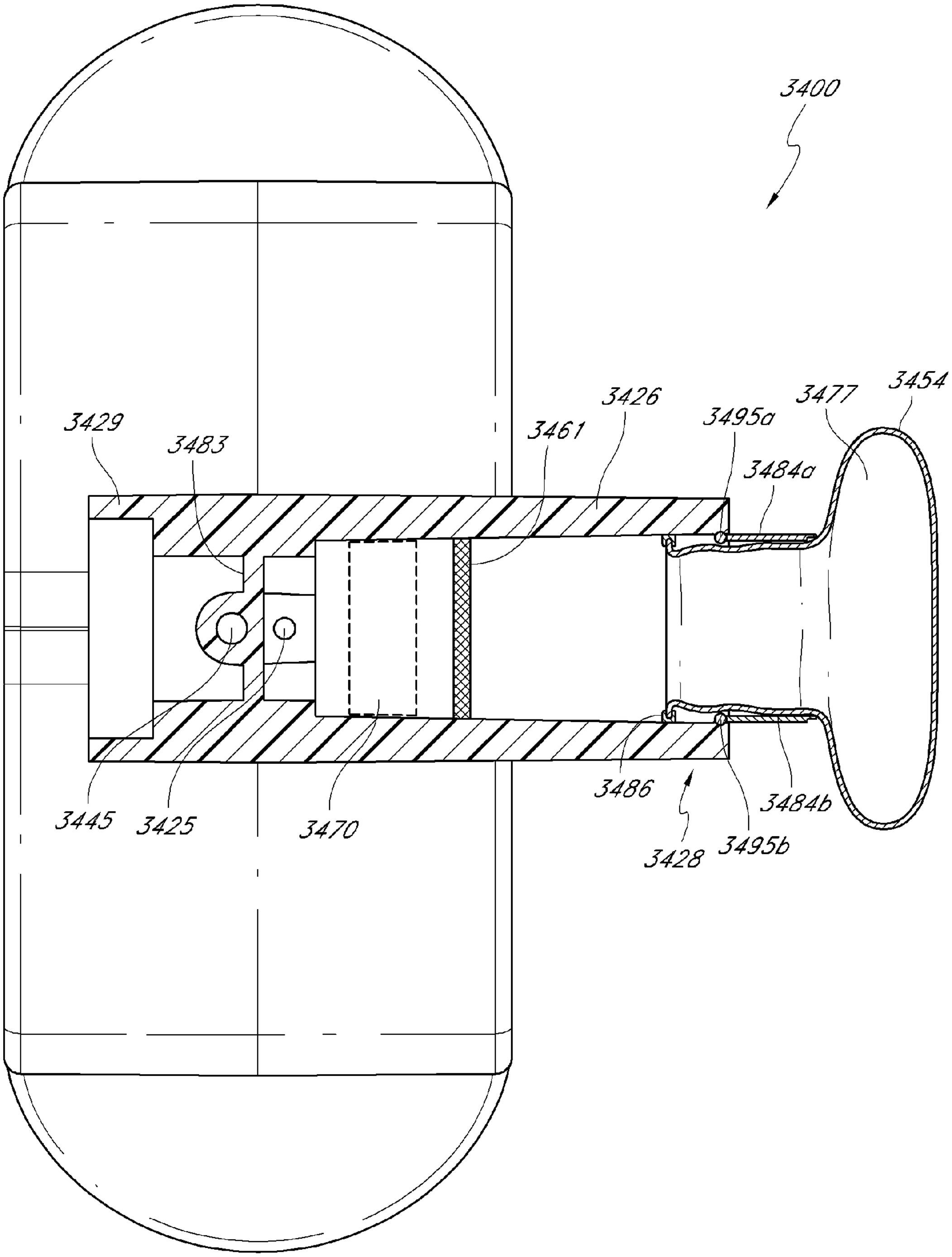
FIG. 26C illustrates a top partial cross-sectional view of the vial adaptor of FIG. 26A along the cut plane 26B-26B, wherein the flexible enclosure is in the expanded position.

FIGS. 26A-26C illustrate an embodiment of a vial adaptor 3400 that can have components or portions that are the same as or similar to the components or portions of other vial adaptors disclosed herein. In some embodiments, the vial adaptor 3400 includes a connector interface 3440 and a piercing member 3420 in partial communication with the connector interface 3440. In some embodiments, the vial adaptor 3400 includes a regulator assembly 3450. Some numerical references to components in FIGS. 26A-26C are the same as or similar to those previously described for the vial adaptor 3300 (e.g., piercing member 3420 v. piercing member 3320). It is to be understood that the components can be the same in function or are similar in function to previously-described components. The adaptor 3400 of FIGS. 26A-26C shows certain variations to the adaptor 3300 of FIGS. 25A-25B.

In some embodiments, the adaptor 3400 includes a flexible enclosure 3454 housed within a lumen 3426 of the adaptor 3400. The adaptor 3400 can include a pair of the enclosure covers 2484*a*, 3484*b* hingedly connected to a lumen 3426 of the adaptor 3400 via a pair of hinges 3495*a*, 3495*b*. The covers 2484*a*, 3484*b* can be figured to engage with each other at a cover engagement point 3496. One or both of the covers 2484*a*, 3484*b* can include a cover engagement feature (e.g., a stepped surface) configured to engage with the other cover 2484*a*, 3484*b*. Engagement between the covers 2484*a*, 3484*b* can help prevent inadvertent opening of the covers 2484*a*, 3484*b*. Expansion of the flexible enclosure 3454 toward the covers 2484*a*, 3484*b* can bring the flexible enclosure 3454 into contact with the covers 2484*a*, 3484*b*. The covers 2484*a*, 3484*b* can be configured to open (e.g., see FIGS. 26B and 26C) upon exertion of pressure from the flexible enclosure 3454. Opening of the covers 2484*a*, 3484*b* can permit the flexible enclosure 3454 to transition to an expanded configuration, as illustrated in FIG. 26C.

Figure 27A:
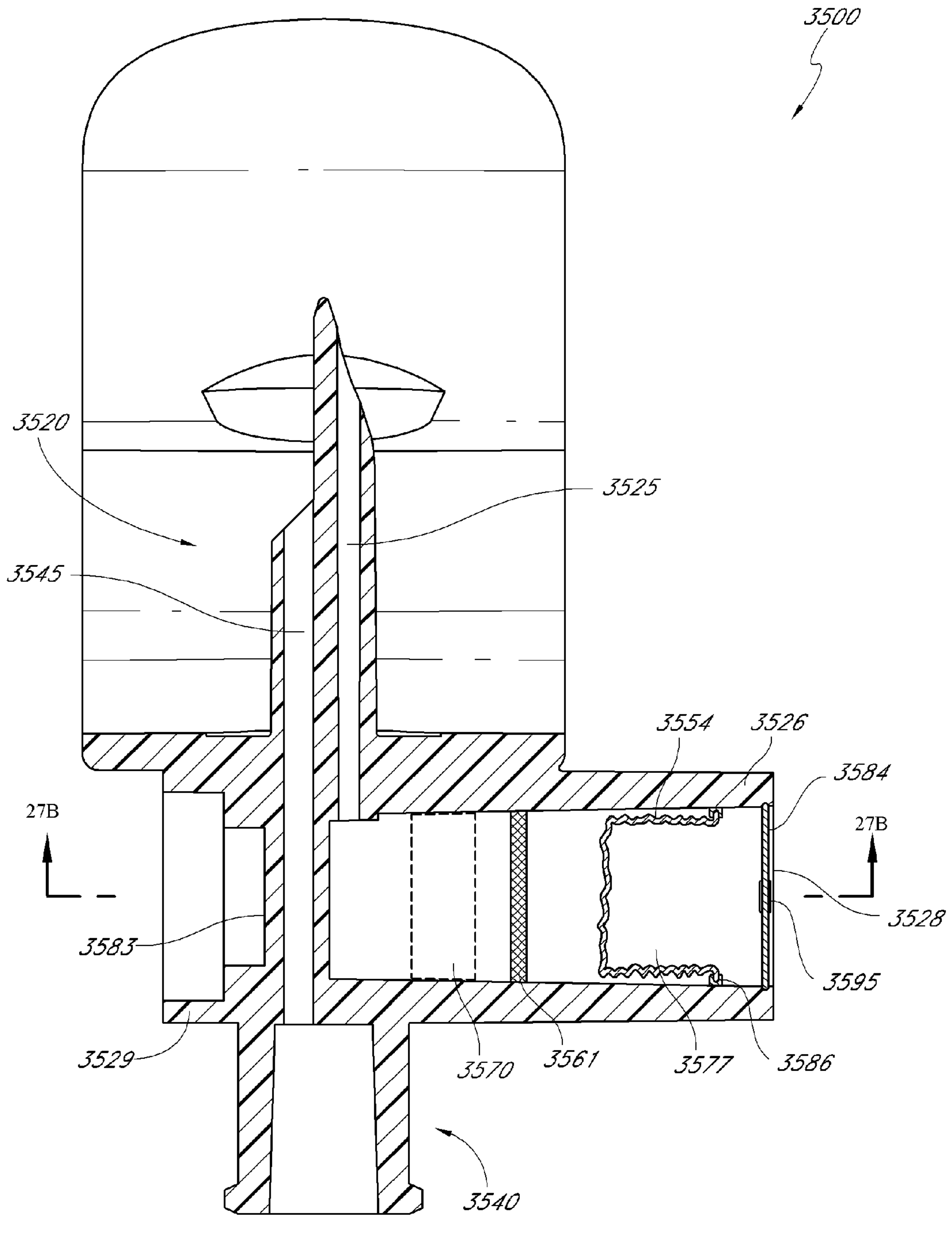
FIG. 27A illustrates a front partial cross-sectional view of another vial adaptor, wherein the flexible enclosure is in the contracted position.
Figure 27B:
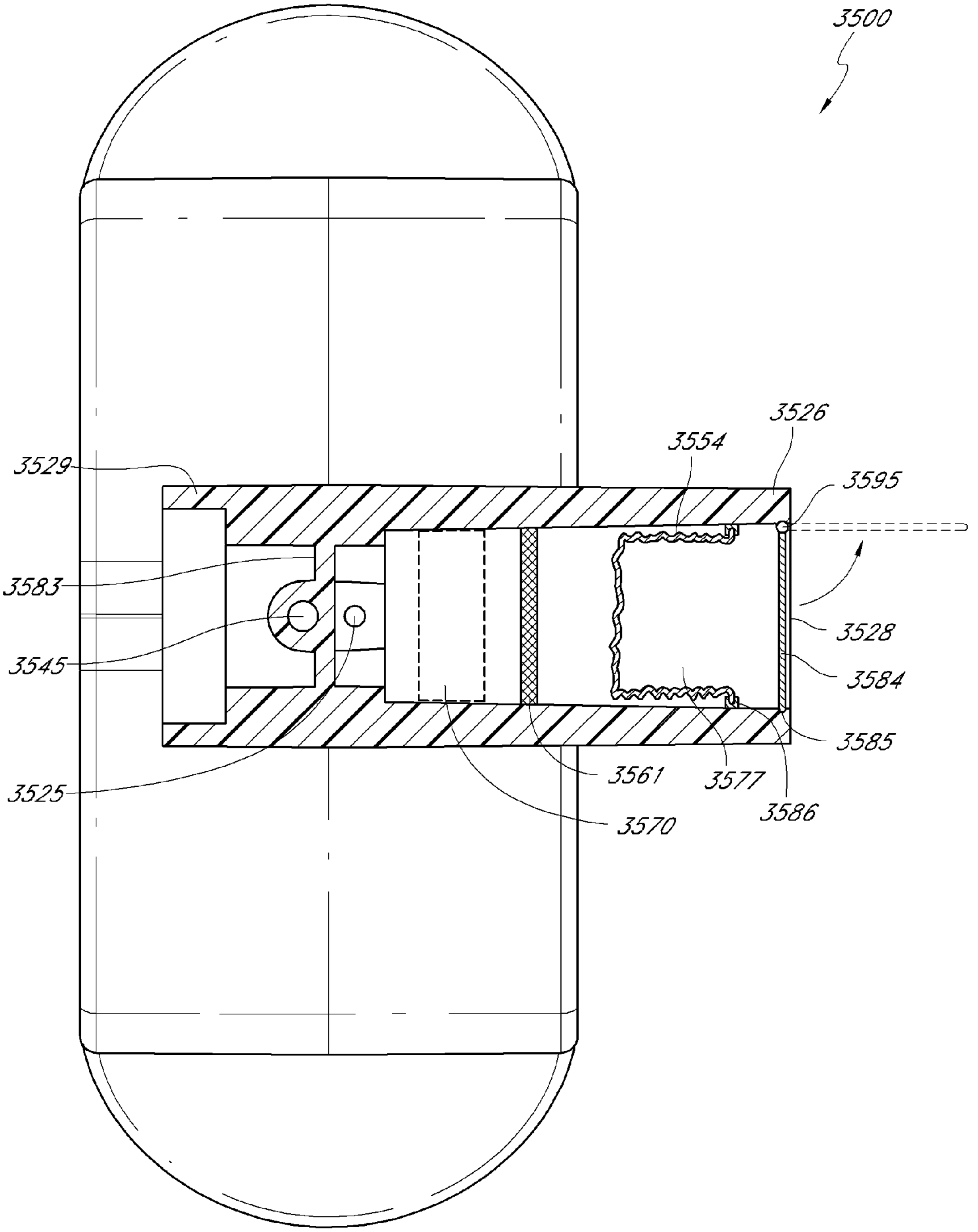
FIG. 27B illustrates a top partial cross-sectional view of the vial adaptor of FIG. 27A along the cut plane 27B-27B, wherein the flexible enclosure is in the contracted position.
Figure 27C:
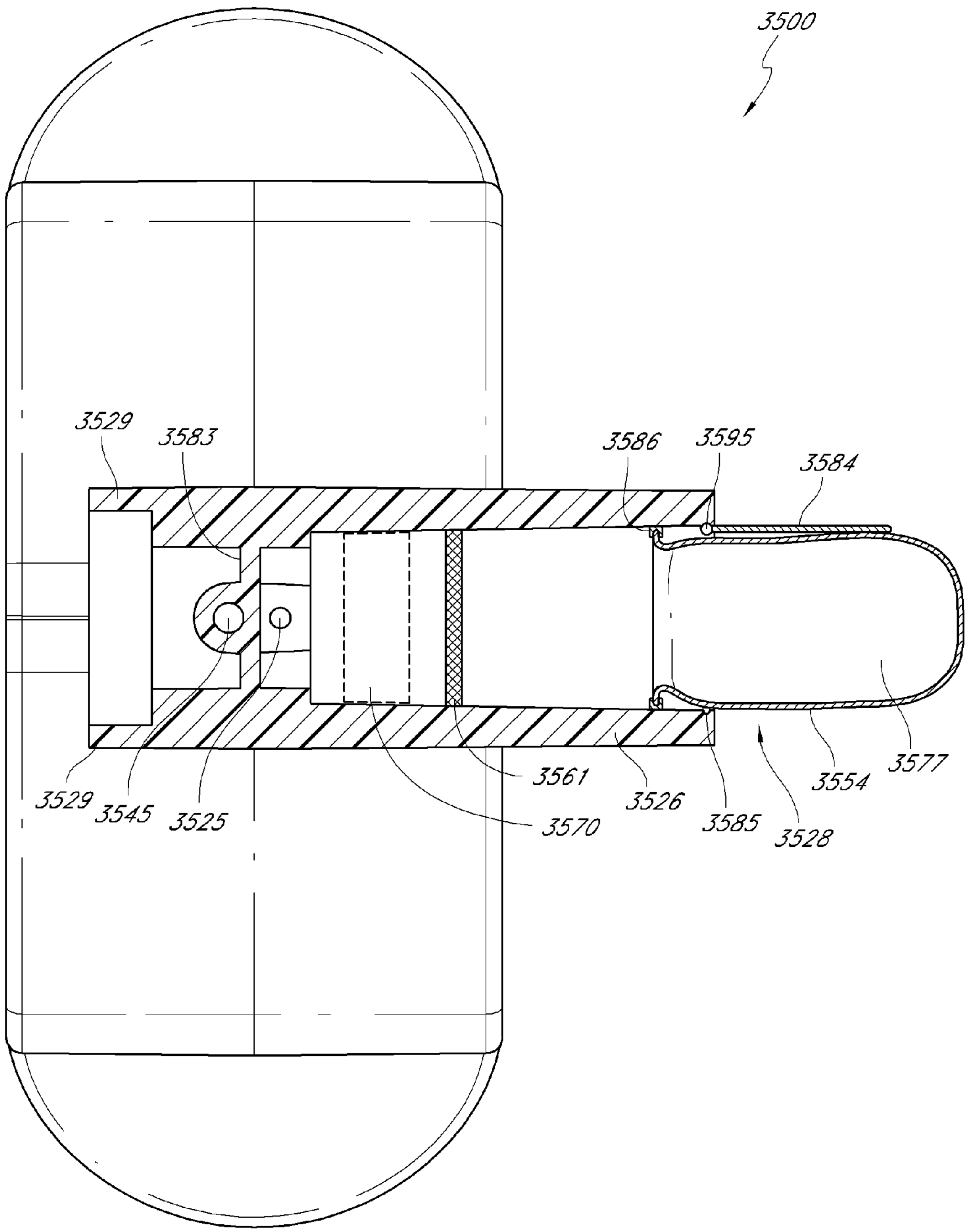
FIG. 27C illustrates a top partial cross-sectional view of the vial adaptor of FIG. 27A along the cut plane 27B-27B, wherein the flexible enclosure is in the expanded position.

FIGS. 27A-27C illustrate an embodiment of a vial adaptor 3500 that can have components or portions that are the same as or similar to the components or portions of other vial adaptors disclosed herein. In some embodiments, the vial adaptor 3500 includes a connector interface 3540 and a piercing member 3520 in partial communication with the connector interface 3540. In some embodiments, the vial adaptor 3500 includes a regulator assembly 3550. Some numerical references to components in FIGS. 27A-27C are the same as or similar to those previously described for the vial adaptor 3400 (e.g., piercing member 3520 v. piercing member 3420). It is to be understood that the components can be the same in function or are similar in function to previously-described components. The adaptor 3500 of FIGS. 27A-27C shows certain variations to the adaptor 3400 of FIGS. 26A-26C.

The adaptor 3500 can include a flexible enclosure 3554 housed within a lumen 3526 of the adaptor 3500. In some embodiments, the adaptor 3500 includes a hinged enclosure cover 3584 attached to the lumen 3526 via a hinge 3595. In some embodiments, the cover 3584 is configured to engage with a recess 3585 in the lumen 3526. Engagement between the cover 3584 and the lumen 3526 can inhibit the cover 3584 from inadvertently opening to expose the flexible enclosure 3554. In some embodiments, pressure exerted by the flexible enclosure 3554 on the interior of the cover 3584 as the flexible enclosure 3554 transitions to an expanded configuration (e.g., see FIG. 27C) can cause the cover 3584 to disengage from the recess 3585. The cover 3584 can be constructed from a resilient, rigid, and/or semi-rigid material.

Figure 2C:
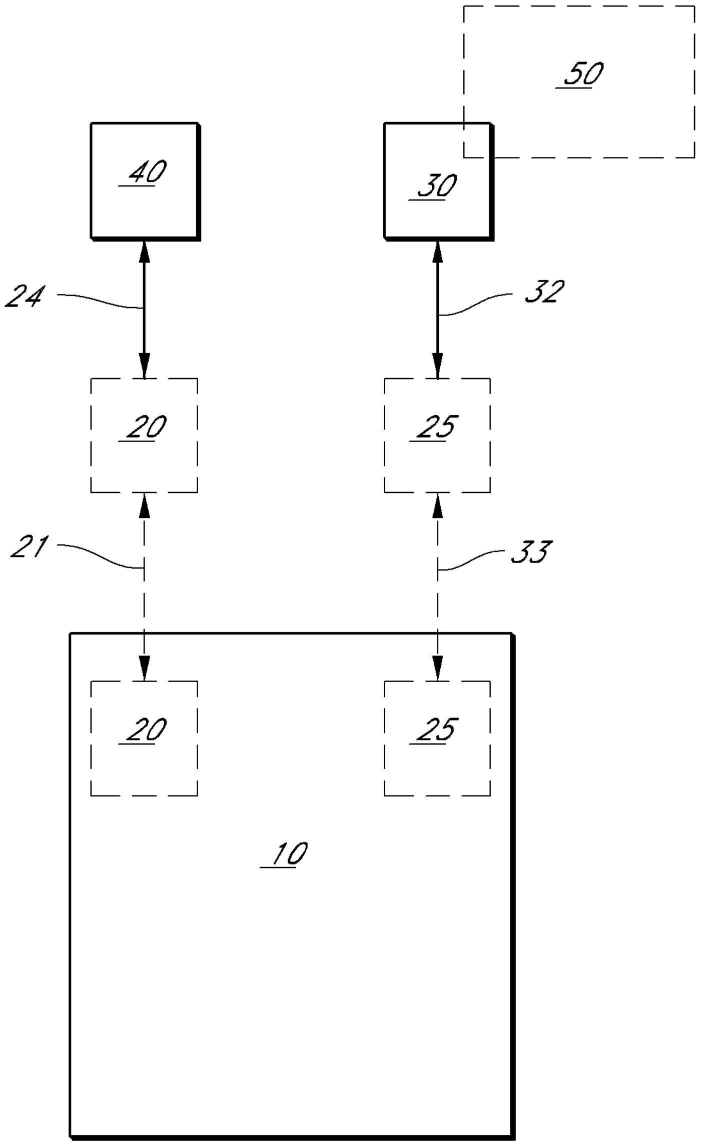
FIG. 2C schematically illustrates the system of FIG. 2B, wherein the flexible enclosure is in an expanded position.
Figure 28A:
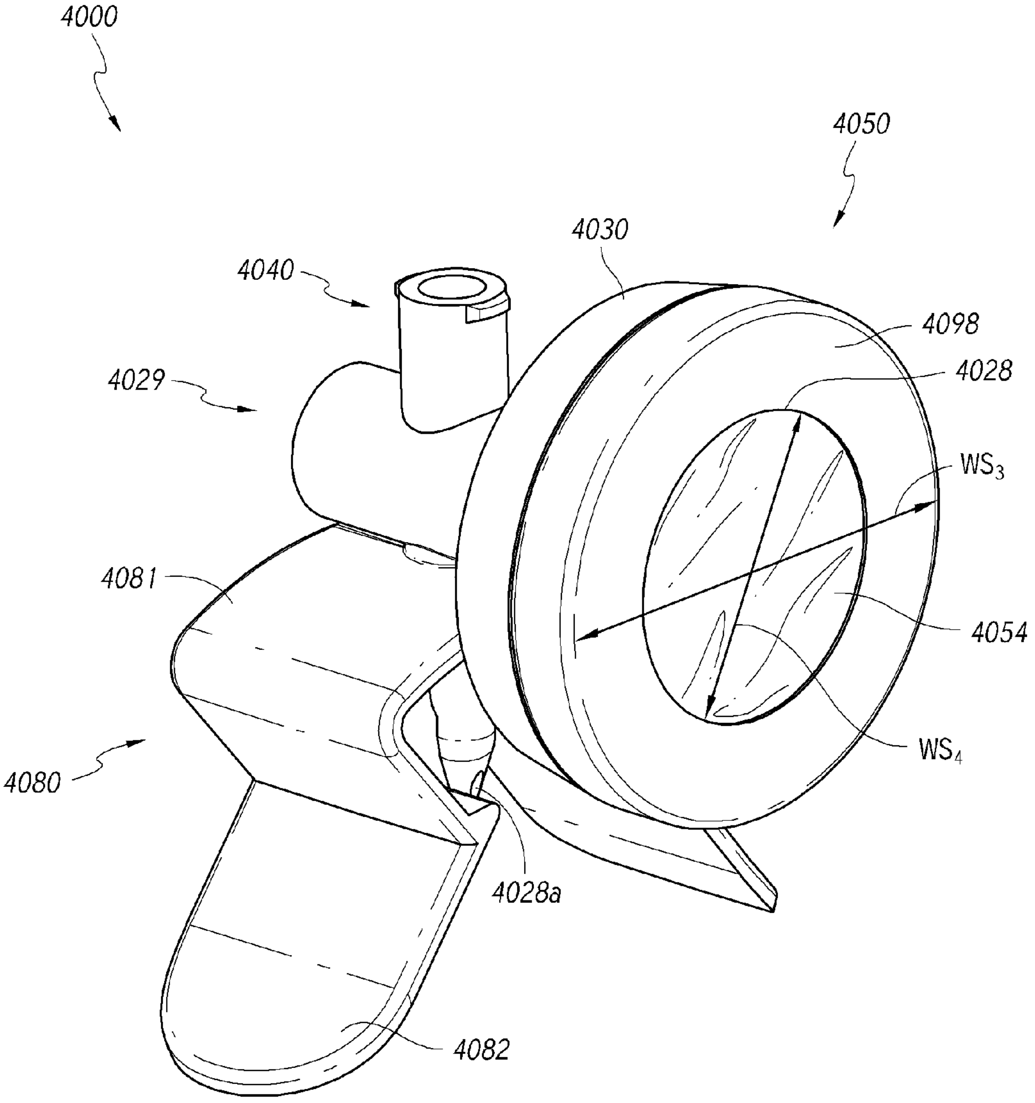
FIG. 28A illustrates a perspective view of another vial adaptor.
Figure 28B:
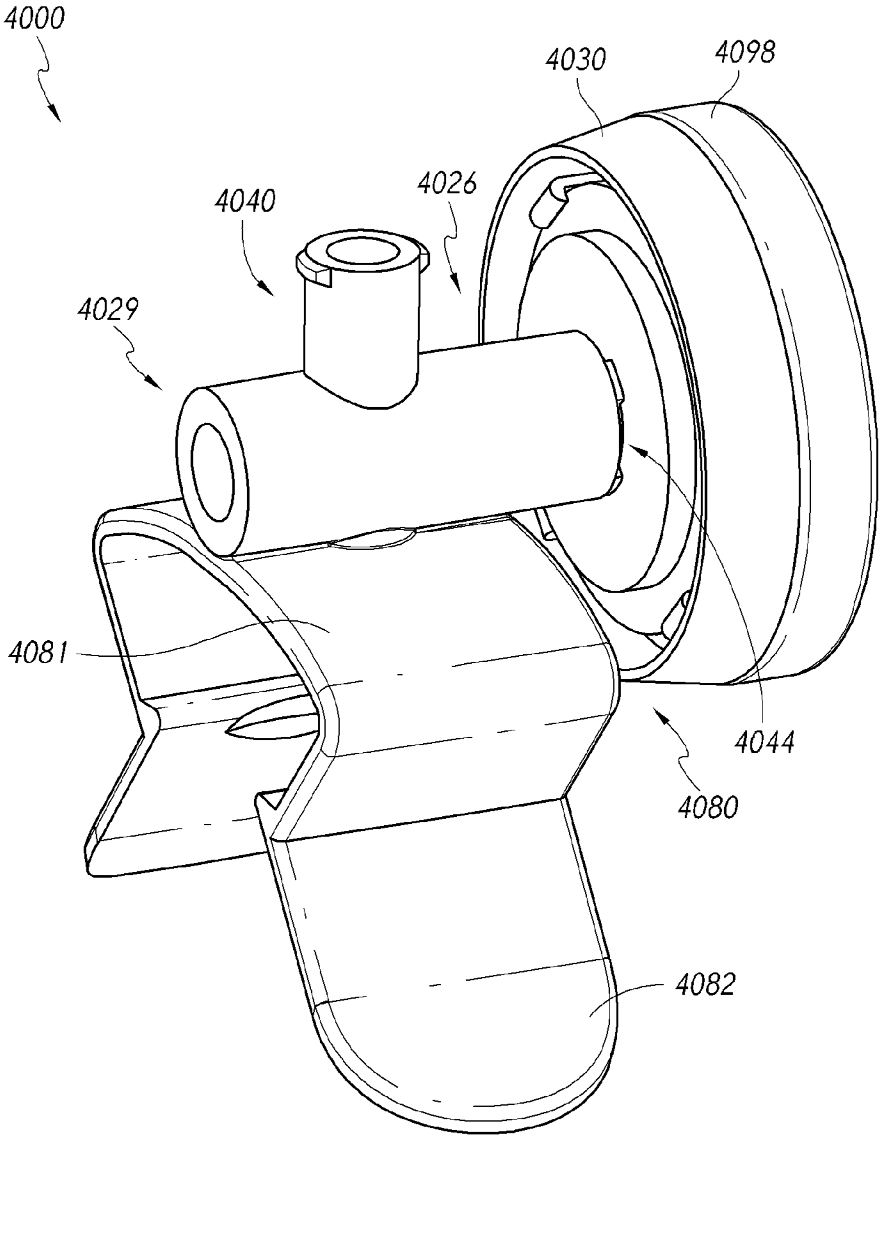
FIG. 28B illustrates another perspective view of the vial adaptor of FIG. 28A.
Figure 28C:
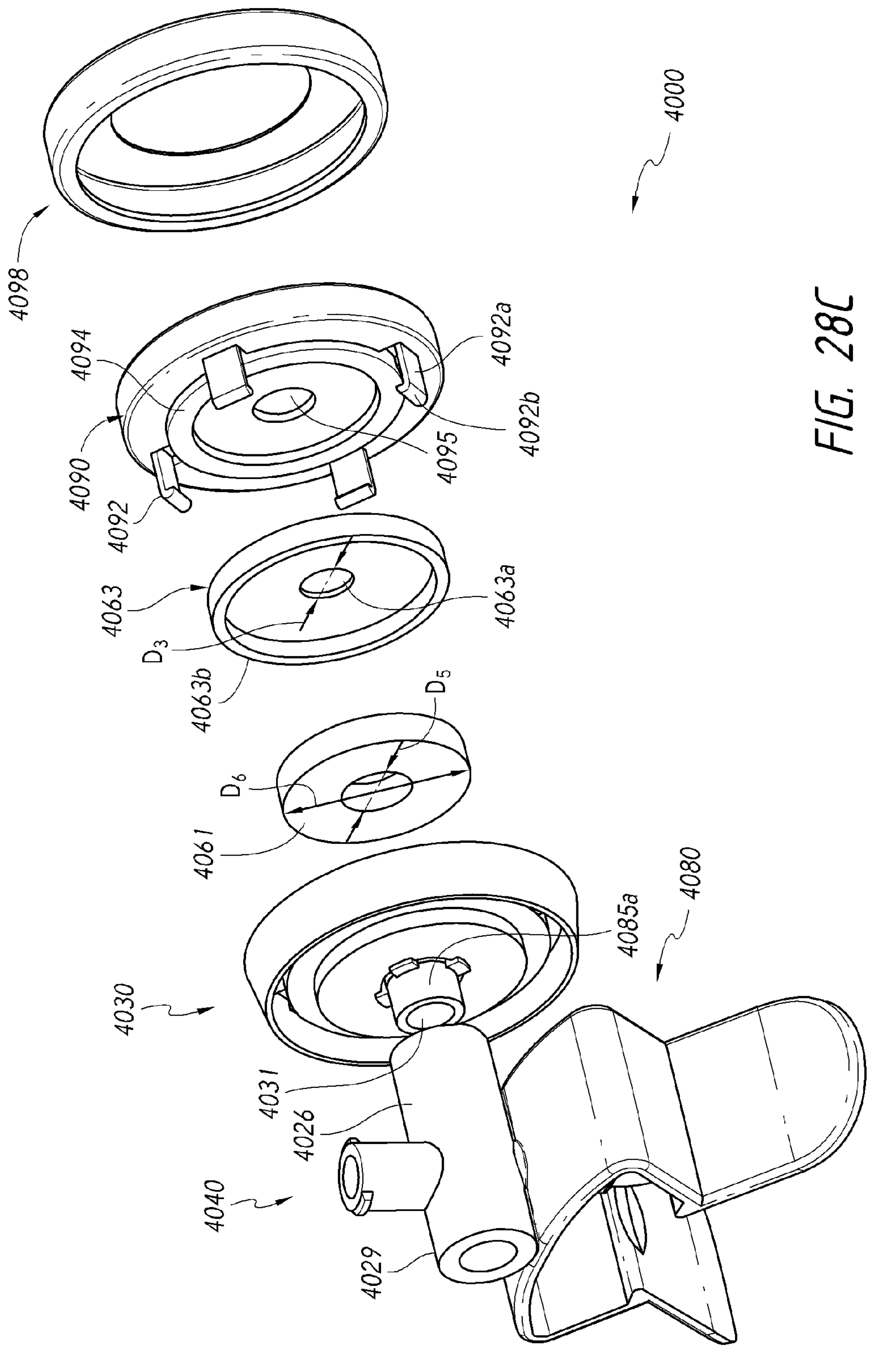
FIG. 28C illustrates an exploded view of the vial adaptor of FIG. 28A.
Figure 28D:
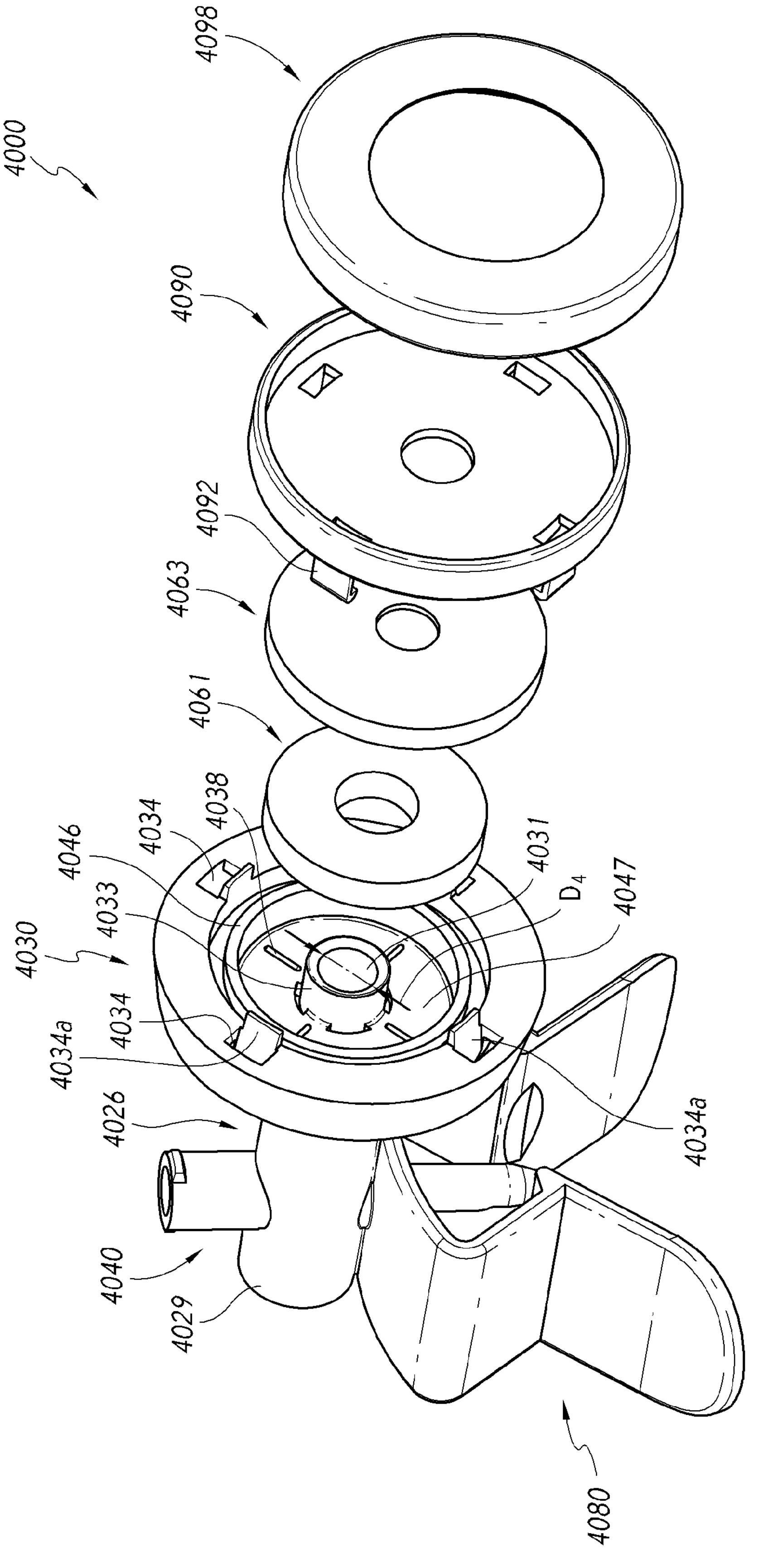
FIG. 28D illustrates another exploded view of the vial adaptor of FIG. 28A.
Figure 28F:
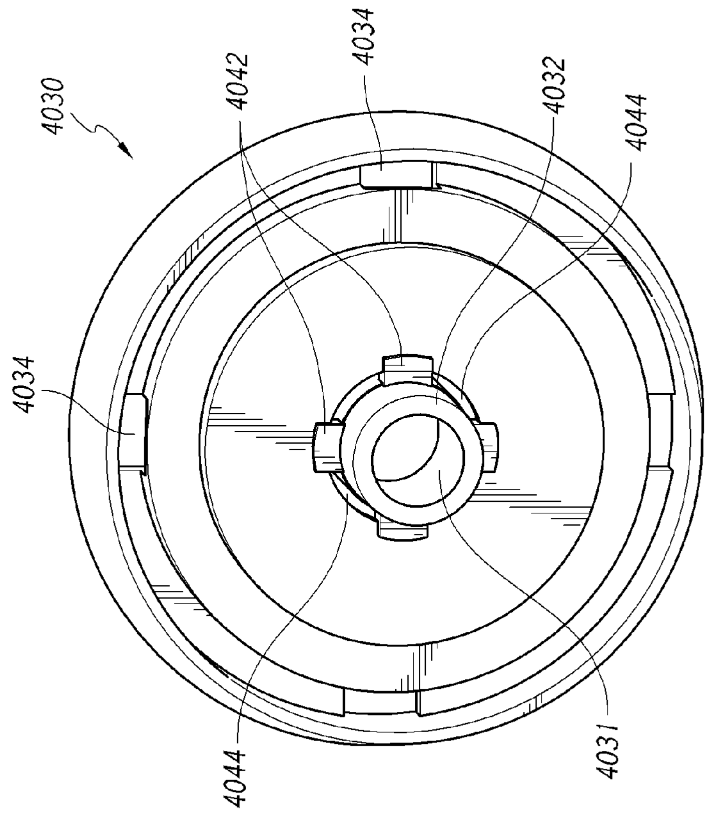
FIG. 28F illustrates another perspective view of the regulator base of FIG. 28E.
Figure 28E:
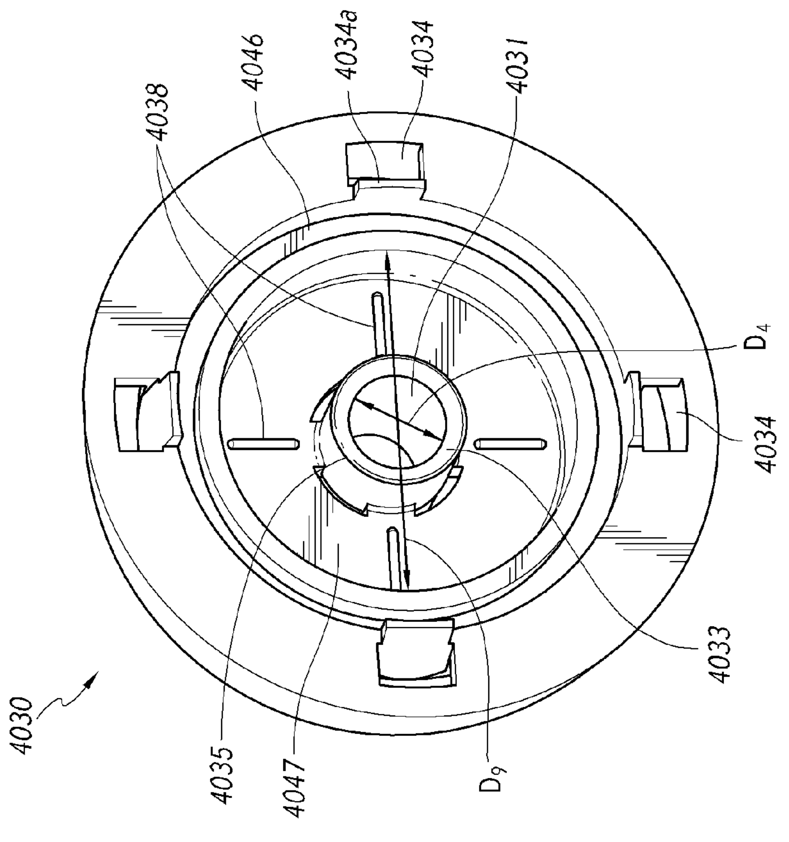
FIG. 28E illustrates a perspective view of a regulator base of the vial adaptor of FIG. 28A.
Figure 28G:
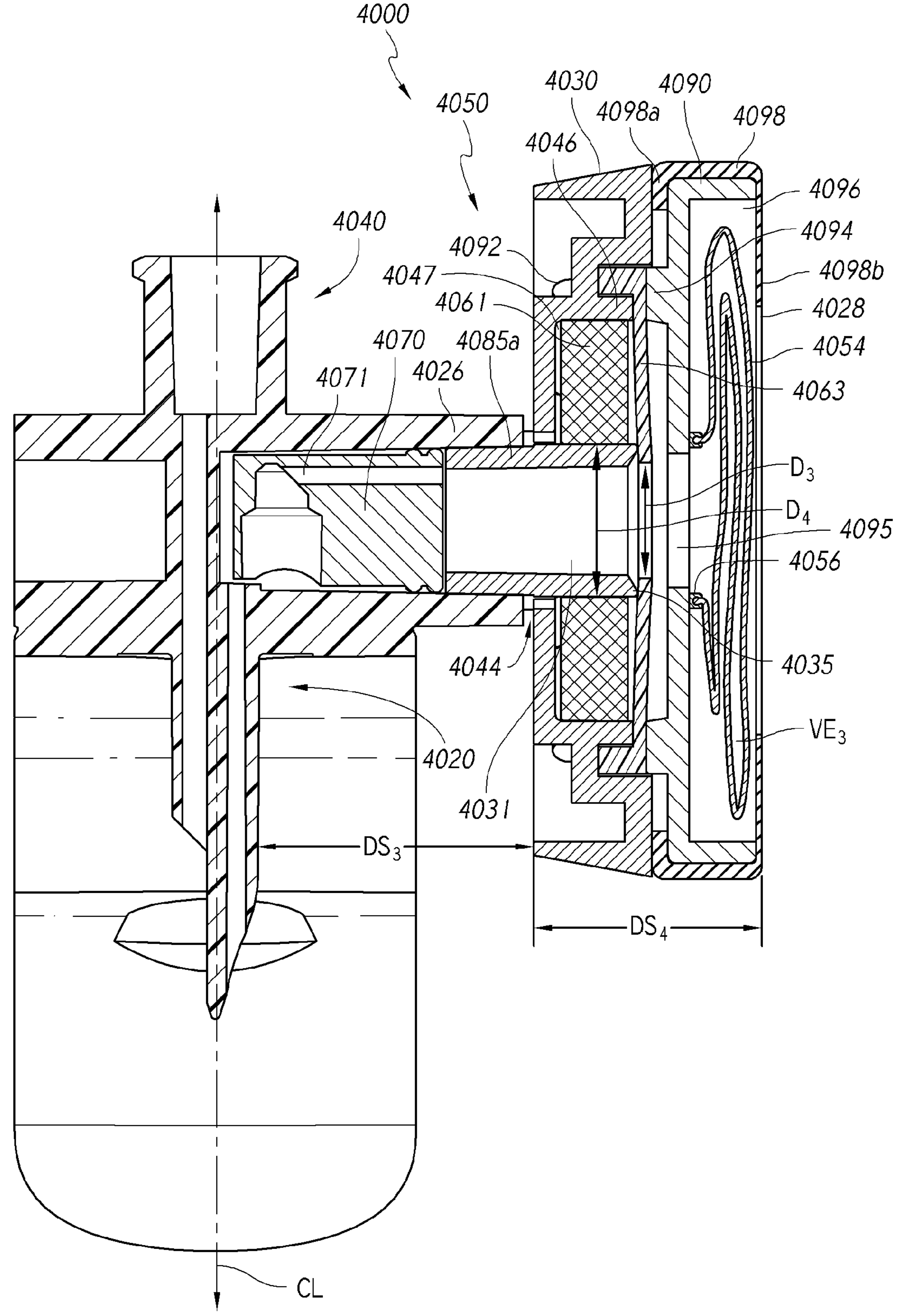
FIG. 28G illustrates a front partial cross-sectional view of the vial adaptor of FIG. 28A.
Figure 28H:
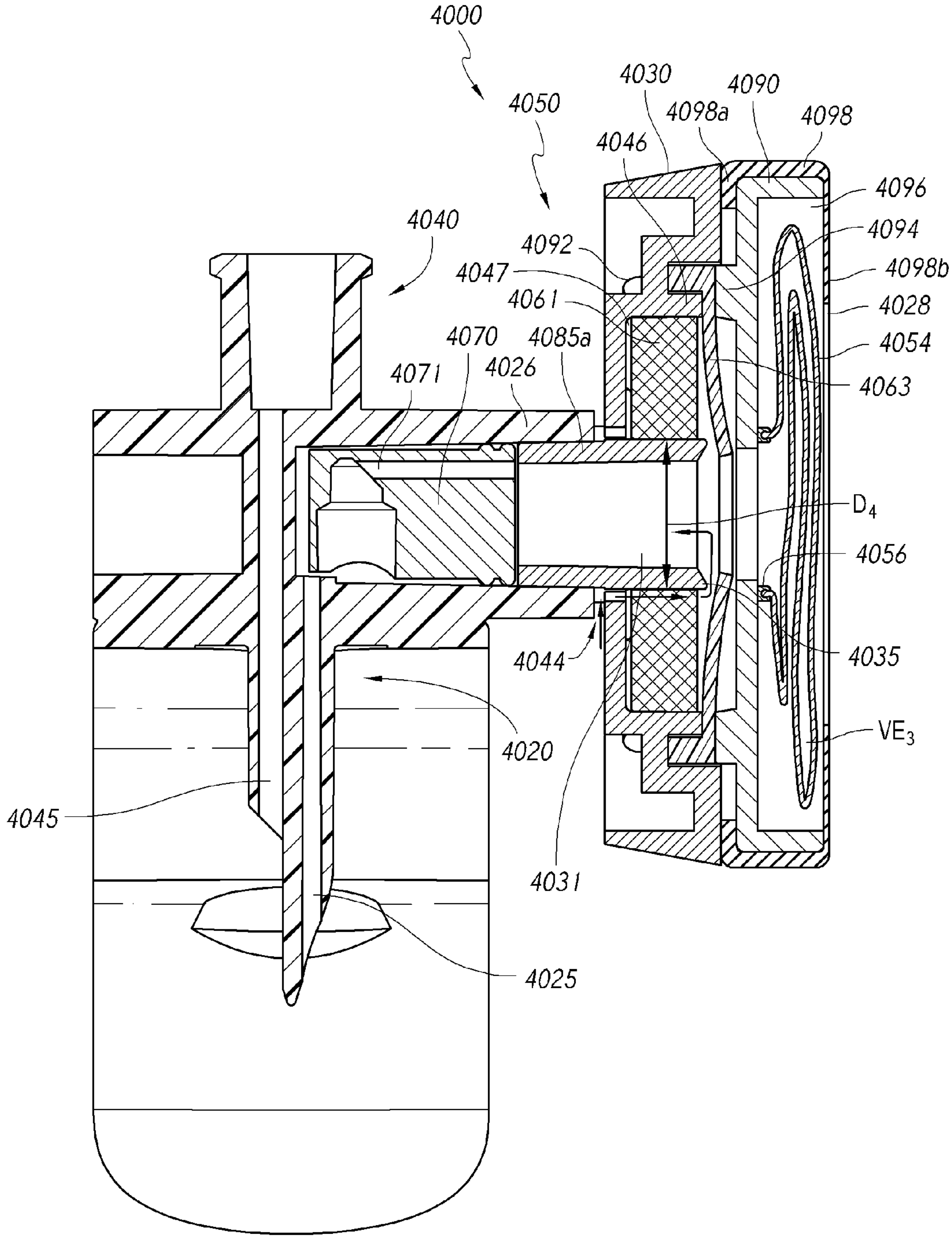
FIG. 28H illustrates a front partial cross-sectional view of the vial adaptor of FIG. 28A with the diaphragm check valve in an open position.
Figure 28I:
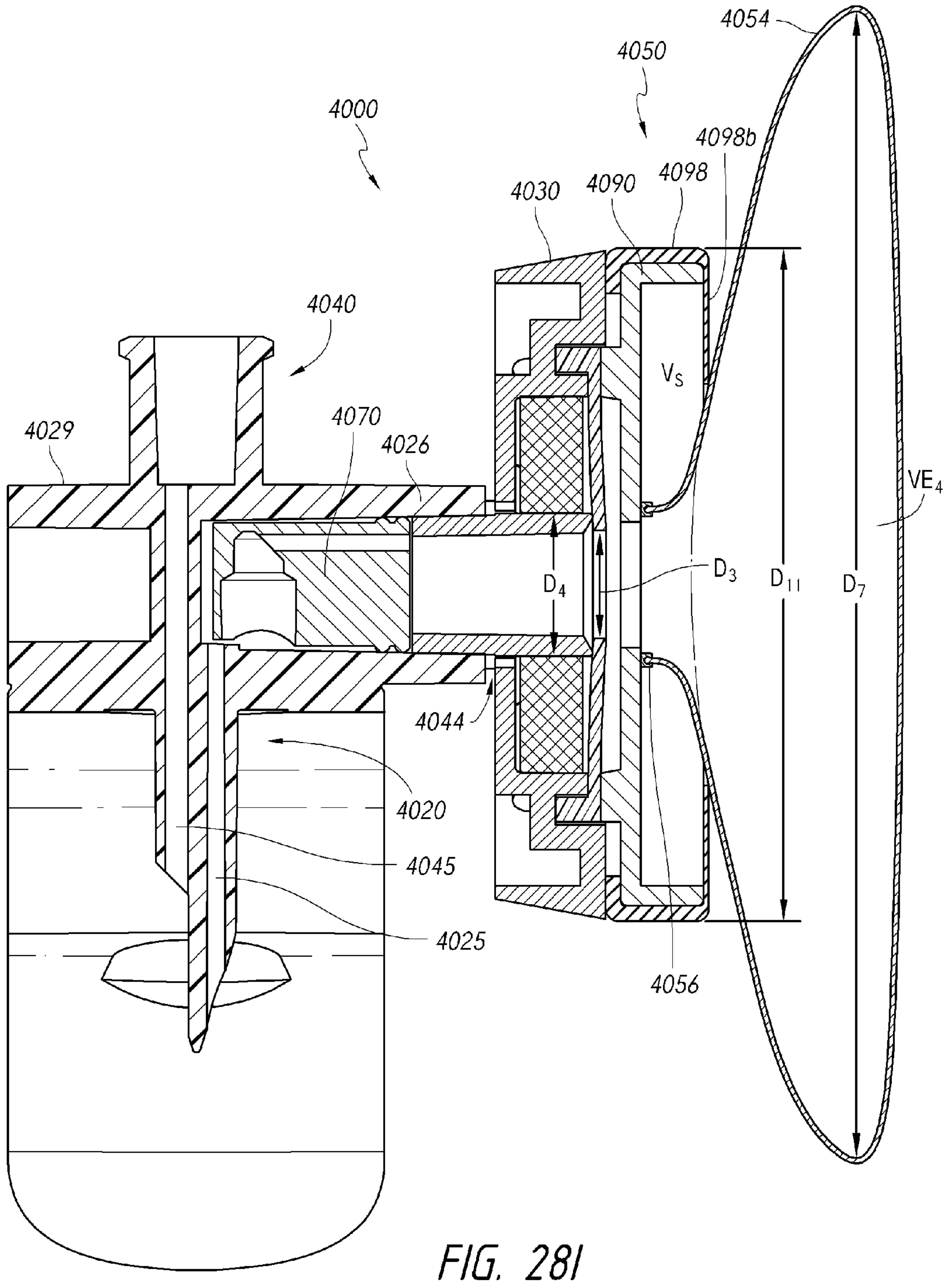
FIG. 28I illustrates a front partial cross-sectional view of the vial adaptor of FIG. 28A with the flexible enclosure in the expanded configuration.
Figure 28J:
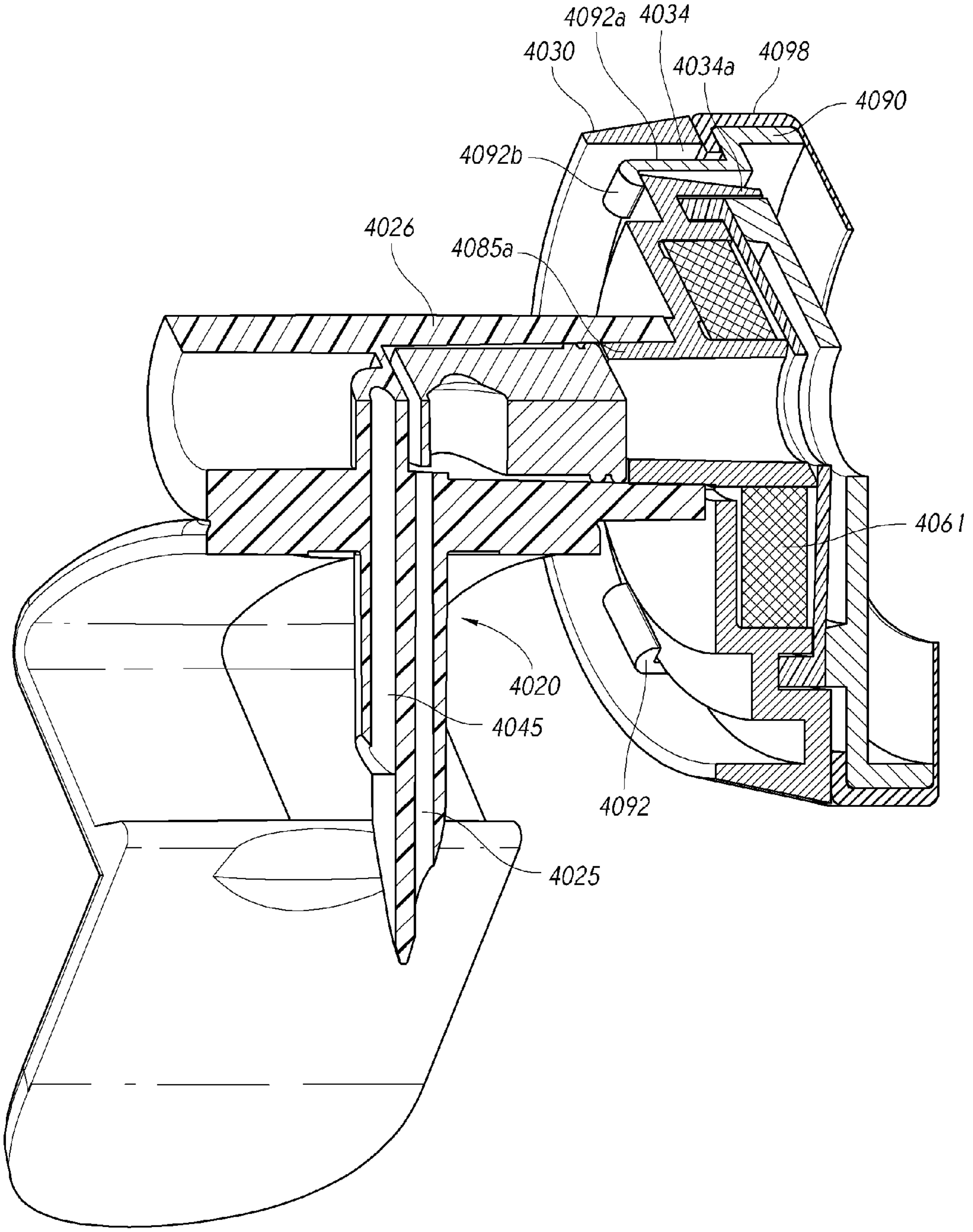
FIG. 28J illustrates a partial perspective cross-sectional view of the vial adaptor of FIG. 28A.

FIGS. 28A-28J illustrate an embodiment of a vial adaptor 4000 that can have components or portions that are the same as or similar to the components or portions of other vial adaptors disclosed herein. In some embodiments, the vial adaptor 4000 includes a connector interface 4040 and a piercing member 4020 in partial communication with the connector interface 4040. In some embodiments, the vial adaptor 4000 includes a regulator assembly 4050. Some numerical references to components in FIGS. 28A-28J are the same as or similar to those previously described for the vial adaptor 3000 (e.g., piercing member 4020 v. piercing member 3020). It is to be understood that the components can be the same in function or are similar in function to previously-described components. The adaptor 4000 of FIGS. 28A-28J shows certain variations to the adaptor 3000 of FIGS. 22A-2C. Some of the views shown in FIGS. 28A-28J, including FIGS. 28C, 28D, and 28J, do not include an illustration of the flexible enclosure 4054 positioned in the storage chamber 4096 of the adaptor 4000, even though the flexible enclosure 4054 is stored in the chamber 4096, as shown in FIGS. 28G-28I.

In some embodiments, the regulator assembly 4000 includes a regulator base configured to couple (e.g., releasably couple or fixedly couple) with a regulator nest 4090. The regulator base 4030 can be constructed from a rigid or semi-rigid material. In some embodiments, the regulator base 4030 is constructed from a polymer (e.g., a polycarbonate plastic). The regulator base 4030 can include a coupling protrusion 4085*a*. In some embodiments, the coupling protrusion 4085*a* defines a coupling passage 4031. The coupling protrusion 4085*a* can be configured to couple with the lumen 4026 of the vial adaptor 4000. For example, the coupling protrusion 4085*a* has an outer cross-sectional shape (e.g., a circle, oval, polygon, or other shape) sized and shaped to generally match an interior cross-section of a lumen 4026 of the vial adaptor 4000. In some embodiments, the coupling protrusion 4085*a* can be configured to friction-fit into the lumen 4026. In some embodiments, one or more attachments are used, such as one or more sonic welds, glues, or adhesives, to affix the coupling protrusion 4085*a* to the lumen 4026. As illustrated in FIG. 28G, coupling passage 4031 can be in fluid communication with the regulator channel 4025 of the vial adaptor 4000 when the coupling protrusion 4085*a* is coupled with or otherwise associated with the lumen 4026.

As illustrated in FIG. 28D, the regulator base 4030 can include a base protrusion 4033 that extends from the regulator base 4030 in a direction generally opposite from the direction in which the coupling protrusion 4085*a* extends. The base protrusion 4033 can have an outer width (e.g. an outer diameter) D4. An inner wall of the base protrusion 4033 can comprise a portion of the coupling passage 4031. The regulator base 4030, in some embodiments, can include an axial projection 4046. The axial projection 4046 can extend from the regulator base 4030 in the same direction as the base protrusion 4033. The axial projection 4046 can, in some embodiments, have a generally annular shape. In some embodiments, the axial projection 4046 has a generally oval shape, generally polygonal shape, generally circular shape, or any other appropriate shape.

In some embodiments, a filter cavity 4047 can be positioned in a space between the base protrusion 4033 and the axial projection 4046. The inner width of the filter cavity can be the width D4 of the base protrusion 4033. The outer width D9 of the filter cavity 4047 can be the inner width of the axial projection. In some embodiments, the filter cavity 4047 has a generally toroidal shape. In some embodiments, the filter cavity 4047 has a generally square, generally rectangular, generally triangular, generally oval shape, or other shape.

A filter 4061 can be sized to fit within the filter cavity 4047. The filter 4061 can have an inner width (e.g., diameter) D5 configured to be less than or equal to about the inner width D4 of the filter cavity 4047. In some embodiments, the inner width D5 of the filter 4061 is greater than the inner width D4 of the filter cavity 4047. In some embodiments, the filter 4061 has an outer width (e.g., diameter) D6 that is greater than or equal to about the outer width D9 of the filter cavity 4047. The filter 4061 can be a hydrophobic and/or an antibacterial filter. In some embodiments, the filter 4061 is constructed from a paper, polymer, foam, or other material, such as a lightweight porous material. In some embodiments, the filter 4061 is constructed from a flexible or semi-flexible material. The filter 4061 can be configured to deform when inserted into the filter cavity 4047. For example, the inner width D5 of the filter 4061 can fit snugly onto or stretch onto the width D4 of the base protrusion 4033. In some embodiments, the outer width D6 of the filter 4061 fits snugly against or is compressed into the outer width D9 of the filter cavity 4047. In some embodiments, a snug fit between the filter 4061 and the filter cavity 4047 can inhibit fluid from flowing into and/or out of the filter cavity 4047 and/or coupling channel 4031 without going through the filter 4061.

The regulator assembly 4050 can include a diaphragm 4063. The diaphragm 4063 can, in some embodiments, have a generally circular or generally annular shape. In some embodiments, the shape of the diaphragm 4063 is configured to generally match the shape of the axial projection 4046 of the regulator base 4030. The diaphragm 4063 can be inserted into or onto the base portion 4030. For example, a lip 4063*b* of the diaphragm 4063 can be configured to fit around the radial (e.g., up and down in FIG. 28H) outside of the axial projection 4046. The diaphragm 4063 can include an inner aperture 4063*a* having a width (e.g., a diameter) D3. In some embodiments, as illustrated, the width D3 can be less than the outer width D4 of the base protrusion 4033.

The regulator nest 4090 can be configured to releasably or otherwise couple with the regulator base 4030. As illustrated in FIG. 28C, the regulator nest 4090 can include one or more fixation members 4092. The fixation members 4092 can be constructed and/or configured to engage with fixation apertures 4034 on the regulator base 4030. The fixation members 4092 can comprise clips, tabs, or other projections configured to insert into the fixation apertures 4034 of the regulator base 4030. For example, the fixation members 4092 can comprise a tab 4092*a* with a hook 4092*b* on the end. The fixation members 4092 can be constructed from a resilient material. For example, tabs 4092*a* of the fixation members 4092 can be configured to deform (e.g., deflect) or otherwise move when a radial (e.g., up and down with respect to FIG. 28H) force is applied to the hooks 4092*b*. The regulator base 4030 can include angled tabs 4034*a* configured to deflect the hooks 4092*b* radially (e.g., up and down with respect to FIG. 28H) outward as the tabs 4092*a* are inserted into the apertures 4034. The hooks 4092*b* can snap back in place upon passing through the fixation apertures 4034 and can engage with the rear side (e.g., the side away from the regulator nest 4090) of the angled tabs 4034*a* to secure the regulator nest 4090 to the regulator base 4030.

As illustrated in FIG. 28G, the regulator nest 4090 can include an axial projection 4094. The axial projection 4094 can extend from the regulator nest 4090 toward the regulator base 4030 when the regulator nest 4090 is coupled with the regulator base 4030. The axial projection 4090 can, in some embodiments, have a generally annular shape. In some embodiments, the axial projection 4094 has a generally oval shape, a generally polygonal shape, a generally circular shape, or any other appropriate shape. The shape of the axial projection 4094 can be similar to or the same as the shape of the axial projection 4046 of the regulator base 4030. As illustrated, the axial projection 4094 can contact at least a portion of the diaphragm 4063 as the regulator nest 4090 is coupled with the regulator base 4030. In some embodiments, contact between the axial projection 4094 of the regulator nest 4090 and the diaphragm 4063 can secure at least a portion of the diaphragm 4063 in position between the axial projection 4094 and the axial projection 4046 of the regulator base 4030. For example, the axial projections 4046, 4094 can secure in position a portion of the diaphragm 4063 adjacent to or near the lip 4063*b*.

As illustrated, in some embodiments the base protrusion 4033 can extend further than the axial projection 4046 in the direction away from the coupling protrusion 4032. In some embodiments, a portion of the diaphragm 4063 adjacent the inner aperture 4063*a* can be deflected or otherwise moved away from the coupling protrusion 4032 when the regulator nest 4090 is coupled to the regulator base 4030. Deflection of the portion of the diaphragm 4063 adjacent the inner aperture 4063*a* can create a biasing force (e.g., a return force within the material of the diaphragm 4063) that can bias the inner aperture 4063*a* of the diaphragm 4063 toward a lip (e.g., the end of the base protrusion 4033 furthest from the regulator base 4030) of the base protrusion 4033. The lip of the base protrusion 4033 can be formed with a configuration to help produce a low amount of interface or surface area of contact on its forward edge (such as an angled or beveled configuration). For example, a valve seat 4035 can be formed on or near the radially (e.g., up and down with respect to FIG. 28H) outward portion of the base protrusion 4033. Engagement between the diaphragm 4063 and the valve seat 4035 can form a one-way diaphragm valve (e.g., a diaphragm check valve) as will be described in more detail below. The valve seat 4035 can be located further from the coupling protrusion 4032 than a radially (e.g., up and down with respect to FIG. 28H) inward portion of the lip. In some embodiments, a beveled lip can inhibit or prevent the diaphragm 4063 from sticking to the valve seat 4035 by producing a low amount of surface area contact or interface between the diaphragm 4063 and the valve seat 4035.

In some embodiments, the vial adaptor 4000 includes an enclosure cover 4098. The enclosure cover 4098 can be constructed from a resilient, flexible, or semi-flexible material. For example, the enclosure cover 4098 can be constructed from rubber, silicone, and/or some other flexible or semi-flexible material. The enclosure cover 4098 can be sized and shaped to fit around the radially (e.g., up and down with respect to FIG. 28H) outward portion of the regulator nest 4090. For example, as illustrated in FIG. 28G, the enclosure cover can include an inner lip 4098*a* configured to wrap around one axial side (e.g., the axial side of the regulator nest 4090 closest to the regulator base 4030 in the assembled regulator assembly 4050) of the regulator nest 4090 and an outer lip 4098*b* configured to wrap around the other axial side of the regulator nest 4090. As illustrated, the inner lip 4098*a* can be about the same thickness as or thicker than the outer lip 4098*b*. In some embodiments, the inner lip 4098*a* of the regulator enclosure cover 4098 can be positioned or wedged between the regulator nest 4090 and the regulator base 4030 when the regulator nest 4090 is coupled with the regulator base 4030. In some embodiments, wedging the inner lip 4098*a* of the enclosure cover 4098 can inhibit or prevent the enclosure cover 4098 from detaching from the regulator nest 4090. In some embodiments, adhesives can be used to adhere the enclosure cover 4098 to the regulator nest 4090. The outer lip 4098*b* of the enclosure cover 4098 can include or define an expansion aperture 4028. For example, the outer lip 4098*b* can define a circular or otherwise shaped opening to define the expansion aperture 4028. The expansion aperture 4028 can have a width WS4 that is less than a width WS3 of the regulator nest 4090.

As illustrated in FIG. 28G, the vial adaptor 4000 can include a flexible enclosure 4054. The flexible enclosure 4054 can be configured to fit within a storage chamber 4096 within the regulator nest 4090 and/or the enclosure cover 4098. In some embodiments, the flexible enclosure 4054 is folded into the storage chamber 4096 when the flexible enclosure 4054 is in a contracted configuration. In some embodiments, as illustrated, the flexible enclosure 4054 is not generally expandable by stretching the material of the flexible enclosure 4054 in the plane of such material, to avoid creating an opposing pressure against the expansion which would tend to encourage gas within the flexible enclosure 4054 to be urged back out of the flexible enclosure 4054. Rather, by primarily unfolding instead of primarily stretching the flexible enclosure 4054 to increase its volume, the gas inside of the flexible enclosure 4054 is not generally urged back out of the flexible enclosure 4054 unless and until one or more other forces in the system act upon it to do so. The flexible enclosure 4054 can be connected to the regulator nest 4090 at an attachment point 4056. For example, an adhesive (e.g., glue, tape, foam tape or other appropriate adhesive) can be used to attach an opening of the flexible enclosure 4054 to the regulator nest 4090. The flexible enclosure 4054 can be connected and/or coupled with the regulator nest 4090 in a fluid tight fashion. For example, the flexible enclosure can define an inner volume VE1, VE2 in communication with the coupling passage 4031 of the regulator base 4030. In some embodiments, the interior volume VE1, VE2 of the flexible enclosure 4054 is not in fluid communication with ambient when the diaphragm check valve is in the closed position.

In some embodiments, as illustrated in FIG. 28H, the regulator assembly 4050 can include one or more intake ports 4044. The intake ports 4044 can be positioned along or near the coupling protrusion 4032. In some embodiments, the intake ports 4044 are positioned in a wall of the regulator base 4030 away from the coupling protrusion 4032. One or more spacers 4044*a* can be located adjacent to the intake ports 4044. The spacers 4044*a* can be configured to limit the extent to which the coupling protrusion 4032 enters into the lumen 4026 when the regulator base 4030 is coupled with the lumen 4026. In some embodiments, the spacers 4044*a* inhibit or prevent intake ports 4044 from being blocked by the regulator base 4030 and/or the lumen 4026.

As illustrated in FIG. 28G, the intake ports 4044 can facilitate communication between ambient and the filter 4061. In some embodiments, upon withdrawal of fluid from a vial onto which the vial adaptor 4000 is attached, a pressure deficit can be realized in the coupling passage 4031. A reduction in pressure in the coupling passage 4031 can create a pressure differential at the interface between the valve seat 4035 and the diaphragm 4063. In some embodiments, the diaphragm 4063 is configured to deflect or otherwise move away from the valve seat 4035 when a predetermined pressure differential (e.g., a pressure differential wherein the pressure in the coupling passage 4031 is lower than the ambient pressure) is applied across the diaphragm 4063. As shown in FIG. 28H, deflection or other movement of the diaphragm 4063 away from the valve seat 4035 can facilitate fluid communication between ambient and the coupling passage 4031. In some embodiments, fluid communication between ambient and the coupling passage 4031 can help to equalize the pressure between the interior of the vial 10 and ambient. Fluid passing from ambient to the coupling passage 4031 can pass through the filter 4061. In some embodiments, the filter 4061 can inhibit or prevent introduction of contaminants (e.g., bacteria, viruses, particulates) into the coupling passage 4031 when the diaphragm check valve is open (e.g., when the diaphragm 4063 is disengaged from the valve seat 4035). The diaphragm 4063 can be configured to return to its engagement with the valve seat 4035 when a predetermined pressure differential (e.g., generally equal pressure, or some other pressure differential) occurs between the interior of the vial (e.g., the coupling passage 4031) and ambient.

In some embodiments, a health care practitioner may withdraw fluid from the vial 10 in a vented manner via the access channel 4045 after coupling the vial adaptor 4000 with the vial 10 both prior to and after injecting fluid into the vial 10 via the access channel 4045. For example, the diaphragm check valve formed by the diaphragm 3063 and the valve seat 4035 can permit fluid withdrawal from the vial 10 via the access channel 4045 in a vented manner (e.g., in a manner that maintains a pre-determined pressure range within the vial 10 during withdrawal of fluid) prior to expansion of the flexible enclosure 4054 by permitting fluid ingress through the intake ports 4044 through the filter 4061. In some embodiments, the gas pressure within the vial is maintained at a generally equal level with ambient air pressure so that fluid within a withdrawing medical implement (such as a syringe connected to the vial adapter) is not unintentionally drawn back into the vial and so that the risk of microspraying, gas release, or other undesirable occurrences during connection or disconnection are substantially reduced or eliminated.

In some embodiments, upon introduction of fluid into the vial 10 via the access channel 4045, an increase in pressure can be realized within the coupling passage 4031. The volume within the flexible enclosure 4054 can be configured to expand in response to an increase in pressure within the coupling passage 4031 to a desirable or predetermined pressure. For example, upon introduction of fluid into the vial via the access channel 4045, the pressure in the coupling channel 4031 can increase to a point that the volume within the flexible enclosure 4054 expands to the expanding configuration, as illustrated in FIG. 28I. In the expanded configuration, the flexible enclosure can have a width (e.g., a diameter) D7. The width D7 of the flexible enclosure 4054 can be greater than a width (e.g., a diameter) D11 of the regulator nest 4090. For example, the width D7 can be greater than about 110% of the width D11 and/or less than about 500% of the width D11. In some embodiments, the width D7 of the expanded flexible enclosure 4054 is approximately 320% of the width D11 of the regulator nest 4090. The expanded volume VE4 of the flexible enclosure 4054 can be greater than the storage chamber volume VS of the storage chamber 4096. For example, the expanded volume DE4 of the flexible enclosure 4054 can be greater than or equal to about 500% of the volume VS of the storage chamber 4096 and/or less than or equal to about 10,000% of the volume VS of the storage chamber 4096. In some embodiments, the expanded volume VE4 of the expanded flexible enclosure 4054 is greater than or equal to about 3,000% of the volume VS of the storage chamber 4096 and/or less than or equal to about 5,500% of the volume VS of the storage chamber 4096. In some embodiments, the expanded volume VE4 of the expanded flexible enclosure 4054 is approximately about 4,300% of the volume VS of the storage chamber 4096. Many variations are possible.

The volume within the flexible enclosure 4054, after transition to the expanded configuration, can be configured to contract to the contracted configuration upon withdrawal of fluid from the vial 10 via the access channel 4045. Contraction of the volume within the flexible enclosure 4054 can facilitate introduction of regulator fluid from the interior volume of the flexible enclosure 4054 to the vial 10 via the regulator channel 4025. Introduction of regulator fluid from the interior volume of the flexible enclosure 4054 to the vial 10 can facilitate maintenance of the pressure within the vial 10 within a desirable or predetermined range.

As illustrated in FIG. 28G, a radial (e.g., with respect to the centerline CL of the piercing member 4020) distance DS3 between the regulator base 4030 and the center line of the vial adaptor 4000 can be greater than the radial distance DS4 between the radially inner edge of the regulator base 4030 and the radially outward edge of the enclosure cover 4098. In some embodiments, the radial distance DS3 is greater than or equal to 110% of the radial distance DS4 and/or less than or equal to 200% of the radial distance DS4. In some embodiments, the radial distance DS3 is approximately 140% of the radial distance DS4.

In some embodiments, the flexible enclosure 4054 is folded and stored within the storage chamber 4096 when the flexible enclosure 4054 is in the contracted configuration. In some embodiments, the flexible enclosure 4054 is folded into a polygonal shape, circular shape, and/or oval shape before being stored in the storage chamber 4096. For example, as illustrated in FIG. 29B, the flexible enclosure 4054 can be folded into a substantially rectangular shape within the storage chamber 4096.

As discussed above, the flexible enclosure 4054 can be configured to transition to an expanded configuration upon introduction of fluid into the vial 10 via the access channel 4045. In some embodiments, the flexible enclosure 4054 is folded and stored within the storage chamber 4096 such that at least a portion of the flexible enclosure 4054 realizes a frictional resistance with a portion of the outer lip 4098*b* of the enclosure cover 4098 as the flexible enclosure 4054 transitions to the expanded configuration from the contracted configuration. Frictional resistance between the folded flexible enclosure 4054 and the outer lip 4098*b* can inhibit or prevent the flexible enclosure 4054 from rapidly transitioning to the expanded configuration. Slowing the transition of the flexible enclosure 4054 from the contracted configuration to the expanded configuration can inhibit or prevent the ball check valve 4070 from accidentally closing (e.g., engagement of the ball with the valve seat of the valve 4070 due to a pulse of fluid from the vial 10 toward the coupling channel 4031) and can generally help diminish stresses within the system of the vial, the vial adaptor, and the medical implement (e.g., syringe) to which vial is being transferred, that may otherwise increase the risk of leaking or other failures.

In some embodiments, the flexible enclosure 4054 is configured to unfold from the contracted configuration in a consistent and/or controlled manner in order to promote a consistent, slow, and predictable expansion of the volume within the flexible enclosure 4054. For example, the flexible enclosure 4054 can be folded in a desirable or predetermined pattern (e.g., the patterns disclosed in FIGS. 30A-31B and described below) and unfolded in a desirable or predetermined pattern (e.g., the folds made in the folding pattern unfold in the reverse order from the order in which they were folded).

In some embodiments, the flexible enclosure 4054 is folded into the storage chamber 4096 such that the folds of the flexible enclosure 4054 form a generally laminate substrate of enclosure layers. For example, as illustrated in FIG. 28G, a plurality of flexible enclosure layers can be positioned between a next aperture 4095 of the regulator nest 4090 and the expansion aperture 4028 of the outer lip 4098*b* of the enclosure cover 4098. In some embodiments, the flexible enclosure layers can substantially reduce, minimize, or eliminate the likelihood of material failure (e.g., puncture, tearing, rupture) of the flexible enclosure 4054 from impact or other external forces on the layer of the folded flexible enclosure 4054 closest to the expansion aperture 4028 (e.g., the layer of the folded flexible enclosure 4054 most exposed to ambient when the flexible enclosure 4054 is in the contracted configuration). For example, the laminate configuration of the folds of the folded flexible enclosure 4054 can increase the effective thickness (e.g., the sum thickness of the laminate layers)

of the flexible enclosure 4054 layers with respect to impact or other forces applied from the exterior of the regulator assembly 4050. In some embodiments, the laminate configuration of the folded flexible enclosure 4054 can reduce, minimize, or eliminate any likelihood that the flexible enclosure 4054 would rupture due to increased pressure from within the vial 10. For example, as described above, the laminate layers can increase the effective thickness of the flexible enclosure 4054 with respect to pressure within the vial 10.

As illustrated in FIG. 28G, the flexible enclosure 4054 can have a very small internal volume VE3 when in the contracted configuration. For example, folding the flexible enclosure 4054 (e.g., according to the processes described below) can diminish the space between the laminate folded layers of the folded flexible enclosure 4054 and can eject much or most of the fluid from within the flexible enclosure 4054. In some embodiments, ejecting much or most of the fluid from the folded flexible enclosure 4054 can increase the volume difference between the contracted flexible enclosure 4054 (e.g., a shown in FIG. 28G) and the expanded flexible enclosure 4054 (e.g., as shown in FIG. 28I). In some embodiments, increasing the volume difference between the contracted flexible enclosure 4054 and the expanded flexible enclosure 4054 can reduce, minimize, or eliminate any need to use a stretchable material for the flexible enclosure 4054. For example, a flexible material with little or no stretchability (e.g. Mylar® film) can be used to construct the flexible enclosure 4054.

Figure 29A:
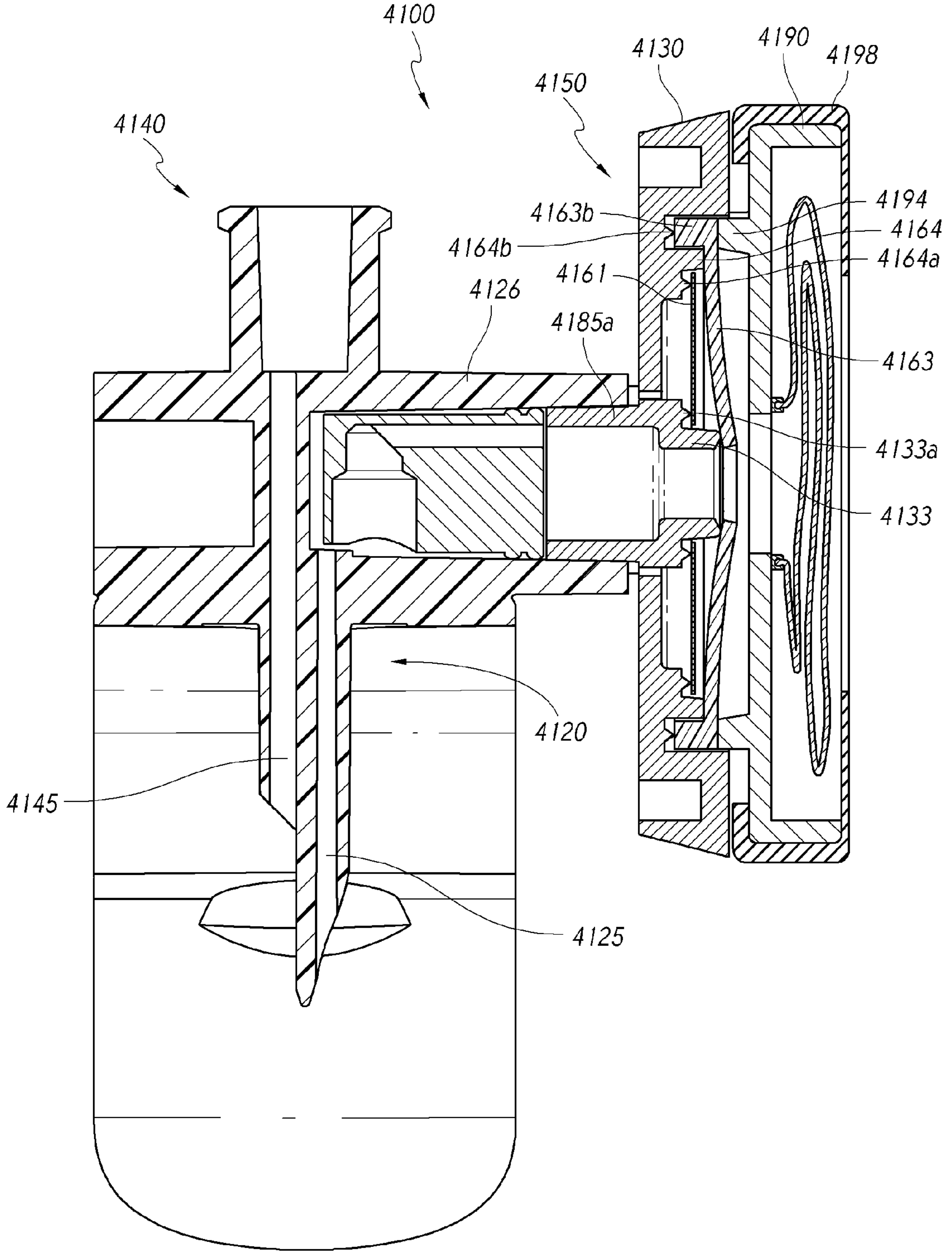
FIG. 29A illustrates a front partial cross-sectional view of another vial adaptor.
Figure 29B:
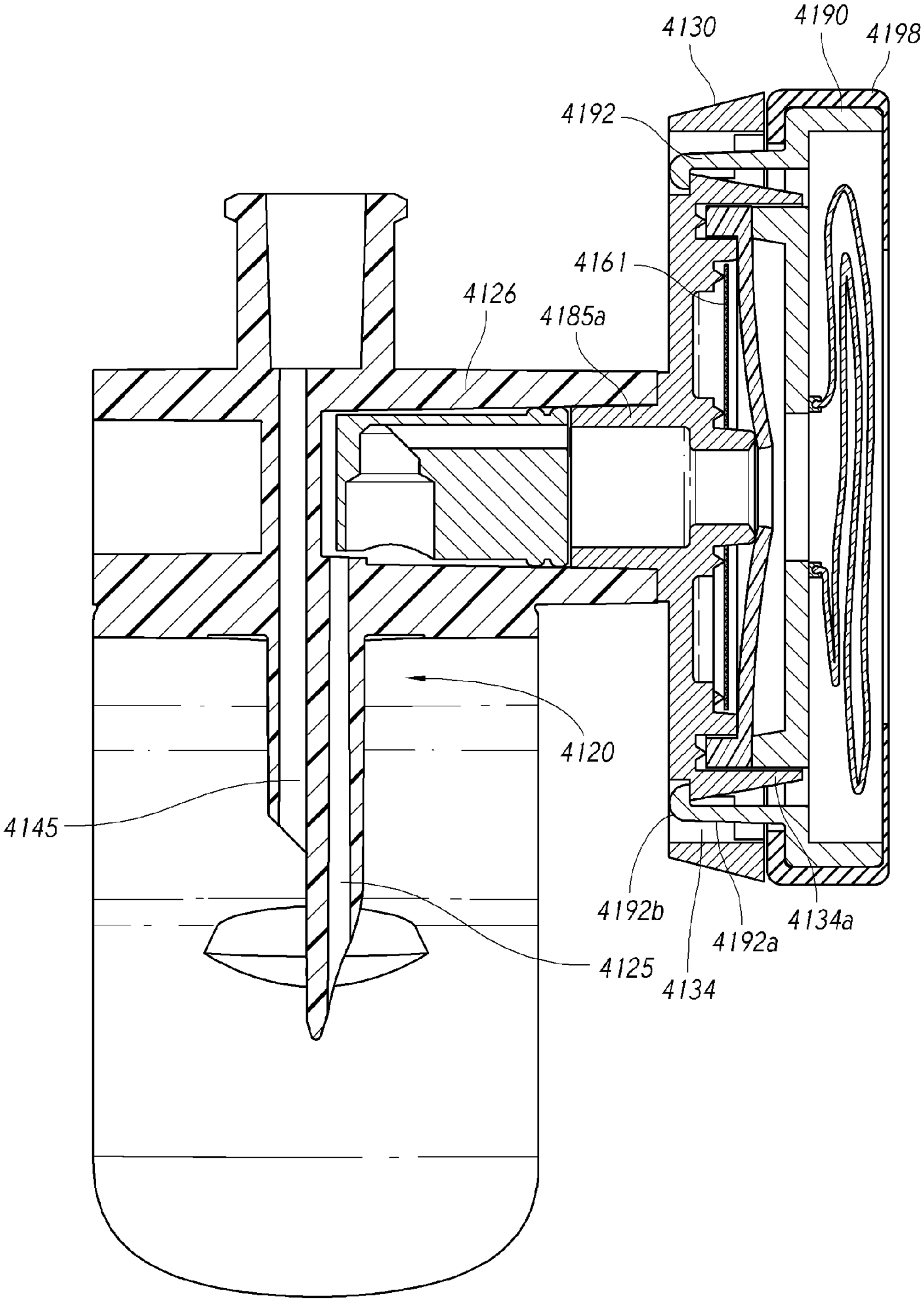
FIG. 29B illustrates a front partial cross-sectional view of the vial adaptor of FIG. 29A with the regulator assembly rotated about its axis by 45°.

FIGS. 29A-29B illustrate an embodiment of a vial adaptor 4100 that can have components or portions that are the same as or similar to the components or portions of other vial adaptors disclosed herein. In some embodiments, the vial adaptor 4100 includes a connector interface 4140 and a piercing member 4120 in partial communication with the connector interface 4140. In some embodiments, the vial adaptor 4100 includes a regulator assembly 4150. Some numerical references to components in FIGS. 29A-29B are the same as or similar to those previously described for the vial adaptor 4000 (e.g., piercing member 4120 v. piercing member 4020). It is to be understood that the components can be the same in function or are similar in function to previously-described components. The adaptor 4100 of FIGS. 29A-29B shows certain variations to the adaptor 4000 of FIGS. 40A-40J.

As illustrated, the filter 4161 of the regulator assembly 4050 can be a thin filter (e.g., substantially thinner than the diameter or cross-section of the filter 4161). The filter 4161 can be hydrophobic and/or antimicrobial. In some embodiments, the filter 4161 is configured to engage with a first filter seat 4133*a* and a second filter seat 4164*a*. One or both of the first filter seat 4133*a* and the second filter seat 4164*a* can be an annular ridge. For example, the first filter seat 4133*a* can be an annular ridge positioned on a stepped portion of the base protrusion 4133 of the regulator base 4030. The second filter seat 4164*a* can be, for example, an annular ridge positioned on a stepped portion of the regulator base 4030. In some embodiments, the filter 4161 is affixed to the first filter seat 4133*a* and/or to the second filter seat 4164*a* via an adhesive of other appropriate fixation compound or technique.

The diaphragm 4163 can be fixed between the regulator nest 4090 and the regulator base 4030. In some embodiments, the lip 4163*b* of the diaphragm 4163 can be positioned or wedged between the axial projection 4194 of the regulator nest 4090 and an base ridge 4164*b*. The base ridge 4164*b* can be a generally annular ridge. The lip 4163*b* of and/or the entire diaphragm 4163 can be constructed from a flexible and/or compressible material. In some embodiments, wedged engagement between the lip 4163*b* of the diaphragm 4163 and the base ridge 4164*b* can reduce, minimize, or eliminate the possibility that fluid will unintentionally bypass the diaphragm 4163 around the lip 4163*b*.

Figure 30A:
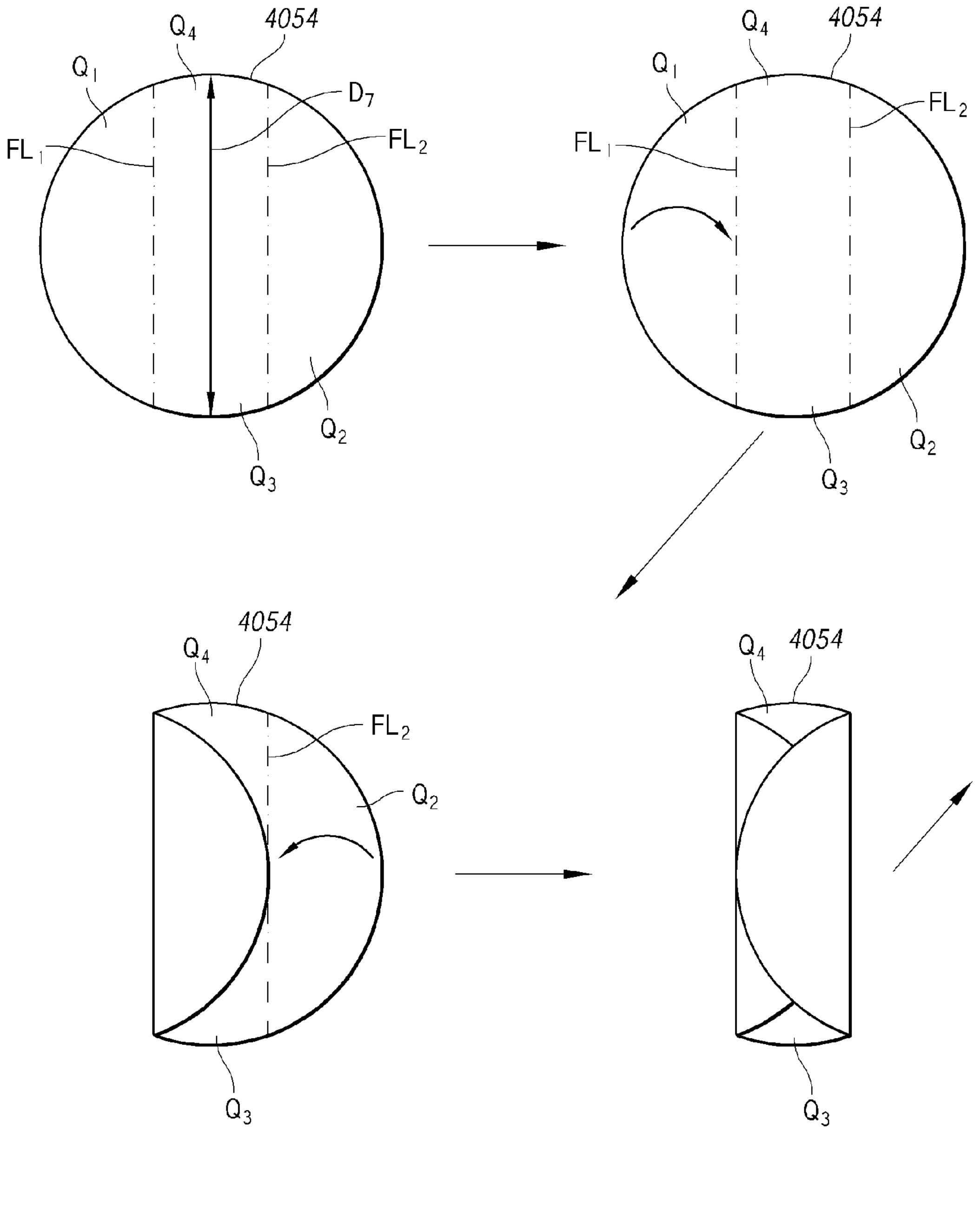
FIG. 30A illustrates an embodiment of a method of folding a flexible enclosure.
Figure 30B:
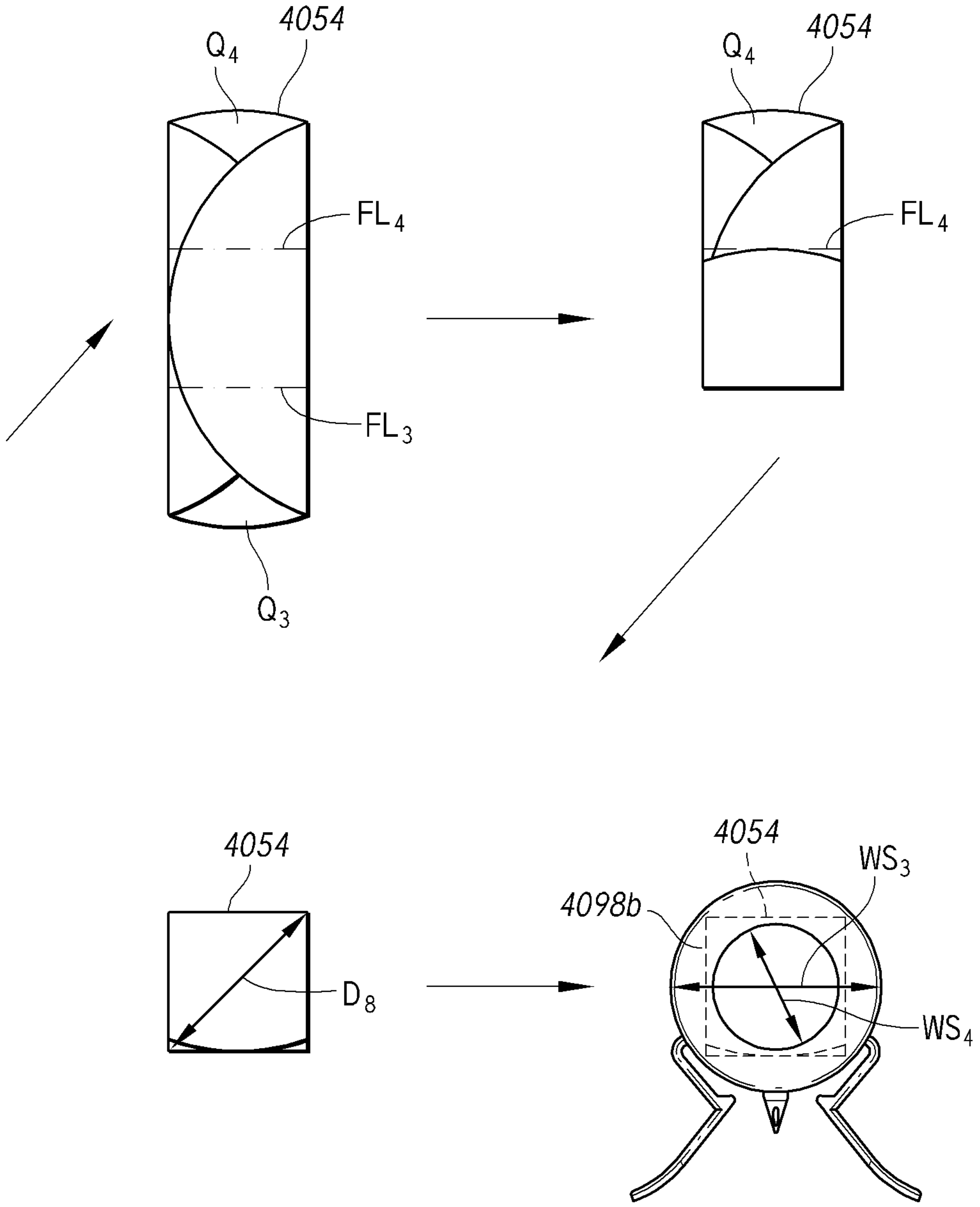
FIG. 30B illustrates steps in an embodiment of the method of FIG. 30A.

FIGS. 30A-30B illustrate an example of a folded flexible enclosure 4054 and an example of a method of folding the flexible enclosure 4054. In some embodiments, the flexible enclosure 4054 can be defined in multiple (e.g., three) horizontal (e.g., left to right with reference to FIG. 30A) portions that have relatively equal horizontal extents. The multiple horizontal portions can be separated by multiple fold lines FL1 and FL2. The method of folding the flexible enclosure 4054 can include folding a first portion or quadrant Q1 of the flexible enclosure 4054 along the fold line FL1. The method can include folding a second portion or quadrant Q2 over the first portion or quadrant Q1 generally along the fold line FL2. As illustrated in 29B, a method of folding the flexible enclosure 4054 can include dividing the flexible enclosure 4054 into multiple (e.g., three) vertical portions (e.g., up and down with respect to FIG. 30B). The multiple vertical portions can be separated by another (e.g., a third) fold line FL3 and yet another (e.g., a fourth) fold line FL4. A method of folding the flexible enclosure 4054 can include folding another (e.g., a third) portion or quadrant along fold line FL3. Yet another portion (e.g., a fourth) or quadrant Q4 can be folded over the previously formed (e.g., third) portion or quadrant Q3 along fold line FL4. Upon folding quadrant 4 over quadrant 3, as illustrated in FIG. 29B, the flexible enclosure can have a generally square or rectangular shape. The square or rectangle of the flexible enclosure 4054 can have a major diagonal line D8. The major diagonal line D8 can be less than or about equal to a width WS3 of the regulator nest 4090. As illustrated in FIG. 29B, the diagonal line D8 can be greater than or about equal to the width WS4 of the expansion aperture 4028.

Figure 31A:
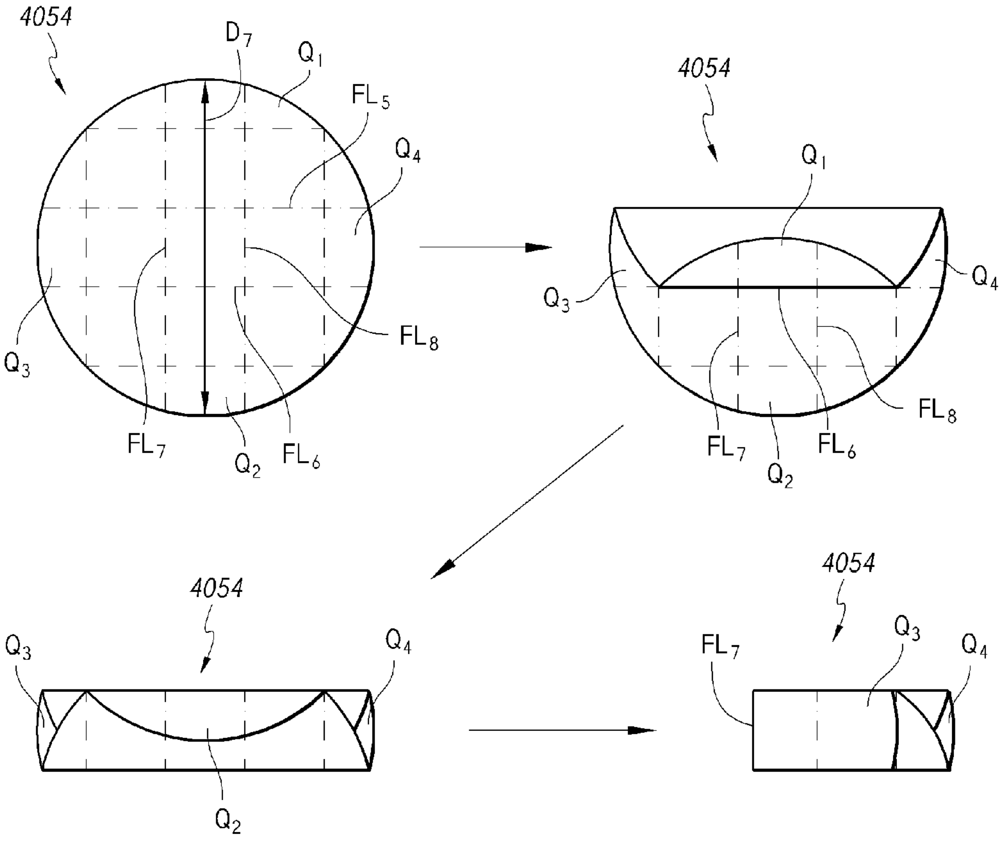
FIG. 31A illustrates an embodiment of a method of folding a flexible enclosure.
Figure 31B:
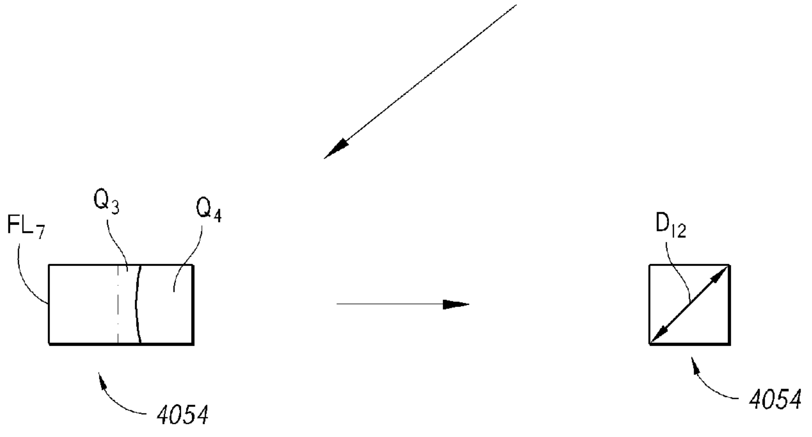
FIG. 31B illustrates steps in an embodiment of the method of FIG. 31A.

FIGS. 31A-31B illustrate a method of folding the flexible enclosure 4054. The fold lines of the method illustrated in FIGS. 31A-31B can generally form a square having a diagonal approximately equal to the width D7 of the expanded flexible enclosure 4054. The method can include folding a first quadrant Q1*a* of the flexible enclosure 4054 toward the second quadrant Q2*a* (e.g., the quadrant on the generally opposite side of the flexible enclosure 4054 from the quadrant Q1*a*) along the first fold line FL1*a*. The first quadrant Q1*a* can then be folded back toward the fold line FL1*a*. In some embodiments, the second quadrant Q2*a* is folded over the first quadrant Q1*a* along the second fold line FL2*a*. The second quadrant Q2*a* can then be folded back toward the fold line FL2*a*. The third quadrant Q3*a* may be folded toward the fourth quadrant Q4*a* along the third fold line FL3*a*. According to some configurations, the fourth quadrant Q4*a* is then folded over the third quadrant Q3*a* along the fourth fold line FL4*a*. The generally stacked or laminated third and fourth quadrants Q3*a*, Q4*a* then can be folded along the fifth fold line FL5 to form a substantially rectangular folded flexible enclosure 4054 having a diagonal D12. The length of diagonal D12 can be greater than the width WS4 of the expansion aperture 4028 and/or less than or equal to about the width WS3 of the regulator nest 4030.

Although the vial adaptor has been disclosed in the context of certain embodiments and examples, it will be understood by those skilled in the art that the vial adaptor extends beyond the specifically disclosed embodiments to other alternative embodiments and/or uses of the embodiments and certain modifications and equivalents thereof. For example, some embodiments are configured to use a regulating fluid that is a liquid (such as water or saline), rather than a gas. As another example, in certain embodiments the bag comprises a bellows. It should be understood that various features and aspects of the disclosed embodiments can be combined with or substituted for one another in order to form varying modes of the vial adaptor. For example, the annular bag shape of FIG. 24 can be incorporated into the embodiment of FIGS. 13-15. Accordingly, it is intended that the scope of the vial adaptor herein-disclosed should not be limited by the particular disclosed embodiments described above, but should be determined only by a fair reading of the claims that follow.

The following is claimed:

1. A medical adaptor capable of coupling with a sealed container, the medical adaptor having a filter chamber surrounding at least a portion of a regulator assembly channel, the medical adaptor comprising:

a housing comprising:

a medical connector interface;

an access channel capable of removing medicinal fluid extending between the medical connector interface and a distal access port; and a regulator channel comprising a distal regulator passageway, a regulator valve, and a proximal regulator passageway; and a regulator assembly comprising:

a regulator interface defining a regulator assembly channel and capable of fluid communication with the proximal regulator passageway;

a storage chamber having a storage height and a storage depth and a storage volume;

a filter chamber in fluid communication with an ambient environment, wherein the filter chamber has an inner diameter at least partially defined by an inner wall, and an outer diameter at least partially defined by an outer wall, and wherein the filter chamber surrounds at least a portion of the regulator assembly channel;

a flexible enclosure capable of fluid communication with the proximal regulator passageway, the flexible enclosure capable of transitioning between a contracted configuration and an expanded configuration;

an intake valve in fluid communication with the flexible enclosure and the proximal regulator passageway when the regulator interface is connected to the proximal regulator aperture, the intake valve capable of transitioning between an opened configuration and a closed configuration, the intake valve comprising an elastomeric member having an inner orifice, the inner orifice defining at least a portion of a fluid path between the flexible enclosure and the proximal regulator passageway when the intake valve is in the closed configuration, wherein the intake valve facilitates fluid communication between an interior of the regulator assembly and the filter chamber when the intake valve is in the opened configuration; and a filter positioned within the filter chamber and filling a space defined between the inner diameter of the filter chamber and the outer diameter of the filter chamber.

2. The adaptor of claim 1, wherein the inner orifice of the elastomeric member is circular.

3. The adaptor of claim 1, wherein the intake valve is a one-way valve, the intake valve capable of inhibiting outflow of fluid through the intake valve from the interior of the interior of the regulator assembly to the ambient environment.

4. The adaptor of claim 1, wherein the filter is a hydrophobic filter.

5. The adaptor of claim 1, wherein the filter is an antimicrobial filter.

6. The adaptor of claim 1, wherein the regulator assembly includes at least one intake port, the intake port facilitating fluid communication between the filter chamber and the ambient environment, the intake port positioned between the inner orifice and the medical connector interface.

7. The adaptor of claim 1, wherein the elastomeric member is in a deflected configuration when the intake valve is in the closed configuration.

8. The adaptor of claim 1, wherein the elastomeric member is biased toward a circular valve seat.

9. The adaptor of claim 1, wherein the elastomeric member is positioned coaxially with at least a portion of the regulator assembly channel.

* * * * *

UNITED STATES PATENT AND TRADEMARK OFFICE

CERTIFICATE OF CORRECTION

PATENT NO. : 9,089,475 B2
APPLICATION NO. : 14/161591
DATED : July 28, 2015
INVENTOR(S) : Thomas F. Fangrow It is certified that error appears in the above-identified patent and that said Letters Patent is hereby corrected as shown below:

In the specification,

In column 23 at line 35, Change “fluid” to --fluid.--.

In column 24 at line 2, Change “member” to --member.--.

In column 24 at line 52, Change “torroidal,” to --toroidal,--.

In column 56 at line 37, Change “and or” to --and/or--.

In column 69 at line 20, Before “shown” change “a” to --as--.

In column 69 at line 62, After “and” change “an” to --a--.

In the claims,

In column 72 at lines 19-20 (approx.), In Claim 3, before “regulator” change “interior of the interior of the” to --interior of the--.

Signed and Sealed this
Thirty-first Day of May, 2016

Michelle K. Lee
*Director of the United States Patent and Trademark Office*